(12) United States Patent
Mogi et al.

(10) Patent No.: US 8,076,332 B2
(45) Date of Patent: Dec. 13, 2011

(54) N-(2-AMINOPHENYL) BENZAMIDE DERIVATIVE HAVING UREA STRUCTURE

(75) Inventors: Hiroyuki Mogi, Ikoma (JP); Hisashi Tajima, Ikoma (JP); Noriko Mishina, Ikoma (JP); Yusuke Yamazaki, Ikoma (JP); Shinji Yoneda, Ikoma (JP); Katsuhiko Watanabe, Ikoma (JP); Junko Fujikawa, Ikoma (JP); Minoru Yamamoto, Ikoma (JP)

(73) Assignee: Santen Pharmaceutical Co., Ltd., Osaka-Shi, Osaka (JP)

( * ) Notice: Subject to any disclaimer, the term of this patent is extended or adjusted under 35 U.S.C. 154(b) by 181 days.

(21) Appl. No.: 12/448,259

(22) PCT Filed: Dec. 26, 2007

(86) PCT No.: PCT/JP2007/074912
§ 371 (c)(1),
(2), (4) Date: Aug. 6, 2009

(87) PCT Pub. No.: WO2008/078762
PCT Pub. Date: Jul. 3, 2008

(65) Prior Publication Data
US 2009/0306077 A1    Dec. 10, 2009

(30) Foreign Application Priority Data
Dec. 26, 2006 (JP) ................... 2006-350263

(51) Int. Cl.
*A61K 31/535* (2006.01)
(52) U.S. Cl. .............. 514/237.2; 514/237.4; 514/424; 514/254.11; 514/596; 544/131; 544/165; 544/377
(58) Field of Classification Search ......... 514/237.2, 514/424, 254.11, 596; 544/131, 165, 377
See application file for complete search history.

(56) References Cited

U.S. PATENT DOCUMENTS
| | | |
|---|---|---|
| 6,174,905 B1 | 1/2001 | Suzuki et al. |
| 6,329,547 B1 | 12/2001 | Shirasawa et al. |
| 6,395,932 B1 | 5/2002 | Shirasawa et al. |

FOREIGN PATENT DOCUMENTS
| | | | |
|---|---|---|---|
| JP | 10-152462 | * | 9/1997 |
| JP | 10-152462 A | | 6/1998 |
| WO | WO 97/30701 A2 | | 8/1997 |
| WO | WO 00/09162 A1 | | 2/2000 |

OTHER PUBLICATIONS

Javvadhi et al. (Kathmandu University Medical Journal (2005) vol. 3, No. 3, Issue 11, 217-221.)*

* cited by examiner

*Primary Examiner* — Andrew D Kosar
*Assistant Examiner* — Valerie Rodriguez-Garcia
(74) *Attorney, Agent, or Firm* — Holtz, Holtz, Goodman & Chick, PC

(57) ABSTRACT

The present invention relates to a study on the synthesis of a novel N-(2-aminophenyl)benzamide derivative having an urea structure and represented by the general formula (1); and the utilization of a pharmacological effect of the derivative. A compound represented by the general formula (1) or a salt thereof has an effect of cellular morphological change on trabecular meshwork cells and is effective in the prevention and/or treatment of a disease considered to be related to intraocular pressure. In the formula, $R^1$ and $R^2$ represent a hydrogen atom, a lower alkyl group, or the like; $R^3$ represents a hydroxy group, a lower alkoxy group, a lower cycloalkyloxy group, an aryloxy group, or the like; $R^4$ and $R^5$ represent a halogen atom, a lower alkyl group, a hydroxy group, a lower alkoxy group, or the like; X represents a lower alkylene group or the like; Y represents a single bond, a lower alkylene group, or the like; l and m represent 0, 1, 2, or the like.

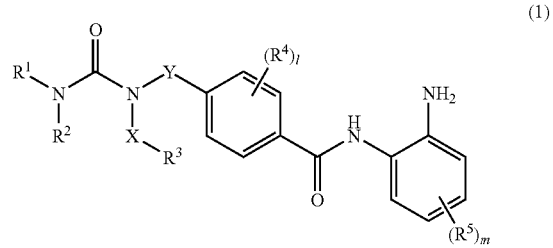

(1)

19 Claims, No Drawings

N-(2-AMINOPHENYL) BENZAMIDE DERIVATIVE HAVING UREA STRUCTURE

This application is the United States national phase application of International Application PCT/JP2007/074912 filed Dec. 26, 2007.

TECHNICAL FIELD

The present invention relates to a novel N-(2-aminophenyl) benzamide derivative having a urea structure or a salt thereof useful as a pharmaceutical. The derivative or a salt thereof has an effect of cellular morphological change on trabecular meshwork cells and is useful as a preventive and/or therapeutic agent for a disease considered to be related to intraocular pressure.

BACKGROUND ART

The circulation of aqueous humor in the eye is closely related to intraocular pressure, and the hindrance of circulation of aqueous humor has a considerable effect on the intraocular pressure. When the circulation of aqueous humor is hindered, the intraocular pressure is increased to cause a disease considered to be related to intraocular pressure such as glaucoma or ocular hypertension.

In general, aqueous humor is produced through filtration or active transport of plasma components and most of aqueous humor flows out of the eyeball through the trabecular outflow pathway. That is, it becomes possible to prevent and/or treat a disease considered to be related to intraocular pressure by changing the morphology of trabecular meshwork cells with a drug or the like to reduce the resistance to aqueous humor outflow and increase aqueous humor outflow.

For example, as drugs for changing the morphology of trabecular meshwork cells to increase aqueous humor outflow, an actin polymerization inhibitor, latrunculin A, a myosin light-chain kinase (MLCK) inhibitor, H-7, a Rho-kinase inhibitor, Y-39983 (WO 97/30701 and WO 00/09162), and the like are known.

On the other hand, a compound having an N-(2-aminophenyl)benzamide structure has been disclosed in JP-A-10-0152462 as a therapeutic agent for a malignant tumor having a differentiation induction promoting effect.

DISCLOSURE OF THE INVENTION

Problems to be Solved

It is a very interesting object to study the synthesis of a novel N-(2-aminophenyl)benzamide derivative having an urea structure or a salt thereof and to study a pharmacological effect of the derivative or a salt thereof.

Means for Solving the Problems

The present inventors made the studies of the synthesis of N-(2-aminophenyl)benzamide derivatives having a novel chemical structure and succeeded in creating a large number of novel compounds.

The derivative has a chemical structural characteristic residing in the combination of (a) and (b) in the following general formula (1):

(a) having an urea structure in A moiety; and
(b) having an alkylene structure attached to a group having an oxygen atom and/or a nitrogen atom in B moiety.

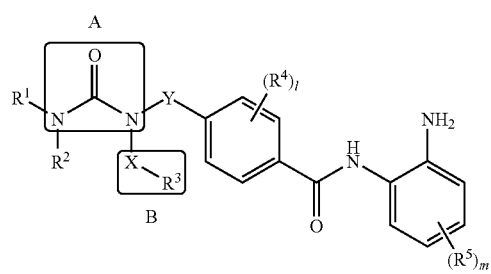

(1)

Further, the present inventors made studies on a pharmacological effect of the derivative or a salt thereof, and as a result, they found that the derivative or a salt thereof has an effect of cellular morphological change on trabecular meshwork cells and is useful as a preventive and/or therapeutic agent for a disease considered to be related to intraocular pressure, and thus, the present invention has been achieved.

That is, the present invention relates to a compound represented by the following general formula (1) or a salt thereof (hereinafter, referred to as "the present compound") and a pharmaceutical composition containing the present compound.

Further, a preferred invention in the medicinal use thereof is an invention relating to a preventive and/or therapeutic agent for a disease considered to be related to intraocular pressure.

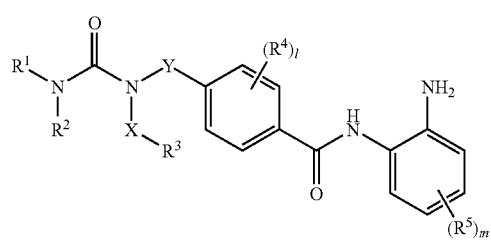

(1)

[$R^1$ and $R^2$ are the same or different and represent a hydrogen atom, a lower alkyl group which may have a substituent, or a group represented by the following general formula (2);

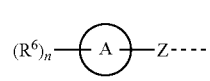

(2)

$R^3$ represents a hydroxy group, a lower alkoxy group which may have a substituent, a lower cycloalkyloxy group which may have a substituent, an aryloxy group which may have a substituent, —NR$^a$R$^b$, or a group represented by the following general formula (3);

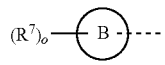
(3)

R$^4$ and R$^5$ are the same or different and represent a halogen atom, a lower alkyl group which may have a substituent, a hydroxy group, or a lower alkoxy group which may have a substituent;

R$^6$ represents a halogen atom, a lower alkyl group which may have a substituent, a lower cycloalkyl group which may have a substituent, an aryl group which may have a substituent, a heterocyclic ring which may have a substituent, a hydroxy group, a lower alkoxy group which may have a substituent, a lower cycloalkyloxy group which may have a substituent, an aryloxy group which may have a substituent, a formyl group, a lower alkylcarbonyl group which may have a substituent, a carboxy group, a lower alkoxycarbonyl group which may have a substituent, a nitro group, a cyano group, —NR$^c$R$^d$, or —NR$^e$(COR$^f$);

R$^7$ represents a lower alkyl group which may have a substituent, a lower cycloalkyl group which may have a substituent, an aryl group which may have a substituent, a hydroxy group, a lower alkoxy group which may have a substituent, a lower cycloalkyloxy group which may have a substituent, or an aryloxy group which may have a substituent;

R$^a$, R$^b$, R$^c$, R$^d$, R$^e$, and R$^f$ are the same or different and represent a hydrogen atom, a lower alkyl group which may have a substituent, a lower cycloalkyl group which may have a substituent, or an aryl group which may have a substituent;

the ring A represents a hydrocarbon ring or a heterocyclic ring;

the ring B represents a heterocyclic ring having one or plural heteroatoms selected from the group consisting of a nitrogen atom, an oxygen atom, and a sulfur atom in the ring;

X represents a lower alkylene group which may have a substituent;

Y and Z are the same or different and represent a single bond or a lower alkylene group which may have a substituent; and l, m, n, and o are the same or different and represent 0, 1, 2, or 3, in the case where l, m, n, and o represent 2 or 3, the respective groups represented by R$^4$, R$^5$, R$^6$, or R$^7$ may be the same or different; hereinafter the same shall apply].

Advantage of the Invention

The present invention provides a novel N-(2-aminophenyl) benzamide derivative having an urea structure or a salt thereof useful as a pharmaceutical. The present compound has an excellent effect of cellular morphological change on trabecular meshwork cells and is useful as a preventive and/or therapeutic agent for a disease considered to be related to intraocular pressure, and particularly useful as an agent for lowering intraocular pressure for preventing and/or treating glaucoma and ocular hypertension.

BEST MODE FOR CARRYING OUT THE INVENTION

Hereinafter, definitions of terms and phrases (atoms, groups, rings, and the like) to be used in this specification will be described in detail. Further, when other definitions of terms and phrases are applied to the definitions of terms and phrases mentioned below, preferred ranges of the respective definitions can also be applied.

The "halogen atom" refers to a fluorine, chlorine, bromine, or iodine atom.

The "lower alkyl group" refers to a straight-chain or branched alkyl group having 1 to 8, preferably 1 to 6 carbon atoms. Specific examples thereof include methyl, ethyl, n-propyl, n-butyl, n-pentyl, n-hexyl, n-heptyl, n-octyl, isopropyl, isobutyl, sec-butyl, tert-butyl, isopentyl groups and the like.

The "lower alkenyl group" refers to a straight-chain or branched alkenyl group having 2 to 8, preferably 2 to 6 carbon atoms. Specific examples thereof include vinyl, propenyl, butenyl, pentenyl, hexenyl, heptenyl, octenyl, isopropenyl, 2-methyl-1-propenyl, 2-methyl-2-butenyl groups and the like.

The "lower alkynyl group" refers to a straight-chain or branched alkynyl group having 2 to 8, preferably 2 to 6 carbon atoms. Specific examples thereof include ethynyl, propynyl, butynyl, pentynyl, hexynyl, heptynyl, octynyl, isobutynyl, isopentynyl groups and the like.

The "lower cycloalkyl group" refers to a cycloalkyl group having 3 to 8, preferably 3 to 6 carbon atoms. Specific examples thereof include cyclopropyl, cyclobutyl, cyclopentyl, cyclohexyl, cycloheptyl, and cyclooctyl groups.

The "aryl group" refers to a residue formed by removing one hydrogen atom from a monocyclic aromatic hydrocarbon group, or bicyclic or tricyclic condensed polycyclic aromatic hydrocarbon having 6 to 14 carbon atoms. Specific examples thereof include phenyl, naphthyl, anthryl, phenanthryl groups and the like.

The "lower alkoxy group" refers to a group formed by substituting the hydrogen atom of a hydroxy group with a lower alkyl group. Specific examples thereof include methoxy, ethoxy, n-propoxy, n-butoxy, n-pentyloxy, n-hexyloxy, n-heptyloxy, n-octyloxy, isopropoxy, isobutoxy, sec-butoxy, tert-butoxy, isopentyloxy groups and the like.

The "lower cycloalkyloxy group" refers to a group formed by substituting the hydrogen atom of a hydroxy group with a lower cycloalkyl group. Specific examples thereof include cyclopropyloxy, cyclobutyloxy, cyclopentyloxy, cyclohexyloxy, cycloheptyloxy, cyclooctyloxy groups and the like.

The "aryloxy group" refers to a group formed by substituting the hydrogen atom of a hydroxy group with an aryl group. Specific examples thereof include phenoxy, naphthoxy, anthryloxy, phenanthryloxy groups and the like.

The "lower alkylcarbonyl group" refers to a group formed by substituting the hydrogen atom of a formyl group with a lower alkyl group. Specific examples thereof include methylcarbonyl, ethylcarbonyl, n-propylcarbonyl, n-butylcarbonyl, n-pentylcarbonyl, n-hexylcarbonyl, n-heptylcarbonyl, n-octylcarbonyl, isopropylcarbonyl, isobutylcarbonyl, sec-butylcarbonyl, tert-butylcarbonyl, isopentylcarbonyl groups and the like.

The "lower alkoxycarbonyl group" refers to a group formed by substituting the hydrogen atom of a formyl group with a lower alkoxy group. Specific examples thereof include methoxycarbonyl, ethoxycarbonyl, n-propoxycarbonyl, n-butoxycarbonyl, n-pentyloxycarbonyl, n-hexyloxycarbonyl, n-heptyloxycarbonyl, n-octyloxycarbonyl, isopropoxycarbonyl, isobutoxycarbonyl, sec-butoxycarbonyl, tert-butoxycarbonyl, isopentyloxycarbonyl groups and the like.

The "heterocyclic ring" refers to a saturated or unsaturated monocyclic heterocyclic ring, or bicyclic or tricyclic condensed polycyclic heterocyclic ring having one or plural heteroatoms selected from a nitrogen atom, an oxygen atom, and a sulfur atom in the ring.

Specific examples of the saturated monocyclic heterocyclic ring include aziridine, azetidine, pyrrolidine, pyrazolidine, imidazolidine, triazolidine, piperidine, hexahydropyridazine, hexahydropyrimidine, piperazine, homopiperidine, and homopiperazine, each of which has a nitrogen atom in the ring; tetrahydrofuran, tetrahydropyran, [1,4]-dioxane, and [1,2]-dioxirane, each of which has an oxygen atom in the ring; tetrahydrothiophene and tetrahydrothiopyran, each of which has a sulfur atom in the ring; oxazolidine, isoxazolidine, and morpholine, each of which has a nitrogen atom and an oxygen atom in the ring; and thiazolidine, isothiazolidine, and thiomorpholine, each of which has a nitrogen atom and a sulfur atom in the ring.

Further, such a saturated monocyclic heterocyclic ring may be condensed with a benzene ring or the like to form a bicyclic or tricyclic condensed polycyclic heterocyclic ring such as dihydroindole, dihydroindazole, dihydrobenzimidazole, tetrahydroquinoline, tetrahydroisoquinoline, tetrahydrocinnoline, tetrahydrophthalazine, tetrahydroquinazoline, tetrahydroquinoxaline, dihydrobenzofuran, dihydroisobenzofuran, chroman, isochroman, benzo[1,3]dioxole, 2,3-dihydrobenzo[1,4]dioxin, dihydrobenzothiophene, dihydroisobenzothiophene, thiochroman, isothiochroman, dihydrobenzoxazole, dihydrobenzisoxazole, dihydrobenzoxazine, dihydrobenzothiazole, dihydrobenzoisothiazole, dihydrobenzothiazine, xanthene, 4a-carbazole, or perimidine.

Specific examples of the unsaturated monocyclic heterocyclic ring include dihydropyrrole, pyrrole, dihydropyrazole, pyrazole, dihydroimidazole, imidazole, dihydrotriazole, triazole, tetrahydropyridine, dihydropyridine, pyridine, tetrahydropyridazine, dihydropyridazine, pyridazine, tetrahydropyrimidine, dihydropyrimidine, pyrimidine, tetrahydropyrazine, dihydropyrazine, and pyrazine, each of which has a nitrogen atom in the ring; dihydrofuran, furan, dihydropyran, and pyran, each of which has an oxygen atom in the ring; dihydrothiophene, thiophene, dihydrothiopyran, and thiopyran, each of which has a sulfur atom in the ring; dihydrooxazole, oxazole, dihydroisoxazole, isoxazole, dihydrooxazine, and oxazine, each of which has a nitrogen atom and an oxygen atom in the ring; dihydrothiazole, thiazole, dihydroisothiazole, isothiazole, dihydrothiazine, and thiazine, each of which has a nitrogen atom and a sulfur atom in the ring.

Further, such an unsaturated monocyclic heterocyclic ring may be condensed with a benzene ring or the like to form a bicyclic or tricyclic condensed polycyclic heterocyclic ring such as indole, indazole, benzimidazole, benzotriazole, dihydroquinoline, quinoline, dihydroisoquinoline, isoquinoline, phenanthridine, dihydrocinnoline, cinnoline, dihydrophthalazine, phthalazine, dihydroquinazoline, quinazoline, dihydroquinoxaline, quinoxaline, benzofuran, isobenzofuran, chromen, isochromen, benzothiophene, isobenzothiophene, thiochromen, isothiochromen, benzoxazole, benzisoxazole, benzoxazine, benzothiazole, 4,5,6,7-tetrahydrobenzothiazole, benzoisothiazole, benzothiazine, phenoxanthine, carbazole, β-carboline, phenanthridine, acridine, phenanthroline, phenazine, phenothiazine, or phenoxazine.

Further, among these heterocyclic rings, in the case where the heterocyclic ring has two hydrogen atoms on the same carbon atom, these hydrogen atoms may be substituted with an oxo group to form a heterocyclic ketone such as 2-pyrrolidone, 4-piperidone, 4-thiazolidone, pyran-4-(4H)-one, or pyrazin-2-(3H)-one, and these heterocyclic ketones are also encompassed in the scope of the heterocyclic ring of the present invention.

The "heterocyclic ring having one or plural heteroatoms selected from the group consisting of a nitrogen atom, an oxygen atom, and a sulfur atom in the ring" refers to a heterocyclic ring having one or plural nitrogen atoms, oxygen atoms, and/or sulfur atoms in the ring among the above-mentioned heterocyclic rings.

The "heterocyclic group" refers to a residue formed by removing one hydrogen atom from a heterocyclic ring.

The "hydrocarbon ring" refers to saturated or unsaturated monocyclic hydrocarbon or bicyclic hydrocarbon having 3 to 10 carbon atoms.

Specific examples of the saturated monocyclic hydrocarbon include cyclopropane, cyclobutane, cyclopentane, cyclohexane, cycloheptane, cyclooctane and the like.

Specific examples of the saturated bicyclic hydrocarbon include octahydropentalene, octahydroindene, decahydronaphthalene and the like.

Specific examples of the unsaturated monocyclic hydrocarbon include cyclopentene, cyclohexene, cyclopentadiene, cyclohexadiene, benzene and the like.

Specific examples of the unsaturated bicyclic hydrocarbon include indan, 1,2,3,4-tetrahydronaphthalene, naphthalene and the like.

The "lower alkylene group" refers to a straight-chain or branched alkylene group having 1 to 8, preferably 1 to 6 carbon atoms. Specific examples thereof include methylene, ethylene, trimethylene, tetramethylene, pentamethylene, hexamethylene, heptamethylene, octamethylene, methylmethylene, ethylmethylene, 2,2-dimethylpropylene groups and the like.

The "lower alkyl group which may have a substituent", "lower alkoxy group which may have a substituent", "lower alkylcarbonyl group which may have a substituent", "lower alkoxycarbonyl group which may have a substituent", and "lower alkylene group which may have a substituent" refer to a "lower alkyl group", a "lower alkoxy group", a "lower alkylcarbonyl group", a "lower alkoxycarbonyl group", and a "lower alkylene group" which may have one or plural substituents selected from the group consisting of a halogen atom, a lower cycloalkyl group, an aryl group, a heterocyclic group, a nitro group, a cyano group, —$OR^p$, —$COR^q$, —$COOR^r$, —$CONR^sR^t$, and —$NR^uR^v$, respectively.

The "lower cycloalkyl group which may have a substituent", "aryl group which may have a substituent", and "heterocyclic group which may have a substituent" refer to a "lower cycloalkyl group", an "aryl group", and a "heterocyclic group" which may have one or plural substituents selected from the group consisting of a halogen atom, a lower alkyl group, a lower alkenyl group, a lower alkynyl group, a lower cycloalkyl group, an aryl group, a heterocyclic group, a nitro group, a cyano group, —$OR^p$, —$COR^q$, —$COOR^r$, —$CONR^sR^t$, and —$NR^uR^v$, respectively.

Here, $R^p$, $R^q$, $R^r$, $R^s$, $R^t$, $R^u$ and $R^v$ are the same or different and represent a group selected from the group consisting of a hydrogen atom, a lower alkyl group, a lower alkenyl group, a lower alkynyl group, a lower cycloalkyl group, an aryl group, and a heterocyclic group.

With regard to the term "plural groups" as used herein, the respective groups may be the same or different, and the number of the groups is preferably 2 or 3, particularly preferably 2. Further, a hydrogen atom and a halogen atom are also encompassed in the concept of the "group" as used herein.

In the present invention, when "l", "m", "n" and/or "o" represents 2 or 3, the respective plural groups represented by $R^4$, $R^5$, $R^6$ and/or $R^7$ may be the same or different. Incidentally, when "l", "m", "n" and/or "o" represents 0, $R^4$, $R^5$, $R^6$ and/or $R^7$ does not exist. That is, it shows that the compound does not have the substituent.

The "agent for enhancing aqueous humor outflow" as used herein refers to a pharmaceutical composition capable of exhibiting a medicinal effect such as reduction of intraocular pressure by enhancing aqueous humor outflow.

Examples of the "disease considered to be related to intraocular pressure" as used herein include glaucoma, ocular hypertension and the like.

The "salt" of the present compound is not particularly limited as long as it is a pharmaceutically acceptable salt, and examples thereof include salts with an inorganic acid such as hydrochloric acid, hydrobromic acid, hydroiodic acid, nitric acid, sulfuric acid, or phosphoric acid; salts with an organic acid such as acetic acid, fumaric acid, maleic acid, succinic acid, citric acid, tartaric acid, adipic acid, gluconic acid, glucoheptonic acid, glucuronic acid, terephthalic acid, methanesulfonic acid, lactic acid, hippuric acid, 1,2-ethanedisulfonic acid, isethionic acid, lactobionic acid, oleic acid, pamoic acid, polygalacturonic acid, stearic acid, tannic acid, trifluoromethanesulfonic acid, benzenesulfonic acid, p-toluenesulfonic acid, lauryl sulfate, methyl sulfate, naphthalene sulfonic acid, or sulfosalicylic acid; quaternary ammonium salts with methyl bromide, methyl iodide, or the like; salts with a halogen ion such as a bromine ion, a chlorine ion, or an iodine ion; salts with an alkali metal such as lithium, sodium, or potassium; salts with an alkaline earth metal such as calcium or magnesium; salts with a metal such as iron or zinc; salts with ammonia; and salts with an organic amine such as triethylenediamine, 2-aminoethanol, 2,2-iminobis(ethanol), 1-deoxy-1-(methylamino)-2-D-sorbitol, 2-amino-2-(hydroxymethyl)-1,3-propanediol, procaine, or N,N-bis(phenylmethyl)-1,2-ethanediamine.

In the case where there are geometrical isomers and/or optical isomers in the present compound, the isomers thereof are also encompassed in the scope of the present invention.

Further, in the case where there are hydrates and/or solvates of the present compound, the hydrates and/or solvates thereof are also encompassed in the scope of the present invention.

Further, in the case where there is proton tautomerism in the present compound, the tautomers thereof are also encompassed in the present invention.

In the case where there are crystalline polymorphisms and/or crystalline polymorphism groups (crystalline polymorphism systems) in the present compound, the polymorphisms and/or crystalline polymorphism groups (crystalline polymorphism systems) thereof are also encompassed in the present invention. Here, the crystalline polymorphism groups (crystalline polymorphism systems) mean individual crystal forms in respective stages when the crystal forms are changed by conditions for the production, crystallization, storage, or the like of the crystals thereof and/or states thereof (the states include also a formulated state) and/or all the processes thereof.

(a) Preferred examples of the present compound include compounds in which the respective groups are as defined below or salts thereof in the compounds represented by the general formula (1) or salts thereof:

(a1) $R^1$ and $R^2$ are the same or different and represent a hydrogen atom, a lower alkyl group, a lower alkyl group having a carboxy group as a substituent, a lower alkyl group having a lower alkoxycarbonyl group as a substituent, or a group represented by the following general formula (2); and/or

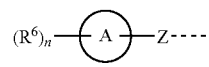

(a2) $R^3$ represents a hydroxy group, a lower alkoxy group, a lower alkoxy group having a hydroxy group as a substituent, a lower alkoxy group having a lower alkoxy group as a substituent, a lower cycloalkyloxy group, an aryloxy group, —$NR^aR^b$, or a group represented by the following general formula (3); and/or

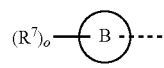

(a3) $R^4$ and $R^5$ are the same or different and represent a halogen atom, a lower alkyl group, a hydroxy group or a lower alkoxy group; and/or (a4) $R^6$ represents a halogen atom, a lower alkyl group, a lower alkyl group having a halogen atom as a substituent, a lower alkyl group having a cyano group as a substituent, a lower cycloalkyl group, an aryl group, a heterocyclic group, a heterocyclic group having a lower alkyl group as a substituent, a hydroxy group, a lower alkoxy group, a lower alkoxy group having a halogen atom as a substituent, a lower alkoxy group having a lower cycloalkyl group as a substituent, a lower alkoxy group having an aryl group as a substituent, a lower cycloalkyloxy group, an aryloxy group, a formyl group, a lower alkylcarbonyl group, a carboxy group, a lower alkoxycarbonyl group, a nitro group, a cyano group, —$NR^cR^d$, or —$NR^e(COR^f)$; and/or (a5) $R^7$ represents a lower alkyl group, a lower cycloalkyl group, an aryl group, a hydroxy group, a lower alkoxy group, a lower cycloalkyloxy group, or an aryloxy group; and/or (a6) $R^a$, $R^b$, $R^c$, $R^d$, $R^e$, and $R^f$ are the same or different and represent a hydrogen atom, a lower alkyl group, a lower alkyl group having —$NR^gR^h$ as a substituent, a lower cycloalkyl group, or an aryl group; and/or (a7) $R^g$ and $R^h$ are the same or different and represent a hydrogen atom or a lower alkyl group; and/or (a8) the ring A represents a hydrocarbon ring or a heterocyclic ring; and/or (a9) the ring B represents a heterocyclic ring having one or plural heteroatoms selected from the group consisting of a nitrogen atom and an oxygen atom in the ring; and/or (a10) X represents a lower alkylene group, a lower alkylene group having a hydroxy group as a substituent, or a lower alkylene group having a lower alkoxy group as a substituent; and/or (a11) Y and Z are the same or different and represent a single bond or a lower alkylene group; and/or (a12) l, m, n, and o are the same or different and represent 0, 1, 2, or 3, in the case where l, m, n, and o represent 2 or 3, the respective groups represented by $R^4$, $R^5$, $R^6$, or $R^7$ may be the same or different.

That is, in the compounds represented by the general formula (1), preferred examples include compounds which comprise one or a combination of two or more selected from the above (a1), (a2), (a3), (a4), (a5), (a6), (a7), (a8), (a9), (a10), (a11), and (a12) or salts thereof.

(b) More preferred examples of the present compound include compounds in which the respective groups are as defined below or salts thereof in the compounds represented by the general formula (1) or salts thereof:

(b1) $R^1$ represents a lower alkyl group, a lower alkyl group having a carboxy group as a substituent, a lower alkyl group having a lower alkoxycarbonyl group as a substituent, or a group represented by the following general formula (2); and/or

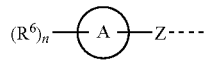
(2)

(b2) $R^2$ represents a hydrogen atom; and/or (b3) $R^3$ represents a hydroxy group, a lower alkoxy group, a lower alkoxy group having a hydroxy group as a substituent, —$NR^aR^b$, or a group represented by the following general formula (3); and/or

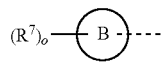
(3)

(b4) $R^5$ represents a halogen atom or a lower alkoxy group; and/or (b5) $R^6$ represents a halogen atom, a lower alkyl group, a lower alkyl group having a halogen atom as a substituent, a lower alkyl group having a cyano group as a substituent, a heterocyclic group, a heterocyclic group having a lower alkyl group as a substituent, a hydroxy group, a lower alkoxy group, a lower alkoxy group having a halogen atom as a substituent, a lower alkoxy group having an aryl group as a substituent, a lower alkylcarbonyl group, a carboxy group, a lower alkoxycarbonyl group, a nitro group, a cyano group, or —$NR^cR^d$; and/or (b6) $R^7$ represents a lower alkyl group or a hydroxy group; and/or (b7) $R^a$, $R^b$, $R^c$, and $R^d$ are the same or different and represent a hydrogen atom or a lower alkyl group; and/or (b8) the ring A represents a hydrocarbon ring or a heterocyclic ring; and/or (b9) the ring B represents a heterocyclic ring having one or plural heteroatoms selected from the group consisting of a nitrogen atom and an oxygen atom in the ring; and/or (b10) X represents a lower alkylene group or a lower alkylene group having a hydroxy group as a substituent; and/or (b11) Y represents a lower alkylene group; and/or (b12) Z represents a single bond or a lower alkylene group; and/or (b13) l represents 0; and/or (b14) m represents 0 or 1; and/or (b15) n represents 0, 1, or 2, in the case where n represents 2, the two groups represented by $R^6$ may be the same or different; and/or (b16) o represents 0 or 1.

That is, in the compounds represented by the general formula (1), more preferred examples include compounds which comprise one or a combination of two or more selected from the above (b1), (b2), (b3), (b4), (b5), (b6), (b7), (b8), (b9), (b10), (b11), (b12), (b13), (b14), (b15), and (b16) or salts thereof.

(c) Preferred examples of the ring A include the following rings.

The ring A represents a ring selected from the group consisting of cyclopentane, benzene, indan, 1,2,3,4-tetrahydronaphthalene, furan, thiophene, isoxazole, thiazole, benzo[1,3]dioxole, 2,3-dihydrobenzo[1,4]dioxin, pyridine, dihydrobenzofuran, benzimidazole, 4,5,6,7-tetrahydrobenzothiazole, and quinoline.

Further, compounds which have the ring A and satisfy the requirements of the above (a) and (b), and/or the following (d) or salts thereof are particularly preferred.

(d) Preferred examples of the ring B include the following rings.

The ring B represents a ring selected from the group consisting of pyrrolidine, morpholine, piperazine, piperidine, 2-pyrrolidone, and pyridine.

Further, compounds which have the ring B and satisfy the requirements of the above (a), (b), and/or (c) or salts thereof are particularly preferred.

(e) Particularly preferred specific examples of the present compound include the following compounds or salts thereof.

N-(2-Aminophenyl)-4-[1-(2-dimethylaminoethyl)-3-phenyl ureidomethyl]benzamide,

N-(2-Aminophenyl)-4-[1-(2,3-dihydroxypropyl)-3-(indan-5-yl)ureidomethyl]benzamide, N-(2-Amino-5-methoxyphenyl)-4-[1-(2-dimethylaminoethyl)-3-(indan-5-yl)ureidomethyl]benzamide, N-(2-Aminophenyl)-4-[3-cyclopentyl-1-(2-methylaminoethyl)ureidomethyl]benzamide, N-(2-Aminophenyl)-4-[3-t-butyl-1-(3-dimethylaminopropyl)ureidomethyl]benzamide, N-(2-Aminophenyl)-4-[3-(4-dimethylaminophenyl)-1-[3-(morpholin-4-yl)propyl]ureidomethyl]benzamide, N-(2-Aminophenyl)-4-[3-(4-cyanomethylphenyl)-1-(3-dimethylamino-2,2-dimethylpropyl)ureidomethyl]benzamide, N-(2-Aminophenyl)-4-[1-(3-aminopropyl)-3-(2,3-dihydrobenzo[1,4]dioxin-6-yl)ureidomethyl]benzamide, N-(2-Aminophenyl)-4-[3-(3,4-difluorophenyl)-1-(3-dimethylaminopropyl)ureidomethyl]benzamide, N-(2-Aminophenyl)-4-[1-(3-dimethylaminopropyl)-3-(4-methoxycarbonylphenyl)ureidomethyl]benzamide, N-(2-Aminophenyl)-4-[3-(4-dimethylaminophenyl)-1-(2-hydroxyethyl)ureidomethyl]benzamide, N-(2-Aminophenyl)-4-[1-(2-hydroxyethyl)-3-phenethylureidomethyl]benzamide, N-(2-Aminophenyl)-4-[3-(2,3-dihydrobenzo[1,4]dioxin-6-yl)-1-(1-ethylpyrrolidin-2-ylmethyl)ureidomethyl]benzamide, N-(2-Aminophenyl)-4-[3-(3-methoxyphenyl)-1-[3-(morpholin-4-yl)propyl]ureidomethyl]benzamide, N-(2-Aminophenyl)-4-[3-(4-difluoromethoxyphenyl)-1-[3-(morpholin-4-yl)propyl]ureidomethyl]benzamide, N-(2-Aminophenyl)-4-[1-(3-dimethylaminopropyl)-3-(3-hydroxyphenyl)ureidomethyl]benzamide, N-(2-Aminophenyl)-4-[3-(3,4-difluorophenyl)-1-[2-(1-methylpyrrolidin-2-yl)ethyl]ureidomethyl]benzamide, N-(2-Aminophenyl)-4-[1-(3-dimethylaminopropyl)-3-(pyridin-3-yl)ureidomethyl]benzamide, N-(2-Aminophenyl)-4-[3-benzyl-1-(2-dimethylaminoethyl) ureidomethyl]benzamide, N-(2-Aminophenyl)-4-[3-(4-chlorophenyl)-1-(piperidin-4-ylmethyl)ureidomethyl]benzamide, N-(2-Aminophenyl)-4-[1-(3-dimethylaminopropyl)-3-(2-methoxyphenyl)ureidomethyl]benzamide, N-(2-Aminophenyl)-4-[1-(3-dimethylaminopropyl)-3-ethoxycarbonylmethylureidomethyl]benzamide, N-(2-Aminophenyl)-4-[3-(4-dimethylaminophenyl)-1-[3-(pyrrolidin-2-on-1-yl)propyl]ureidomethyl]benzamide, N-(2-Aminophenyl)-4-[1-(4-dimethylaminobutyl)-3-(4-dimethylaminophenyl)ureidomethyl]benzamide, N-(2-Aminophenyl)-4-[3-[2-(benzo[1,3]dioxol-5-yl)ethyl]-1-[3-(morpholin-4-yl)propyl]ureidomethyl]benzamide, N-(2-Aminophenyl)-4-[3-(4-aminophenyl)-1-[3-(morpholin-4-yl)propyl]ureidomethyl]benzamide, N-(2-Aminophenyl)-4-[3-(3-benzyloxyphenyl)-1-(3-dimethylaminopropyl)ureidomethyl]benzamide, N-(2-Aminophenyl)-4-[1-(2-dimethylaminoethyl)-3-phenethylureidomethyl]benzamide, N-(2-Aminophenyl)-4-[3-(2,3-dihydrobenzo[1,4]dioxin-6-yl)-1-(2-methylaminoethyl)ureidomethyl]benzamide, N-(2-Aminophenyl)-4-[1-(3-dimethylaminopropyl)-3-phenethylureidomethyl]benzamide, N-(2-Aminophenyl)-4-[3-(3,4-dimethoxyphenyl)-1-(3-dimethylamino-2,2-dimethylpropyl)ureidomethyl]benzamide, N-(2-Aminophenyl)-4-[3-(2,3-dihydrobenzo[1,4]dioxin-6-yl)-1-(2-dimethylaminoethyl)ureidomethyl]benzamide, N-(2-Aminophenyl)-4-[3-(2,3-dihydrobenzo[1,4]dioxin-6-yl)-1-[2-(4-methylpiperazin-1-yl)ethyl]ureidomethyl]benzamide, N-(2-Aminophenyl)-4-[1-(3-dimethylaminopropyl)-3-(4-fluoro-3-nitrophenyl)ureidomethyl]benzamide, N-(2-Aminophenyl)-4-[3-(2,3-dihydrobenzo[1,4]dioxin-6-yl)-1-[3-(pyrrolidin-1-yl)propyl]ureidomethyl]benzamide, N-(2-Aminophenyl)-4-[3-(3,4-difluorophenyl)-1-[2-(4-methylpiperazin-1-yl)ethyl]ureidomethyl]benzamide, N-(2-Aminophenyl)-4-[1-[3-(morpholin-4-yl)propyl-3-(3-phenylpropyl)]ureidomethyl]benzamide, N-(2-Aminophenyl)-4-[3-(2,3-dihydrobenzo[1,4]dioxin-6-yl)-1-[3-(4-methylpiperidin-1-yl)propyl]ureidomethyl]benzamide, N-(2-Aminophenyl)-4-[1-[3-(morpholin-4-yl)propyl]-3-(thiophen-3-yl)ureidomethyl]benzamide, N-(2-Aminophenyl)-4-[3-(4-fluoro-3-methylphenyl)-1-[3-(morpholin-4-yl)propyl]ureidomethyl]benzamide, N-(2-Aminophenyl)-4-[1-[3-(morpholin-4-yl)propyl]-3-(5-nitrothiazol-2-yl)ureidomethyl]benzamide The compounds of this invention can be prepared according to the following methods. Each specific process for preparing the present compounds will be described in detail in the following Examples (section of Production Examples). The term "Boc" used in the following synthetic routes represents a tert-butoxycarbonyl group. In the case where an oxygen atom, a nitrogen atom, a sulfur atom, and so on are contained in $R^1$, $R^2$, $R^3$, $R^4$ and $R^5$ of the following scheme, they can be protected or deprotected by generally used methods.

The processes for preparing the compounds of this invention are divided roughly into the methods described below, and the suitable method can be selected according to the kind of substituent.

1) The compound of this invention (Ia, $R^2$=H) can be synthesized according to the synthetic route 1. Namely, this (Ia) can be given by the treatment of the compound (IIa, $R^2$=H) in an organic solvent such as methanol in the presence of an acid such as hydrogen chloride ethyl acetate solution at 0° C. to room temperature for 30 minutes to 3 hours.

Synthetic Route 1

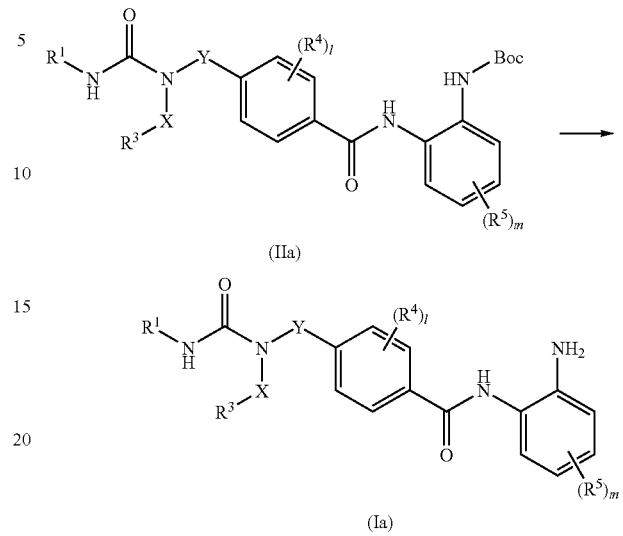

The compound (IIa) can be synthesized according to the synthetic route 1-1. Namely, this can be given by the reaction of the compound (III) with isocyanate (IV) in an organic solvent such as dichloromethane at 0° C. to room temperature for 30 minutes to 24 hours.

Synthetic Route 1-1

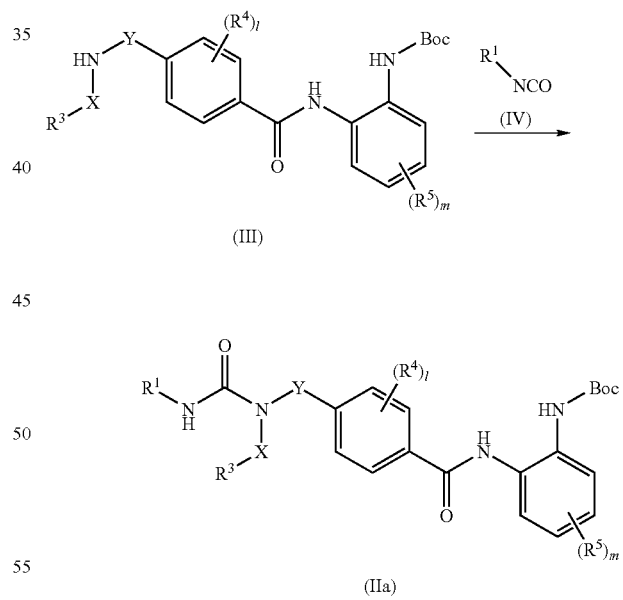

The compound (III) can be synthesized according to the synthetic route 1-2. Namely, the intermediate (VII) can be given by the reaction of the compound (V) with methanesulfonyl chloride (VI) in an organic solvent such as dichloromethane in the presence of a base such as triethylamine at 0° C. to room temperature for 30 minutes to 3 hours. Additionally, the compound (III) can be given by the reaction of the obtained the intermediate (VII) with the amine (VIII) at 0° C. to room temperature for 30 minutes to 24 hours.

Synthetic Route 1-2

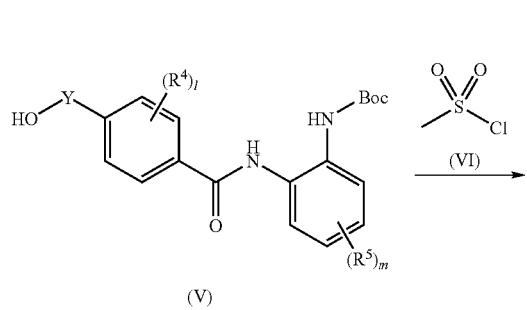

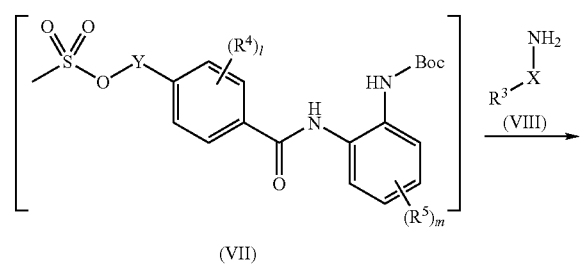

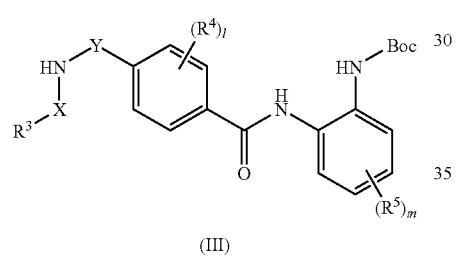

The compound (V) can be synthesized according to the synthetic route 1-3. Namely, it can be given by the reaction of the compound (IX) with the compound (X) in an organic solvent such as N,N-dimethylformamide (hereinafter referred to as DMF) in the presence of a condensing agent such as O-(7-azabenzotriazol-1-yl)-1,1,3,3-tetramethyluronium hexafluorophosphate (hereinafter referred to as HATU) and a base such as N,N-diisopropylethylamine at room temperature for 1 hour to 24 hours.

Synthetic Route 1-3

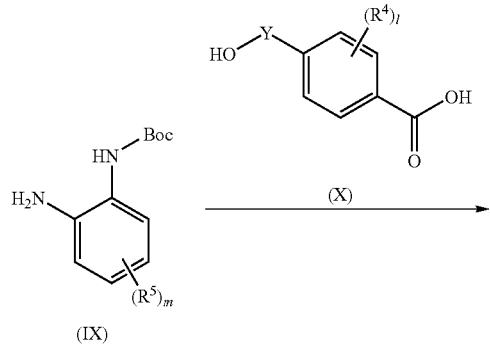

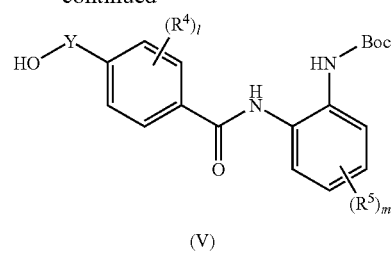

The compound (IX) can be synthesized according to the synthetic route 1-4. Namely, this can be given by the reaction of the compound (XI) with di-tert-butyl dicarbonate (XII) in an organic solvent such as tetrahydrofuran (hereinafter referred to as THF) in the presence of a base such as triethylamine at room temperature for 1 hour to 24 hours.

Synthetic Route 1-4

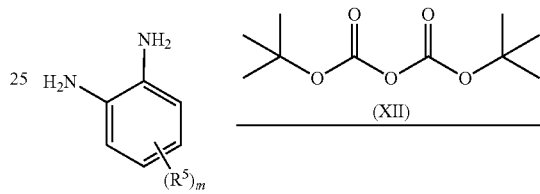

2) The compound (II) can be synthesized according to the synthetic route 2. Namely, this can be given by the reaction of the compound (III) with the compound (XIII) in an organic solvent such as dimethylsulfoxide (hereinafter referred to as DMSO) at 0° C. to room temperature for 30 minutes to 24 hours.

Synthetic Route 2

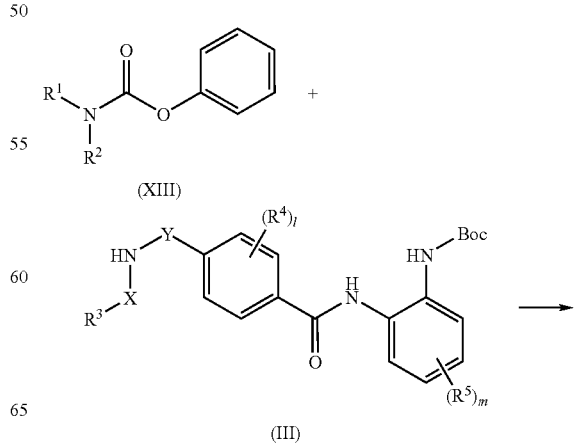

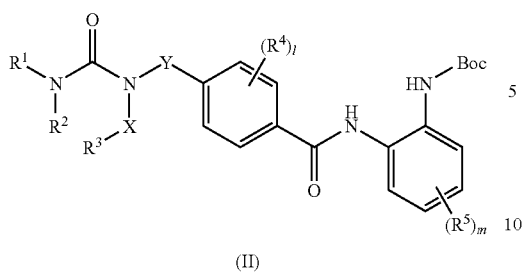

(II)

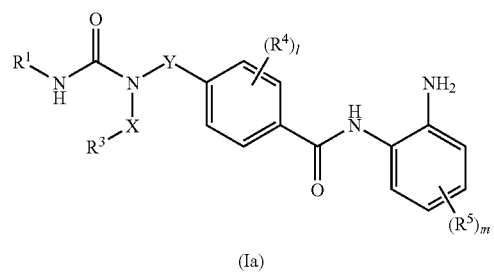

(Ia)

The compound (XIII) can be synthesized according to the synthetic route 2-1. Namely, this can be given by the reaction of the amine (XIV) with phenyl chloroformate (XV) in an organic solvent such as THF in the presence of a base such as pyridine at 0° C. to room temperature for 30 minutes to 24 hours.

Synthetic Route 2-1

The compound (XVIa) can be synthesized according to the synthetic route 3-1. Namely, this can be given by the treatment of the compound (XVIIa, $R^2$=H) under a hydrogen atmosphere in the presence of a catalyst such as palladium on carbon in an organic solvent such as methanol at room temperature for 1 hour to 72 hours.

Synthetic Route 3-1

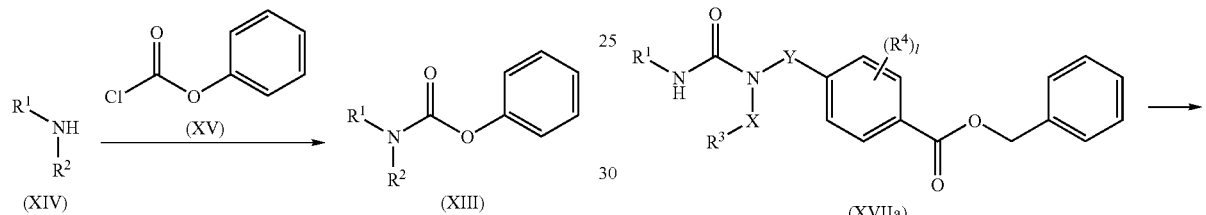

3) The compound of this invention (Ia, $R^2$=H) can be synthesized according to the synthetic route 3. Namely, this can be given by the reaction of the compound (XVIa, $R^2$=H) with the compound (XI) in an organic solvent such as DMF in the presence of a condensing agent such as HATU in the presence of a base such as N,N-diisopropylethylamine at room temperature for 1 hour to 24 hours.

Synthetic Route 3

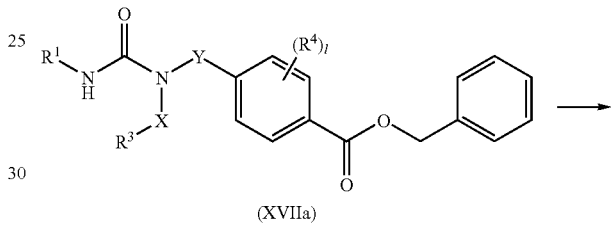

(XVIa)

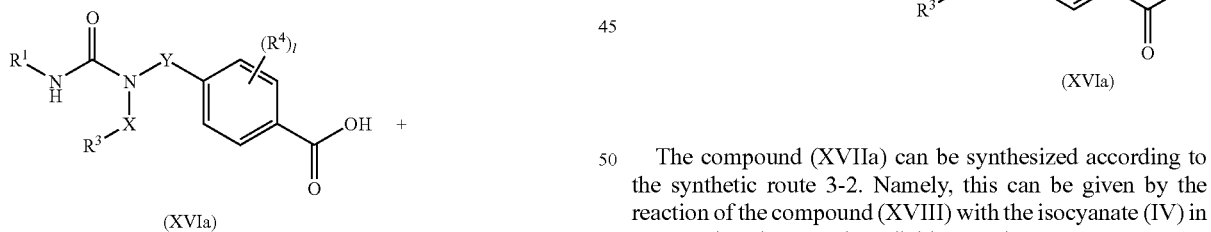

The compound (XVIIa) can be synthesized according to the synthetic route 3-2. Namely, this can be given by the reaction of the compound (XVIII) with the isocyanate (IV) in an organic solvent such as dichloromethane at 0° C. to room temperature for 30 minutes to 24 hours.

Synthetic Route 3-2

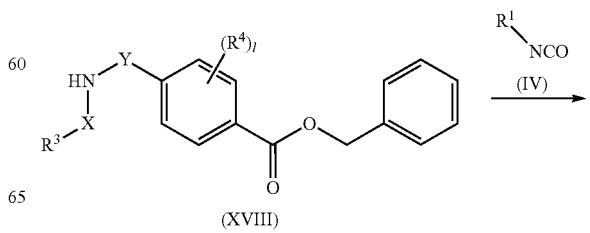

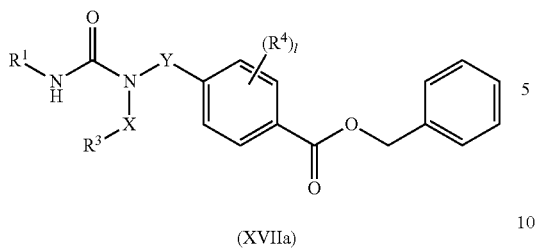

(XVIIa)

The compound (XVIII) can be synthesized according to the synthetic route 3-3. Namely, this can be given by the reaction of the compound (XIX) with the amine (VIII) in an organic solvent such as DMF, and in the presence of a base such as triethylamine at 0° C. to room temperature for 30 minutes to 3 hours.

Synthetic Route 3-3

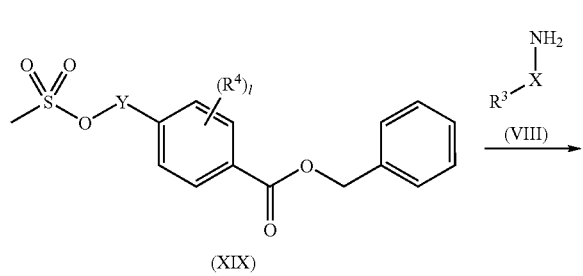

(XVIII)

The compound (XIX) can be synthesized according to the synthetic route 3-4. Namely, this can be given by the reaction of the compound (XX) with methanesulfonyl chloride (VI) in an organic solvent such as dichloromethane in the presence of a base such as triethylamine at 0° C. to room temperature for 30 minutes to 3 hours.

Synthetic Route 3-4

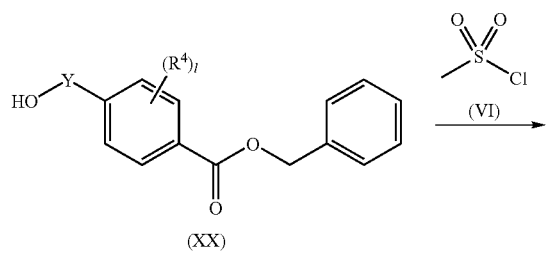

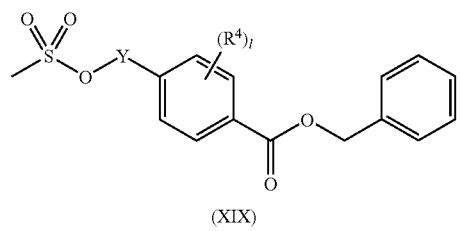

(XIX)

4) The compound (II) can be synthesized according to the synthetic route 4. Namely, this can be given by the reaction of the amine (XIV) with carbonyldiimidazole in an organic solvent such as THF at 0° C. to room temperature for 30 minutes to 12 hours, and then with the compound (III) at 40° C. to 60° C. for 1 hour to 24 hours.

Synthetic Route 4

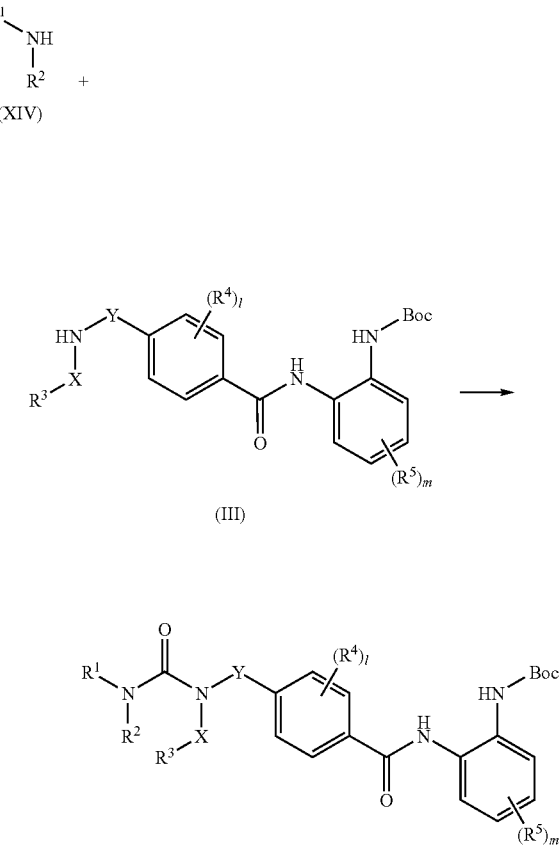

5) The compound (IIb, $R^3$=$NR^6R^7$) can be synthesized according to the synthetic route 5. Namely, the intermediate (IIc, $R^3$=$OSO_2Me$) can be given by the reaction of the compound (IId, $R^3$=$OH$) with methanesulfonyl chloride in the presence of a base such as triethylamine in an organic solvent such as THF at 0° C. to room temperature for 30 minutes to 12 hours. The compound (IIb) can be given by the reaction of the intermediate (IIc) with the amine (XXI) in an organic solvent such as dichloromethane at room temperature for 1 hour to 24 hours.

Synthetic Route 5

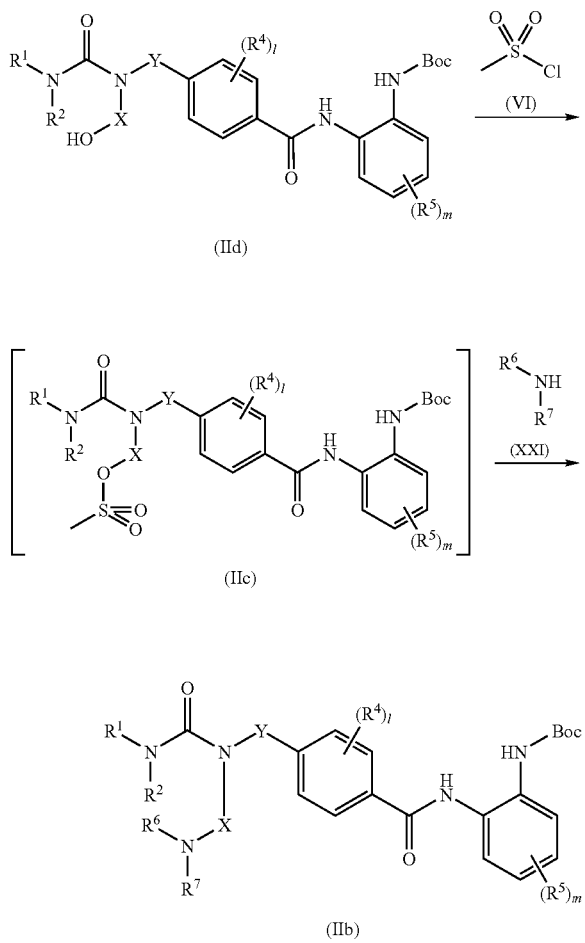

As described above, the present compound has an excellent effect of cellular morphological change on trabecular meshwork cells and is useful as a preventive or therapeutic agent for a disease considered to be related to intraocular pressure, particularly as an agent for lowering intraocular pressure for preventing or treating glaucoma and ocular hypertension.

Further, as will be described in detail in the "section of Pharmacological Test" in the Examples mentioned below, when an effect of morphological change of the present compound on trabecular meshwork cells was evaluated in an evaluation system using the cell shape index (hereinafter referred to as "CSI") which has been reported in The Journal of Clinical Investigation, 103, 1141-1150 (1999) as an index, the present compound exhibited an excellent effect of cellular morphological change on trabecular meshwork cells.

The present compound can be administered orally or parenterally. Examples of the dosage form for administration include a tablet, a capsule, a granule, a powder, an injection, and an eye drop, and such a preparation can be prepared by a widely used technique.

For example, an oral preparation such as a tablet, a capsule, a granule, or a powder can be prepared by optionally adding a necessary amount of an excipient such as lactose, mannitol, starch, crystalline cellulose, light silicic anhydride, calcium carbonate, or calcium hydrogen phosphate; a lubricant such as stearic acid, magnesium stearate, or talc; a binder such as starch, hydroxypropyl cellulose, hydroxypropylmethyl cellulose, or polyvinylpyrrolidone; a disintegrant such as carboxymethyl cellulose, low-substituted hydroxypropylmethyl cellulose, or calcium citrate; a coating agent such as hydroxypropylmethyl cellulose, macrogol, or a silicone resin; a stabilizer such as ethyl parahydroxybenzoate or benzyl alcohol; a corrigent such as a sweetener, a sour agent, or a flavor, or the like.

Further, a parenteral preparation such as an injection or an eye drop can be prepared by optionally adding a necessary amount of a tonicity agent such as sodium chloride, concentrated glycerin, propylene glycol, polyethylene glycol, potassium chloride, sorbitol, or mannitol; a buffer such as sodium phosphate, sodium hydrogen phosphate, sodium acetate, citric acid, glacial acetic acid, or trometamol; a surfactant such as polysorbate 80, polyoxy 40 stearate, or polyoxyethylene hydrogenated castor oil 60; a stabilizer such as sodium citrate or sodium edetate; a preservative such as benzalkonium chloride, paraben, benzethonium chloride, parahydroxybenzoic acid ester, sodium benzoate, chlorobutanol, or sorbic acid; a pH adjusting agent such as hydrochloric acid, citric acid, phosphoric acid, glacial acetic acid, sodium hydroxide, sodium carbonate, or sodium hydrogen carbonate; a soothing agent such as benzyl alcohol, or the like.

The present invention also relates to a method for preventing and/or treating a disease considered to be related to intraocular pressure comprising administering to a patient (human patient) in need thereof an pharmaceutically effective amount of the present compound.

The dose of the present compound can be appropriately selected depending on the symptoms, age, dosage form, or the like. For example, in the case of an oral preparation, it can be administered in an amount of generally from 0.01 to 1000 mg, preferably from 1 to 100 mg per day in a single dose or several divided doses. Further, in the case of an eye drop, a preparation containing the present compound at a concentration of generally from 0.0001 to 10% (w/v), preferably from 0.01 to 5% (w/v) can be administered in a single dose or several divided doses.

Hereinafter, production examples of the present compound, preparation examples, and results of pharmacological tests will be described. However, these examples are described for the purpose of understanding the present invention better and are not meant to limit the scope of the present invention.

PRODUCTION EXAMPLES

Reference Example 1

2-Aminophenylcarbamic acid t-butyl ester
(Reference Compound No. 1-1)

A solution of di-t-butyl dicarbonate (44 g, 200 mmol) in THF (50 mL) was added dropwise to a solution of o-phenylenediamine (22 g, 200 mmol) and triethylamine (30 mL) in THF (150 mL), and then the mixture was stirred at room temperature for 15 hours. The reaction mixture was concentrated, the obtained solid was filtered with ethyl acetate, and then the solid was dried under reduced pressure to give 21 g of the title reference compound as a white solid. Additionally, another solid which was obtained by concentration of the filtrate was collected by filtration with ethyl acetate, and the solid was dried under reduced pressure to give 11 g of the title reference compound as a white solid. (Yield 76%)

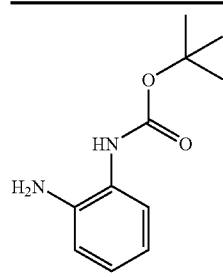

$^1$H-NMR (400 MHz, DMSO-$d_6$) δ (1.48 (s, 9H), 4.84 (s, 2H), 6.55 (td, J = 7.6, 1.4 Hz, 1H), 6.70 (dd, J = 7.6, 1.3 Hz, 1H), 6.86 (td, J = 7.6, 1.5 Hz, 1H), 7.20 (d, J = 7.6 Hz, 1H), 8.30 (br s, 1H)

Reference Example 2

N-(2-t-Butoxycarbonylaminophenyl)-4-methoxycarbonylbenzamide (Reference Compound No. 2-1)

Under ice cooling, terephthalic acid monomethylester chloride (1.1 g, 5.0 mmol) was added to a solution of 2-aminophenylcarbamic acid t-butyl ester (Reference Compound No. 1-1, 1.1 g, 5.0 mmol) and triethylamine (30 mL) in dichloromethane (15 mL), and then the mixture was stirred at room temperature for 4 hours. Water (50 mL) was added thereto, and the whole was extracted with ethyl acetate (40 mL) twice. The organic layer was dried over anhydrous magnesium sulfate, and then the solvent was evaporated under reduced pressure. The resulting solid was collected by filtration with a mixed solvent (hexane (10 mL) and ethyl acetate (5 mL)), and the whole was dried under reduced pressure to give 1.8 g of the title reference compound as a white solid. (Yield 99%)

Reference Example 3

N-(2-t-Butoxycarbonylaminophenyl)-4-hydroxymethylbenzamide (Reference Compound No. 3-1)

Under ice cooling, lithium borohydride (73 mg, 3.6 mmol) was added to a solution of N-(2-t-butoxycarbonylaminophenyl)-4-methoxycarbonylbenzamide (Reference Compound No. 2-1, 1.1 g, 3.0 mmol) in THF (15 mL), and then the mixture was stirred at room temperature overnight. Under ice cooling, water (20 mL) and 2.0 M hydrochloric acid (20 mL) were added thereto, the whole was extracted with ethyl acetate (40 mL) twice, and then the organic layer was washed with saturated aqueous sodium hydrogen carbonate solution (50 mL) and brine (50 mL). The organic layer was dried over anhydrous magnesium sulfate, and then the solvent was evaporated under reduced pressure. The residue was purified by silica gel column chromatography (hexane-ethyl acetate) to give 890 mg of the title reference compound as a white solid. (Yield 87%)

In addition, the title reference compound can be also synthesized by the following method.

HATU (17 g, 45 mmol) was added to a solution of 2-aminophenylcarbamic acid t-butyl ester (Reference Compound No. 1-1, 8.3 g, 40 mmol), 4-hydroxymethylbenzoic acid (6.2 g, 41 mmol) and N,N-diisopropylethylamine (21 mL, 120 mmol) in anhydrous DMF (200 mL), and then the mixture was stirred at room temperature for 16 hours. Water (500 mL) was added thereto, the whole was extracted with ethyl acetate (500 mL) twice, and then the organic layer was washed with brine (500 mL) twice. The organic layer was dried over anhydrous sodium sulfate, and then the solvent was evaporated under reduced pressure. The residue was purified by silica gel column chromatography (chloroform-methanol) to give 1.7 g of the title reference compound as a pale yellow solid. (Yield 42%)

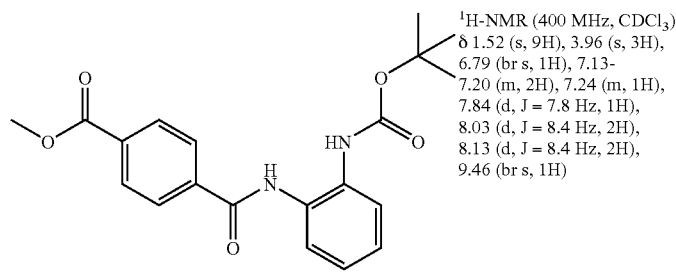

$^1$H-NMR (400 MHz, CDCl$_3$) δ 1.52 (s, 9H), 3.96 (s, 3H), 6.79 (br s, 1H), 7.13-7.20 (m, 2H), 7.24 (m, 1H), 7.84 (d, J = 7.8 Hz, 1H), 8.03 (d, J = 8.4 Hz, 2H), 8.13 (d, J = 8.4 Hz, 2H), 9.46 (br s, 1H)

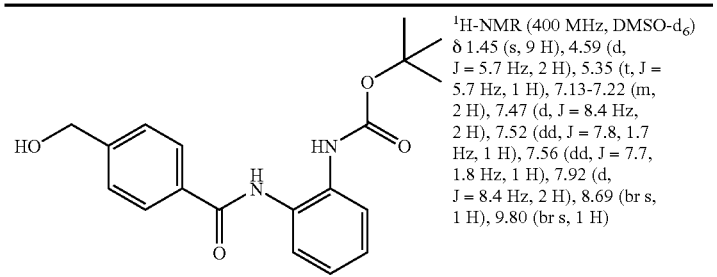

¹H-NMR (400 MHz, DMSO-d₆)
δ 1.45 (s, 9 H), 4.59 (d, J = 5.7 Hz, 2 H), 5.35 (t, J = 5.7 Hz, 1 H), 7.13-7.22 (m, 2 H), 7.47 (d, J = 8.4 Hz, 2 H), 7.52 (dd, J = 7.8, 1.7 Hz, 1 H), 7.56 (dd, J = 7.7, 1.8 Hz, 1 H), 7.92 (d, J = 8.4 Hz, 2 H), 8.69 (br s, 1 H), 9.80 (br s, 1 H)

Reference Example 4

N-(2-t-Butoxycarbonylaminophenyl)-4-[3-(4-methylpiperazin-1-yl)propylaminomethyl]benzamide (Reference Compound No. 4-1)

Under ice cooling, methanesulfonyl chloride (0.25 mL, 3.2 mmol) was added to a solution of N-(2-t-butoxycarbonylaminophenyl)-4-hydroxymethylbenzamide (Reference Compound No. 3-1, 1.0 g, 2.9 mmol) and triethylamine (0.61 mL, 4.4 mmol) in anhydrous dichloromethane (15 mL), and then the mixture was stirred for 40 minutes. 1-(3-Aminopropyl)-4-methylpiperazine (2.3 mL, 4.4 mmol) was added to the reaction mixture, and then stirred at room temperature for 2.5 hours additionally. Water (200 mL) was added thereto, the whole was extracted with ethyl acetate (200 mL) twice, and then the organic layer was washed with brine (200 mL). The organic layer was dried over anhydrous sodium sulfate, and then the solvent was evaporated under reduced pressure. The residue was purified by silica gel column chromatography (NH-modified silica gel, chloroform-methanol) to give 470 mg of the title reference compound as a colorless amorphous product. (Yield 33%)

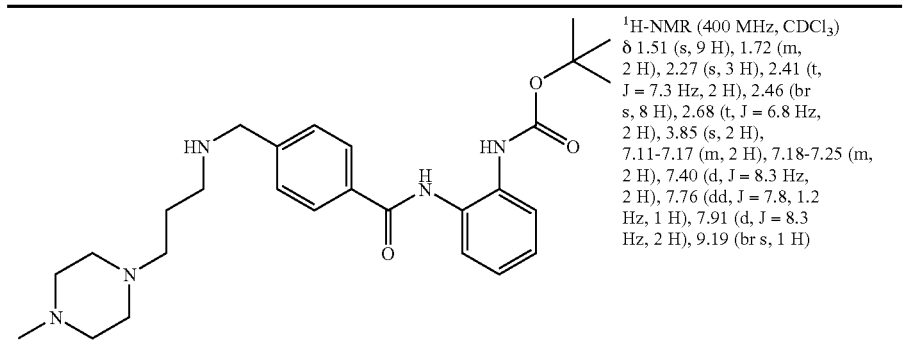

¹H-NMR (400 MHz, CDCl₃)
δ 1.51 (s, 9 H), 1.72 (m, 2 H), 2.27 (s, 3 H), 2.41 (t, J = 7.3 Hz, 2 H), 2.46 (br s, 8 H), 2.68 (t, J = 6.8 Hz, 2 H), 3.85 (s, 2 H), 7.11-7.17 (m, 2 H), 7.18-7.25 (m, 2 H), 7.40 (d, J = 8.3 Hz, 2 H), 7.76 (dd, J = 7.8, 1.2 Hz, 1 H), 7.91 (d, J = 8.3 Hz, 2 H), 9.19 (br s, 1 H)

By using any compounds selected from Reference Compound No. 3-1, commercially available compounds, and known compounds, the following Reference Compounds No. 4-2 to 4-26 were obtained by a method similar to that of Reference Compound No. 4-1.

| | | ¹H-NMR (400 MHz, CDCl₃) |
|---|---|---|
| N-(2-t-Butoxycarbonylamino phenyl)-4-(2-dimethylamino ethylaminomethyl)benzamide (Reference Compound No. 4-2) | 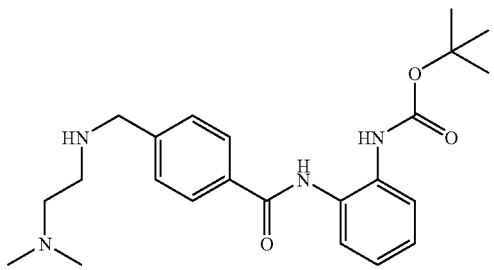 | δ 1.52 (s, 9 H), 2.21 (s, 6 H), 2.44 (t, J = 6.0 Hz, 2 H), 2.69 (t, J = 6.0 Hz, 2 H), 3.88 (s, 2 H), 6.94 (br s, 1 H), 7.16 (td, J = 7.8, 1.7 Hz, 1 H), 7.21-7.27 (m, 2 H), 7.42 (d, J = 8.4 Hz, 2 H), 7.79 (dd, J = 7.8, 1.0 Hz, 1 H), 7.91 (d, J = 8.4 Hz, 2 H), 9.13 (br s, 1 H) |

| | |
|---|---|
| N-(2-t-Butoxycarbonylamino phenyl)-4-(2-methoxyethyl-aminomethyl)benzamide (Reference Compound No. 4-3) 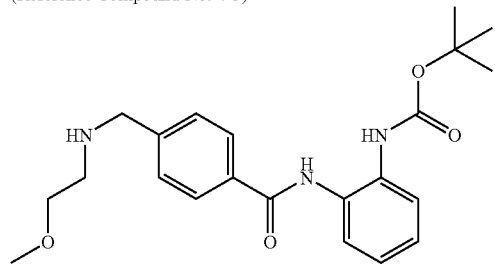 | $^1$H-NMR (400 MHz, DMSO-d$_6$) δ 1.45 (s, 9 H), 2.64 (t, J = 5.7 Hz, 2 H), 3.24 (s, 3 H), 3.41 (t, J = 5.7 Hz, 2 H), 3.79 (s, 2 H), 7.13-7.22 (m, 2 H), 7.48 (d, J = 8.3 Hz, 2 H), 7.52 (dd, J = 7.8, 1.7 Hz, 1 H), 7.55 (dd, J = 7.8, 1.7 Hz, 1 H), 7.90 (d, J = 8.3 Hz, 2 H), 8.66 (br s, 1 H), 9.78 (s, 1 H) |
| N-(2-t-Butoxycarbonylamino phenyl)-4-(3-hydroxypropyl aminomethyl)benzamide (Reference Compound No. 4-4) 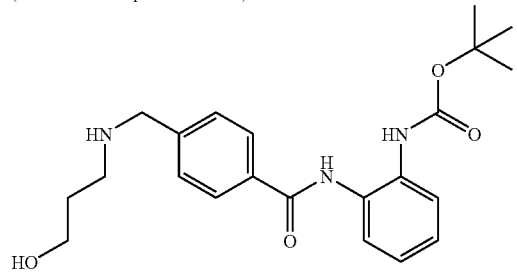 | $^1$H-NMR (400 MHz, DMSO-d$_6$) δ 1.45 (s, 9 H), 1.60 (m, 2 H), 2.57 (t, J = 6.9 Hz, 2 H), 3.47 (t, J = 6.2 Hz, 2 H), 3.79 (s, 2 H), 7.12-7.22 (m, 2 H), 7.49 (d, J = 8.3 Hz, 2 H), 7.51-7.56 (m, 2 H), 7.90 (d, J = 8.3 Hz, 2 H), 8.69 (s, 1 H), 9.80 (s, 1 H) |
| N-(2-t-Butoxycarbonylamino phenyl)-4-(3-dimethylamino propylaminomethyl)benzamide (Reference Compound No. 4-5) 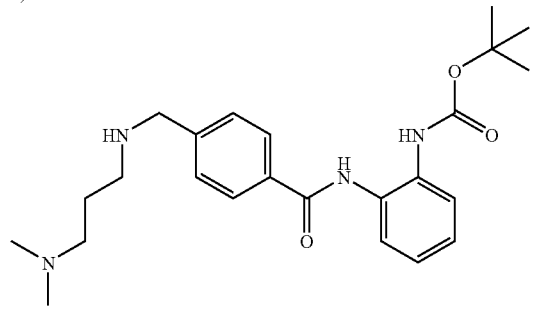 | $^1$H-NMR (400 MHz, CDCl$_3$) δ 1.50 (s, 9 H), 1.70 (m, 2 H), 1.77 (br s, 1 H), 2.26 (s, 6 H), 2.33 (t, J = 7.2 Hz, 2 H), 2.68 (t, J = 6.9 Hz, 2 H), 3.86 (s, 2 H), 6.97 (s, 1 H), 7.16 (dd, J = 7.8, 1.7 Hz, 1 H), 7.21 (dd, J = 7.8, 1.7 Hz, 1 H), 7.25 (m, 1 H), 7.41 (d, J = 8.4 Hz, 2 H), 7.78 (m, 1 H), 7.91 (d, J = 8.4 Hz, 2 H), 9.14 (s, 1 H) |
| 4-(2-t-Butoxycarbonylamino ethylaminomethyl)N-(2-t-butoxycarbonylaminophenyl) benzamide (Reference Compound No. 4-6) 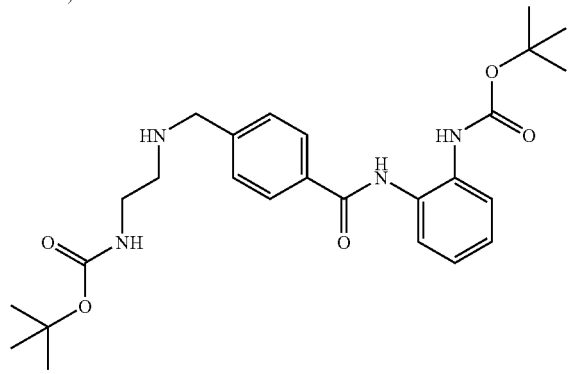 | $^1$H-NMR (500 MHz, CDCl$_3$) δ 1.45 (s, 9 H), 1.52 (s, 9 H), 2.76 (t, J = 5.8 Hz, 2 H), 3.25 (m, 2 H), 3.86 (s, 2 H), 4.90 (br s, 1 H), 6.78 (br s, 1 H), 7.17 (td, J = 7.8, 1.5 Hz, 1 H), 7.22-7.28 (m, 2 H), 7.42 (d, J = 8.4 Hz, 2 H), 7.81 (d, J = 7.8 Hz, 1 H), 7.93 (d, J = 8.4 Hz, 2 H), 9.10 (br s, 1 H) |

-continued

| | |
|---|---|
| N-(2-t-Butoxycarbonylamino phenyl)-4-[2-(N'-t-butoxy-carbonyl-N'-methylamino)ethyl aminomethyl]benzamide (Reference Compound No. 4-7) 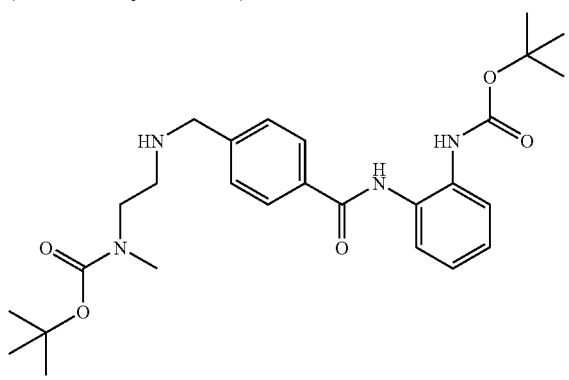 | $^1$H-NMR (500 MHz, CDCl$_3$) δ 1.46 (s, 9 H), 1.52 (s, 9 H), 2.80 (t, J = 6.4 Hz, 2 H), 2.87 (br s, 3 H), 3.38 (br s, 2 H), 3.88 (s, 2 H), 6.77 (br s, 1 H), 7.17 (td, J = 7.8, 1.5 Hz, 1 H), 7.22-7.29 (m, 2 H), 7.43 (d, J = 7.9 Hz, 2 H), 7.81 (d, J = 7.8 Hz, 1 H), 7.92 (d, J = 7.9 Hz, 2 H), 9.08 (br s, 1 H) |
| N-(2-t-Butoxycarbonylamino phenyl)-4-(2-diethylamino ethylaminomethyl)benzamide (Reference Compound No. 4-8) 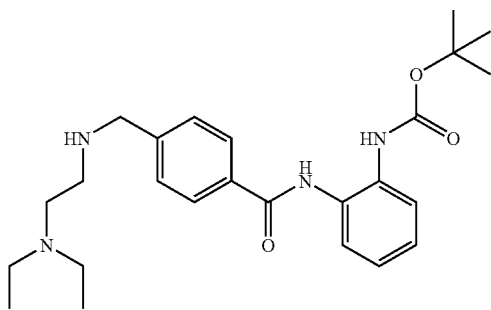 | $^1$H-NMR (400 MHz, CDCl$_3$) δ 1.10 (t, J = 7.1 Hz, 6 H), 1.52 (s, 9 H), 2.62-2.71 (m, 6 H), 2.77 (m, 2 H), 3.89 (s, 2 H), 6.86 (s, 1 H), 7.18 (dd, J = 7.6, 1.5 Hz, 1 H), 7.22-7.28 (m, 2 H), 7.44 (d, J = 8.2 Hz, 2 H), 7.79 (d, J = 7.6 Hz, 1 H), 7.92 (d, J = 8.2 Hz, 2 H), 9.12 (s, 1 H) |
| N-(2-t-Butoxycarbonylamino phenyl)-4-(3-dimethylamino 2,2-dimethylpropylamino-methyl)benzamide (Reference Compound No. 4-9) 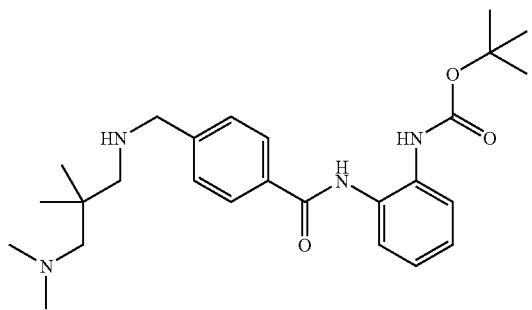 | $^1$H-NMR (400 MHz, CDCl$_3$) δ 0.95 (s, 6 H), 1.51 (s, 9 H), 2.23 (s, 2 H), 2.28 (s, 6 H), 2.53 (s, 2 H), 3.90 (s, 2 H), 6.92 (s, 1 H), 7.17 (ddd, J = 7.8, 7.5, 1.5 Hz, 1 H), 7.23 (ddd, J = 7.5, 7.5, 1.5 Hz, 1 H), 7.27 (dd, J = 7.5, 1.5 Hz, 1 H), 7.46 (d, J = 8.2 Hz, 2 H), 7.79 (d, J = 7.8 Hz, 1 H), 7.93 (d, J = 8.2 Hz, 2 H), 9.19 (s, 1 H) |

| | |
|---|---|
| N-(2-t-Butoxycarbonylamino phenyl)-4-[2-(2-hydroxy-ethoxy)ethylaminomethyl] benzamide (Reference Compound No. 4-10) 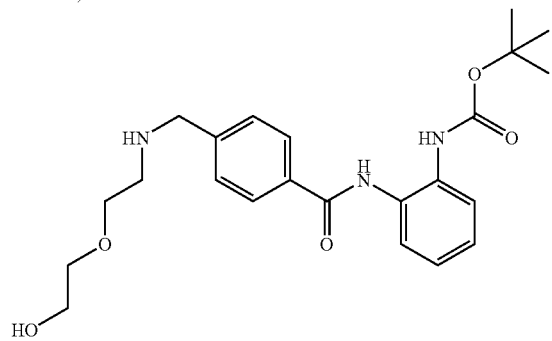 | $^1$H-NMR (500 MHz, CDCl$_3$) δ 1.52 (s, 9 H), 2.86 (t, J = 5.0 Hz, 2 H), 3.60 (t, J = 4.5 Hz, 2 H), 3.67 (d, J = 5.0 Hz, 2 H), 3.74 (t, J = 4.5 Hz, 2 H), 3.90 (s, 2 H), 6.88 (s, 1 H), 7.18 (dd, J = 8.2, 7.7 Hz, 1 H), 7.23 (dd, J = 8.2, 7.7 Hz, 1 H), 7.29 (d, J = 8.2 Hz, 1 H), 7.45 (d, J = 7.9 Hz, 2 H), 7.78 (d, J = 8.2 Hz, 1 H), 7.92 (d, J = 7.9 Hz, 2 H), 9.16 (s, 1 H) |
| N-(2-t-Butoxycarbonylamino phenyl)-4-[3-(morpholin-4-yl)propylaminomethyl] benzamide (Reference Compound No. 4-11) 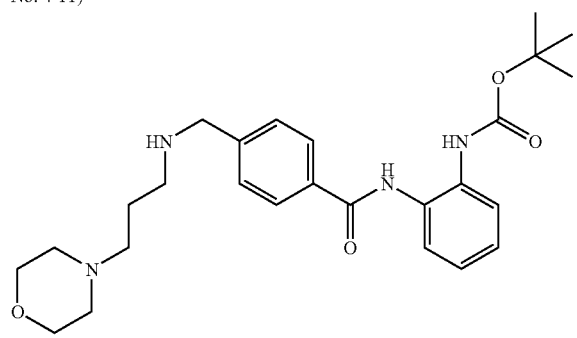 | $^1$H-NMR (500 MHz, CDCl$_3$) δ 1.52 (s, 9 H), 1.72 (m, 2 H), 2.39-2.49 (m, 6 H), 2.69 (t, J = 6.7 Hz, 2 H), 3.70 (t, J = 4.6 Hz, 4 H), 3.86 (s, 2 H), 6.78 (br s, 1 H), 7.18 (td, J = 7.9, 1.5 Hz, 1 H), 7.23-7.28 (m, 2 H), 7.42 (d, J = 8.2 Hz, 2 H), 7.81 (d, J = 7.9 Hz, 1 H), 7.93 (d, J = 8.2 Hz, 2 H), 9.09 (br s, 1 H) |
| N-(2-t-Butoxycarbonylamino phenyl)-4-(1-t-butoxy-carbonylpiperidin-4-ylmethyl-aminomethyl)benzamide Reference Compound No. 4-12) 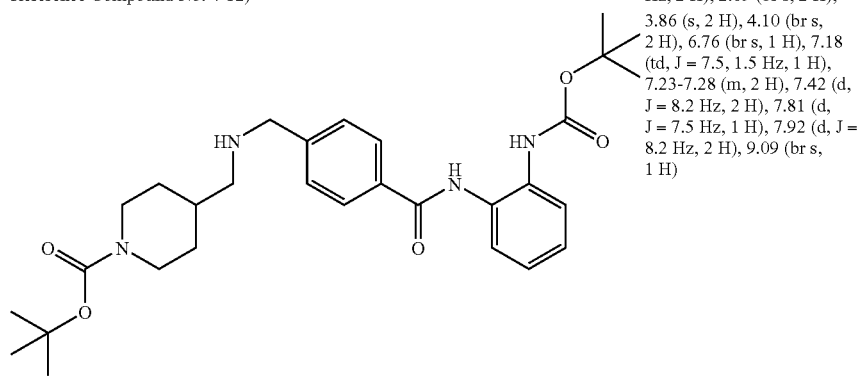 | $^1$H-NMR (500 MHz, CDCl$_3$) δ 1.12 (m, 2 H), 1.45 (s, 9 H), 1.52 (s, 9 H), 1.55-1.75 (m, 3 H), 2.51 (d, J = 6.7 Hz, 2 H), 2.69 (br s, 2 H), 3.86 (s, 2 H), 4.10 (br s, 2 H), 6.76 (br s, 1 H), 7.18 (td, J = 7.5, 1.5 Hz, 1 H), 7.23-7.28 (m, 2 H), 7.42 (d, J = 8.2 Hz, 2 H), 7.81 (d, J = 7.5 Hz, 1 H), 7.92 (d, J = 8.2 Hz, 2 H), 9.09 (br s, 1 H) |

| | |
|---|---|
| 4-(3-t-Butoxycarbonylamino propylaminomethyl)-N-(2-t-butoxycarbonylaminophenyl) benzamide (Reference Compound No. 4-13)<br>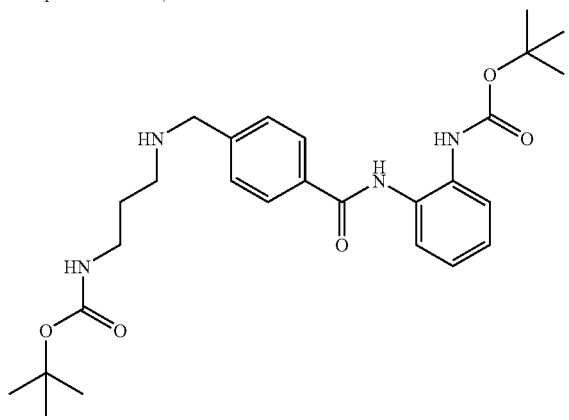 | $^1$H-NMR (400 MHz, CDCl$_3$) δ 1.45 (s, 9 H), 1.52 (s, 9 H), 1.69 (m, 2 H), 2.71 (t, J = 6.5 Hz, 2 H), 3.23 (m, 2 H), 3.85 (s, 2 H), 5.16 (br s, 1 H), 6.77 (br s, 1 H), 7.18 (td, J = 7.9, 1.5 Hz, 1 H), 7.22-7.29 (m, 2 H), 7.43 (d, J = 8.3 Hz, 2 H), 7.80 (d, J = 7.9 Hz, 1 H), 7.92 (d, J = 8.3 Hz, 2 H), 9.07 (br s, 1 H) |
| N-(2-t-Butoxycarbonylamino phenyl)-4-[3-(pyrrolidin-2-on-1-yl)propylaminomethyl] benzamide (Reference Compound No. 4-14)<br>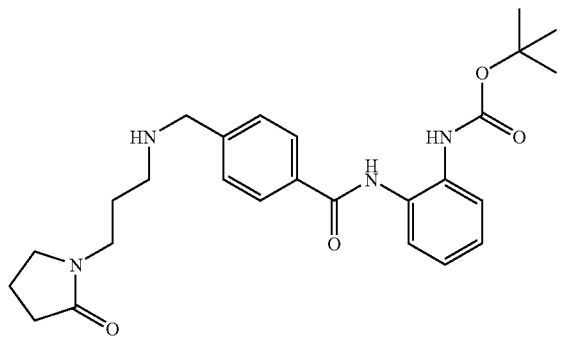 | $^1$H-NMR (400 MHz, CDCl$_3$) δ 1.52 (s, 9 H), 1.74 (m, 2 H), 2.01 (m, 2 H), 2.38 (t, J = 8.1 Hz, 2 H), 2.61 (t, J = 6.8 Hz, 2 H), 3.34-3.39 (m, 4 H), 3.85 (s, 2 H), 6.78 (br s, 1 H), 7.18 (td, J = 7.7, 1.5 Hz, 1 H), 7.22-7.30 (m, 2 H), 7.43 (d, J = 8.3 Hz, 2 H), 7.80 (d, J = 7.7 Hz, 1 H), 7.92 (d, J = 8.3 Hz, 2 H), 9.06 (br s, 1 H) |
| N-(2-t-Butoxycarbonylamino phenyl)-4-(2-hydroxyethyl-aminomethyl)benzamide Reference Compound No. 4-15)<br>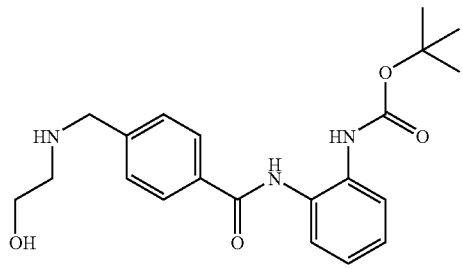 | $^1$H-NMR (400 MHz, CDCl$_3$) δ 1.52 (s, 9 H), 2.83 (t, J = 5.1 Hz, 2 H), 3.68 (t, J = 5.1 Hz, 2 H), 3.89 (s, 2 H), 6.82 (br s, 1 H), 7.17 (t, J = 7.4 Hz, 1 H), 7.22-7.26 (m, 2 H), 7.42 (d, J = 7.8 Hz, 2 H), 7.80 (d, J = 7.8 Hz, 1 H), 7.92 (d, J = 8.1 Hz, 2 H), 9.14 (br s, 1 H) |

| | |
|---|---|
| N-(2-t-Butoxycarbonylamino phenyl)-4-(4-dimethylamino butylaminomethyl)benzamide (Reference Compound No. 4-16) 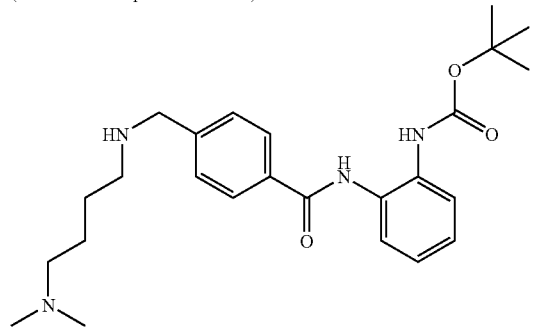 | ¹H-NMR (400 MHz, CDCl₃) δ 1.46-1.59 (m, 4 H), 1.52 (s, 9 H), 2.21 (s, 6 H), 2.26 (t, J = 7.1 Hz, 2 H), 2.65 (t, J = 6.7 Hz, 2 H), 3.86 (s, 2 H), 6.87 (br s, 1 H), 7.17 (td, J = 7.8, 1.5 Hz, 1 H), 7.21-7.28 (m, 2 H), 7.42 (d, J = 8.2 Hz, 2 H), 7.80 (d, J = 7.8 Hz, 1 H), 7.92 (d, J = 8.2 Hz, 2 H), 9.10 (br s, 1 H) |
| N-(2-t-Butoxycarbonylamino phenyl)-4-(1-ethylpyrrolidin-2-ylmethylaminomethyl) benzamide (Reference Compound No. 4-17) 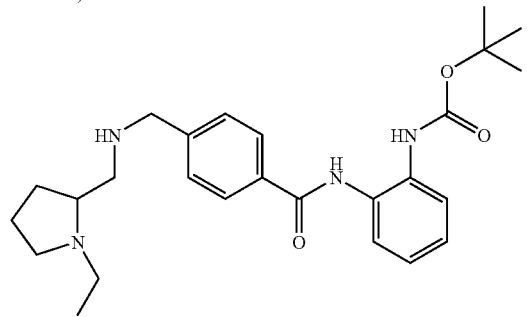 | ¹H-NMR (400 MHz, CDCl₃) δ 1.09 (t, J = 7.2 Hz, 3 H), 1.52 (s, 9 H), 1.64-1.78 (m, 3 H), 1.90 (m, 1 H), 2.12-2.24 (m, 2 H), 2.46-2.84 (m, 4 H), 3.15 (m, 1 H), 3.88 (s, 2 H), 6.96 (br s, 1 H), 7.15 (td, J = 7.8, 1.6 Hz, 1 H), 7.22 (td, J = 7.8, 1.7 Hz, 1 H), 7.26 (d, J = 7.8 Hz, 1 H), 7.42 (d, J = 8.3 Hz, 2 H), 7.77 (d, J = 7.8 Hz, 1 H), 7.91 (d, J = 8.3 Hz, 2 H), 9.13 (br s, 1 H) |
| N-(2-t-Butoxycarbonylamino phenyl)-4-(pyridin-4-yl-methylaminomethyl)benzamide (Reference Compound No. 4-18) 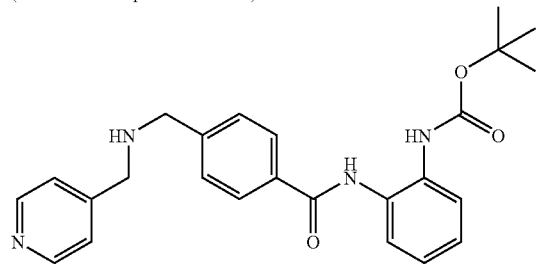 | ¹H-NMR (400 MHz, CDCl₃) δ 1.52 (s, 9 H), 3.83 (s, 2 H), 3.88 (s, 2 H), 6.77 (br s, 1 H), 7.17 (t, J = 7.8 Hz, 1 H), 7.23-7.27 (m, 2 H), 7.30 (d, J = 6.0 Hz, 2 H), 7.45 (d, J = 8.1 Hz, 2 H), 7.83 (d, J = 7.8 Hz, 1 H), 7.94 (d, J = 8.1 Hz, 2 H), 8.57 (d, J = 6.0 Hz, 2 H), 9.13 (br s, 1 H) |
| N-(2-t-Butoxycarbonylamino phenyl)-4-[2-(pyridin-4-yl)-ethylaminomethyl]benzamide (Reference Compound No. 4-19) 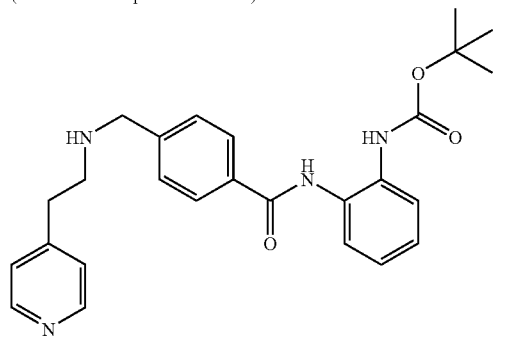 | ¹H-NMR (400 MHz, CDCl₃) δ 1.52 (s, 9 H), 2.82 (t, J = 7.0 Hz, 2 H), 2.92 (m, 2 H), 3.88 (s, 2 H), 6.81 (br s, 1 H), 7.14 (dd, J = 4.4, 1.7 Hz, 2 H), 7.17 (td, J = 7.8, 1.5 Hz, 1 H), 7.22-7.28 (m, 2 H), 7.38 (d, J = 8.4 Hz, 2 H), 7.82 (d, J = 7.8 Hz, 1 H), 7.91 (d, J = 8.4 Hz, 2 H), 8.51 (dd, J = 4.4, 1.7 Hz, 2 H), 9.10 (br s, 1 H) |

N-(2-t-Butoxycarbonylamino phenyl)-4-[2-(morpholin-4-yl)ethylaminomethyl] benzamide (Reference Compound No. 4-20)

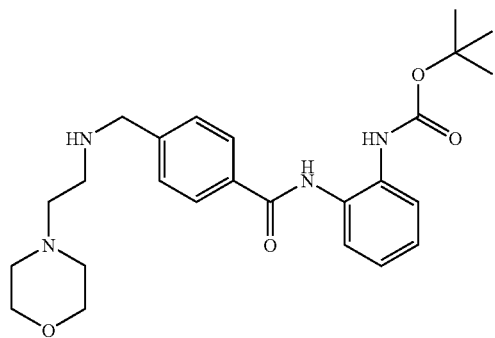

$^1$H-NMR (400 MHz, CDCl$_3$) δ 1.52 (s, 9 H), 2.42 (m, 4 H), 2.53 (m, 2 H), 2.71 (m, 2 H), 3.69 (m, 4 H), 3.88 (s, 2 H), 6.89 (s, 1 H), 7.16 (ddd, J = 7.6, 7.6, 1.5 Hz, 1 H), 7.21-7.28 (m, 2 H), 7.42 (d, J = 8.3 Hz, 2 H), 7.81 (d, J = 8.1 Hz, 1 H), 7.92 (d, J = 8.3 Hz, 2 H), 9.14 (s, 1 H)

N-(2-t-Butoxycarbonylamino phenyl)-4-[2-(4-methyl-piperazin-1-yl)ethylaminomethyl] benzamide (Reference Compound No. 4-21)

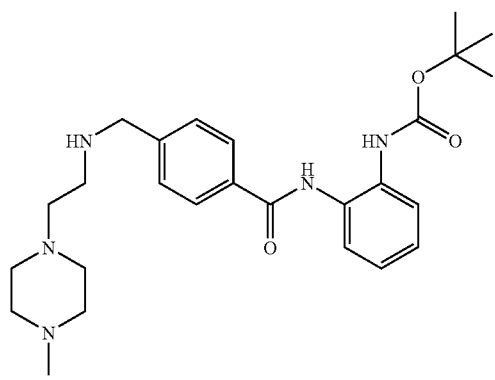

$^1$H-NMR (500 MHz, CDCl$_3$) δ 1.52 (s, 9 H), 2.31 (s, 3 H), 2.50 (br s, 8 H), 2.56 (t, J = 6.1 Hz, 2 H), 2.73 (t, J = 6.1 Hz, 2 H), 3.89 (s, 2 H), 6.93 (br s, 1 H), 7.17 (td, J = 7.8, 1.6 Hz, 1 H), 7.23 (td, J = 7.8, 1.6 Hz, 1 H), 7.28 (d, J = 7.8 Hz, 1 H), 7.44 (d, J = 8.0 Hz, 2 H), 7.79 (d, J = 7.8 Hz, 1 H), 7.92 (d, J = 8.0 Hz, 2 H), 9.17 (br s, 1 H)

N-(2-t-Butoxycarbonylamino phenyl)-4-[2-(1-methyl-pyrrolidin-2-yl)ethylamino-methyl]benzamide (Reference Compound No. 4-22)

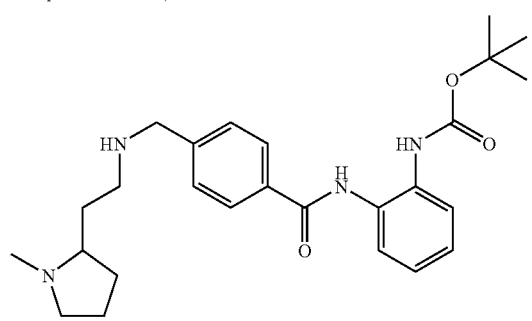

$^1$H-NMR (400 MHz, CDCl$_3$) δ 1.41-1.80 (m, 4 H), 1.52 (s, 9 H), 1.85-1.95 (m, 2 H), 2.05-2.15 (m, 2 H), 2.32 (s, 3 H), 2.60-2.74 (m, 2 H), 3.05 (m, 1 H), 3.85 (d, J = 13.8 Hz, 1 H), 3.89 (d, J = 13.8 Hz, 1 H), 6.85 (s, 1 H), 7.17 (td, J = 7.8, 1.6 Hz, 1 H), 7.20-7.29 (m, 2 H), 7.42 (d, J = 8.4 Hz, 2 H), 7.80 (d, J = 7.8 Hz, 1 H), 7.92 (d, J = 8.4 Hz, 2 H), 9.11 (br s, 1 H)

| | |
|---|---|
| N-(2-t-Butoxycarbonylamino phenyl)-4-[3-(4-hydroxy-piperidin-1-yl)propylamino-methyl]benzamide (Reference Compound No. 4-23)<br>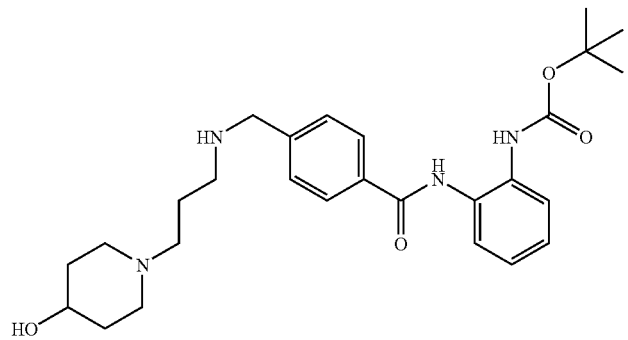 | $^1$H-NMR (500 MHz, CDCl$_3$) δ 1.51 (s, 9 H), 1.56 (m, 2 H), 1.70 (m, 2 H), 1.87 (m, 2 H), 2.07 (t, J = 9.5 Hz, 2 H), 2.39 (t, J = 7.2 Hz, 2 H), 2.67 (t, J = 6.9 Hz, 2 H), 2.76 (m, 2 H), 3.69 (m, 1 H), 3.85 (s, 2 H), 7.06 (s, 1 H), 7.15 (td, J = 7.6, 1.5 Hz, 1 H), 7.21 (td, J = 7.6, 1.5 Hz, 1 H), 7.26 (dd, J = 7.6, 1.5 Hz, 1 H), 7.41 (d, J = 8.2 Hz, 2 H), 7.77 (d, J = 7.6 Hz, 1 H), 7.91 (d, J = 8.2 Hz, 2 H), 9.16 (s, 1 H) |
| N-(2-t-Butoxycarbonylamino phenyl)-4-[2-hydroxy-3-(morpholin-4-yl)propylamino-methyl]benzamide (Reference Compound No. 4-24)<br>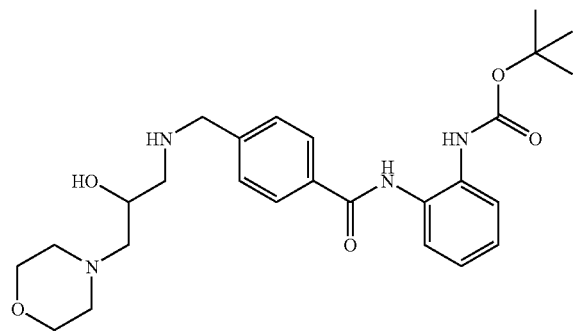 | $^1$H-NMR (500 MHz, CDCl$_3$) δ 1.52 (s, 9 H), 2.34 (dd, J = 12.2, 3.4 Hz, 1 H), 2.42 (m, 2 H), 2.45 (dd, J = 12.2, 10.1 Hz, 1 H), 2.58 (dd, J = 11.9, 7.3 Hz, 1 H), 2.64 (m, 2 H), 2.72 (dd, J = 11.9, 3.4 Hz, 1 H), 3.67-3.76 (m, 4 H), 3.85-3.93 (m, 3 H), 6.76 (br s, 1 H), 7.18 (td, J = 7.9, 1.5 Hz, 1 H), 7.23-7.28 (m, 2 H), 7.43 (d, J = 8.6 Hz, 2 H), 7.81 (d, J = 7.9 Hz, 1 H), 7.93 (d, J = 8.6 Hz, 2 H), 9.08 (br s, 1 H) |
| N-(2-t-Butoxycarbonylamino phenyl)-4-[3-(pyrrolidin-1-yl)propylaminomethyl] benzamide (Reference Compound No. 4-25)<br>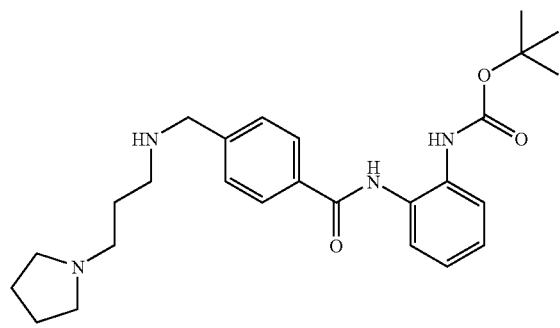 | $^1$H-NMR (400 MHz, CDCl$_3$) δ 1.50 (s, 9 H), 1.95 (m, 4 H), 2.03 (m, 2 H), 2.85 (t, J = 6.5 Hz, 2 H), 2.91-2.96 (m, 4 H), 3.22 (m, 2 H), 3.90 (s, 2 H), 7.12-7.21 (m, 3 H), 7.37 (dd, J = 7.6, 1.5 Hz, 1 H), 7.48 (d, J = 8.3 Hz, 2 H), 7.75 (dd, J = 7.6, 1.5 Hz, 1 H), 7.95 (d, J = 8.3 Hz, 2 H), 9.51 (s, 1 H) |

| | |
|---|---|
| N-(2-t-Butoxycarbonylamino phenyl)-4-[3-(4-methyl-piperidin-1-yl)propylamino-methyl]benzamide (Reference Compound No. 4-26) 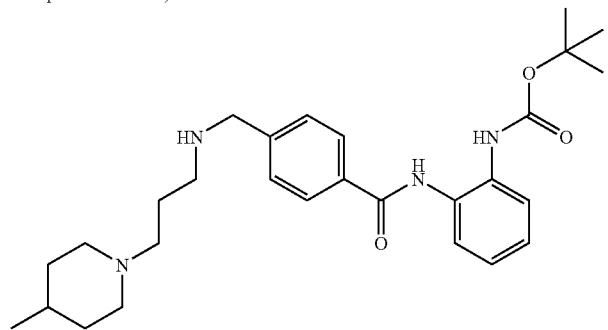 | $^1$H-NMR (400 MHz, CDCl$_3$) δ 0.91 (d, J = 6.3 Hz, 3 H), 1.19-1.27 (m, 2 H), 1.35 (m, 1 H), 1.52 (s, 9 H), 1.62 (m, 2 H), 1.75 (m, 2 H), 1.92 (m, 2 H), 2.41 (t, J = 7.2 Hz, 2 H), 2.70 (t, J = 6.7 Hz, 2 H), 2.93 (m, 2 H), 3.86 (s, 2 H), 6.86 (br s, 1 H), 7.15-7.28 (m, 3 H), 7.43 (d, J = 8.3 Hz, 2 H), 7.80 (d, J = 7.8 Hz, 1 H), 7.92 (d, J = 8.3 Hz, 2 H), 9.12 (br s, 1 H) |

Reference Example 5

1-Benzyloxy-3-(phenoxycarbonylamino)benzene (Reference Compound No. 5-1)

Under ice cooling, after a solution of phenyl chloroformate (2.0 mL, 16 mmol) in THF (2.0 mL) was added dropwise to a solution of 3-benzyloxyaniline (3.7 g, 16 mmol) and pyridine (6.0 mL) in DMF (25 mL), the mixture was stirred at room temperature for 3 hours. Ethyl acetate (200 mL) was added thereto, and then the whole was washed with water (200 mL) twice and brine (200 mL) twice. The organic layer was dried over anhydrous magnesium sulfate, and then the solvent was evaporated under reduced pressure. The resulting solid was collected by filtration with diisopropyl ether, and dried under reduced pressure to give 3.7 g of the title reference compound as a white solid. (Yield 73%)

| | |
|---|---|
| 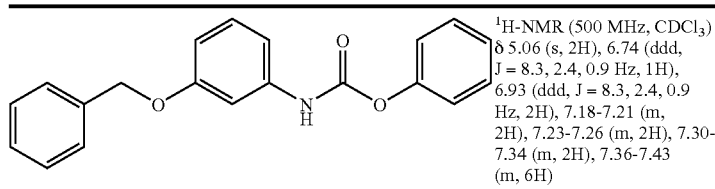 | $^1$H-NMR (500 MHz, CDCl$_3$) δ 5.06 (s, 2H), 6.74 (ddd, J = 8.3, 2.4, 0.9 Hz, 1H), 6.93 (ddd, J = 8.3, 2.4, 0.9 Hz, 2H), 7.18-7.21 (m, 2H), 7.23-7.26 (m, 2H), 7.30-7.34 (m, 2H), 7.36-7.43 (m, 6H) |

By using any compounds selected from commercially available compounds and known compounds, the following Reference Compounds No. 5-2 to 5-4 were obtained by a method similar to that of Reference Compound No. 5-1.

| | |
|---|---|
| 1-Benzyloxy-4-(phenoxycar-bonylamino)benzene (Reference Compound No. 5-2) 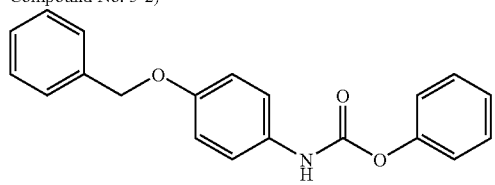 | $^1$H-NMR (400 MHz, CDCl$_3$) δ 5.05 (s, 2H), 6.81 (s, 1H), 6.95 (d, J = 9.1 Hz, 2H), 7.17-7.20 (m, 2H), 7.21-7.27 (m, 2H), 7.31-7.44 (m, 8H) |
| 4-(4-Merthylpiperazin-1-yl)-1-(phenoxycarbonylamino)-benzene (Reference Compound No. 5-3) 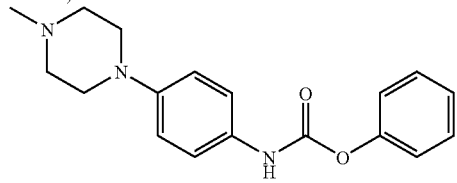 | $^1$H-NMR (400 MHz, DMSO-d$_6$) δ 2.80 (s, 3H), 3.16 (br s, 4H), 3.42 (br s, 2H), 3.71 (br s, 2H), 6.98 (d, J = 9.0 Hz, 2H), 7.20 (d, J = 9.0 Hz, 2H), 7.25 (dd, J = 7.4, 7.4 Hz, 1H), 7.34-7.48 (m, 4H), 10.04 (s, 1H) |

| | |
|---|---|
| 3-Dimethylamino-1-(phenoxy carbonylamino)benzene (Reference Compound No. 5-4) 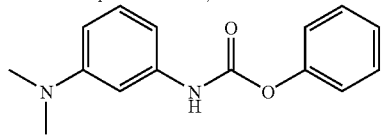 | $^1$H-NMR (400 MHz, CDCl$_3$) δ 2.95 (s, 6H), 6.48 (dd, J = 8.3, 2.2 Hz, 1H), 6.64 (dd, J = 8.1, 1.5 Hz, 1H), 6.88 (br s, 1H), 7.04 (br s, 1H), 7.15-7.26 (m, 4H), 7.39 (m, 2H) |

Reference Example 6

4-Hydroxymethylbenzoic acid benzyl ester (Reference Compound No. 6-1)

Benzyl bromide (7.8 mL, 66 mmol) was added to a suspension of 4-hydroxymethylbenzoic acid (10 g, 66 mmol) and cesium carbonate (11 g, 33 mmol) in a mixed solvent (DMF (100 mL)-methanol (30 mL)-water (30 mL)), and then the mixture was stirred at room temperature for 2 hours. Water (500 mL) was added thereto, the whole was extracted with ethyl acetate (500 mL), and then the organic layer was washed with saturated aqueous sodium hydrogen carbonate solution (300 mL) twice and water (300 mL) twice. The organic layer was dried over anhydrous magnesium sulfate, and then the solvent was evaporated under reduced pressure. The resulting solid was collected by filtration with hexane, and dried at 35° C. under reduced pressure to give 13 g of the title reference compound as a white solid. (Yield 81%)

| | |
|---|---|
| 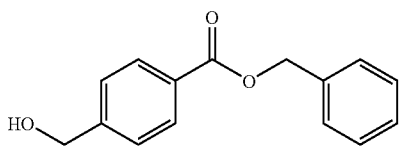 | $^1$H-NMR (400 MHz, DMSO-d$_6$) δ 4.58 (d, J = 5.8 Hz, 2H), 5.35 (s, 2H), 5.38 (t, J = 5.8 Hz, 1H), 7.33-7.44 (m, 4H), 7.46 (m, 1H), 7.47 (d, J = 8.2 Hz, 2H), 7.96 (d, J = 8.2 Hz, 2H) |

Reference Example 7

4-Methanesulfonyloxymethylbenzoic acid benzyl ester (Reference Compound No. 7-1)

Under ice cooling, after methanesulfonyl chloride (2.1 mL, 27 mmol) was added to a solution of 4-hydroxymethylbenzoic acid benzyl ester (Reference Compound No. 6-1, 6.0 g, 25 mmol) and triethylamine (7.6 mL, 54 mmol) in dichloromethane (60 mL), the reaction mixture was stirred at room temperature for 50 minutes. Brine (300 mL) was added thereto, and then the whole was extracted with chloroform (150 mL) four times. The organic layer was dried over anhydrous magnesium sulfate, and then the solvent was evaporated under reduced pressure to give 1.8 g of the title reference compound as yellow oil. (Yield 73%)

| | |
|---|---|
| 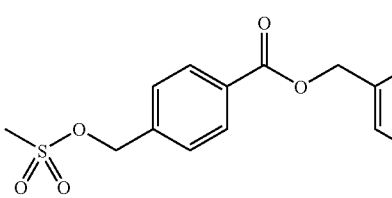 | $^1$H-NMR (400 MHz, CDCl$_3$) δ 2.97 (s, 3H), 5.28 (s, 2H), 5.38 (s, 2H), 7.35-7.41 (m, 5H), 7.49 (d, J = 8.2 Hz, 2H), 8.12 (d, J = 8.2 Hz, 2H) |

Reference Example 8

4-(2-Dimethylaminoethylaminomethyl)benzoic acid benzyl ester (Reference Compound No. 8-1)

N,N-Dimethylethylenediamine (0.87 mL, 7.9 mmol) was added to a solution of 4-methanesulfonyloxymethylbenzoic acid benzyl ester (Reference Compound No. 7-1, 2.3 g, 7.2 mmol) and triethylamine (3.0 mL, 22 mmol) in DMF (10 mL), and then the reaction mixture was stirred at room temperature for 2 hours. Saturated aqueous sodium hydrogen carbonate solution (150 mL) was added thereto, and then the whole was extracted with chloroform (100 mL) three times. The organic layer was dried over anhydrous magnesium sulfate, and then the solvent was evaporated under reduced pressure to give 1.2 g of a mixture, which contains the title reference compound as yellow oil.

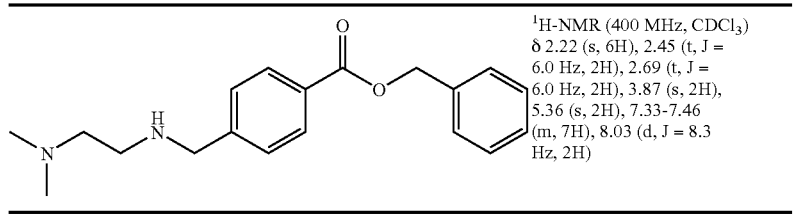

$^1$H-NMR (400 MHz, CDCl$_3$) δ 2.22 (s, 6H), 2.45 (t, J = 6.0 Hz, 2H), 2.69 (t, J = 6.0 Hz, 2H), 3.87 (s, 2H), 5.36 (s, 2H), 7.33-7.46 (m, 7H), 8.03 (d, J = 8.3 Hz, 2H)

By using any compounds selected from Reference Compound No. 7-1, commercially available compounds, and known compounds, the following Reference Compounds No. 8-2 to 8-3 were obtained by a method similar to that of Reference Compound No. 8-1.

4-(2-Hydroxyethylaminomethyl)benzoic acid benzyl ester (Reference Compound No. 8-2)

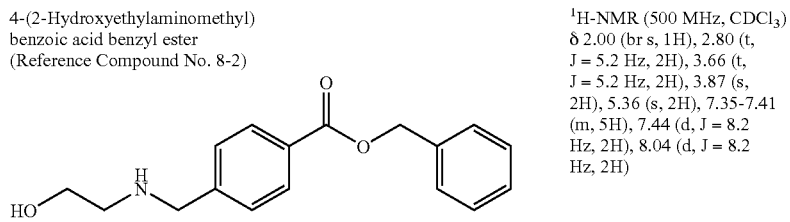

$^1$H-NMR (500 MHz, CDCl$_3$) δ 2.00 (br s, 1H), 2.80 (t, J = 5.2 Hz, 2H), 3.66 (t, J = 5.2 Hz, 2H), 3.87 (s, 2H), 5.36 (s, 2H), 7.35-7.41 (m, 5H), 7.44 (d, J = 8.2 Hz, 2H), 8.04 (d, J = 8.2 Hz, 2H)

4-(3-Dimethylaminopropyl-aminomethyl)benzoic acid benzyl ester (Referemce Compound No. 8-3)

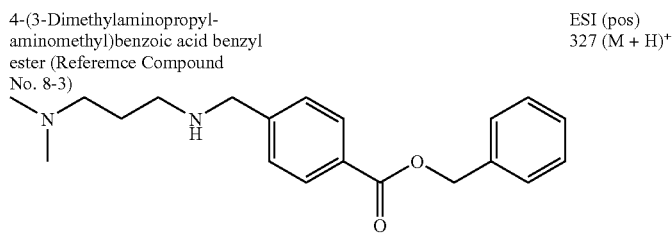

ESI (pos) 327 (M + H)$^+$

Reference Example 9

4-[1-(2-Dimethylaminoethyl)-3-(indan-5-yl)ureidomethyl]benzoic acid benzyl ester (Reference Compound No. 9-1)

Indan-5-yl isocyanate (0.61 mL, 4.2 mmol) was added to a solution of the mixture containing 4-(2-dimethylaminoethylaminomethyl)benzoic acid benzyl ester (Reference Compound No. 8-1, 1.2 g, 3.8 mmol) in dichloromethane (10 mL), and then the reaction mixture was stirred at room temperature for 15 hours. The reaction mixture was concentrated, and then the residue was purified by silica gel column chromatography (chloroform-methanol) to give 0.98 g of the title reference compound as colorless oil. (Yield 29% in 2 steps)

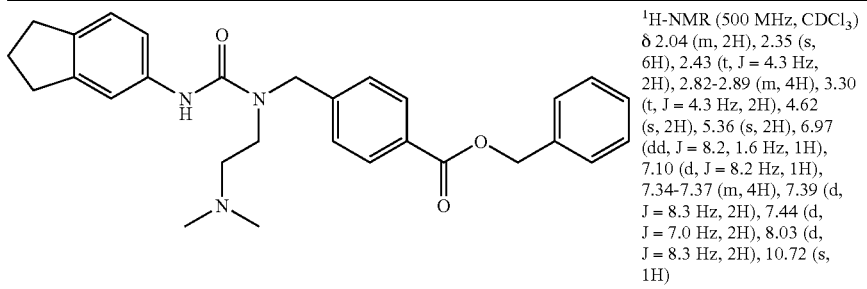

$^1$H-NMR (500 MHz, CDCl$_3$) δ 2.04 (m, 2H), 2.35 (s, 6H), 2.43 (t, J = 4.3 Hz, 2H), 2.82-2.89 (m, 4H), 3.30 (t, J = 4.3 Hz, 2H), 4.62 (s, 2H), 5.36 (s, 2H), 6.97 (dd, J = 8.2, 1.6 Hz, 1H), 7.10 (d, J = 8.2 Hz, 1H), 7.34-7.37 (m, 4H), 7.39 (d, J = 8.3 Hz, 2H), 7.44 (d, J = 7.0 Hz, 2H), 8.03 (d, J = 8.3 Hz, 2H), 10.72 (s, 1H)

By using any compounds selected from Reference Compound No. 8-2 to 8-3, commercially available compounds, and known compounds, the following Reference Compounds to 9-6 were obtained by a method similar to that of Reference Compound No. 9-1.

4-[3-(3,4-Difluorophenyl)-1-(3-dimethylaminopropyl)ureidomethyl]benzoic acid benzyl ester (Reference Compound No. 9-2)

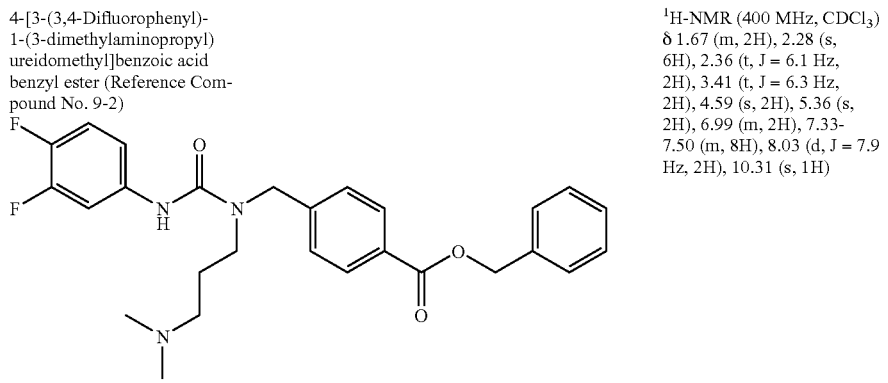

$^1$H-NMR (400 MHz, CDCl$_3$) δ 1.67 (m, 2H), 2.28 (s, 6H), 2.36 (t, J = 6.1 Hz, 2H), 3.41 (t, J = 6.3 Hz, 2H), 4.59 (s, 2H), 5.36 (s, 2H), 6.99 (m, 2H), 7.33-7.50 (m, 8H), 8.03 (d, J = 7.9 Hz, 2H), 10.31 (s, 1H)

4-[1-(3-Dimethylaminopropyl)-3-(2-methoxyphenyl)ureidomethyl]benzoic acid benzyl ester (Reference Compound No. 9-3)

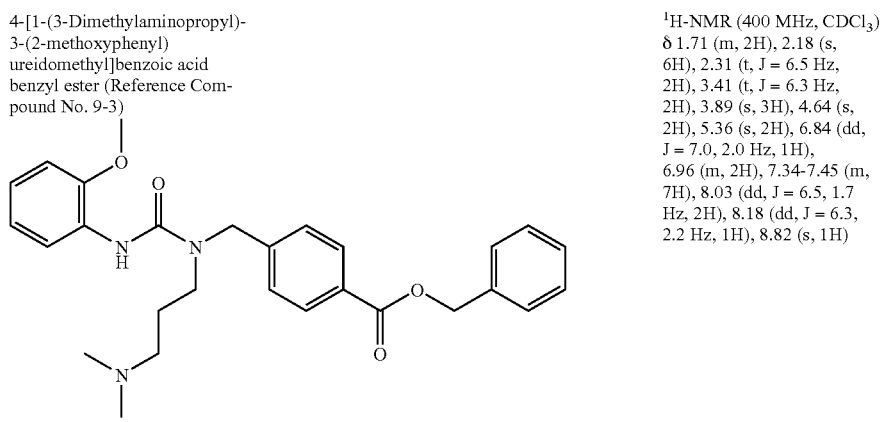

$^1$H-NMR (400 MHz, CDCl$_3$) δ 1.71 (m, 2H), 2.18 (s, 6H), 2.31 (t, J = 6.5 Hz, 2H), 3.41 (t, J = 6.3 Hz, 2H), 3.89 (s, 3H), 4.64 (s, 2H), 5.36 (s, 2H), 6.84 (dd, J = 7.0, 2.0 Hz, 1H), 6.96 (m, 2H), 7.34-7.45 (m, 7H), 8.03 (dd, J = 6.5, 1.7 Hz, 2H), 8.18 (dd, J = 6.3, 2.2 Hz, 1H), 8.82 (s, 1H)

| | |
|---|---|
| 4-[1-(3-Dimethylaminopropyl)-3-ethoxycarbonylmethyl-ureidomethyl]benzoic acid benzyl ester (Reference Compound No. 9-4) 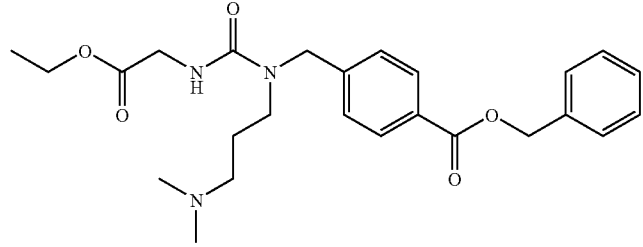 | $^1$H-NMR (400 MHz, CDCl$_3$) δ 1.29 (t, J = 7.2 Hz, 3H), 1.58 (m, 2H), 2.19 (s, 6H), 2.31 (t, J = 6.1 Hz, 2H), 3.27 (t, J = 5.7 Hz, 2H), 3.92 (d, J = 5.5 Hz, 2H), 4.20 (q, J = 7.2 Hz, 2H), 4.56 (s, 2H), 5.35 (s, 2H), 7.32-7.35 (m, 3H), 7.37-7.40 (m, 2H), 7.44 (d, J = 7.0 Hz, 2H), 8.01 (d, J = 6.7 Hz, 2H), 8.21 (s, 1H) |
| 4-[3-t-Butyl-1-(3-dimethyl aminopropyl)ureidomethyl] benzoic acid benzyl ester (Reference Compound No. 9-5) 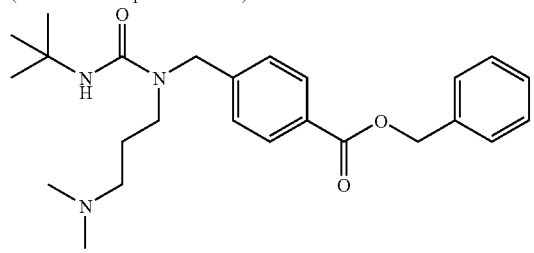 | $^1$H-NMR (500 MHz, CDCl$_3$) δ 1.34 (s, 9H), 1.56 (m, 2H), 2.18 (s, 6H), 2.23 (t, J = 6.1 Hz, 2H), 3.19 (t, J = 5.9 Hz, 2H), 4.50 (s, 2H), 5.35 (s, 2H), 6.91 (s, 1H), 7.32 (d, J = 7.9 Hz, 2H), 7.34 (m, 1H), 7.38 (m, 2H), 7.44 (m, 2H), 8.01 (d, J = 7.9 Hz, 2H) |
| 4-[1-(2-Hydroxyethyl)-3-(indan-5-yl)ureidomethyl] benzoic acid benzyl ester (Reference Compound No. 9-6) 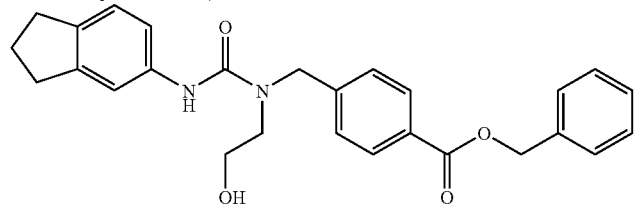 | $^1$H-NMR (400 MHz, CDCl$_3$) δ 2.05 (m, 2H), 2.83-2.87 (m, 4H), 3.37 (t, J = 4.4 Hz, 2H), 3.67 (m, 2H), 3.80 (t, J = 4.6 Hz, 1H), 4.44 (s, 2H), 5.36 (s, 2H), 7.05 (dd, J = 8.0, 2.2 Hz, 1H), 7.10 (d, J = 8.0 Hz, 1H), 7.29 (d, J = 8.5 Hz, 2H), 7.32-7.45 (m, 6H), 8.02 (d, J = 8.5 Hz, 2H), 8.11 (s, 1H) |

Reference Example 10

4-[1-(2-Dimethylaminoethyl)-3-(indan-5-yl)ureidomethyl]benzoic acid (Reference Compound No. 10-1)

10% Palladium on carbon (100 mg) was added to a solution of 4-[1-(2-dimethylaminoethyl)-3-(indan-5-yl)ureidomethyl]benzoic acid benzyl ester (Reference Compound No. 9-1, 970 mg, 2.1 mmol) in methanol (20 mL), and then the reaction mixture was stirred under a hydrogen atmosphere at room temperature for 29 hours. The insoluble was filtered off, and then the solvent was evaporated under reduced pressure. The resulting solid was collected by filtration with ethyl acetate to give 0.78 g of the title reference Compound as a white solid quantitatively.

| | |
|---|---|
| 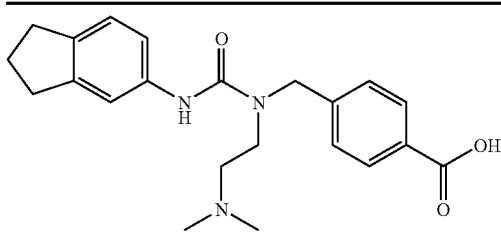 | $^1$H-NMR (500 MHz, DMSO-d$_6$) δ 1.99 (m, 2H), 2.34 (s, 6H), 1.57 (br s, 2H), 2.75-2.82 (m, 4H), 3.39 (t, J = 5.2 Hz, 2H), 4.62 (s, 2H), 7.07-7.09 (m, 2H), 7.31 (s, 1H), 7.38 (d, J = 8.2 Hz, 2H), 7.92 (d, J = 8.2 Hz, 2H), 9.68 (s, 1H) |

By using any compounds selected from Reference Compound No. 9-2 to 9-6, commercially available compounds, and known compounds, the following Reference Compounds No. 10-2 to 10-6 were obtained by a method similar to that of Reference Compound No. 10-1.

4-[3-(3,4-Difluorophenyl)-1-(3-dimethylaminopropyl)-ureidomethyl]benzoic acid (Reference Compound No. 10-2)

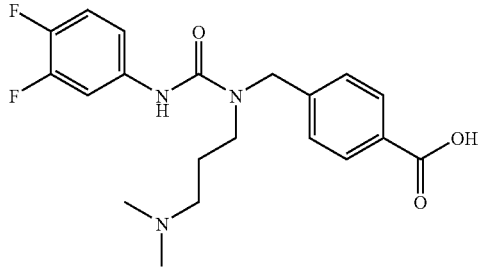

$^1$H-NMR (400 MHz, DMSO-$d_6$) δ 1.66 (m, 2H), 2.18 (s, 6H), 2.25 (t, J = 6.2 Hz, 2H), 3.34 (br s, 2H), 4.48 (s, 2H), 7.10 (m, 1H), 7.27 (m, 1H), 7.36 (d, J = 8.3 Hz, 2H), 7.68 (m, 1H), 7.90 (d, J = 8.3 Hz, 2H), 9.80 (s, 1H)

4-[1-(3-Dimethylaminopropyl)-3-(2-methoxyphenyl)-ureidomethyl]benzoic acid (Reference Compound No. 10-3)

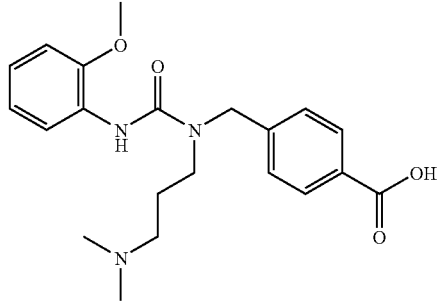

$^1$H-NMR (500 MHz, DMSO-$d_6$) δ 1.58 (m, 2H), 2.09 (s, 6H), 2.21 (t, J = 6.6 Hz, 2H), 3.34 (br s, 2H), 3.78 (s, 3H), 4.53 (s, 2H), 6.85 (m, 1H), 6.93-6.97 (m, 2H), 7.29 (d, J = 7.6 Hz, 2H), 7.78-7.95 (m, 2H), 7.99 (d, J = 7.6 Hz, 2H)

4-[1-(3-Dimethylaminopropyl)-3-ethoxycarbonylmethyl-ureidomethyl]benzoic acid (Reference Compound No. 10-4)

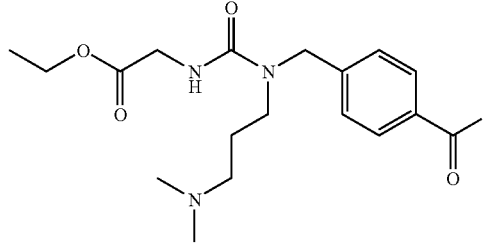

$^1$H-NMR (400 MHz, DMSO-$d_6$) δ 1.20 (t, J = 7.1 Hz, 3H), 1.58 (tt, J = 6.8, 6.6 Hz, 2H), 2.09 (s, 6H), 2.21 (t, J = 6.6 Hz, 2H), 3.16 (t, J = 6.8 Hz, 2H), 3.76 (d, J = 4.6 Hz, 2H), 4.09 (q, J = 7.1 Hz, 2H), 4.49 (s, 2H), 7.31 (d, J = 8.3 Hz, 2H), 7.50 (br s, 1H), 7.87 (d, J = 8.3 Hz, 2H)

4-[3-t-Butyl-1-(3-dimethylaminopropyl)ureidomethyl]benzoic acid (Reference Compound No. 10-5)

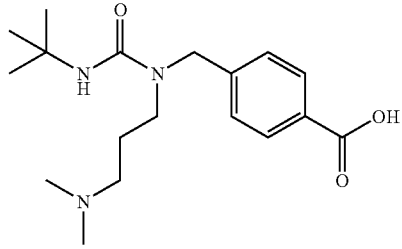

$^1$H-NMR (500 MHz, DMSO-$d_6$) δ 1.23 (s, 9H), 1.61 (m, 2H), 2.26 (s, 6H), 2.36 (m, 2H), 3.16 (m, 2H), 4.46 (s, 2H), 6.47 (s, 1H), 7.31 (d, J = 8.3 Hz, 2H), 7.89 (d, J = 8.3 Hz, 2H), 12.28 (s, 1H)

| | |
|---|---|
| 4-[1-(2-Hydroxyethyl)-3-(indan-5-yl)ureidomethyl]benzoic acid (Reference Compound No. 10-6) 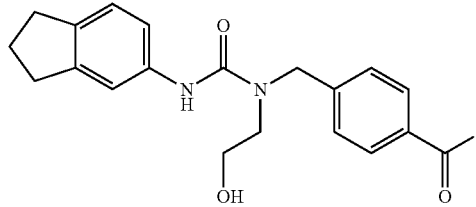 | $^1$H-NMR (500 MHz, DMSO-$d_6$) δ 1.98 (m, 2H), 2.76-2.82 (m, 4H), 3.38 (t, J = 5.1 Hz, 2H), 3.56 (br s, 2H), 4.64 (s, 2H), 5.30 (br s, 1H), 7.06 (d, J = 8.3 Hz, 1H), 7.10 (dd, J = 8.3, 1.8 Hz, 1H), 7.31 (s, 1H), 7.38 (d, J = 8.3 Hz, 2H), 7.91 (d, J = 8.3 Hz, 2H), 8.61 (s, 1H), 12.83 (br s, 1H) |

Reference Example 11

4-Methoxy-2-nitrophenylcarbamic acid t-butyl ester (Reference Compound No. 11-1)

4-Methoxy-2-nitroaniline (1.3 g, 7.7 mmol) was added to a suspension of sodium hydride (1.1 g, 46 mmol) in THF (35 mmol), a solution of di-t-butyl dicarbonate (2.0 g, 9.2 mmol) in THF (10 mL) was dropwised thereto, and then the reaction mixture was stirred at room temperature for 18 hours. Under ice cooling, 1.0 M hydrochloric acid (50 mL) was added thereto, the whole was extracted with ethyl acetate (40 mL) three times, and then the organic layer was washed with saturated aqueous sodium hydrogen carbonate solution (50 mL) and brine (50 mL). The organic layer was dried over anhydrous magnesium sulfate, and then the solvent was evaporated under reduced pressure. The residue was purified by silica gel column chromatography (hexane-ethyl acetate) to give 1.7 g of the title reference compound as orange oil. (Yield 86%)

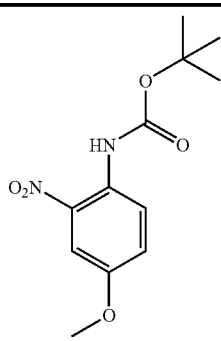

$^1$H-NMR (400 MHz, CDCl$_3$) δ 1.53 (s, 9H), 3.84 (s, 3H), 7.21 (dd, J = 9.5, 3.2 Hz, 1H), 7.64 (d, J = 3.2 Hz, 1H), 8.44 (d, J = 9.5 Hz, 1H), 9.41 (s, 1H)

Reference Example 12

2-Amino-4-methoxyphenylcarbamic acid t-butyl ester (Reference Compound No. 12-1)

10% Palladium on carbon (120 mg) was added to a solution of 4-methoxy-2-nitrophenylcarbamic acid t-butyl ester (Reference Compound No. 11-1, 1.3 g, 4.8 mmol) in methanol (20 mL), and then the reaction mixture was stirred under a hydrogen atmosphere at room temperature for 9 hours. The insoluble was filtered off, and then the solvent was evaporated under reduced pressure. The resulting solid was collected by filtration with hexane to give 1.1 g of the title reference compound as a pale brown solid quantitatively.

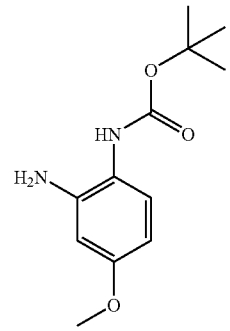

$^1$H-NMR (400 MHz, CDCl$_3$) δ 1.49 (s, 9H), 3.75 (s, 3H), 3.82 (s, 2H), 5.97 (br s, 1H), 6.31-6.33 (m, 2H), 7.05 (d, J = 9.0 Hz, 1H)

Reference Example 13

N-(2-t-Butoxycarbonylaminophenyl)-4-[3-(2,3-dihydrobenzo[1,4]dioxin-6-yl)-1-[3-(4-methylpiperazin-1-yl)propyl]ureidomethyl]benzamide (Reference Compound No. 13-1)

2,3-Dihydrobenzo[1,4]dioxin-6-ylisocyanate (0.11 mL, 0.80 mmol) was added to a solution of N-(2-t-butoxycarbonylaminophenyl)-4-[3-(4-methylpiperazin-1-yl)propylaminomethyl]benzamide (Reference Compound No. 4-1, 350 mg, 0.73 mmol) in anhydrous dichloromethane (15 mL), and then the reaction mixture was stirred at room temperature for 40 minutes. The reaction mixture was concentrated under reduced pressure, and then the residue was purified by silica gel column chromatography (chloroform-methanol) to give 460 mg of the title reference compound as a colorless amorphous product. (Yield 94%)

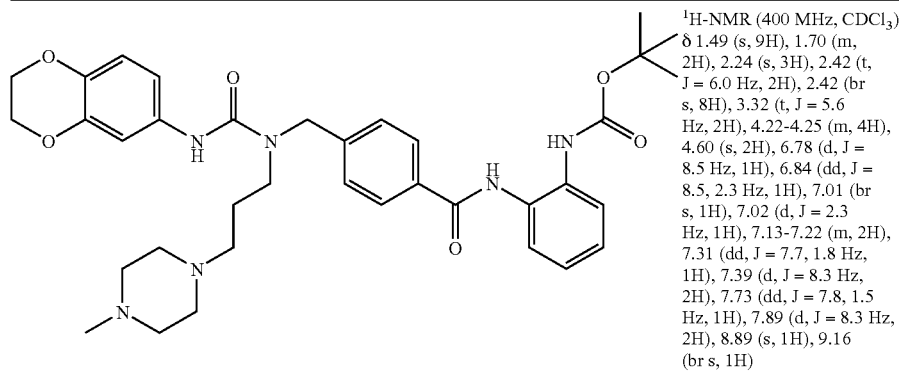

| | ¹H-NMR (400 MHz, CDCl₃) δ 1.49 (s, 9H), 1.70 (m, 2H), 2.24 (s, 3H), 2.42 (t, J = 6.0 Hz, 2H), 2.42 (br s, 8H), 3.32 (t, J = 5.6 Hz, 2H), 4.22-4.25 (m, 4H), 4.60 (s, 2H), 6.78 (d, J = 8.5 Hz, 1H), 6.84 (dd, J = 8.5, 2.3 Hz, 1H), 7.01 (br s, 1H), 7.02 (d, J = 2.3 Hz, 1H), 7.13-7.22 (m, 2H), 7.31 (dd, J = 7.7, 1.8 Hz, 1H), 7.39 (d, J = 8.3 Hz, 2H), 7.73 (dd, J = 7.8, 1.5 Hz, 1H), 7.89 (d, J = 8.3 Hz, 2H), 8.89 (s, 1H), 9.16 (br s, 1H) |

By using any compounds selected from Reference Compound No. 4-1 to 4-26, commercially available compounds, and known compounds, the following Reference Compounds No. 13-2 to 13-158 were obtained by a method similar to that of Reference Compound No. 13-1.

N-(2-t-Butoxycarbonylaminophenyl)-4-[3-(3,5-dimethoxybenzyl)-1-(2-dimethylaminoethyl)ureidomethyl]benzamide
(Reference Compound No. 13-2)

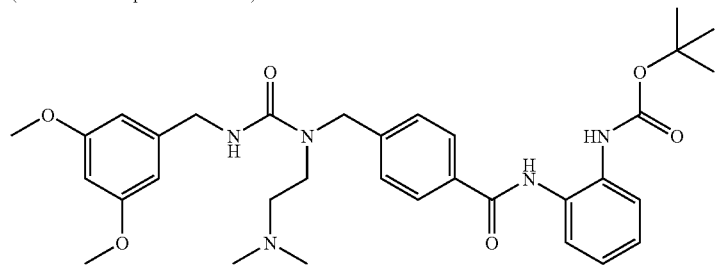

¹H-NMR (500 MHz, CDCl₃)
δ 1.51 (s, 9H), 2.09 (s, 6H), 2.35 (t, J = 4.4 Hz, 2H), 3.23 (t, J = 4.4 Hz, 2H), 3.78 (s, 6H), 4.34 (d, J = 4.9 Hz, 2H), 4.60 (s, 2H), 6.35 (t, J = 2.3 Hz, 1H), 6.48 (s, 1H), 6.48 (s, 1H), 6.80 (s, 1H), 7.18 (td, J = 7.6, 1.5 Hz, 1H), 7.23-7.29 (m, 2H), 7.38 (d, J = 8.1 Hz, 2H), 7.80 (d, J = 7.6 Hz, 1H), 7.91 (d, J = 8.1 Hz, 2H), 8.17 (s, 1H), 9.10 (s, 1H)

N-(2-t-Butoxycarbonylaminophenyl)-4-[1-(2-dimethylaminoethyl)-3-phenylureidomethyl]benzamide
(Reference Compound No. 13-3)

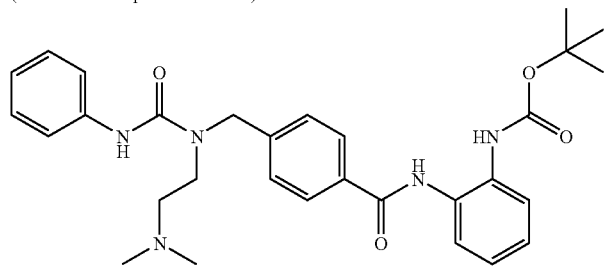

¹H-NMR (500 MHz, DMSO-d₆)
δ 1.44 (s, 9H), 2.27 (s, 6H), 2.46 (t, J = 5.2 Hz, 2H), 3.38 (t, J = 5.2 Hz, 2H), 4.63 (s, 2H), 6.93 (t, J = 7.6 Hz, 1H), 7.15 (td, J = 8.1, 1.5 Hz, 1H), 7.20 (td, J = 8.1, 1.5 Hz, 1H), 7.25 (t, J = 7.6 Hz, 2H), 7.38 (dd, J = 8.1, 1.5 Hz, 2H), 7.45 (d, J = 8.2 Hz, 2H), 7.53 (t, J = 7.6 Hz, 2H), 7.93 (d, J = 8.2 Hz, 2H), 8.66 (s, 1H), 9.81 (s, 1H), 10.19 (s, 1H)

N-(2-t-Butoxycarbonylaminophenyl)-4-[3-(4-chlorophenyl)-1-(2-dimethylaminoethyl)ureidomethyl]benzamide
(Reference Compound No. 13-4)

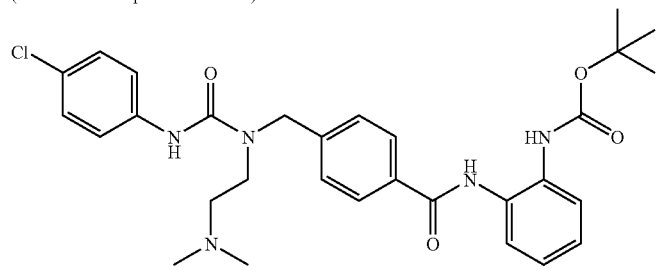

¹H-NMR (500 MHz, DMSO-d₆)
δ 1.43 (s, 9H), 2.26 (s, 6H), 2.46 (t, J = 5.2 Hz, 2H), 3.38 (t, J = 5.2 Hz, 2H), 4.63 (s, 2H), 7.15 (td, J = 7.6, 1.5 Hz, 1H), 7.20 (td, J = 7.6, 1.5 Hz, 1H), 7.29 (d, J = 8.9 Hz, 2H), 7.42 (d, J = 8.9 Hz, 2H), 7.45 (d, J = 8.2 Hz, 2H), 7.53 (dd, J = 7.6, 1.5 Hz, 1H), 7.54 (dd, J = 7.6, 1.5 Hz, 1H), 7.93 (d, J = 8.2 Hz, 2H), 8.66 (s, 1H), 9.81 (s, 1H), 10.33 (br s, 1H)

N-(2-t-Butoxycarbonylaminophenyl)-4-[1-(2-dimethylaminoethyl)-3-phenethylureidomethyl]-benzamide
(Reference Compound No. 13-5)

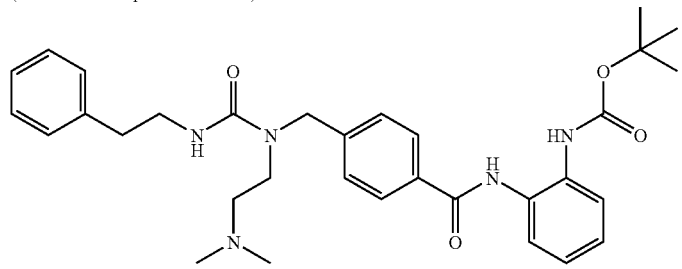

$^1$H-NMR (500 MHz, DMSO-d$_6$)
δ 1.44 (s, 9H), 2.07 (s, 6H), 2.27 (t, J = 6.3 Hz, 2H), 2.74 (t, J = 7.2 Hz, 2H), 3.18 (m, 2H), 3.32 (m, 2H), 4.52 (s, 2H), 6.90 (br s, 1H), 7.16 (td, J = 7.6, 1.5 Hz, 1H), 7.18-7.22 (m, 4H), 7.28 (d, J = 7.3 Hz, 2H), 7.33 (d, J = 8.2 Hz, 2H), 7.53 (dd, J = 7.6, 1.5 Hz, 1H), 7.90 (d, J = 8.2 Hz, 2H), 8.68 (s, 1H), 9.80 (s, 1H)

4-[3-Benzyl-1-(2-dimethylaminoethyl)ureidomethyl]-N-(2-t-butoxycarbonylaminophenyl)benzamide
(Reference Compound No. 13-6)

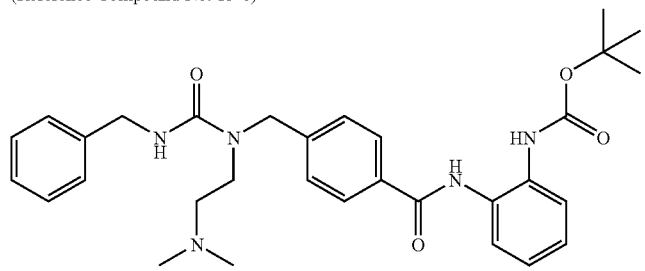

$^1$H-NMR (500 MHz, DMSO-d$_6$)
δ 1.44 (s, 9H), 2.10 (s, 6H), 2.34 (t, J = 6.4 Hz, 2H), 3.28 (t, J = 6.4 Hz, 2H), 4.27 (d, J = 5.5 Hz, 2H), 4.58 (s, 2H), 7.16 (td, J = 7.3, 1.5 Hz, 1H), 7.18-7.25 (m, 4H), 7.30 (d, J = 7.3 Hz, 2H), 7.38 (d, J = 7.9 Hz, 2H), 7.43 (br s, 1H), 7.52-7.55 (m, 2H), 7.92 (d, J = 7.9 Hz, 2H), 8.67 (s, 1H), 9.81 (s, 1H)

N-(2-t-Butoxycarbonylaminophenyl)-4-[3-cyclopentyl-1-(2-dimethylaminoethyl)ureidomethyl]benzamide
(Reference Compound No. 13-7)

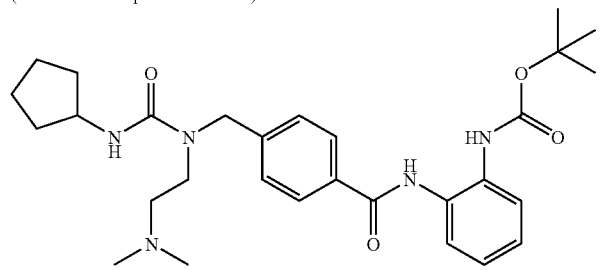

$^1$H-NMR (400 MHz, DMSO-d$_6$)
δ 1.38 (m, 2H), 1.51 (s, 9H), 1.54-1.63 (m, 4H), 1.95 (m, 2H), 2.23 (s, 6H), 2.35 (t, J = 4.6 Hz, 2H), 3.18 (t, J = 4.6 Hz, 2H), 4.08 (m, 1H), 4.56 (s, 2H), 6.85 (br s, 1H), 7.15-7.31 (m, 3H), 7.36 (d, J = 8.2 Hz, 2H), 7.78 (d, J = 7.3 Hz, 1H), 7.78 (m, 1H), 7.90 (d, J =8.2 Hz, 2H), 9.13 (s, 1H)

4-[3-(Benzo[1,3]dioxol-5-yl)-1-(2-dimethylaminoethyl)ureidomethyl]-N-(2-t-butoxycarbonylaminophenyl)benzamide
(Reference Compound No. 13-8)

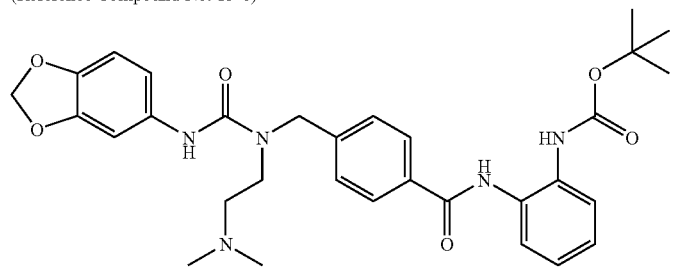

$^1$H-NMR (400 MHz, CDCl$_3$)
δ 1.51 (s, 9H), 2.36 (s, 6H), 2.45 (t, J = 4.2 Hz, 2H), 3.31 (m, 2H), 4.63 (s, 2H), 5.91 (s, 2H), 6.65 (dd, J = 8.3, 2.1 Hz, 1H), 6.72 (d, J = 8.3 Hz, 1H), 6.80 (s, 1H), 7.10 (d, J = 2.1 Hz, 1H), 7.15-7.28 (m, 3H), 7.41 (d, J = 8.3 Hz, 2H), 7.80 (d, J = 7.1 Hz, 1H), 7.92 (d, J = 8.3 Hz, 2H), 9.14 (s, 1H), 10.84 (s, 1H)

| | |
|---|---|
| N-(2-t-Butoxycarbonylaminophenyl)-4-[1-(2-dimethylaminoethyl)-3-(5,6,7,8-tetrahydronaphthalen-1-yl)ureidomethyl]benzamide (Reference Compound No. 13-9)<br>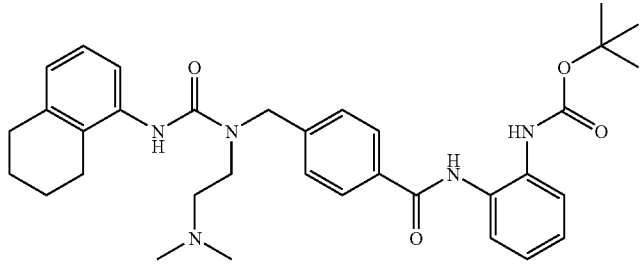 | $^1$H-NMR (400 MHz, DMSO-$d_6$)<br>δ 1.44 (m, 2H), 1.45 (s, 9H), 1.70-1.71 (m, 4H), 2.22 (s, 6H), 2.46 (t, J = 5.4 Hz, 2H), 2.72 (m, 2H), 3.38 (t, J = 5.4 Hz, 2H), 4.62 (s, 2H), 6.81 (d, J = 7.4 Hz, 1H), 7.02 (t, J = 7.4 Hz, 1H), 7.10 (d, J = 7.4 Hz, 1H), 7.16 (td, J = 7.6, 1.7 Hz, 1H), 7.20 (td, J = 7.6, 1.7 Hz, 1H), 7.46 (d, J = 8.2 Hz, 2H), 7.52 (dd, J = 7.6, 1.7 Hz, 1H), 7.56 (dd, J = 7.6, 1.7 Hz, 1H), 7.95 (d, J = 8.2 Hz, 2H), 8.70 (s, 1H), 8.89 (s, 1H), 9.82 (s, 1H) |
| N-(2-t-Butoxycarbonylaminophenyl)-4-[1-(2-hydroxyethyl)-3-phenylureidomethyl]benzamide (Reference Compound No. 13-10)<br>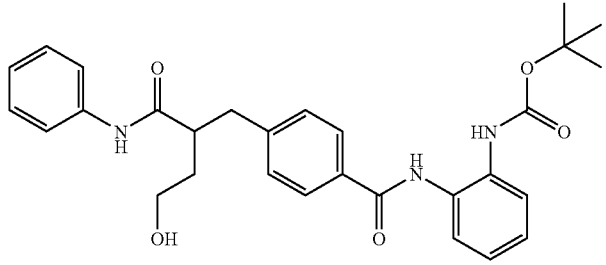 | $^1$H-NMR (400 MHz, CDCl$_3$)<br>δ 1.28 (m, 1H), 1.49 (s, 9H), 3.48 (br s, 2H), 3.64 (br s, 2H), 4.53 (s, 2H), 6.99 (t, J = 7.1 Hz, 1H), 7.08 (s, 1H), 7.18-7.23 (m, 2H), 7.24-7.30 (m, 7H), 7.37 (m, 1H), 7.74 (d, J = 7.6 Hz, 2H), 8.55 (br s, 1H), 9.28 (br s, 1H) |
| 4-[3-(Benzo[1,3]dioxol-5-yl)-1-(2-hydroxyethyl)ureidomethyl]-N-(2-t-butoxycarbonylaminophenyl)benzamide (Reference Compound No. 13-11)<br>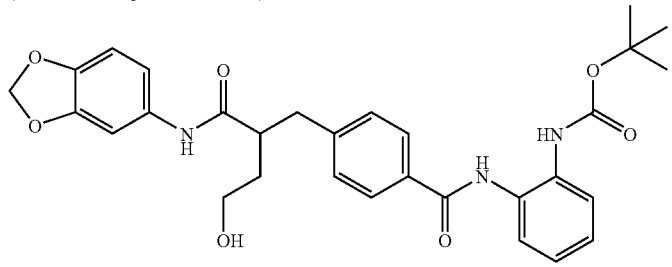 | $^1$H-NMR (400 MHz, CDCl$_3$)<br>δ 1.30 (t, J = 5.1 Hz, 1H), 1.49 (s, 9H), 3.43-3.49 (m, 2H), 3.66 (br s, 2H), 4.55 (s, 2H), 5.89 (s, 2H), 6.57 (dd, J = 8.3, 2.2 Hz, 1H), 6.65 (d, J = 8.3 Hz, 1H), 6.96 (s, 1H), 7.12 (s, 1H), 7.16-7.23 (m, 2H), 7.29 (d, J = 7.8 Hz, 2H), 7.38 (m, 1H), 7.70 (d, J = 5.9 Hz, 1H), 7.76 (d, J = 7.8 Hz, 2H), 8.38 (br s, 1H), 9.30 (br s, 1H) |
| N-(2-t-Butoxycarbonylaminophenyl)-4-[1-(2-methoxyethyl)-3-phenylureidomethyl]benzamide (Reference Compound No. 13-12)<br>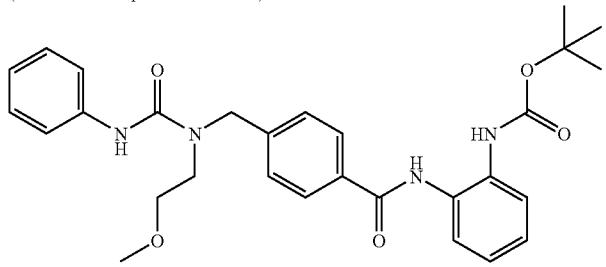 | $^1$H-NMR (400 MHz, CDCl$_3$)<br>δ 1.51 (s, 9H), 3.46 (s, 3H), 3.50 (s, 4H), 4.68 (s, 2H), 6.71 (br s, 1H), 7.00 (m, 1H), 7.18 (td, J = 7.7, 1.5 Hz, 1H), 7.23-7.31 (m, 4H), 7.36 (dd, J = 8.5, 1.2 Hz, 2H), 7.44 (d, J = 8.2 Hz, 2H), 7.83 (d, J = 7.7 Hz, 1H), 7.94 (d, J = 8.2 Hz, 2H), 8.33 (br s, 1H), 9.12 (br s, 1H) |

| | |
|---|---|
| N-(2-t-Butoxycarbonylaminophenyl)-4-[3-(indan-5-yl)-1-(2-methoxymethyl)ureidomethyl]benzamide (Reference Compound No. 13-13)<br />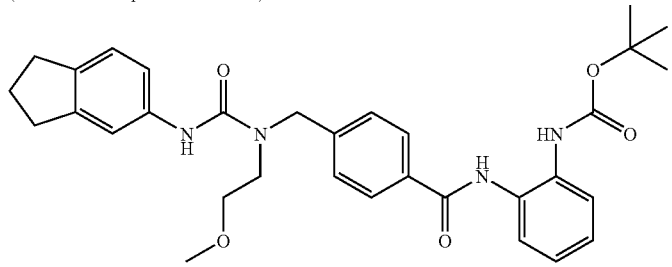 | $^1$H-NMR (400 MHz, CDCl$_3$)<br />δ 1.51 (s, 9H), 2.06 (m, 2H), 2.83-2.90 (m, 4H), 3.45 (s, 3H), 3.49 (s, 4H), 4.67 (s, 2H), 6.70 (br s, 1H), 7.01 (dd, J = 8.2, 1.8 Hz, 1H), 7.12 (d, J = 8.2 Hz, 1H), 7.18 (td, J = 7.8, 1.5 Hz, 1H), 7.23-7.34 (m, 3H), 7.44 (d, J = 8.3 Hz, 2H), 7.82 (d, J = 7.8 Hz, 1H), 7.93 (d, J = 8.3 Hz, 2H), 8.17 (br s, 1H), 9.10 (br s, 1H) |
| 4-[3-Benzo[1,3]dioxol-5-yl)-1-(2-methoxyethyl)ureidomethyl]-N-(2-t-butoxycarbonylaminophenyl)benzamide (Reference Compound No. 13-14)<br />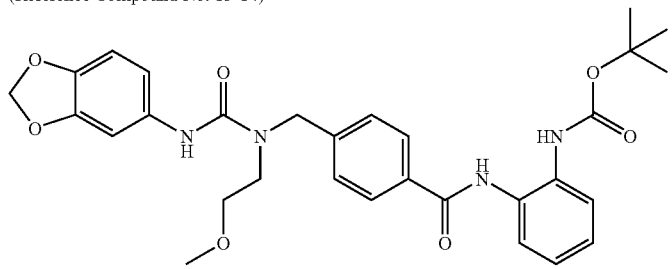 | $^1$H-NMR (400 MHz, CDCl$_3$)<br />δ 1.51 (s, 9H), 3.44 (s, 3H), 3.48 (s, 4H), 4.66 (s, 2H), 5.92 (s, 2H), 6.63 (dd, J = 8.3, 2.2 Hz, 1H), 6.71 (br s, 1H), 6.72 (d, J = 8.3 Hz, 1H), 7.08 (d, J = 2.2 Hz, 1H), 7.18 (td, J = 7.6, 1.5 Hz, 1H), 7.22-7.29 (m, 2H), 7.43 (d, J = 8.4 Hz, 2H), 7.82 (d, J = 7.6 Hz, 1H), 7.94 (d, J = 8.4 Hz, 2H), 8.17 (br s, 1H), 9.11 (br s, 1H) |
| N-(2-t-Butoxycarbonylaminophenyl)-4-[1-(3-hydroxypropyl)-3-(indan-5-yl)ureidomethyl]benzamide (Reference Compound No. 13-15)<br />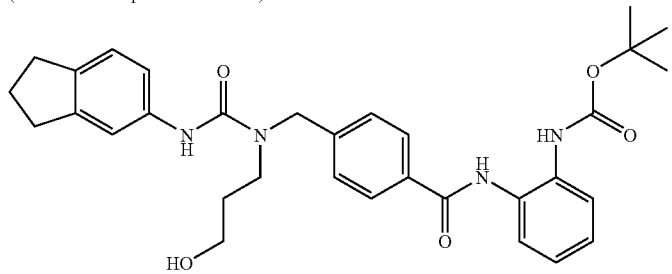 | $^1$H-NMR (400 MHz, CDCl$_3$)<br />δ 1.50 (s, 9H), 1.73 (m, 2H), 2.03 (m, 2H), 2.76-2.87 (m, 4H), 3.01 (br s, 1H), 3.53 (t, J = 5.7 Hz, 2H), 3.70 (t, J = 5.1 Hz, 2H), 4.60 (s, 2H), 6.87 (s, 1H), 7.00 (d, J =7.8 Hz, 1H), 7.08 (d, J = 8.0 Hz, 1H), 7.17-7.28 (m, 5H), 7.39 (d, J = 8.2 Hz, 2H), 7.78 (d, J = 7.8 Hz, 1H), 7.93 (d, J = 8.2 Hz, 2H), 9.23 (s, 1H) |
| N-(2-t-Butoxycarbonylaminophenyl)-4-[1-(3-dimethylaminopropyl)-3-(indan-5-yl)ureidomethyl]benzamide (Reference Compound No. 13-16)<br />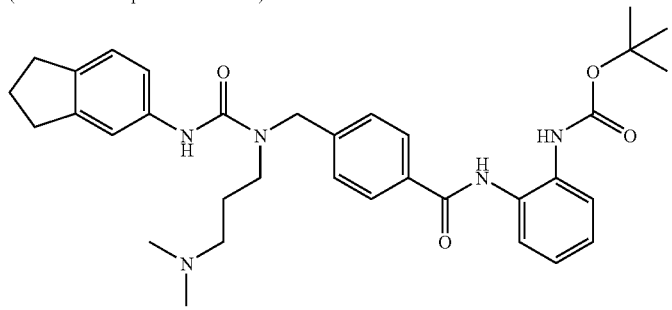 | $^1$H-NMR (400 MHz, CDCl$_3$)<br />δ 1.51 (s, 9H), 1.68 (br s, 2H), 2.05 (m, 2H), 2.30 (s, 6H), 2.38 (br s, 2H), 2.81-2.90 (m, 4H), 3.38 (t, J = 5.5 Hz, 2H), 4.62 (s, 2H), 6.78 (s, 1H), 7.04 (dd, J = 8.1, 2.0 Hz, 1H), 7.11 (d, J = 8.1 Hz, 1H), 7.15-7.28 (m, 2H), 7.43 (d, J = 8.3 Hz, 2H), 7.49 (s, 1H), 7.53 (m, 1H), 7.78 (d, J = 7.8 Hz, 1H), 7.91 (s, J = 8.3 Hz, 2H), 9.06 (s, 1H), 9.89 (s, 1H) |

-continued

| | |
|---|---|
| 4-[1-(2-t-Butoxycarbonylaminoethyl)-3-phenylureidomethyl]-N-(2-t-butoxycarbonylaminophenyl)-benzamide (Reference Compound No. 13-17)<br>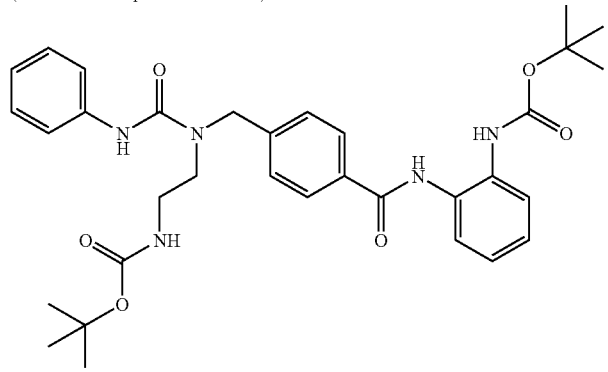 | $^1$H-NMR (400 MHz, CDCl$_3$)<br>δ 1.46 (s, 9H), 1.50 (s, 9H), 3.12 (m, 2H), 3.43 (t, J = 7.4 Hz, 2H), 4.67 (s, 2H), 4.89 (t, J = 5.9 Hz, 1H), 6.79 (br s, 1H), 7.02 (m, 1H), 7.17 (td, J = 7.8, 1.6 Hz, 1H), 7.22-7.32 (m, 4H), 7.40 (d, J = 8.3 Hz, 2H), 7.63 (d, J = 7.8 Hz, 2H), 7.81 (d, J = 7.8 Hz, 1H), 7.93 (d, J = 8.3 Hz, 2H), 8.22 (br s, 1H), 9.20 (br s, 1H) |
| 4-[1-(2-t-Butoxycarbonylaminoethyl)-3-(indan-5-yl)ureidomethyl]-N-(2-t-butoxycarbonylaminophenyl)benzamide (Reference Compound No. 13-18)<br>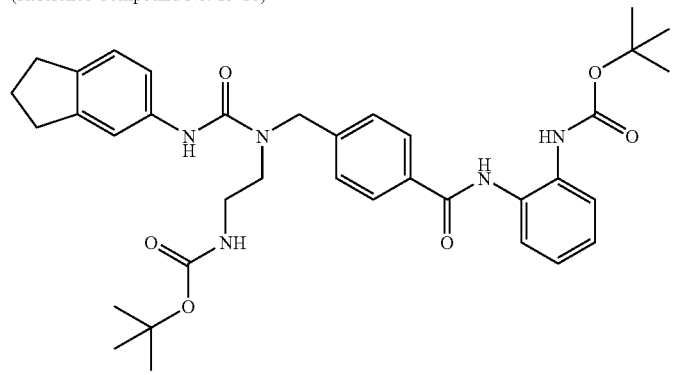 | $^1$H-NMR (400 MHz, CDCl$_3$)<br>δ 1.45 (s, 9H), 1.51 (s, 9H), 2.05 (m, 2H), 2.83-2.90 (m, 4H), 3.14 (m, 2H), 3.44 (t, J = 7.3 Hz, 2H), 4.67 (s, 2H), 4.88 (m, 1H), 6.73 (br s, 1H), 7.13 (d, J = 8.1 Hz, 1H), 7.18 (td, J = 7.4, 1.7 Hz, 1H), 7.22-7.29 (m, 3H), 7.41 (d, J = 8.1 Hz, 2H), 7.54 (br s, 1H), 7.82 (d, J = 7.4 Hz, 1H), 7.94 (d, J = 8.1 Hz, 2H), 7.94 (br s, 1H), 9.16 (br s, 1H) |
| 4-[1-(2-t-Butoxycarbonylaminoethyl)-3-(4-dimethylaminophenyl)ureidomethyl]-N-(2-t-butoxycarbonylaminophenyl)benzamide (Reference Compound No. 13-19)<br>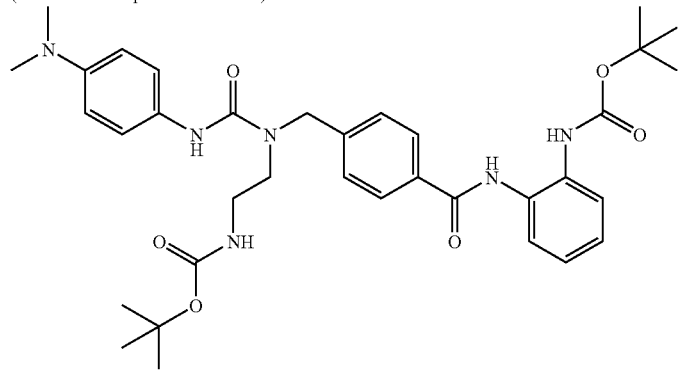 | $^1$H-NMR (400 MHz, CDCl$_3$)<br>δ 1.45 (s, 9H), 1.50 (s, 9H), 2.89 (s, 6H), 3.14 (m, 2H), 3.43 (t, J = 7.2 Hz, 2H), 4.66 (s, 2H), 4.91 (m, 1H), 6.72 (d, J = 9.0 Hz, 2H), 6.79 (s, 1H), 7.17 (td, J = 7.7, 1.5 Hz, 1H), 7.21-7.29 (m, 2H), 7.36-7.49 (m, 4H), 7.73 (br s, 1H), 7.80 (d, J = 7.7 Hz, 1H), 7.93 (d, J = 8.1 Hz, 2H), 9.17 (br s, 1H) |

N-(2-t-Butoxycarbonylaminophenyl)-4-[1-[2-(N'-t-butoxycarbonyl-N'-methylamino)ethyl]-3-(indan-5-yl)ureidomethyl]benzamide
(Reference Compound No. 13-20)

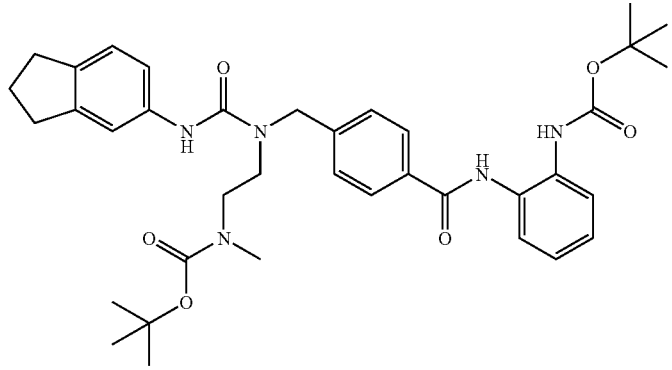

$^1$H-NMR (500 MHz, CDCl$_3$)
δ 1.47 (s, 9H), 1.51 (s, 9H), 2.05 (m, 2H), 2.80-2.92 (m, 7H), 3.21 (br s, 2H), 3.43 (br s, 2H), 4.68 (s, 2H), 6.71 (s, 1H), 7.13 (d, J = 7.9 Hz, 1H), 7.18 (td, J = 7.2, 1.6 Hz, 1H), 7.23-7.36 (m, 3H), 7.42 (d, J = 7.8 Hz, 2H), 7.62 (br s, 1H), 7.83 (d, J = 7.2 Hz, 1H), 7.94 (d, J = 7.8 Hz, 2H), 8.38 (br s, 1H), 9.12 (br s, 1H)

N-(2-t-Butoxycarbonylaminophenyl)-4-[1-[2-(N'-t-butoxycarbonyl-N'-methylamino)ethyl]-3-cyclopentylureidomethyl]benzamide
(Reference Compound No. 13-21)

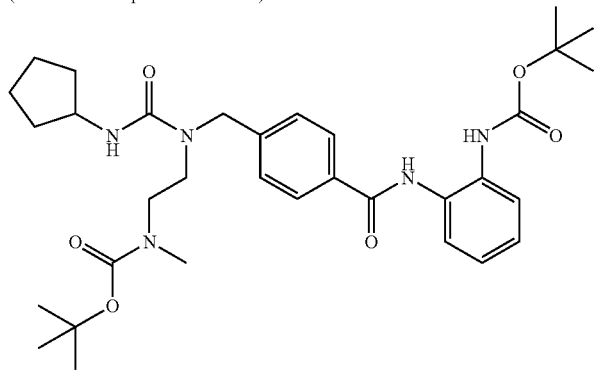

$^1$H-NMR (400 MHz, CDCl$_3$)
δ 1.45 (s, 9H), 1.47-2.00 (m, 8H), 1.52 (s, 9H), 2.81 (s, 3H), 3.14 (m, 2H), 3.27 (m, 2H), 4.14 (m, 1H), 4.58 (s, 2H), 6.10 (br s, 1H), 6.75 (s, 1H), 7.18 (td, J = 7.2, 1.5 Hz, 1H), 7.23-7.28 (m, 2H), 7.35 (d, J = 7.8 Hz, 2H), 7.82 (d, J = 7.2 Hz, 1H), 7.92 (d, J = 7.8 Hz, 2H), 9.14 (br s, 1H)

N-(2-t-Butoxycarbonylaminophenyl)-4-[1-[2-(N'-butoxycarbonyl-N'-methylamino)ethyl]-3-(2,3-dihydroxybenzo[1,4]dioxin-6-yl)ureidomethyl]benzamide
(Reference Compound No. 13-22)

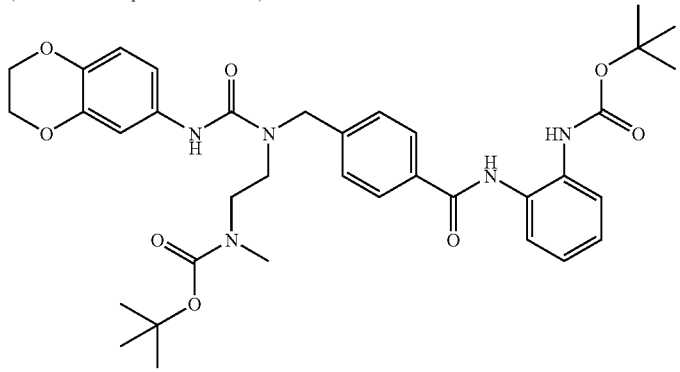

$^1$H-NMR (400 MHz, CDCl$_3$)
δ 1.47 (s, 9H), 1.51 (s, 9H), 2.84 (s, 3H), 3.18 (br s, 2H), 3.40 (br s, 2H), 4.20-4.25 (m, 4H), 4.67 (s, 2H), 6.74 (s, 1H), 6.78 (d, J = 8.8 Hz, 1H), 7.10 (m, 1H), 7.18 (td, J = 7.7, 1.7 Hz, 1H), 7.22-7.31 (m, 3H), 7.40 (d, J = 8.3 Hz, 2H), 7.82 (d, J = 7.7 Hz, 1H), 7.93 (d, J = 8.3 Hz, 2H), 8.39 (br s, 1H), 9.14 (br s, 1H)

| | |
|---|---|
| N-(2-t-Butoxycarbonylaminophenyl)-4-[1-(2-diethylaminoethyl)-3-(indan-5-yl)ureidomethyl]benzamide<br>(Reference Compound No. 13-23)<br>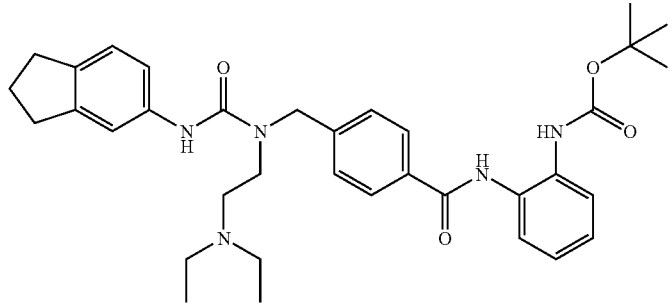 | $^1$H-NMR (400 MHz, CDCl$_3$)<br>δ 1.07 (t, J = 7.2 Hz, 6H), 1.51 (s, 9H), 2.05 (m, 2H), 2.51 (t, J = 4.0 Hz, 2H), 2.60-2.66 (m, 4H), 2.85 (m, 4H), 3.34 (t, J = 4.0 Hz, 2H), 4.65 (s, 2H), 6.74 (s, 1H), 6.98 (dd, J = 8.2, 2.0 Hz, 1H), 7.11 (d, J = 8.2 Hz, 1H), 7.19 (dd, J = 7.8, 1.6 Hz, 1H), 7.24 (dd, J = 7.8, 1.6 Hz, 1H), 7.28 (m, 1H), 7.39 (s, 1H), 7.44 (d, J = 8.1 Hz, 2H), 7.81 (s, J = 8.3 Hz, 1H), 7.92 (d, J = 8.1 Hz, 2H), 9.09 (s, 1H), 10.76 (s, 1H) |
| N-(2-t-Butoxycarbonylaminophenyl)-4-[1-(3-dimethylamino2,2-dimethylpropyl)-3-(indan-5-yl)ureidomethyl]benzamide<br>(Reference Compound No. 13-24)<br>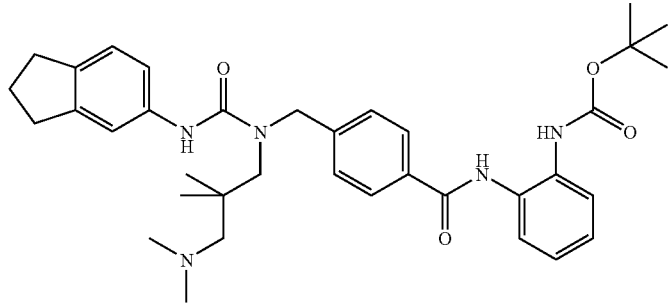 | $^1$H-NMR (400 MHz, CDCl$_3$)<br>δ 1.03 (s, 6H), 1.50 (s, 9H), 2.04 (m, 2H), 2.29 (s, 2H), 2.36 (s, 6H), 2.81- 2.91 (m, 4H), 3.23 (s, 2H), 4.73 (s, 2H), 6.77 (s, 1H), 7.06 (dd, J = 7.9, 2.0 Hz, 1H), 7.11 (d, J = 7.9 Hz, 1H), 7.16-7.25 (m, 2H), 7.30 (dd, J = 7.8, 1.7 Hz, 1H), 7.37 (d, J = 8.2 Hz, 2H), 7.53 (s, 1H), 7.76 (d, J = 7.1 Hz, 1H), 7.90 (d, J = 8.2 Hz, 2H), 8.98 (s, 1H), 10.39 (s, 1H) |
| N-(2-t-Butoxycarbonylaminophenyl)-4-[1-[2-(2-hydroxyethoxy)ethyl]-3-(indan-5-yl)ureidomethyl]benzamide<br>(Reference Compound No. 13-25)<br>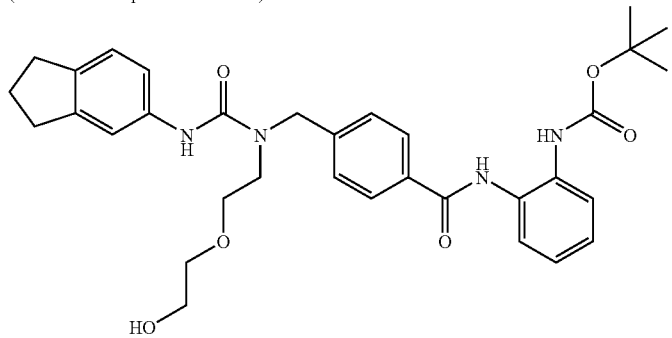 | $^1$H-NMR (400 MHz, CDCl$_3$)<br>δ 1.51 (s, 9H), 1.88 (br s, 1H), 2.05 (m, 2H), 2.81-2.88 (m, 4H), 3.53 (m, 2H), 3.59-3.66 (m, 4H), 3.81 (m, 2H), 4.67 (s, 2H), 6.81 (s, 1H), 7.01 (dd, J = 8.0, 2.1 Hz, 1H), 7.11 (d, J = 8.0 Hz, 1H), 7.17-7.28 (m, 3H), 7.36 (s, 1H), 7.42 (d, J = 8.3 Hz, 2H), 7.79 (d, J = 8.0 Hz, 1H), 7.92 (d, J = 8.3 Hz, 2H), 7.92 (s, 1H), 9.13 (s, 1H) |
| N-(2-t-Butoxycarbonylaminophenyl)-4-[3-(2,3-dihydroxobenzo[1,4]dioxin-6-yl)-1-(3-di-methylaminopropyl)ureidomethyl]benzamide<br>(Reference Compound No. 13-26)<br>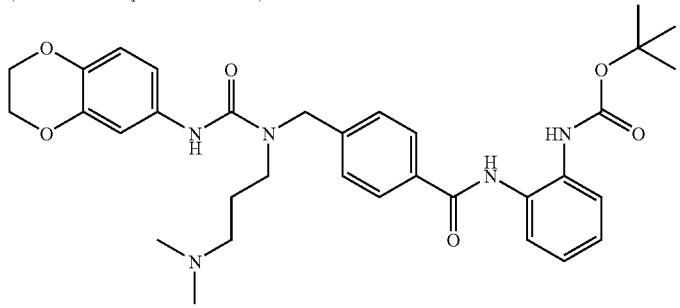 | $^1$H-NMR (400 MHz, CDCl$_3$)<br>δ 1.51 (s, 9H), 1.67 (m, 2H), 2.28 (s, 6H), 2.34 (t, J = 6.1 Hz, 2H), 3.35 (t, J = 5.5 Hz, 2H), 4.21-4.25 (m, 4H), 4.61 (s, 2H), 6.72 (s, 1H), 6.76 (d, J = 8.8 Hz, 1H), 6.89 (dd, J = 8.8, 2.7 Hz, 1H), 7.05 (d, J = 2.7 Hz, 1H), 7.19 (dd, J = 7.6, 1.7 Hz, 1H), 7.23-7.29 (m, 2H), 7.43 (d, J = 8.3 Hz, 2H), 7.79 (d, J = 7.1 Hz, 1H), 7.90 (d, J = 8.3 Hz, 2H), 9.01 (s, 1H), 9.90 (s, 1H) |

-continued

N-(2-t-Butoxycarbonylaminophenyl)-4-[1-(3-dimethylaminopropyl)-3-phenethylureidomethyl]benzamide
(Reference Compound No. 13-27)

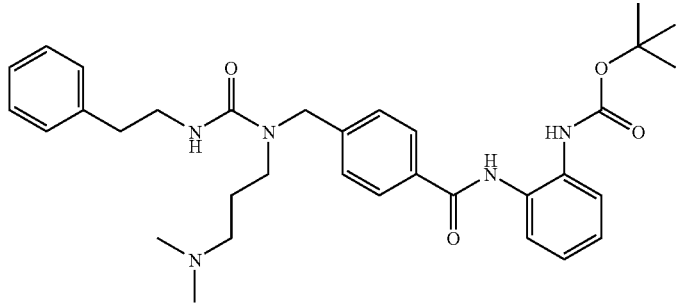

$^1$H-NMR (400 MHz, CDCl$_3$)
δ 1.51 (s, 9H), 1.67 (br s, 2H), 2.16 (s, 6H), 2.29 (br s, 2H), 2.82 (t, J = 7.1 Hz, 2H), 3.21 (br s, 2H), 3.50 (m, 2H), 4.53 (s, 2H), 6.84 (s, 1H), 7.13-7.33 (m, 10H), 7.79 (d, J = 8.1 Hz, 1H), 7.90 (d, J = 8.3 Hz, 2H), 8.00 (m, 1H), 9.11 (s, 1H)

N-(2-t-Butoxycarbonylaminophenyl)-4-[3-(indan-5-yl)-1-[3-(morpholin-4-yl)propyl]ureidomethyl]benzamide
(Reference Compound No. 13-28)

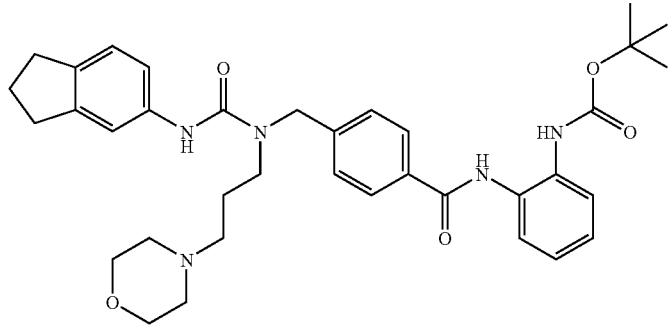

$^1$H-NMR (400 MHz, CDCl$_3$)
δ 1.50 (s, 9H), 1.73 (m, 2H), 2.06 (m, 2H), 2.41-2.48 (m, 6H), 2.84-2.91 (m, 4H), 3.37 (t, J = 5.7 Hz, 2H), 3.68 (t, J = 4.6 Hz, 4H), 4.64 (s, 2H), 6.76 (br s, 1H), 7.07 (dd, J = 8.1, 2.0 Hz, 1H), 7.14 (d, J = 8.1 Hz, 1H), 7.18 (td, J = 7.7, 1.5 Hz, 1H), 7.21-7.33 (m, 2H), 7.39 (s, 1H), 7.43 (d, J = 8.3 Hz, 2H), 7.79 (d, J = 7.7 Hz, 1H), 7.91 (d, J = 8.3 Hz, 2H), 8.65 (br s, 1H), 9.08 (br s, 1H)

N-(2-t-Butoxycarbonylaminophenyl)-4-[3-cyclopentyl-1-[3-(morpholin-4-yl)propyl]ureidomethyl]benzamide
(Reference Compound No. 13-29)

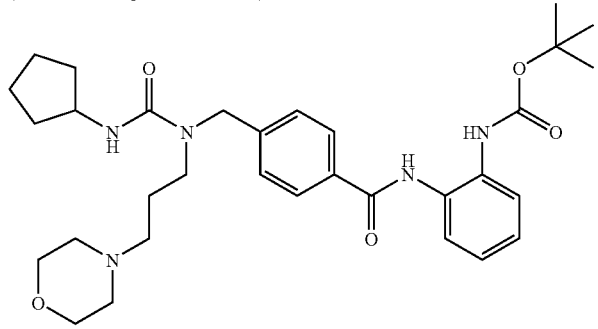

$^1$H-NMR (400 MHz, CDCl$_3$)
δ 1.32 (m, 2H), 1.51 (s, 9H), 1.55-1.72 (m, 6H), 2.04 (m, 2H), 2.35 (t, J = 6.3 Hz, 2H), 2.43 (br s, 4H), 3.23 (t, J = 6.3 Hz, 2H), 3.73 (t, J = 4.8 Hz, 4H), 4.11 (m, 1H), 4.55 (s, 2H), 5.59 (d, J = 7.3 Hz, 1H), 6.83 (br s, 1H), 7.17 (td, J = 7.7, 1.7 Hz, 1H), 7.21-7.30 (m, 2H), 7.36 (d, J = 8.3 Hz, 2H), 7.80 (d, J = 7.7 Hz, 1H), 7.91 (d, J = 8.3 Hz, 2H), 9.14 (br s, 1H)

N-(2-t-Butoxycarbonylaminophenyl)-4-[3-(4-dimethylaminophenyl)-1-[3-(morpholin-4-yl)propyl]ureidomethyl]benzamide
(Reference Compound No. 13-30)

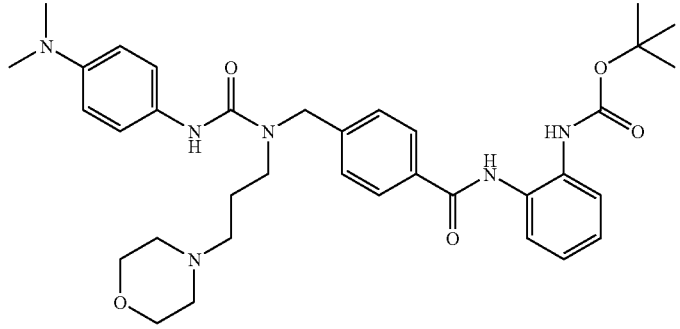

$^1$H-NMR (400 MHz, CDCl$_3$)
δ 1.50 (s, 9H), 1.71 (m, 2H), 2.38-2.48 (m, 6H), 2.91 (s, 6H), 3.36 (t, J = 5.6 Hz, 2H), 3.63 (t, J = 4.5 Hz, 4H), 4.63 (s, 2H), 6.71 (d, J = 8.9 Hz, 2H), 6.77 (br s, 1H), 7.18 (td, J = 7.8, 1.7 Hz, 1H), 7.22-7.30 (m, 2H), 7.25 (d, J = 8.9 Hz, 2H), 7.44 (d, J = 8.3 Hz, 2H), 7.78 (d, J = 7.8 Hz, 1H), 7.91 (d, J = 8.3 Hz, 2H), 8.70 (br s, 1H), 9.06 (br s, 1H)

| | |
|---|---|
| N-(2-t-Butoxycarbonylaminophenyl)-4-[1-(1-t-butoxycarbonylpiperidin-4-ylmethyl)-3-(indan-5-yl)ureidomethyl]benzamide (Reference Compound No. 13-31)<br>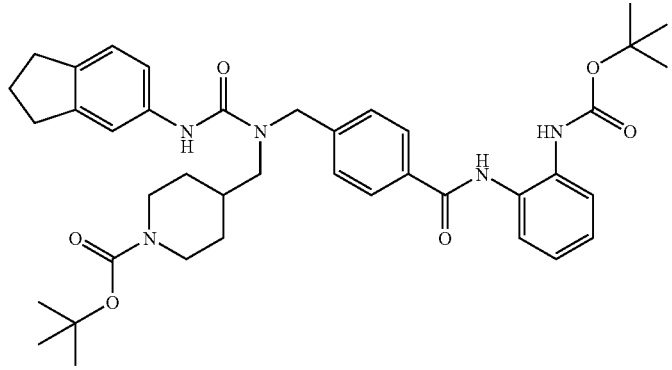 | $^1$H-NMR (400 MHz, CDCl$_3$)<br>δ 1.20 (m, 2H), 1.45 (s, 9H), 1.50 (s, 9H), 1.73 (m, 2H), 1.92 (m, 1H), 2.04 (m, 2H), 2.69 (t, J = 11.2 Hz, 2H), 2.83 (t, J = 7.4 Hz, 2H), 2.86 (t, J = 7.4 Hz, 2H), 3.29 (br s, 2H), 4.14 (br s, 2H), 4.65 (s, 2H), 6.21 (s, 1H), 6.75 (s, 1H), 6.91 (dd, J = 8.1, 2.0 Hz, 1H), 7.09 (d, J = 8.1 Hz, 1H), 7.17 (m, 1H), 7.21-7.28 (m, 3H), 7.38 (d, J = 8.3 Hz, 2H), 7.83 (d, J = 7.8 Hz, 1H), 7.97 (d, J = 8.3 Hz, 2H), 9.25 (br s, 1H) |
| N-(2-t-Butoxycarbonylaminophenyl)-4-[1-(1-t-butoxycarbonylpiperidin-4-ylmethyl)-4-cyclopentylureidomethyl]benzamide (Reference Compound No. 13-32)<br>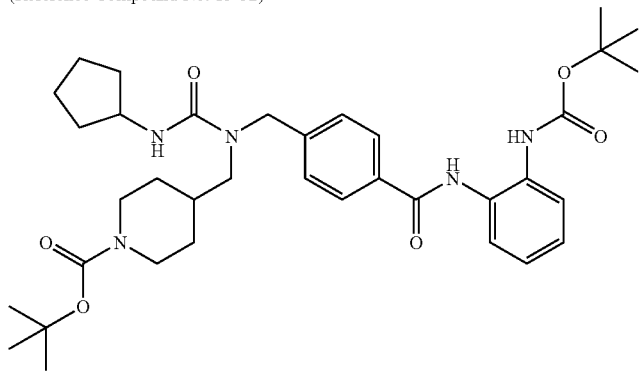 | $^1$H-NMR (400 MHz, CDCl$_3$)<br>δ 1.10-1.29 (m, 4H), 1.45 (s, 9H), 1.49-1.60 (m, 4H), 1.52 (s, 9H), 1.67 (m, 2H), 1.82 (m, 1H), 1.94 (m, 2H), 2.67 (t, J = 11.6 Hz, 2H), 3.17 (br s, 2H), 4.04-4.22 (m, 4H), 4.52 (s, 2H), 6.74 (br s, 1H), 7.18 (td, J = 8.1, 1.5 Hz, 1H), 7.22-7.28 (m, 2H), 7.31 (d, J = 8.3 Hz, 2H), 7.85 (d, J = 8.1 Hz, 1H), 7.95 (d, J = 8.3 Hz, 2H), 9.23 (br s, 1H) |
| N-(2-t-Butoxycarbonylaminophenyl)-4-[1-(1-t-butoxycarbonylpiperidin-4-ylmethyl)-3-(4-chlorophenyl)ureidomethyl]benzamide (Reference Compound No. 13-33)<br>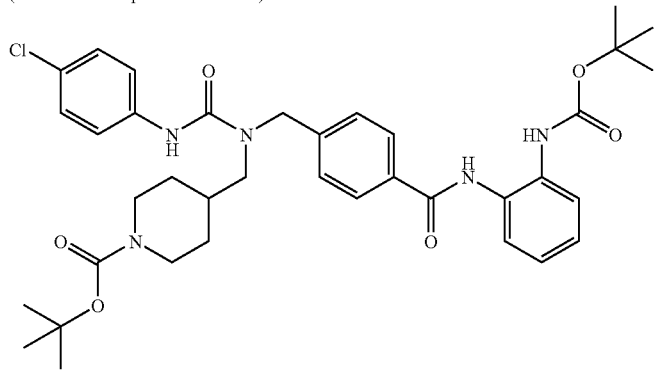 | $^1$H-NMR (400 MHz, CDCl$_3$)<br>δ 1.22 (m, 2H), 1.46 (s, 9H), 1.49 (s, 9H), 1.73 (m, 2H), 1.92 (m, 1H), 2.69 (t, J = 11.2 Hz, 2H), 3.30 (br s, 2H), 4.14 (br s, 2H), 4.65 (s, 2H), 6.29 (s, 1H), 6.72 (s, 1H), 7.16-7.28 (m, 7H), 7.37 (d, J = 8.3 Hz, 2H), 7.84 (d, J = 7.8 Hz, 1H), 7.98 (d, J = 8.3 Hz, 2H), 9.30 (br s, 1H) |

| | |
|---|---|
| N-(2-t-Butoxycarbonylaminophenyl)-4-[1-(3-dimethylamino2,2-dimethylpropyl)-3-(4-nitrophenyl)ureidomethyl]benzamide<br>(Reference Compound No. 13-34)<br>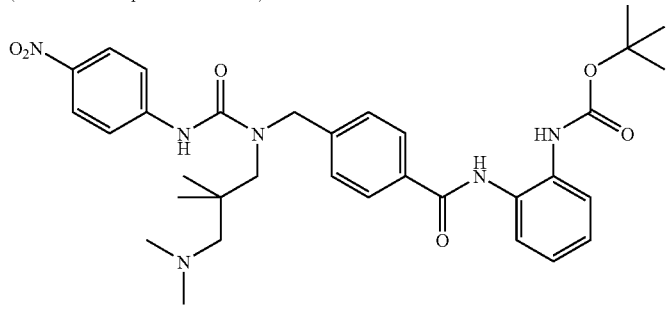 | $^1$H-NMR (500 MHz, CDCl$_3$)<br>δ 1.07 (s, 6H), 1.51 (s, 9H), 2.36 (br s, 2H), 2.42 (s, 6H), 3.29 (br s, 2H), 4.76 (s, 2H), 6.70 (s, 1H), 7.19 (dd, J = 7.6, 7.3 Hz, 1H), 7.20-7.28 (m, 3H), 7.31 (d, J = 7.9 Hz, 1H), 7.37 (d, J = 7.9 Hz, 1H), 7.60 (d, J = 9.1 Hz, 1H), 7.85 (m, 1H), 7.94 (d, J = 8.2 Hz, 2H), 8.16 (d, J = 8.2 Hz, 2H), 9.16 (s, 1H), 11.47 (s, 1H) |
| N-(2-t-Butoxycarbonylaminophenyl)-4-[3-(3,4-dimethoxyphenyl)-1-(3-dimethylamino-2,2-dimethylpropyl)ureidomethyl]benzamide<br>(Reference Compound No. 13-35)<br>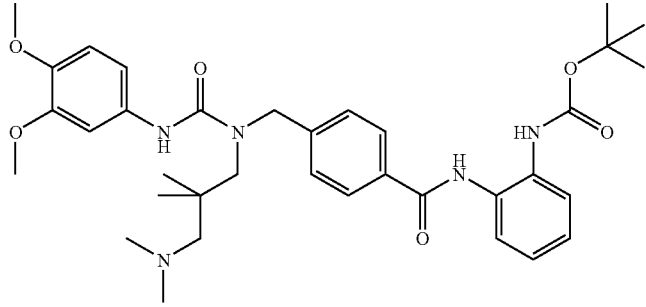 | $^1$H-NMR (500 MHz, CDCl$_3$)<br>δ 1.03 (s, 6H), 1.50 (s, 9H), 2.30 (br s, 2H), 2.37 (s, 6H), 3.24 (br s, 2H), 3.68 (s, 3H), 3.76 (s, 3H), 4.75 (s, 2H), 6.73 (s, 1H), 6.76-6.80 (m, 2H), 7.02 (m, 1H), 7.19 (ddd, J = 7.6, 7.6, 1.2 Hz, 1H), 7.22-7.26 (m, 2H), 7.31-7.34 (m, 2H), 7.80 (m, 1H), 7.92 (d, J = 8.2 Hz, 2H), 9.14 (s, 1H), 10.47 (s, 1H) |
| N-(2-t-Butoxycarbonylaminophenyl)-4-[1-(3-dimethylamino-2,2-dimethylpropyl)-3-(4-fluorophenyl)ureidomethyl]benz-amide<br>(Reference Compound No. 13-36)<br>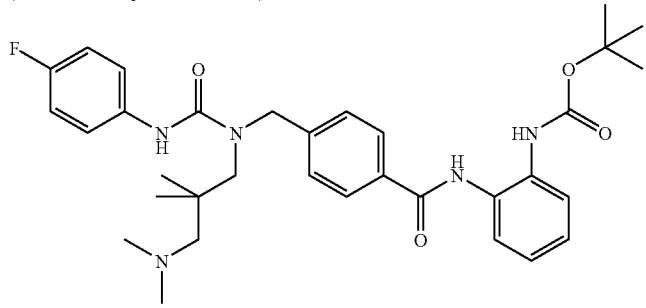 | $^1$H-NMR (500 MHz, CDCl$_3$)<br>δ 1.04 (s, 6H), 1.49 (s, 9H), 2.30 (s, 2H), 2.35 (s, 6H), 3.23 (s, 2H), 4.74 (s, 2H), 6.70 (s, 1H), 6.95-6.99 (m, 2H), 7.18 (ddd, J = 7.7, 7.4, 1.6 Hz, 1H), 7.23-7.29 (m, 2H), 7.37 (d, J = 8.1 Hz, 2H), 7.41-7.46 (m, 2H), 7.78 (d, J = 7.4 Hz, 1H), 7.91 (d, J = 8.1 Hz, 2H), 8.98 (s, 1H), 10.58 (s, 1H) |
| N-(2-t-Butoxycarbonylaminophenyl)-4-[3-(4-cyanomethylphenyl)-1-(3-dimethylamino-2,2-dimethylpropyl)ureidomethyl]benzamide<br>(Reference Compound No. 13-37)<br>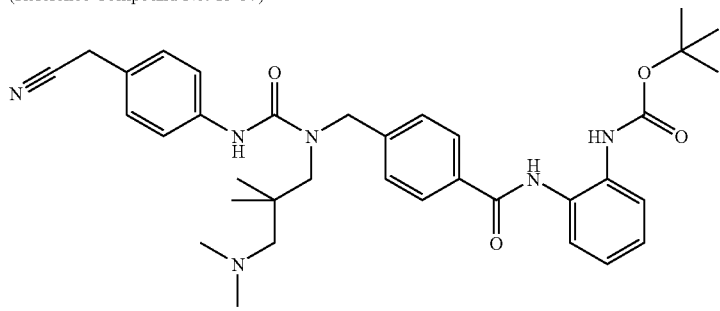 | $^1$H-NMR (500 MHz, CDCl$_3$)<br>δ 1.04 (s, 6H), 1.50 (s, 9H), 2.30 (s, 2H), 2.35 (s, 6H), 3.11 (s, 2H), 3.23 (s, 2H), 4.74 (s, 2H), 6.73 (s, 1H), 7.15-7.35 (m, 7H), 7.50 (d, J = 8.1 Hz, 2H), 7.78 (d, J = 7.4 Hz, 1H), 7.91 (d, J = 8.1 Hz, 2H), 8.99 (s, 1H), 10.73 (s, 1H) |

| | |
|---|---|
| N-(2-t-Butoxycarbonylaminophenyl)-4-[1-(3-t-butoxycarbonylaminopropyl)-3-(2,3-dihydrobenzo[1,4]dioxin-6-yl)ureidomethyl]benzamide (Reference Compound No. 13-38) 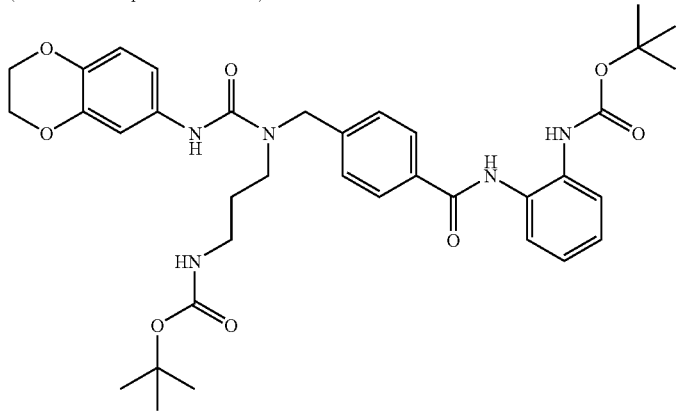 | $^1$H-NMR (500 MHz, CDCl$_3$) δ 1.44 (s, 9H), 1.51 (s, 9H), 1.77 (m, 2H), 3.18 (m, 2H), 3.48 (t, J = 6.6 Hz, 2H), 4.19-4.23 (m, 4H), 4.61 (s, 2H), 5.15 (br s, 1H), 6.55 (br s, 1H), 6.71 (dd, J = 8.6, 2.4 Hz, 1H), 6.71 (br s, 1H), 6.75 (d, J = 8.6 Hz, 1H), 6.94 (d, J = 2.4 Hz, 1H), 7.18 (t, J = 7.8 Hz, 1H), 7.22-7.29 (m, 2H), 7.39 (d, J = 8.1 Hz, 2H), 7.84 (d, J = 7.8 Hz, 1H), 7.97 (d, J = 8.1 Hz, 2H), 9.20 (br s, 1H) |
| N-(2-t-Butoxycarbonylaminophenyl)-4-[1-(3-t-butoxycarbonylaminopropyl)-3-(4-dimethylaminophenyl)ureidomethyl]benzamide (Reference Compound No. 13-39) 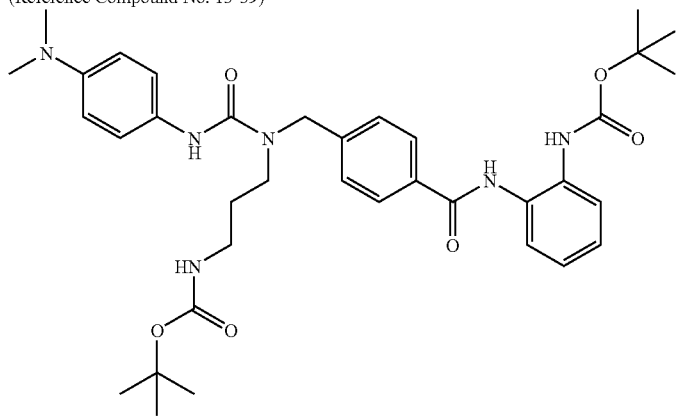 | $^1$H-NMR (500 MHz, CDCl$_3$) δ 1.44 (s, 9H), 1.51 (s, 9H), 1.77 (m, 2H), 2.89 (s, 6H), 3.18 (m, 2H), 3.49 (t, J = 6.6 Hz, 2H), 4.61 (s, 2H), 5.21 (br s, 1H), 6.36 (br s, 1H), 6.68 (d, J = 9.2 Hz, 2H), 6.72 (s, 1H), 7.13 (d, J = 9.2 Hz, 2H), 7.18 (t, J = 7.8 Hz, 1H), 7.23-7.30 (m, 2H), 7.40 (d, J = 8.2 Hz, 2H), 7.84 (d, J = 7.8 Hz, 1H), 7.97 (d, J = 8.2 Hz, 2H), 9.21 (br s, 1H) |
| N-(2-t-Butoxycarbonylaminophenyl)-4-[1-(3-t-butoxycarbonylaminopropyl)-3-phenethylureidomethyl]benzamide (Reference Compound No. 13-40) 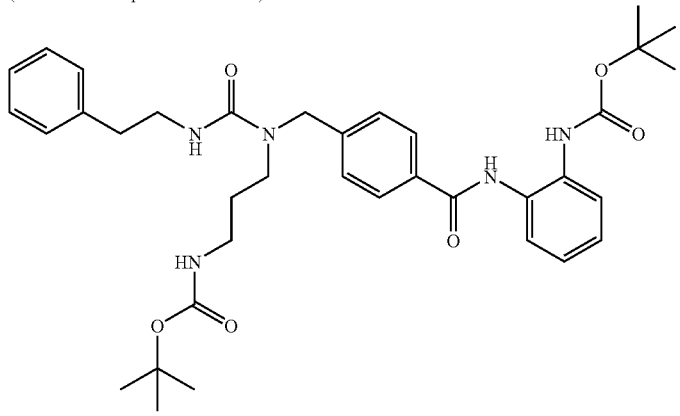 | $^1$H-NMR (500 MHz, CDCl$_3$) δ 1.44 (s, 9H), 1.52 (s, 9H), 1.63 (m, 2H), 2.78 (t, J = 6.7 Hz, 2H), 3.08 (m, 2H), 3.34 (t, J = 6.6 Hz, 2H), 3.49 (m, 2H), 4.40 (s, 2H), 4.44 (br s, 1H), 5.11 (br s, 1H), 6.76 (br s, 1H), 7.09 (d, J = 7.0 Hz, 2H), 7.17-7.28 (m, 8H), 7.84 (d, J = 7.9 Hz, 1H), 7.90 (d, J = 8.2 Hz, 2H), 9.19 (br s, 1H) |

| | |
|---|---|
| N-(2-t-Butoxycarbonylaminophenyl)-4-[3-(2,3-dihydrobenzo[1,4]dioxin-6-yl)-1-[3-(pyrrolidin-2-on-1-yl)propyl]ureidomethyl]benzamide (Reference Compound No. 13-41) 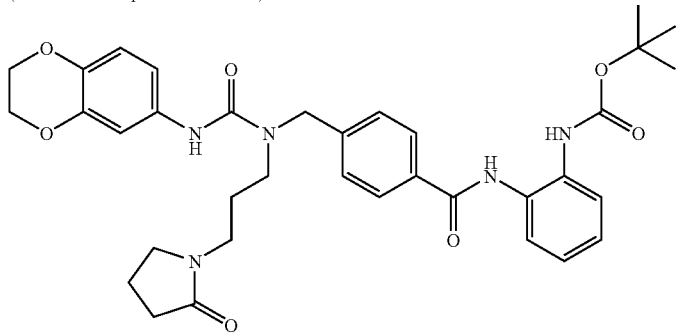 | $^1$H-NMR (500 MHz, CDCl$_3$) δ 1.51 (s, 9H), 1.83 (m, 2H), 2.03 (m, 2H), 2.40 (t, J = 8.2 Hz, 2H), 3.31 (t, J = 6.3 Hz, 2H), 3.37-3.41 (m, 4H), 4.19-4.23 (m, 4H), 4.64 (s, 2H), 6.75 (d, J = 8.7 Hz, 1H), 6.80 (br s, 1H), 6.83 (dd, J = 8.7, 2.4 Hz, 1H), 7.02 (d, J = 2.4 Hz, 1H), 7.18 (td, J = 7.6, 1.5 Hz, 1H), 7.20 (br s, 1H), 7.23-7.29 (m, 2H), 7.39 (d, J = 8.2 Hz, 2H), 7.81 (d, J = 7.6 Hz, 1H), 7.94 (d, J = 8.2 Hz, 2H), 9.17 (br s, 1H) |
| N-(2-t-Butoxycarbonylaminophenyl)-4-[3-(4-dimethylaminophenyl)-1-[3-(pyrrolidin-2-on-1-yl)propyl]ureidomethyl]benzamide (Reference Compound No. 13-42) 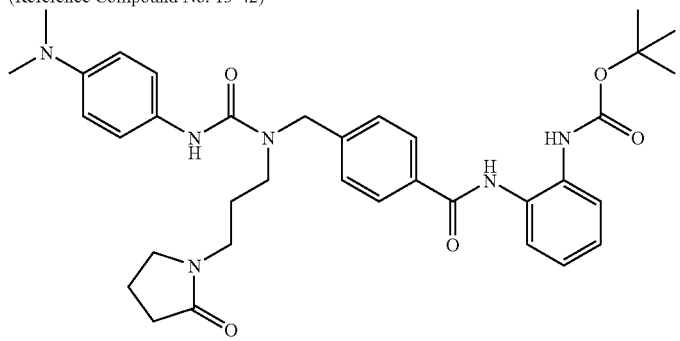 | $^1$H-NMR (400 MHz, CDCl$_3$) δ 1.51 (s, 9H), 1.85 (m, 2H), 2.03 (m, 2H), 2.39 (t, J = 8.2 Hz, 2H), 2.88 (s, 6H), 3.32 (t, J = 6.6 Hz, 2H), 3.37-3.42 (m, 4H), 4.65 (s, 2H), 6.69 (d, J = 9.0 Hz, 2H), 6.77 (br s, 1H), 6.84 (br s, 1H), 7.16-7.29 (m, 5H), 7.41 (d, J = 7.8 Hz, 1H), 7.95 (d, J = 8.4 Hz, 2H), 9.16 (br s, 1H) |
| N-(2-t-Butoxycarbonylaminophenyl)-4-[3-phenethyl-1-[3-(pyrrolidin-2-on-1-yl)propyl]ureidomethyl]benzamide (Reference Compound No. 13-43) 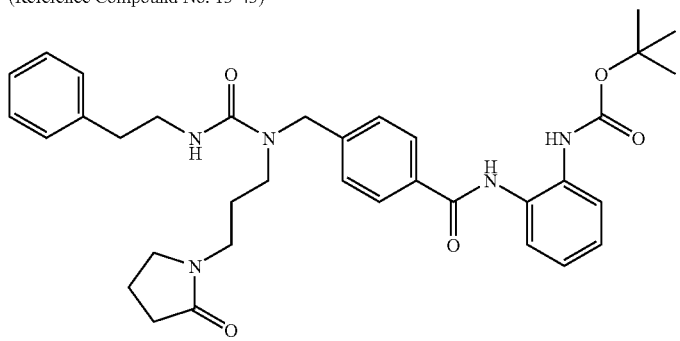 | $^1$H-NMR (400 MHz, CDCl$_3$) δ 1.52 (s, 9H), 1.71 (m, 2H), 2.00 (m, 2H), 2.36 (t, J = 8.1 Hz, 2H), 2.80 (t, J = 6.8 Hz, 2H), 3.21-3.26 (m, 4H), 3.32 (t, J = 7.0 Hz, 2H), 3.50 (m, 2H), 4.48 (s, 2H), 4.75 (t, J = 5.2 Hz, 1H), 6.80 (br s, 1H), 7.12 (d, J = 6.8 Hz, 2H), 7.17-7.30 (m, 8H), 7.82 (d, J = 7.8 Hz, 1H), 7.89 (d, J = 8.3 Hz, 2H), 9.17 (br s, 1H) |
| N-(2-t-Butoxycarbonylaminophenyl)-4-[1-(3-dimethylaminopropyl)-3-(4-methylphenyl)ureidomethyl]benzamide (Reference Compound No. 13-44) 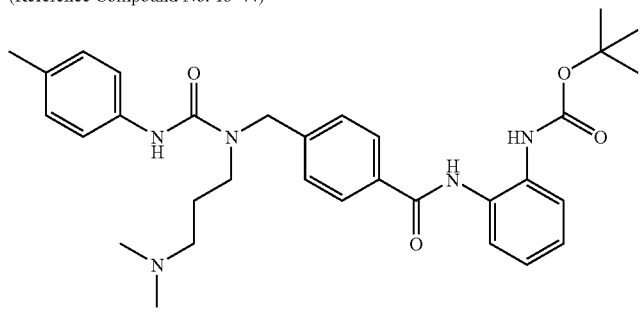 | $^1$H-NMR (400 MHz, CDCl$_3$) δ 1.49 (s, 9H), 1.78 (br s, 2H), 2.17 (s, 6H), 2.28 (s, 3H), 2.46 (br s, 2H), 3.42 (br s, 2H), 4.61 (s, 2H), 6.94 (br s, 1H), 7.07 (d, J = 8.1 Hz, 2H), 7.15-7.28 (m, 6H), 7.38 (d, J = 8.1 Hz, 2H), 7.74 (d, J = 7.6 Hz, 1H), 7.91 (d, J = 8.3 Hz, 2H), 9.19 (s, 1H) |

| | |
|---|---|
| N-(2-t-Butoxycarbonylaminophenyl)-4-[1-(3-dimethylaminopropyl)-3-(4-methoxycarbonylphenyl)ureidomethyl]benzamide (Reference Compound No. 13-45) 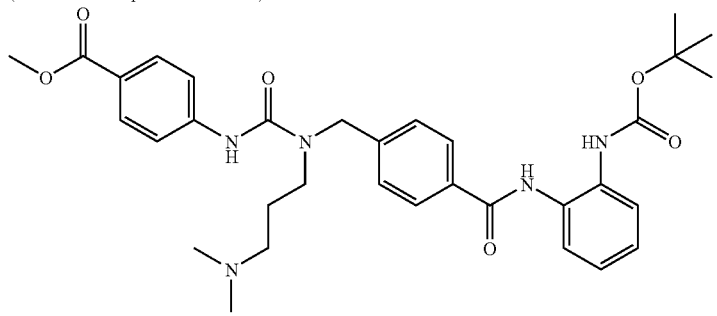 | $^1$H-NMR (500 MHz, CDCl$_3$) δ 1.50 (s, 9H), 1.76 (br s, 2H), 2.17 (s, 6H), 2.41 (br s, 2H), 3.42 (br s, 2H), 3.88 (s, 3H), 4.62 (s, 2H), 6.83 (br s, 1H), 7.16-7.28 (m, 4H), 7.41 (d, J = 8.2 Hz, 2H), 7.47 (d, J = 8.2 Hz, 2H), 7.79 (d, J = 7.6 Hz, 1H), 7.91-7.96 (m, 4H), 9.16 (s, 1H) |
| N-(2-t-Butoxycarbonylaminophenyl)-4-[3-(4-dimethylaminophenyl)-1-(2-hydroxyethyl)ureidomethyl]benzamide (Reference Compound No. 13-46) 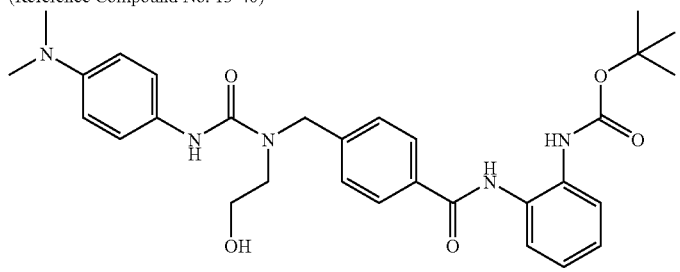 | $^1$H-NMR (500 MHz, CDCl$_3$) δ 1.50 (s, 9H), 2.87 (s, 6H), 3.51 (t, J = 4.3 Hz, 2H), 3.69 (br s, 2H), 3.80 (br s, 1H), 4.57 (s, 2H), 6.67 (d, J = 9.2 Hz, 2H), 7.01 (br s, 1H), 7.15 (d, J = 9.2 Hz, 2H), 7.17-7.24 (m, 2H), 7.32 (d, J = 8.0 Hz, 2H), 7.35 (dd, J = 7.6, 1.5 Hz, 1H), 7.74 (d, J = 7.6 Hz, 1H), 7.80 (d, J = 8.0 Hz, 2H), 7.85 (br s, 1H), 9.24 (br s, 1H) |
| N-(2-t-Butoxycarbonylaminophenyl)-4-[3-(3,4-difluorophenyl)-1-(2-hydroxyethyl)ureidomethyl]benzamide (Reference Compound No. 13-47) 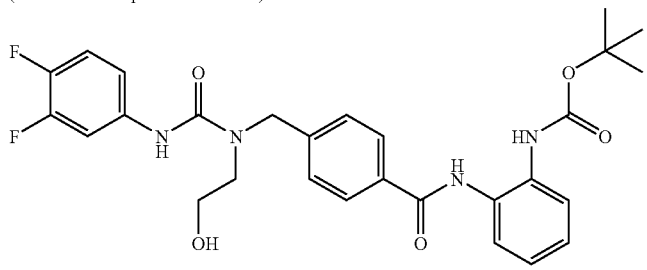 | $^1$H-NMR (400 MHz, CDCl$_3$) δ 1.50 (s, 9H), 3.49 (t, J = 4.3 Hz, 2H), 3.58 (br s, 1H), 3.70 (t, J = 4.3 Hz, 2H), 4.59 (s, 2H), 6.88 (m, 1H), 6.95 (br s, 1H), 7.00 (m, 1H), 7.16-7.25 (m, 2H), 7.29-7.35 (m, 4H), 7.75 (d, J = 7.3 Hz, 1H), 7.82 (d, J = 8.1 Hz, 2H), 8.59 (br s, 1H), 9.27 (br s, 1H) |
| N-(2-t-Butoxycarbonylaminophenyl)-4-[1-(2-hydroxyethyl)-3-phenethylureidomethyl]benzamide (Reference Compound No. 13-48) 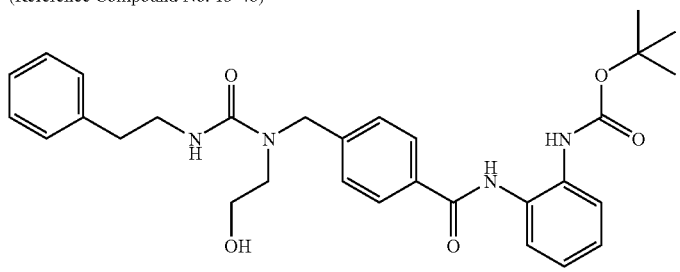 | $^1$H-NMR (400 MHz, CDCl$_3$) δ 1.51 (s, 9H), 2.80 (t, J = 6.8 Hz, 2H), 2.90 (br s, 1H), 3.42 (t, J = 4.8 Hz, 2H), 3.48 (m, 2H), 3.67 (m, 2H), 4.49 (s, 2H), 5.08 (br s, 1H), 6.83 (br s, 1H), 7.11-7.13 (m, 2H), 7.16-7.28 (m, 8H), 7.82 (d, J = 7.8 Hz, 1H), 7.90 (d, J = 8.3 Hz, 2H), 9.22 (br s, 1H) |

| | |
|---|---|
| N-(2-t-Butoxycarbonylaminophenyl)-4-[3-(2,3-dihydrobenzo[1,4]dioxin-6-yl)-1-(1-ethylpyrrolidin-2-ylmethyl)ureidomethyl]benzamide (Reference Compound No. 13-49) 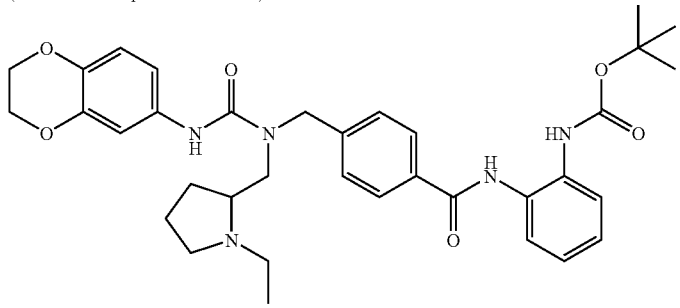 | $^1$H-NMR (400 MHz, DMSO-$d_6$) δ 1.00 (t, J = 7.1 Hz, 3H), 1.44 (s, 9H), 1.47 (m, 1H), 1.63-1.89 (m, 3H), 2.31-2.46 (m, 2H), 2.75 (m, 1H), 2.84 (m, 1H), 3.11 (m, 1H), 3.20-3.34 (m, 2H), 4.15-4.23 (m, 4H), 4.49 (d, J = 15.9 Hz, 1H), 4.69 (d, J = 15.9 Hz, 1H), 6.69-6.76 (m, 2H), 6.97 (d, J = 2.2 Hz, 1H), 7.15 (td, J = 7.6, 1.7 Hz, 1H), 7.20 (td, J = 7.6, 1.6 Hz, 1H), 7.44 (d, J = 8.3 Hz, 2H), 7.51-7.56 (m, 2H), 7.92 (d, J = 8.3 Hz, 2H), 8.67 (br s, 1H), 9.81 (s, 1H), 10.66 (br s, 1H) |
| N-(2-t-Butoxycarbonyaminophenyl)-4-[3-(4-dimethylaminophenyl)-1-(1-ethylpyrrolidin-2-ylmethyl)ureidomethyl]benzamide (Reference Compound No. 13-50) 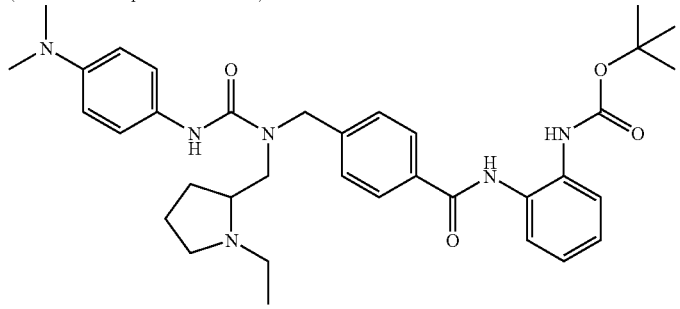 | $^1$H-NMR (400 MHz, DMSO-$d_6$) δ 1.01 (t, J = 7.2 Hz, 3H), 1.44 (s, 9H), 1.51 (m, 1H), 1.64-1.88 (m, 3H), 2.31-2.41 (m, 2H), 2.73-2.86 (m, 2H), 2.81 (s, 6H), 3.13 (m, 1H), 3.26-3.35 (m, 2H), 4.49 (d, J = 15.9 Hz, 1H), 4.72 (d, J = 15.9 Hz, 1H), 6.68 (d, J = 9.0 Hz, 2H), 7.13-7.23 (m, 2H), 7.18 (d, J = 9.0 Hz, 2H), 7.44 (d, J = 8.2 Hz, 2H), 7.51-7.56 (m, 2H), 7.92 (d, J = 8.2 Hz, 2H), 8.67 (s, 1H), 9.81 (s, 1H), 10.42 (br s, 1H) |
| N-(2-t-Butoxycarbonylaminophenyl)-4-[3-(3,4-difluorophenyl)-1-(1-ethylpyrrolidin-2-ylmethyl)ureidomethyl]benzamide (Reference Compound No. 13-51) 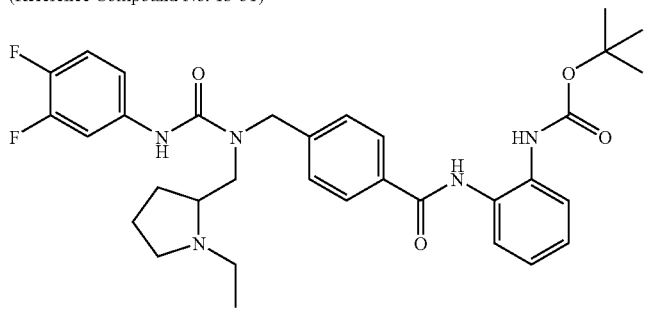 | $^1$H-NMR (400 MHz, DMSO-$d_6$) δ 1.00 (t, J = 7.2 Hz, 3H), 1.44 (s, 9H), 1.46 (m, 1H), 1.65-1.90 (m, 3H), 2.36-2.49 (m, 2H), 2.74 (m, 1H), 2.88 (m, 1H), 3.14 (m, 1H), 3.21-3.41 (m, 2H), 4.54 (d, J = 15.9 Hz, 1H), 4.71 (d, J = 15.9 Hz, 1H), 6.98 (m, 1H), 7.15 (td, J = 7.6, 1.7 Hz, 1H), 7.20 (td, J = 7.6, 1.8 Hz, 1H), 7.32 (dd, J = 19.7, 9.2 Hz, 1H), 7.45 (d, J = 8.3 Hz, 2H), 7.52-7.56 (m, 2H), 7.60 (m, 1H), 7.93 (d, J = 8.3 Hz, 2H), 8.67 (s, 1H), 9.81 (s, 1H), 11.21 (br s, 1H) |
| N-(2-t-Butoxycarbonylaminophenyl)-4-[1-(4-dimethylaminobutyl)-3-(4-dimethylaminophenyl)ureidomethyl]benzamide (Reference Compound No. 13-52) 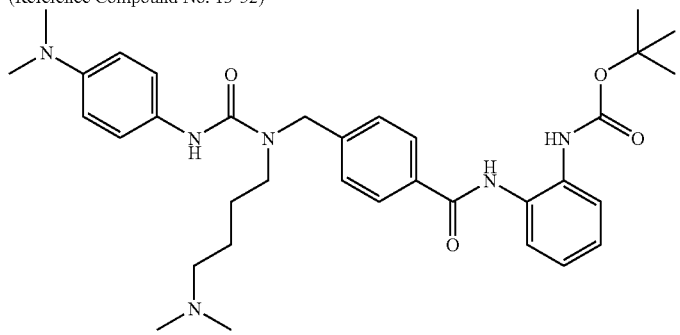 | $^1$H-NMR (400 MHz, CDCl$_3$) δ 1.49 (m, 2H), 1.51 (s, 9H), 1.66 (m, 2H), 2.19 (s, 6H), 2.32 (t, J = 6.6 Hz, 2H), 2.90 (s, 6H), 3.25 (t, J = 8.2 Hz, 2H), 4.65 (s, 2H), 6.70 (d, J = 9.0 Hz, 2H), 6.87 (br s, 1H), 7.15-7.25 (m, 2H), 7.17 (d, J = 9.0 Hz, 2H), 7.29 (dd, J = 7.7, 1.6 Hz, 1H), 7.42 (d, J = 8.4 Hz, 2H), 7.47 (br s, 1H), 7.77 (d, J = 8.1 Hz, 1H), 7.93 (d, J = 8.4 Hz, 2H), 9.13 (br s, 1H) |

N-(2-t-Butoxycarbonylaminophenyl)-4-[3-(4-cyanomethylphenyl)-1-(4-dimethylaminobutyl)ureidomethyl]benzamide
(Reference Compound No. 13-53)

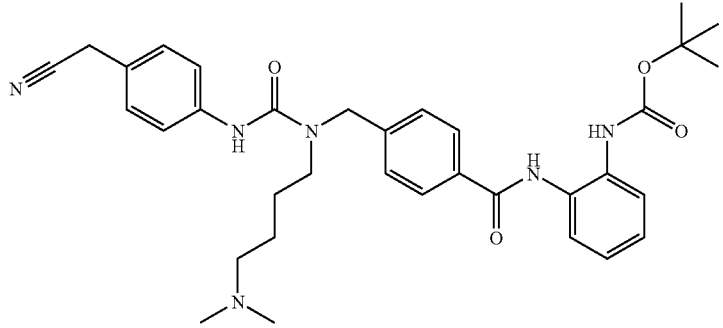

¹H-NMR (400 MHz, CDCl₃)
δ 1.51 (s, 9H), 1.52 (m, 2H), 1.68 (m, 2H), 2.23 (s, 6H), 2.34 (t, J = 6.6 Hz, 2H), 3.27 (t, J = 8.2 Hz, 2H), 3.71 (s, 2H), 4.67 (s, 2H), 6.77 (br s, 1H), 7.18 (td, J = 7.8, 1.5 Hz, 1H), 7.22-7.29 (m, 4H), 7.36 (d, J = 8.5 Hz, 2H), 7.42 (d, J = 8.3 Hz, 2H), 7.70 (br s, 1H), 7.81 (d, J = 7.8 Hz, 1H), 7.94 (d, J = 8.3 Hz, 2H), 9.14 (br s, 1H)

N-(2-t-Butoxycarbonylaminophenyl)-4-[1-[3-(morpholin-4-yl)propyl]phenethylureidomethyl]benzamide
(Reference Compound No. 13-54)

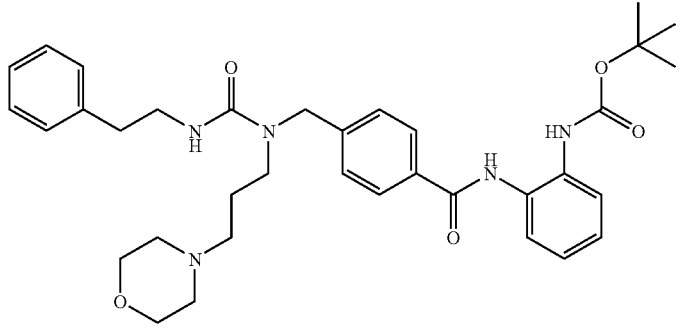

¹H-NMR (400 MHz, CDCl₃)
δ 1.51 (s, 9H), 1.58 (m, 2H), 2.22-2.32 (m, 6H), 2.86 (t, J = 6.7 Hz, 2H), 3.15 (t, J = 5.9 Hz, 2H), 3.44-3.58 (m, 6H), 4.56 (s, 2H), 6.82 (s, 1H), 6.91 (br s, 1H), 7.15-7.32 (m, 8H), 7.34 (d, J = 8.4 Hz, 2H), 7.80 (d, J = 6.8 Hz, 1H), 7.91 (d, J = 8.4 Hz, 2H), 9.13 (br s, 1H)

N-(2-t-Butoxycarbonylaminophenyl)-4-[3-(4-methoxyphenyl)-1-[3-(morpholin-4-yl)propyl]ureidomethyl]benzamide
(Reference Compound No. 13-55)

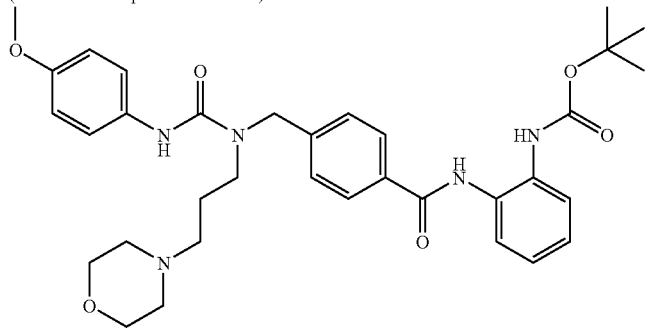

¹H-NMR (400 MHz, CDCl₃)
δ 1.50 (s, 9H), 1.72 (m, 2H), 2.36-2.49 (m, 6H), 3.36 (t, J = 5.7 Hz, 2H), 3.62 (t, J = 4.6 Hz, 4H), 3.79 (s, 3H), 4.62 (s, 2H), 6.85 (d, J = 9.0 Hz, 2H), 6.88 (s, 1H), 7.17 (td, J = 7.6, 1.7 Hz, 1H), 7.22 (td, J = 7.6, 1.8 Hz, 1H), 7.27-7.34 (m, 3H), 7.41 (d, J = 8.3 Hz, 2H), 7.75 (d, J = 7.6 Hz, 1H), 7.90 (d, J = 8.3 Hz, 2H), 8.82 (br s, 1H), 9.14 (br s, 1H)

N-(2-t-Butoxycarbonylaminophenyl)-4-[3-(2-methoxyphenyl)-1-[3-(morpholin-4-yl)propyl]ureidomethyl]benzamide
(Reference Compound No. 13-56)

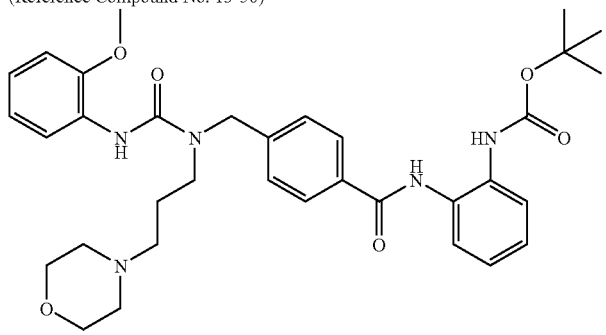

¹H-NMR (400 MHz, CDCl₃)
δ 1.47 (s, 9H), 1.78 (m, 2H), 2.36-2.43 (m, 6H), 3.42 (t, J = 6.6 Hz, 2H), 3.61 (t, J = 4.5 Hz, 4H), 3.76 (s, 3H), 4.63 (s, 2H), 6.82 (d, J = 7.9 Hz, 1H), 6.90 (td, J = 7.9, 1.4 Hz, 1H), 6.99 (td, J = 7.9, 1.7 Hz, 1H), 7.08-7.15 (m, 2H), 7.29-7.38 (m, 4H), 7.65 (m, 1H), 7.87 (br s, 1H), 7.88-7.96 (m, 3H), 9.40 (br s, 1H)

N-(2-t-Butoxycarbonylaminophenyl)-4-[3-(3-methoxyphenyl)-1-[3-(morpholin-4-yl)propyl]ureidomethyl]benzamide
(Reference Compound No. 13-57)

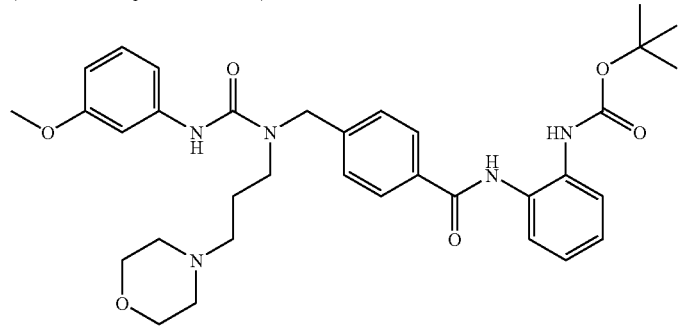

¹H-NMR (400 MHz, CDCl₃)
δ 1.47 (s, 9H), 1.71 (m, 2H), 2.39-2.46 (m, 6H), 3.34 (t, J = 5.6 Hz, 2H), 3.69 (t, J = 4.5 Hz, 4H), 3.77 (s, 3H), 4.59 (s, 2H), 6.61 (ddd, J = 8.3, 2.7, 0.7 Hz, 1H), 6.94 (ddd, J = 8.1, 2.0, 0.7 Hz, 1H), 7.08-7.15 (m, 2H), 7.15-7.21 (m, 2H), 7.30-7.35 (m, 4H), 7.64 (m, 1H), 7.87 (d, J = 8.3 Hz, 2H), 8.76 (br s, 1H), 9.36 (br s, 1H)

4-[3-[2-(Benzo[1,3]dioxol-5-yl)ethyl]-1-[3-(morpholin-4-yl)propyl]ureidomethyl]-N-(2-t-butoxycarbonylaminophenyl)benzamide
(Reference Compound No. 13-58)

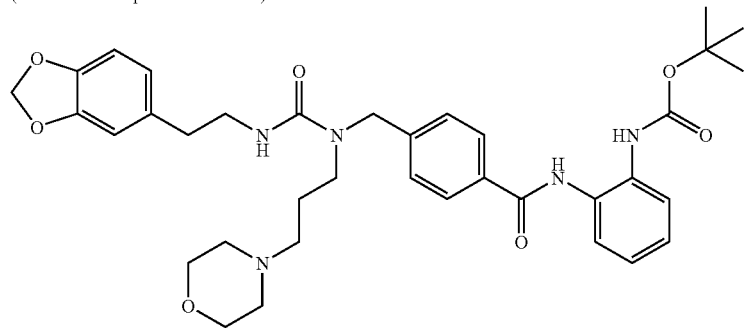

¹H-NMR (400 MHz, CDCl₃)
δ 1.57 (s, 9H), 1.57 (m, 2H), 2.24-2.36 (m, 6H), 2.74 (t, J = 6.7 Hz, 2H), 3.15 (t, J = 5.7 Hz, 2H), 3.41 (m, 2H), 3.58 (br s, 4H), 4.52 (s, 2H), 5.89 (s, 2H), 6.60 (dd, J = 8.0, 1.5 Hz, 1H), 6.67 (d, J = 1.5 Hz, 1H), 6.72 (d, J = 8.0 Hz, 1H), 6.85 (br s, 1H), 7.09-7.16 (m, 2H), 7.25 (d, J = 8.2 Hz, 2H), 7.36 (dd, J = 7.6, 2.0 Hz, 1H), 7.47 (br s, 1H), 7.68 (dd, J = 7.6, 2.0 Hz, 1H), 7.89 (d, J = 8.2 Hz, 2H), 9.43 (br s, 1H)

N-(2-t-Butoxycarbonylaminophenyl)-4-[3-(4-difluoromethoxyphenyl)-1-[3-(morpholin-4-yl)propyl]ureidomethyl]benzamide
(Reference Compound No. 13-59)

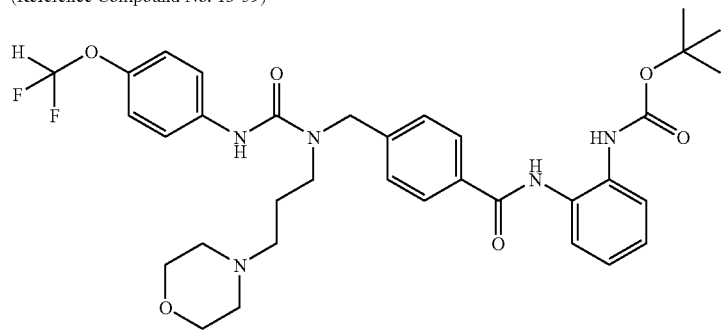

¹H-NMR (500 MHz, CDCl₃)
δ 1.48 (s, 9H), 1.72 (m, 2H), 2.40-2.45 (m, 6H), 3.35 (t, J = 5.8 Hz, 2H), 3.64 (t, J = 4.6 Hz, 4H), 4.59 (s, 2H), 6.45 (t, J = 74.2 Hz, 1H), 7.05 (d, J = 8.9 Hz, 2H), 7.10-7.16 (m, 2H), 7.20 (br s, 1H), 7.30 (dd, J = 7.6, 1.8 Hz, 1H), 7.35 (d, J = 8.4 Hz, 2H), 7.41 (d, J = 8.9 Hz, 2H), 7.66 (dd, J = 7.8, 1.7 Hz, 1H), 7.87 (d, J = 8.4 Hz, 2H), 8.90 (br s, 1H), 9.30 (br s, 1H)

N-(2-t-Butoxycarbonylaminophenyl)-4-[3-(3,4-dimethoxyphenyl)-1-[3-(morpholin-4-yl)propyl]ureidomethyl]benzamide
(Reference Compound No. 13-60)

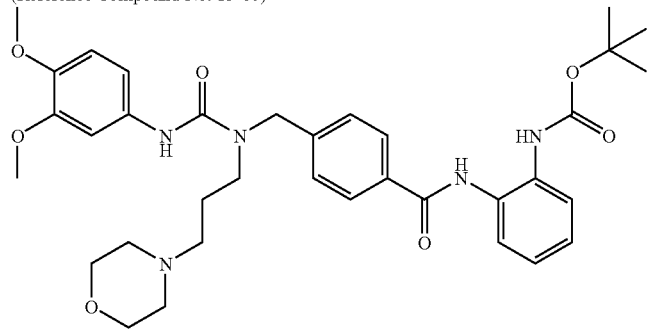

¹H-NMR (500 MHz, CDCl₃)
δ 1.50 (s, 9H), 1.73 (m, 2H), 2.41-2.48 (m, 6H), 3.38 (t, J = 5.7 Hz, 2H), 3.66 (t, J = 4.4 Hz, 4H), 3.86 (s, 3H), 3.90 (s, 3H), 4.65 (s, 2H), 6.73 (br s, 1H), 6.79-6.82 (m, 2H), 7.18 (td, J = 7.8, 1.5 Hz, 1H), 7.22-7.29 (m, 3H), 7.43 (d, J = 8.1 Hz, 2H), 7.80 (d, J = 7.8 Hz, 1H), 7.92 (d, J = 8.1 Hz, 2H), 8.81 (br s, 1H), 9.08 (br s, 1H)

N-(2-t-Butoxycarbonylaminophenyl)-4-[3-(3,4-difluorophenyl)-1-[3-(morpholin-4-yl)propyl]ureidomethyl]benzamide
(Reference Compound No. 13-61)

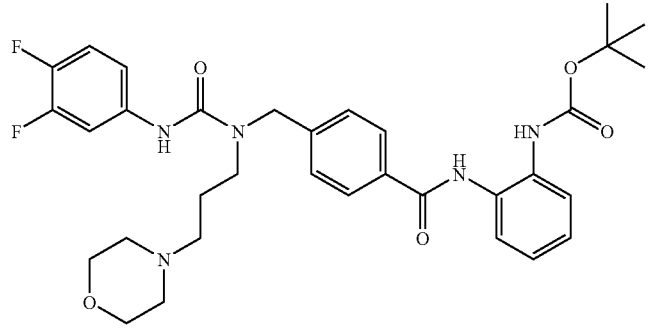

¹H-NMR (500 MHz, CDCl₃)
δ 1.51 (s, 9H), 1.74 (m, 2H), 2.41-2.48 (m, 6H), 3.37 (t, J = 5.8 Hz, 2H), 3.67 (t, J = 4.6 Hz, 4H), 4.63 (s, 2H), 6.70 (br s, 1H), 7.00-7.11 (m, 2H), 7.18 (td, J = 7.8, 1.5 Hz, 1H), 7.22-7.28 (m, 2H), 7.42 (d, J = 8.2 Hz, 2H), 7.52 (m, 1H), 7.82 (d, J = 7.8 Hz, 1H), 7.93 (d, J = 8.2 Hz, 2H), 8.93 (br s, 1H), 9.11 (br s, 1H)

N-(2-t-Butoxycarbonylaminophenyl)-4-[1-[3-(morpholin-4-yl)propyl]-3-(4-nitrophenyl)ureidomethyl]benzamide
(Reference Compound No. 13-62)

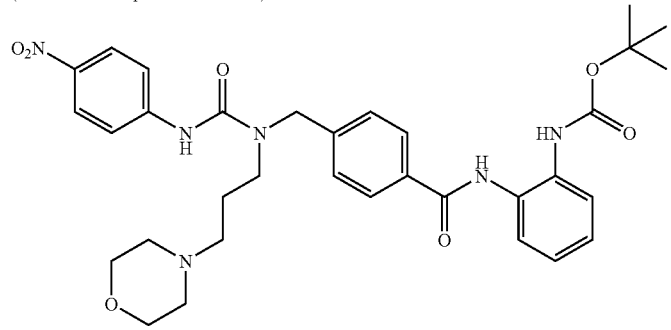

¹H-NMR (400 MHz, CDCl₃)
δ 1.51 (s, 9H), 1.79 (m, 2H), 2.44-2.53 (m, 6H), 3.41 (t, J = 5.7 Hz, 2H), 3.76 (t, J = 4.6 Hz, 4H), 4.65 (s, 2H), 6.72 (br s, 1H), 7.18 (td, J = 8.3, 1.5 Hz, 1H), 7.22-7.28 (m, 2H), 7.42 (d, J = 8.3 Hz, 2H), 7.69 (d, J = 9.2 Hz, 2H), 7.82 (d, J = 8.3 Hz, 1H), 7.94 (d, J = 8.3 Hz, 2H), 8.20 (d, J = 9.2 Hz, 2H), 9.16 (br s, 2H)

N-(2-t-Butoxycarbonylaminophenyl)-4-[1-[3-(morpholin-4-yl)propyl]-3-(pyridin-3-yl)ureidomethyl]benzamide
Reference Compound No. 13-63)

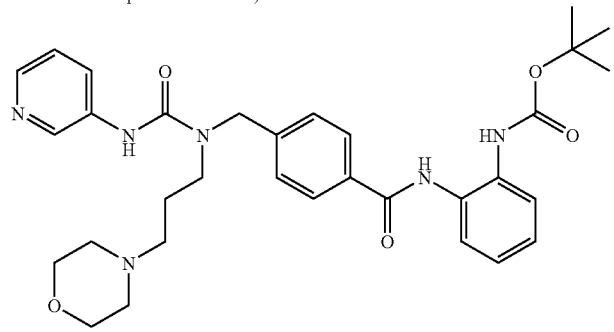

¹H-NMR (400 MHz, CDCl₃)
δ 1.50 (s, 9H), 1.76 (m, 2H), 2.43-2.50 (m, 6H), 3.40 (t, J = 5.7 Hz, 2H), 3.68 (t, J = 4.6 Hz, 4H), 4.64 (s, 2H), 6.82 (br s, 1H), 7.17 (td, J = 7.4, 1.5 Hz, 1H), 7.21-7.28 (m, 3H), 7.42 (d, J = 8.3 Hz, 2H), 7.79 (d, J = 7.4 Hz, 1H), 7.92 (d, J = 8.3 Hz, 2H), 8.05 (ddd, J = 8.3, 2.2, 1.5 Hz, 1H), 8.32 (dd, J = 4.6, 1.5 Hz, 1H), 8.57 (d, J = 2.2 Hz, 1H), 9.05 (br s, 1H), 9.15 (br s, 1H)

N-(2-t-Butoxycarbonylaminophenyl)-4-[3-(3-ethoxyphenyl)-1-[3-(morpholin-4-yl)propyl]ureidomethyl]benzamide
(Reference Compound No. 13-64)

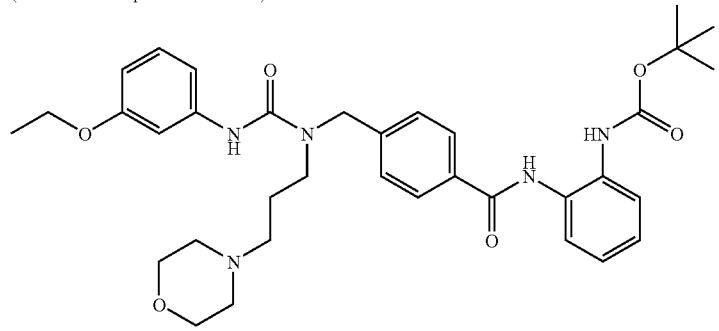

¹H-NMR (500 MHz, CDCl₃)
δ 1.40 (t, J = 6.9 Hz, 3H), 1.51 (s, 9H), 1.74 (m, 2H), 2.41-2.48 (m, 6H), 3.38 (t, J = 5.7 Hz, 2H), 3.71 (t, J = 4.6 Hz, 4H), 4.04 (q, J = 6.9 Hz, 2H), 4.64 (s, 2H), 6.62 (dd, J = 8.2, 2.4 Hz, 1H), 6.72 (br s, 1H), 6.92 (d, J = 7.9 Hz, 1H), 7.15-7.29 (m, 5H), 7.43 (d, J = 8.1 Hz, 2H), 7.81 (d, J = 7.9 Hz, 1H), 7.92 (d, J = 8.1 Hz, 2H), 8.65 (br s, 1H), 9.07 (br s, 1H)

N-(2-t-Butoxycarbonylaminophenyl)-4-[3-(3,5-dimethoxy-phenyl)-1-[3-(morpholin-4-yl)propyl]ureidomethyl]benzamide
(Reference Compound No. 13-65)

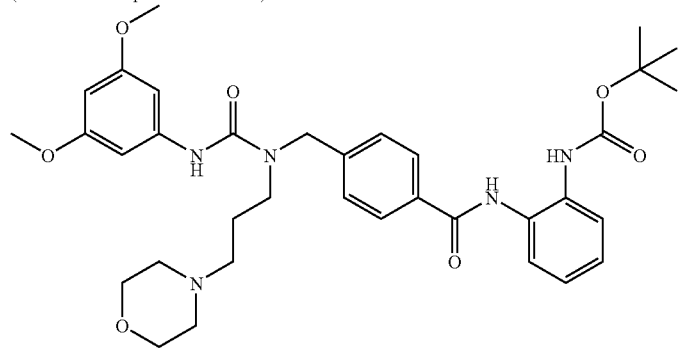

$^{1}$H-NMR (500 MHz, CDCl$_3$)
δ 1.47 (s, 9H), 1.71 (m, 2H), 2.40-2.46 (m, 6H), 3.34 (t, J = 5.8 Hz, 2H), 3.71 (t, J = 4.7 Hz, 4H), 3.75 (s, 6H), 4.60 (s, 2H), 6.19 (t, J = 2.1 Hz, 1H), 6.71 (d, J = 2.1 Hz, 2H), 7.09-7.14 (m, 2H), 7.31-7.34 (m, 2H), 7.33 (d, J = 8.2 Hz, 2H), 7.65 (d, J = 7.0 Hz, 1H), 7.87 (d, J = 8.2 Hz, 2H), 8.69 (br s, 1H), 9.34 (br s, 1H)

N-(2-t-Butoxycarbonylaminophenyl)-4-[3-(2,3-dihydrobenzo[1,4]dioxin-6-yl)-1-(pyridin-4-ylmethyl)ureidomethyl]benzamide
(Reference Compound No. 13-66)

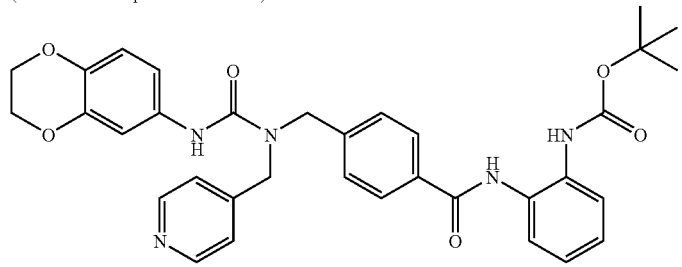

$^{1}$H-NMR (400 MHz, CDCl$_3$)
δ 1.51 (s, 9H), 4.19-4.23 (m, 4H), 4.62 (s, 2H), 4.63 (s, 2H), 6.11 (s, 1H), 6.64 (dd, J = 8.7, 2.5 Hz, 1H), 6.71 (br s, 1H), 6.75 (d, J = 8.7 Hz, 1H), 6.87 (d, J = 2.5 Hz, 1H), 7.16-7.29 (m, 5H), 7.39 (d, J = 8.2 Hz, 2H), 7.86 (d, J = 7.6 Hz, 1H), 7.98 (d, J = 8.2 Hz, 2H), 8.61 (dd, J = 4.4, 1.7 Hz, 2H), 9.26 (br s, 1H)

N-(2-t-Butoxycarbonylaminophenyl)-4-[3-(4-dimethylphenyl)-1-(pyridin-4-ylmethyl)ureidomethyl]benzamide
(Reference Compound No. 13-67)

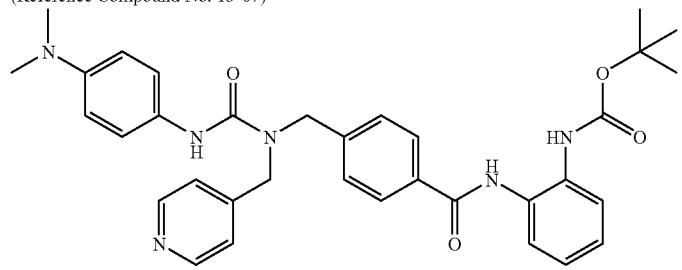

$^{1}$H-NMR (400 MHz, CDCl$_3$)
δ 1.51 (s, 9H), 2.89 (s, 6H), 4.62 (s, 2H), 4.64 (s, 2H), 6.08 (s, 1H), 6.67 (d, J = 9.0 Hz, 2H), 6.71 (br s, 1H), 7.10 (d, J = 9.0 Hz, 2H), 7.16-7.29 (m, 5H), 7.40 (d, J = 8.4 Hz, 2H), 7.86 (d, J = 7.8 Hz, 1H), 7.98 (d, J = 8.4 Hz, 2H), 8.60 (dd, J = 4.4, 1.7 Hz, 2H), 9.25 (br s, 1H)

N-(2-t-Butoxycarbonylaminophenyl)-4-[3-(3,4-difluorophenyl)-1-(pyridin-4-ylmethyl)ureidomethyl]benzamide
(Reference Compound No. 13-68)

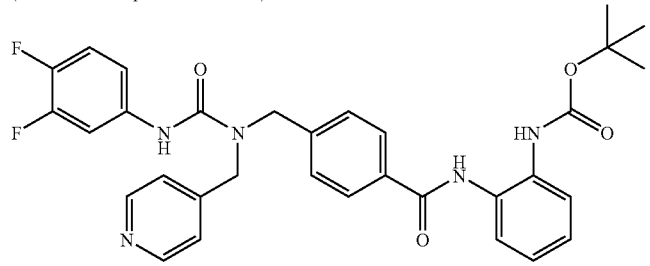

$^{1}$H-NMR (400 MHz, CDCl$_3$)
δ 1.51 (s, 9H), 4.64 (s, 2H), 4.64 (s, 2H), 6.34 (br s, 1H), 6.72 (br s, 1H), 6.78 (m, 1H), 7.02 (m, 1H), 7.16-7.29 (m, 5H), 7.35-7.41 (m, 3H), 7.87 (d, J = 8.1 Hz, 1H), 7.99 (d, J = 8.3 Hz, 2H), 8.62 (dd, J = 4.4, 1.7 Hz, 2H), 9.34 (br s, 1H)

4-[3-[2-(Benzo[1,3]dioxol-5-yl)ethyl]-1-[2-(pyridin-4-yl)ethyl]ureidomethyl]-N-(2-t-butoxycarbonylaminophenyl)benzamide
(Reference Compound 13-69)

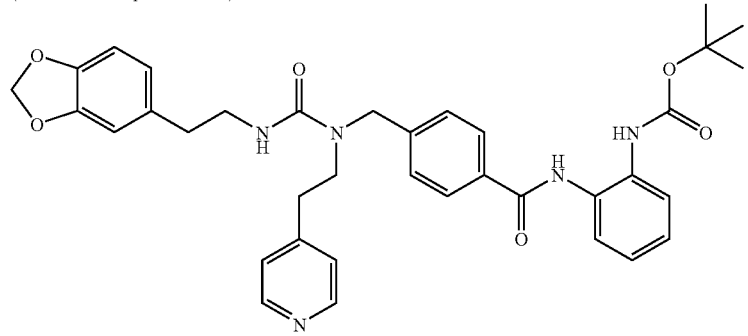

¹H-NMR (500 MHz, CDCl₃)
δ 1.51 (s, 9H), 2.69 (t, J = 6.6 Hz, 2H), 2.83 (t, J = 7.5 Hz, 2H), 3.44 (m, 2H), 3.53 (t, J = 7.5 Hz, 2H), 4.20 (t, J = 5.7 Hz, 1H), 4.33 (s, 2H), 5.90 (s, 2H), 6.52 (dd, J = 7.8, 1.7 Hz, 1H), 6.56 (d, J = 1.7 Hz, 1H), 6.67 (d, J = 7.8 Hz, 1H), 6.82 (s, 1H), 7.06 (dd, J = 4.4, 1.5 Hz, 2H), 7.17-7.21 (m, 3H), 7.24-7.29 (m, 2H), 7.84 (d, J = 7.6 Hz, 1H), 7.88 (d, J = 8.2 Hz, 2H), 8.50 (dd, J = 4.4, 1.5 Hz, 2H), 9.13 (br s, 1H)

N-(2-t-Butoxycarbonylaminophenyl)-4-[3-(4-dimethylaminophenyl)-1-[2-(pyridin-4-yl)ethyl]ureidomethyl]benzamide
(Reference Compound No. 13-70)

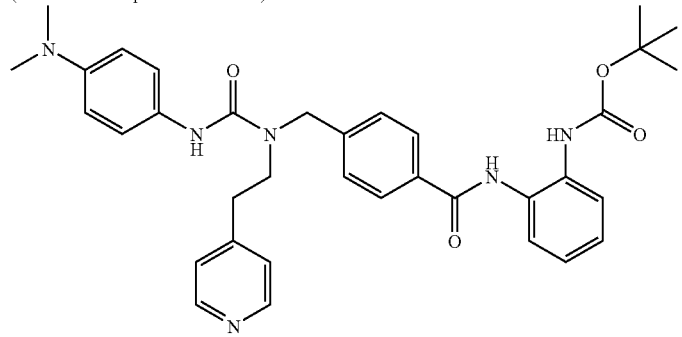

¹H-NMR (500 MHz, CDCl₃)
δ 1.50 (s, 9H), 2.89 (s, 6H), 2.96 (t, J = 7.3 Hz, 2H), 3.67 (t, J = 7.3 Hz, 2H), 4.54 (s, 2H), 5.92 (s, 1H), 6.67 (d, J = 8.9 Hz, 2H), 6.78 (s, 1H), 7.04 (d, J = 8.9 Hz, 2H), 7.15 (d, J = 5.7 Hz, 2H), 7.18 (t, J = 7.7 Hz, 1H), 7.23-7.30 (m, 2H), 7.36 (d, J = 8.1 Hz, 2H), 7.86 (d, J = 7.7 Hz, 1H), 7.95 (d, J = 8.1 Hz, 2H), 8.53 (d, J = 5.7 Hz, 2H), 9.21 (br s, 1H)

N-(2-t-Butoxycarbonylaminophenyl)-4-[3-(3,4-difluorophenyl)-1-[2-(pyridin-4-yl)ethyl]ureidomethyl]benzamide
(Reference Compound No. 13-71)

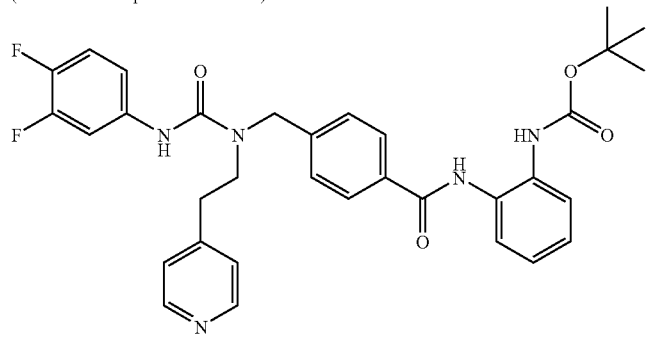

¹H-NMR (500 MHz, CDCl₃)
δ 1.50 (s, 9H), 2.96 (t, J = 7.3 Hz, 2H), 3.69 (t, J = 7.3 Hz, 2H), 4.54 (s, 2H), 6.08 (s, 1H), 6.68 (m, 1H), 6.74 (s, 1H), 7.01 (m, 1H), 7.16 (dd, J = 4.6, 1.5 Hz, 2H), 7.17-7.33 (m, 4H), 7.35 (d, J = 8.4 Hz, 2H), 7.88 (d, J = 7.9 Hz, 1H), 7.97 (d, J = 8.4 Hz, 2H), 8.55 (dd, J = 4.6, 1.5 Hz, 2H), 9.30 (br s, 1H)

N-(2-t-Butoxycarbonylaminophenyl)-4-[3-(2,3-dihydrobenzo[1,4]dioxin-6-yl)-1-[2-(pyridin-4-yl)ethyl]ureidomethyl]benzamide
(Reference Compound No. 13-72)

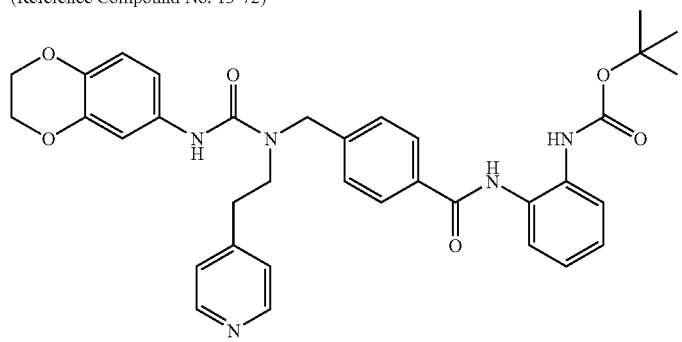

¹H-NMR (400 MHz, CDCl₃)
δ 1.49 (s, 9H), 2.95 (t, J = 7.3 Hz, 2H), 3.66 (t, J = 7.3 Hz, 2H), 4.19-4.23 (m, 4H), 4.52 (s, 2H), 6.01 (s, 1H), 6.59 (dd, J = 8.7, 2.5 Hz, 1H), 6.74 (d, J = 8.7 Hz, 1H), 6.82 (d, J = 2.5 Hz, 1H), 6.85 (s, 1H), 7.14 (dd, J = 4.4, 1.7 Hz, 2H), 7.17 (td, J = 7.7, 1.7 Hz, 1H), 7.22-7.27 (m, 2H), 7.34 (d, J = 8.4 Hz, 2H), 7.84 (d, J = 7.7 Hz, 1H), 7.94 (d, J = 8.4 Hz, 2H), 8.52 (dd, J = 4.4, 1.7 Hz, 2H), 9.26 (br s, 1H)

N-(2-t-Butoxycarbonylaminophenyl)-4-[3-(4-dimethylaminophenyl)-1-[2-(morpholin-4-yl)ethyl]ureidomethyl]benzamide
(Reference Compound No. 13-73)

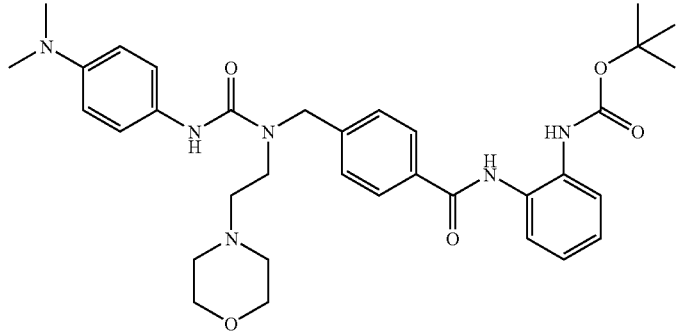

$^1$H-NMR (400 MHz, CDCl$_3$)
δ 1.51 (s, 9H), 2.49 (m, 2H), 2.58 (br s, 4H), 2.91 (s, 6H), 3.37 (t, J = 4.2 Hz, 2H), 3.75 (t, J = 4.6 Hz, 4H), 4.64 (s, 2H), 6.73-6.76 (m, 3H), 7.16 (m, 1H), 7.26-7.29 (m, 4H), 7.43 (d, J = 8.2 Hz, 2H), 7.81 (d, J = 8.3 Hz, 1H), 7.93 (d, J = 8.2 Hz, 2H), 9.11 (s, 1H), 9.35 (s, 1H)

N-(2-t-Butoxycarbonylaminophenyl)-4-[3-(2,3-dihydrobenzo[1,4]dioxin-6-yl)-1-[2-(morpholin-4-yl)ethyl]ureidomethyl]benzamide
(Reference Compound No. 13-74)

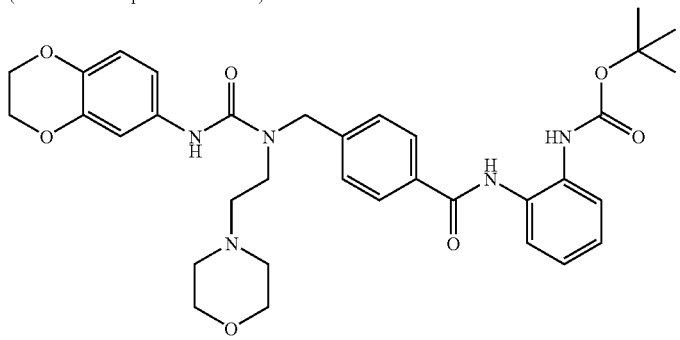

$^1$H-NMR (400 MHz, CDCl$_3$)
δ 1.52 (s, 9H), 2.49 (m, 2H), 2.59 (br s, 4H), 3.36 (m, 2H), 3.76 (t, J = 4.6 Hz, 4H), 4.22-4.26 (m, 4H), 4.63 (s, 2H), 6.70 (s, 1H), 6.80 (d, J = 8.8 Hz, 1H), 6.86 (dd, J = 8.8, 2.4 Hz, 1H), 7.00 (d, J = 2.4 Hz, 1H), 7.24-7.29 (m, 3H), 7.43 (d, J = 8.3 Hz, 2H), 7.83 (d, J = 7.8 Hz, 1H), 7.93 (d, J = 8.3 Hz, 2H), 9.09 (s, 1H), 9.50 (s, 1H)

N-(2-t-Butoxycarbonylaminophenyl)-4-[1-(2-dimethylaminoethyl)-3-(4-dimethylaminophenyl)ureidomethyl]benzamide
(Reference Compound No. 13-75)

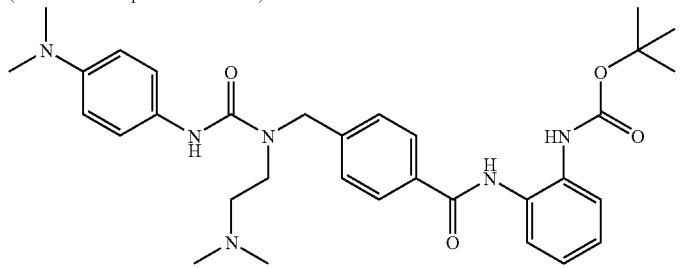

$^1$H-NMR (400 MHz, CDCl$_3$)
δ 1.51 (s, 9H), 2.35 (s, 6H), 2.44 (t, J = 4.2 Hz, 2H), 2.89 (s, 6H), 3.30 (t, J = 4.2 Hz, 2H), 4.64 (s, 2H), 6.74 (d, J = 9.0 Hz, 2H), 6.77 (m, 1H), 7.15-7.28 (m, 5H), 7.42 (d, J = 8.3 Hz, 2H), 7.80 (d, J = 7.8 Hz, 1H), 7.91 (d, J = 8.3 Hz, 2H), 9.11 (s, 1H), 10.54 (s, 1H)

N-(2-t-Butoxycarbonylaminophenyl)-4-[3-(2,3-dihydrobenzo[1,4]dioxin-6-yl)-1-(2-dimethylaminoethyl)ureidomethyl]benzamide
(Reference Compound No. 13-76)

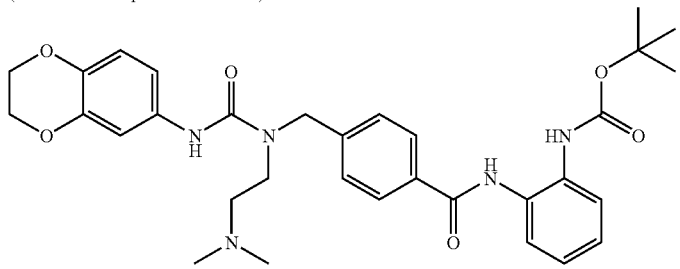

$^1$H-NMR (400 MHz, CDCl$_3$)
δ 1.51 (s, 9H), 2.35 (s, 6H), 2.44 (t, J = 4.2 Hz, 2H), 3.30 (t, J = 4.2 Hz, 2H), 4.21-4.25 (m, 4H), 4.63 (s, 2H), 6.76-6.82 (m, 3H), 6.94 (d, J = 2.2 Hz, 1H), 7.16-7.28 (m, 3H), 7.42 (d, J = 8.3 Hz, 2H), 7.81 (d, J = 8.1 Hz, 1H), 7.92 (d, J = 8.3 Hz, 2H), 9.10 (s, 1H), 10.76 (s, 1H)

N-(2-t-Butoxycarbonylaminophenyl)-4-[3-(4-dimethylaminophenyl)-1-[3-(4-methylpiperazin-1-yl)propyl]ureidomethyl]benzamide
(Reference Compound No. 13-77)

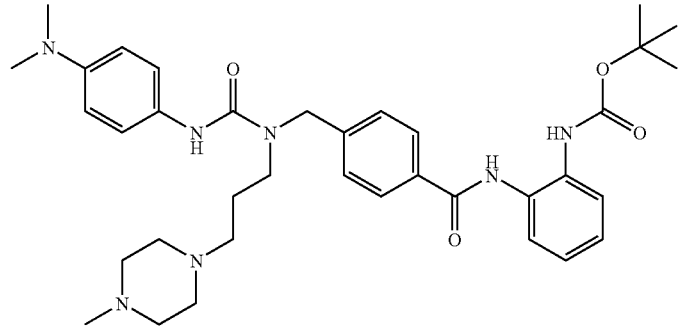

$^1$H-NMR (400 MHz, CDCl$_3$)
δ 1.50 (s, 9H), 1.70 (m, 2H), 2.22 (s, 3H), 2.39 (br s, 8H), 2.44 (t, J = 6.1 Hz, 2H), 2.91 (s, 6H), 3.34 (t, J = 5.6 Hz, 2H), 4.62 (s, 2H), 6.72 (d, J = 9.0 Hz, 2H), 6.80 (br s, 1H), 7.18 (td, J = 7.7, 1.6 Hz, 1H), 7.21-7.31 (m, 2H), 7.26 (d, J = 9.0 Hz, 2H), 7.44 (d, J = 8.3 Hz, 2H), 7.77 (d, J = 7.7 Hz, 1H), 7.90 (d, J = 8.3 Hz, 2H), 8.77 (br s, 1H), 9.05 (br s, 1H)

N-(2-t-Butoxycarbonaminophenyl)-4-[3-(3,4-difluorophenyl)-1-[3-(4-methylpiperazin-1-yl)propyl]ureidomethyl]benzamide
(Reference Compound No. 13-78)

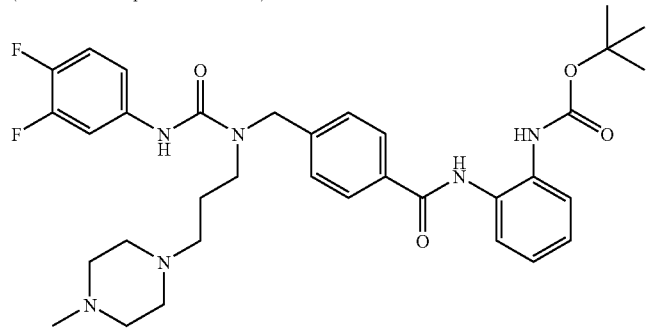

$^1$H-NMR (400 MHz, CDCl$_3$)
δ 1.51 (s, 9H), 1.73 (m, 2H), 2.27 (s, 3H), 2.35-2.55 (m, 8H), 2.44 (t, J = 6.0 Hz, 2H), 3.35 (t, J = 5.7 Hz, 2H), 4.61 (s, 2H), 6.75 (s, 1H), 7.04-7.13 (m, 2H), 7.17 (td, J = 7.8, 1.5 Hz, 1H), 7.22-7.28 (m, 2H), 7.42 (d, J = 8.4 Hz, 2H), 7.49 (m, 1H), 7.80 (d, J = 7.8 Hz, 1H), 7.92 (d, J = 8.4 Hz, 2H), 9.10 (br s, 1H), 9.15 (br s, 1H)

N-(2-t-Butoxycarbonylaminophenyl)-4-[3-(4-dimethylaminophenyl)-1-(3-hydroxypropyl)ureidomethyl]benzamide
(Reference Compound No. 13-79)

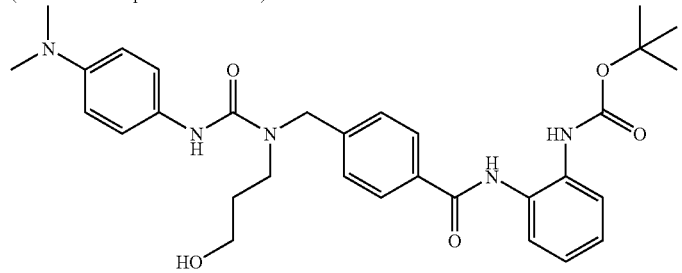

$^1$H-NMR (500 MHz, CDCl$_3$)
δ 1.50 (s, 9H), 1.73 (m, 2H), 2.88 (s, 6H), 3.09 (br s, 1H), 3.55 (t, J = 6.0 Hz, 2H), 3.71 (m, 2H), 4.61 (s, 2H), 6.68 (d, J = 9.2 Hz, 2H), 6.79 (s, 1H), 7.00 (br s, 1H), 7.16-7.20 (m, 3H), 7.23-7.28 (m, 2H), 7.41 (d, J = 8.2 Hz, 2H), 7.81 (d, J = 7.3 Hz, 1H), 7.95 (d, J = 8.2 Hz, 2H), 9.20 (br s, 1H)

N-(2-t-Butoxycarbonylaminophenyl)-4-[3-(3,4-difluorophenyl)-1-[2-(morpholin-4-yl)ethyl]ureidomethyl]benzamide
(Reference Compound No. 13-80)

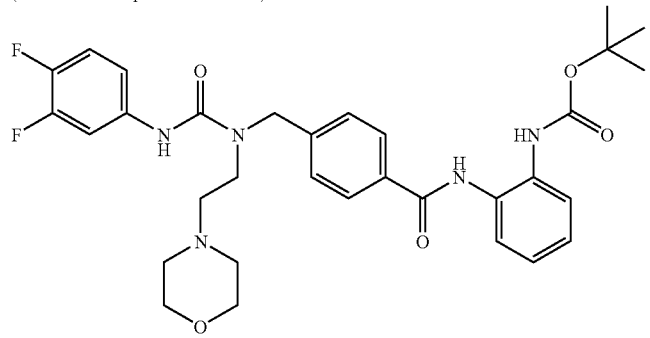

$^1$H-NMR (500 MHz, DMSO-d$_6$)
δ 1.43 (s, 9H), 2.43-2.46 (m, 6H), 3.44 (t, J = 5.6 Hz, 2H), 3.54 (t, J = 4.5 Hz, 4H), 4.69 (s, 2H), 7.14-7.21 (m, 3H), 7.30 (dd, J = 19.4, 9.0 Hz, 1H), 7.43 (d, J = 8.4 Hz, 2H), 7.51-7.56 (m, 2H), 7.65 (m, 1H), 7.93 (d, J = 8.4 Hz, 2H), 8.68 (s, 1H), 9.05 (s, 1H), 9.81 (s, 1H)

N-(2-t-Butoxycarbonylaminophenyl)-4-[3-(3,4-difluorophenyl)-1-(2-dimethylaminoethyl)ureidomethyl]benzamide
(Reference Compound No. 13-81)

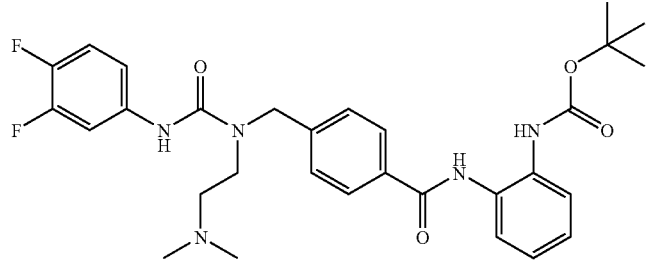

¹H-NMR (500 MHz, DMSO-d₆)
δ 1.43 (s, 9H), 2.26 (s, 6H), 2.46 (m, 2H), 3.35 (m, 2H), 4.63 (s, 2H), 7.06 (m, 1H), 7.12-7.21 (m, 2H), 7.30 (dd, J = 19.5, 9.0 Hz, 1H), 7.44 (d, J = 8.2 Hz, 2H), 7.51-7.56 (m, 2H), 7.61 (m, 1H), 7.93 (d, J = 8.2 Hz, 2H), 8.68 (s, 1H), 9.81 (s, 1H), 10.38 (s, 1H)

N-(2-t-Butoxycarbonylaminophenyl)-4-[3-(2,3-dihydrobenzo[1,4]dioxin-6-yl)-1-[3-(morpholin-4-yl)propyl]ureidomethyl]benzamide
(Reference Compound No. 13-82)

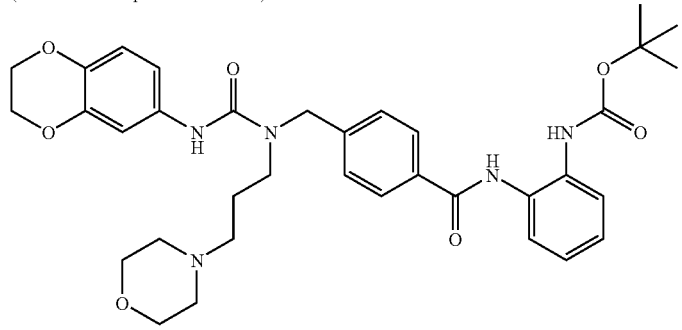

¹H-NMR (400 MHz, CDCl₃)
δ 1.51 (s, 9H), 1.71 (t, J = 5.7 Hz, 2H), 2.42-2.46 (m, 6H), 3.35 (t, J = 5.7 Hz, 2H), 3.65 (t, J = 4.6 Hz, 4H), 4.23 (s, 4H), 4.62 (s, 2H), 6.75 (s, 2H), 6.79-6.84 (m, 2H), 7.00 (s, 1H), 7.18 (ddd, J = 7.8, 7.2, 1.5 Hz, 1H), 7.24-7.29 (m, 2H), 7.43 (d, J = 8.3 Hz, 2H), 7.79 (d, J = 8.0 Hz, 1H), 7.91 (d, J = 8.3 Hz, 2H), 8.74 (s, 1H), 9.07 (s, 1H)

N-(2-t-Butoxycarbonylaminophenyl)-4-[3-(4-cyanomethylphenyl)-1-[3-(morpholin-4-yl)propyl]ureidomethyl]benzamide
(Reference Compound No. 13-83)

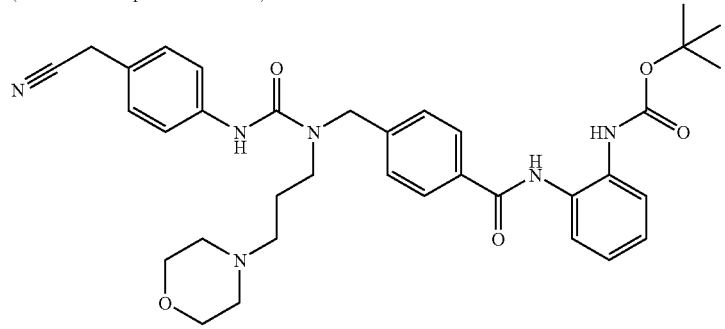

¹H-NMR (500 MHz, CDCl₃)
δ 1.51 (s, 9H), 1.75 (t, J = 5.7 Hz, 2H), 2.44-2.47 (m, 6H), 3.39 (t, J = 5.7 Hz, 2H), 3.69 (t, J = 4.6 Hz, 4H), 3.72 (s, 2H), 4.64 (s, 2H), 6.71 (s, 1H), 7.18 (ddd, J = 7.8, 7.2, 1.5 Hz, 1H) 7.24-7.29 (m, 4H), 7.43 (d, J = 8.2 Hz, 2H), 7.49 (d, J = 8.3 Hz, 2H), 7.81 (d, J = 7.6 Hz, 1H), 7.92 (d, J = 8.3 Hz, 2H), 8.83 (s, 1H), 9.10 (s, 1H)

N-(2-t-Butoxycarbonylaminophenyl)-4-[3-(4-dimethylaminophenyl)-1-(3-dimethylaminopropyl)ureidomethyl]benzamide
(Reference Compound No. 13-84)

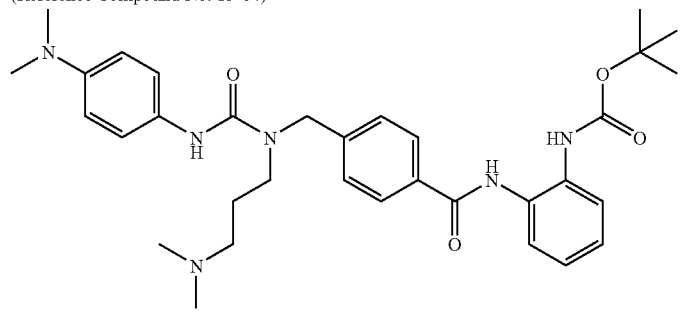

¹H-NMR (500 MHz, CDCl₃)
δ 1.51 (s, 9H), 1.66 (br s, 2H), 2.28 (s, 6H), 2.37 (br s, 2H), 2.89 (s, 6H), 3.38 (br s, 2H), 4.62 (s, 2H), 6.73 (d, J = 9.0 Hz, 2H), 6.74 (s, 1H), 7.18 (ddd, J = 7.9, 7.6, 1.5 Hz, 1H), 7.24 (ddd, J = 7.8, 7.6, 1.5 Hz, 1H), 7.29 (d, J = 7.9 Hz, 1H), 7.32 (d, J = 9.0 Hz, 2H), 7.44 (d, J = 8.3 Hz, 2H), 7.79 (d, J = 7.8 Hz, 1H), 7.91 (d, J = 8.3 Hz, 2H), 9.02 (s, 1H), 9.72 (s, 1H)

N-(2-t-Butoxycarbonylaminophenyl)-4-[3-(3,4-difluorophenyl)-1-(3-dimethylamino-2,2-dimethylpropyl)ureidomethyl]benzamide
(Reference Compound No. 13-85)

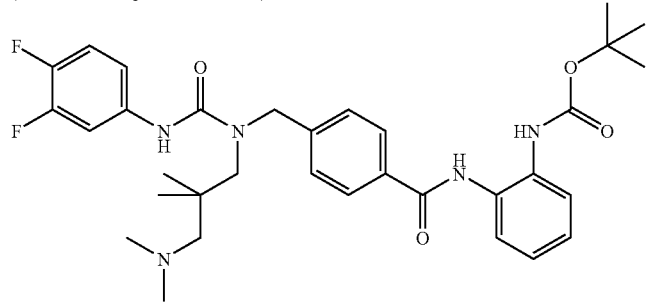

$^1$H-NMR (400 MHz, CDCl$_3$)
δ 1.05 (s, 6H), 1.49 (s, 9H), 2.32 (s, 2H), 2.37 (s, 6H), 3.25 (s, 2H), 4.72 (s, 2H), 6.80 (m, 1H), 6.95-7.08 (m, 3H), 7.14-7.24 (m, 2H), 7.33 (d, J = 8.3 Hz, 2H), 7.58 (s, 1H), 7.75 (m, 1H), 7.90 (d, J = 8.3 Hz, 2H), 9.24 (s, 1H), 10.98 (s, 1H)

N-(2-t-Butoxycarbonylaminophenyl)-4-[3-(2,3-dihydrobenzo[1,4]dioxin-6-yl)-1-(3-dimethylamino-2,2-dimethylpropyl)ureidomethyl]benzamide
(Reference Compound No. 13-86)

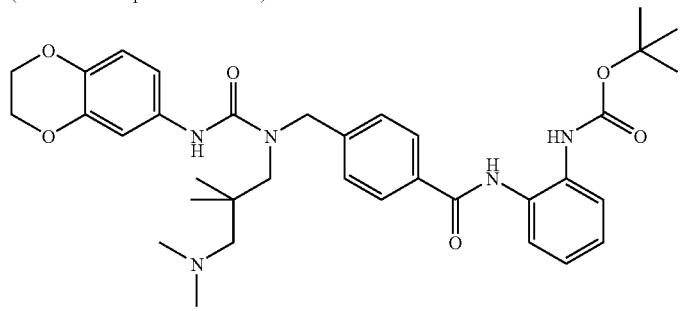

$^1$H-NMR (400 MHz, CDCl$_3$)
δ 1.03 (s, 6H), 1.50 (s, 9H), 2.28 (s, 2H), 2.36 (s, 6H), 3.21 (s, 2H), 4.21-4.24 (m, 4H), 4.72 (s, 2H), 6.78 (s, 1H), 6.80-6.90 (m, 2H), 7.07 (d, J = 2.4 Hz, 1H), 7.14-7.24 (m, 2H), 7.32 (m, 1H), 7.35 (d, J = 8.3 Hz, 2H), 7.74 (d, J = 6.6 Hz, 1H), 7.89 (d, J = 8.3 Hz, 2H), 9.03 (s, 1H), 10.43 (s, 1H)

N-(2-t-Butoxycarbonylaminophenyl)-4-[1-(3-dimethylamino-2,2-dimethylpropyl)-3-(4-dimethylaminophenyl)ureidomethyl]benzamide
(Reference Compound No. 13-87)

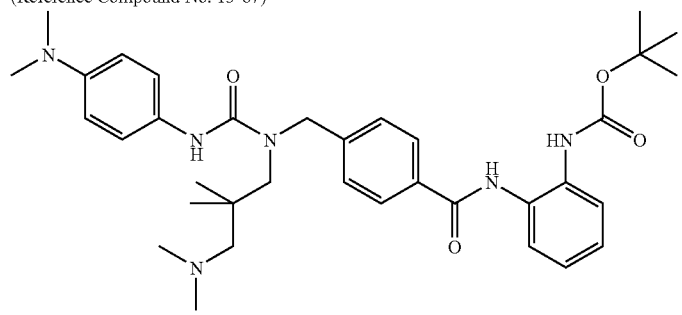

$^1$H-NMR (400 MHz, CDCl$_3$)
δ 1.02 (s, 6H), 1.50 (s, 9H), 2.27 (s, 2H), 2.34 (s, 6H), 2.89 (s, 6H), 3.21 (s, 2H), 4.73 (s, 2H), 6.73 (d, J = 9.0 Hz, 2H), 6.76 (s, 1H), 7.15-7.25 (m, 2H), 7.28-7.40 (m, 5H), 7.76 (d, J = 9.3 Hz, 1H), 7.89 (d, J = 8.3 Hz, 2H), 8.96 (s, 1H), 10.21 (s, 1H)

N-(2-t-Butoxycarbonylaminophenyl)-4-[3-(2,3-dihydrobenzo[1,4]dioxin-6-yl)-1-[2-(4-methylpiperazin-1-yl)ethyl]ureidomethyl]benzamide
(Reference Compound No. 13-88)

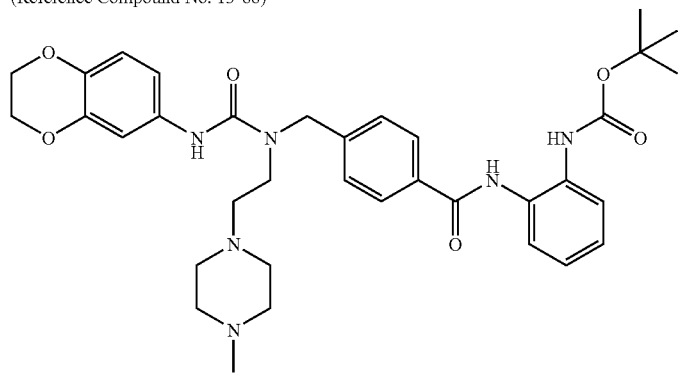

$^1$H-NMR (400 MHz, CDCl$_3$)
δ 1.51 (s, 9H), 2.31 (s, 3H), 2.49 (t, J = 4.2 Hz, 2H), 2.61 (br s, 8H), 3.34 (t, J = 4.2 Hz, 2H), 4.22-4.26 (m, 4H), 4.62 (s, 2H), 6.79 (d, J = 8.8 Hz, 1H), 6.79 (br s, 1H), 6.88 (dd, J = 8.8, 2.4 Hz, 1H), 7.04 (d, J = 2.4 Hz, 1H), 7.15-7.28 (m, 3H), 7.42 (d, J = 8.3 Hz, 2H), 7.80 (d, J = 7.8 Hz, 1H), 7.92 (d, J = 8.3 Hz, 2H), 9.13 (br s, 1H), 9.72 (br s, 1H)

N-(2-t-Butoxycarbonylaminophenyl)-4-[3-(2,3-dihydrobenzo[1,4]dioxin-6-yl)-1-[2-(1-methylpyrrolidin-2-yl)ethyl]ureidomethyl]benzamide
(Reference Compound No. 13-89)

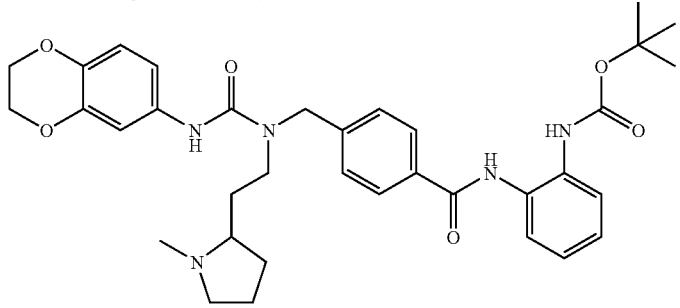

¹H-NMR (400 MHz, CDCl₃)
δ 1.51 (s, 9H), 1.57-1.79 (m, 4H), 1.81-1.94 (m, 2H), 2.26-2.44 (m, 5H), 3.15-3.46 (m, 3H), 4.20-4.25 (m, 4H), 4.53 (d, J = 15.6 Hz, 1H), 4.70 (d, J = 15.6 Hz, 1H), 6.77 (d, J = 8.8 Hz, 1H), 6.81 (s, 1H), 6.86 (dd, J = 8.8, 2.4 Hz, 1H), 7.01 (d, J = 2.4 Hz, 1H), 7.17 (td, J = 7.7, 1.7 Hz, 1H), 7.21-7.30 (m, 2H), 7.43 (d, J = 8.3 Hz, 2H), 7.79 (d, J = 7.7 Hz, 1H), 7.92 (d, J = 8.3 Hz, 2H), 9.09 (br s, 1H), 9.45 (br s, 1H)

N-(2-t-Butoxycarbonylaminophenyl)-4-[3-(4-dimethylaminophenyl)-1-[2-(1-methylpyrrolidin-2-yl)ethyl]ureidomethyl]benzamide
(Reference Compound No. 13-90)

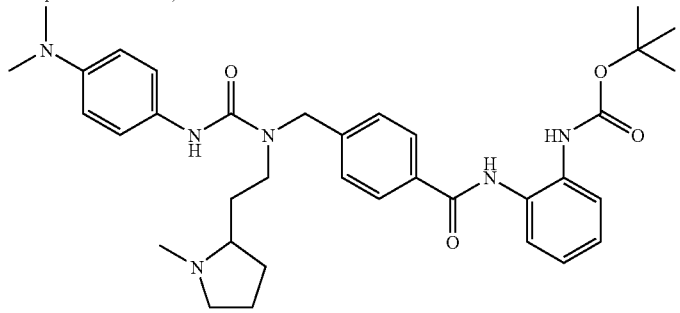

¹H-NMR (400 MHz, CDCl₃)
δ 1.51 (s, 9H), 1.55-1.80 (m, 4H), 1.81-1.96 (m, 2H), 2.24-2.42 (m, 5H), 2.89 (s, 6H), 3.13-3.47 (m, 3H), 4.56 (d, J = 15.6 Hz, 1H), 4.71 (d, J = 15.6 Hz, 1H), 6.73 (d, J = 9.0 Hz, 2H), 6.77 (s, 1H), 7.18 (td, J = 7.6, 1.6 Hz, 1H), 7.22-7.30 (m, 2H), 7.28 (d, J = 9.0 Hz, 2H), 7.44 (d, J = 8.3 Hz, 2H), 7.79 (d, J = 7.6 Hz, 1H), 7.92 (d, J = 8.3 Hz, 2H), 9.08 (br s, 2H)

N-(2-t-Butoxycarbonylaminophenyl)-4-[3-(3,4-difluorophenyl)-1-[2-(1-methylpyrrolidin-2-yl)ethyl]ureidomethyl]benzamide
(Reference Compound No. 13-91)

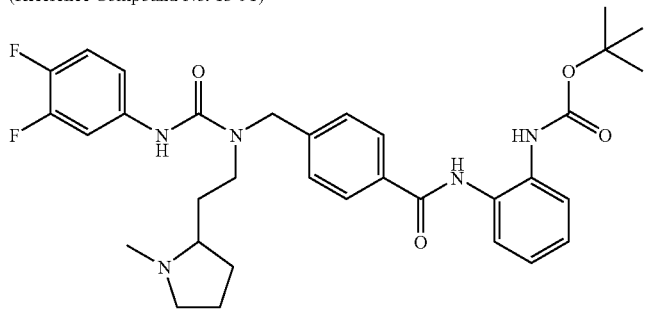

¹H-NMR (400 MHz, CDCl₃)
δ 1.51 (s, 9H), 1.58-1.80 (m, 4H), 1.83-1.95 (m, 2H), 2.31-2.49 (m, 5H), 3.13-3.48 (m, 3H), 4.51 (d, J = 15.4 Hz, 1H), 6.83 (s, 1H), 6.96 (m, 1H), 7.04 (dd, J = 18.8, 8.8 Hz, 1H), 7.17 (td, J = 7.7, 1.5 Hz, 1H), 7.21-7.29 (m, 2H), 7.42 (d, J = 8.3 Hz, 2H), 7.51 (m, 1H), 7.79 (d, J = 7.7 Hz, 1H), 7.92 (d, J = 8.3 Hz, 2H), 9.15 (br s, 1H), 10.05 (br s, 1H)

N-(2-t-Butoxycarbonylaminophenyl)-4-[3-(4-methoxycarbonylphenyl)-1-[3-(morpholin-4-yl)propyl]ureidomethyl]benzamide
(Reference Compound No. 13-92)

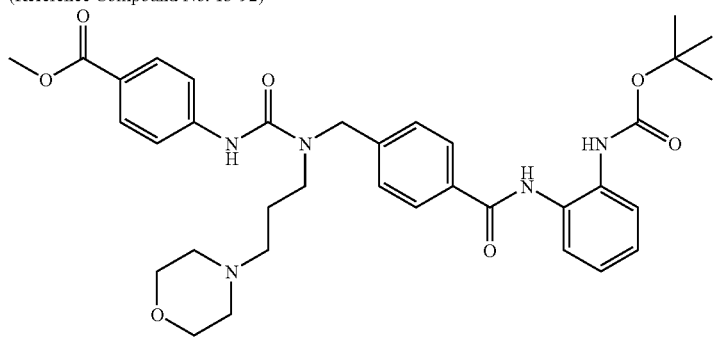

¹H-NMR (400 MHz, CDCl₃)
δ 1.51 (s, 9H), 1.77 (m, 2H), 2.43-2.50 (m, 6H), 3.40 (t, J = 5.6 Hz, 2H), 3.74 (t, J = 4.5 Hz, 4H), 3.90 (s, 3H), 4.65 (s, 2H), 6.70 (s, 1H), 7.18 (td, J = 7.8, 1.7 Hz, 1H), 7.23-7.28 (m, 2H), 7.43 (d, J = 8.3 Hz, 2H), 7.59 (d, J = 8.8 Hz, 2H), 7.82 (d, J = 7.8 Hz, 1H), 7.93 (d, J = 8.3 Hz, 2H), 8.00 (d, J = 8.8 Hz, 2H), 8.90 (br s, 1H), 9.12 (br s, 1H)

4-[3-(Benzo[1,3]dioxol-5-yl)-1-[3-(morpholin-4-yl)propyl]ureidomethyl]-N-(2-t-butoxycarbonylaminophenyl)benzamide
(Reference Compound No. 13-93)

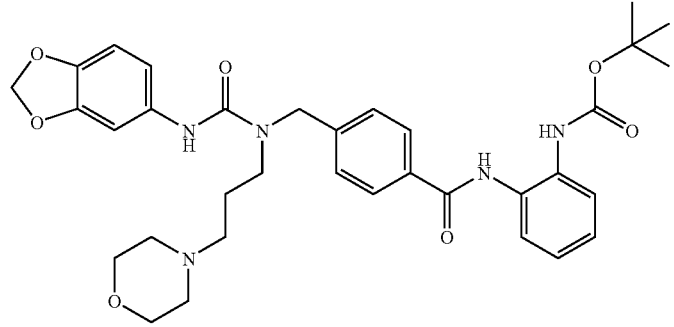

¹H-NMR (400 MHz, CDCl₃)
δ 1.50 (s, 9H), 1.72 (m, 2H), 2.39-2.49 (m, 6H), 3.35 (t, J = 5.6 Hz, 2H), 3.64 (t, J = 4.5 Hz, 4H), 4.62 (s, 2H), 5.94 (s, 2H), 6.70 (dd, J = 8.3, 2.0 Hz, 1H), 6.74 (d, J = 8.3 Hz, 1H), 6.80 (s, 1H), 7.09 (d, J = 2.0 Hz, 1H), 7.17 (td, J = 7.8, 1.7 Hz, 1H), 7.21-7.29 (m, 2H), 7.42 (d, J = 8.3 Hz, 2H), 7.78 (d, J = 7.8 Hz, 1H), 7.91 (d, J = 8.3 Hz, 2H), 8.87 (br s, 1H), 9.11 (br s, 1H)

N-(2-t-Butoxycarbonylaminophenyl)-4-[3-(4-methylphenyl)-1-[3-(morpholin-4-yl)propyl]ureidomethyl]benzamide
(Reference Compound No. 13-94)

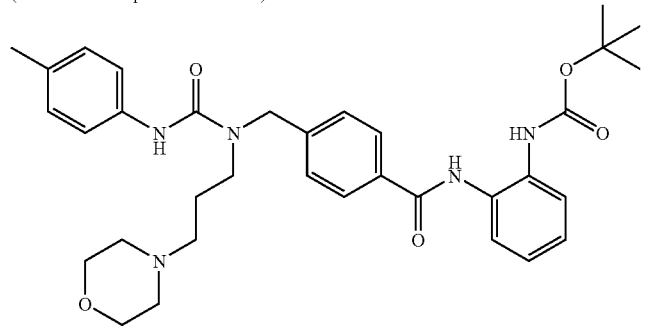

¹H-NMR (400 MHz, CDCl₃)
δ 1.50 (s, 9H), 1.73 (m, 2H), 2.31 (s, 3H), 2.39-2.48 (m, 6H), 3.37 (t, J = 5.6 Hz, 2H), 3.67 (t, J = 4.6 Hz, 4H), 4.63 (s, 2H), 6.78 (s, 1H), 7.11 (d, J = 8.2 Hz, 2H), 7.17 (td, J = 7.7, 1.7 Hz, 1H), 7.21-7.29 (m, 2H), 7.32 (d, J = 8.2 Hz, 2H), 7.43 (d, J = 8.3 Hz, 2H), 7.78 (d, J = 7.7 Hz, 1H), 7.91 (d, J = 8.3 Hz, 2H), 8.70 (br s, 1H), 9.10 (br s, 1H)

N-(2-t-Butoxycarbonylaminophenyl)-4-[1-(3-dimethylaminopropyl)-3-(3-ethoxyphenyl)ureidomethyl]benzamide
(Reference Compound No. 13-95)

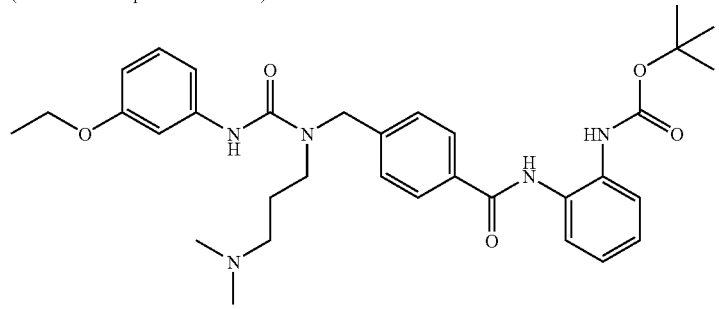

¹H-NMR (500 MHz, CDCl₃)
δ 1.40 (t, J = 7.0 Hz, 3H), 1.51 (s, 9H), 1.67 (m, 2H), 2.30 (s, 6H), 2.36 (t, J = 5.5 Hz, 2H), 3.38 (t, J = 6.0 Hz, 2H), 4.04 (q, J = 7.0 Hz, 2H), 4.62 (s, 2H), 6.53 (ddd, J = 8.3, 2.4, 0.9 Hz, 1H), 6.71 (s, 1H), 6.89 (ddd, J = 7.9, 2.4, 0.9 Hz, 1H), 7.13-7.16 (m, 2H), 7.18-7.30 (m, 3H), 7.44 (d, J = 8.3 Hz, 2H), 7.80 (d, J = 7.9 Hz, 1H), 7.91 (d, J = 8.3 Hz, 2H), 9.04 (s, 1H), 10.12 (s, 1H)

N-(2-t-Butoxycarbonylaminophenyl)-4-[1-(3-dimethylaminopropyl)-3-(4-fluoro-3-nitrophenyl)ureidomethyl]benzamide
(Reference Compound No. 13-96)

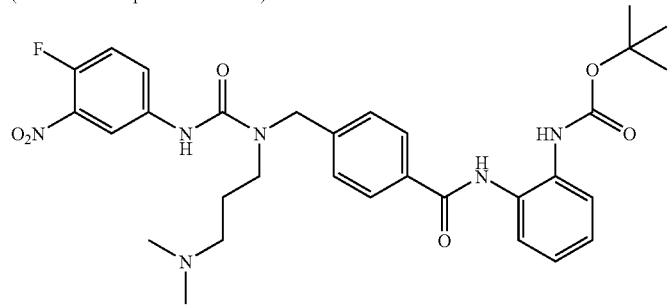

¹H-NMR (500 MHz, CDCl₃)
δ 1.51 (s, 9H), 1.71 (m, 2H), 2.33 (s, 6H), 2.39 (t, J = 5.9 Hz, 2H), 3.39 (t, J = 5.7 Hz, 2H), 4.62 (s, 2H), 6.74 (s, 1H), 7.14-7.20 (m, 2H), 7.23-7.28 (m, 2H), 7.43 (d, J = 8.3 Hz, 2H), 7.82 (d, J = 8.3 Hz, 1H), 7.87 (m, 1H), 7.93 (d, J = 8.3 Hz, 2H), 8.06 (dd, J = 7.7, 2.8 Hz, 1H), 9.13 (s, 1H), 10.72 (s, 1H)

| | |
|---|---|
| N-(2-t-Butoxycarbonylaminophenyl)-4-[3-(4-cyanophenyl)-1-(3-dimethylaminopropyl)ureidomethyl]benzamide (Reference Compound No. 13-97) 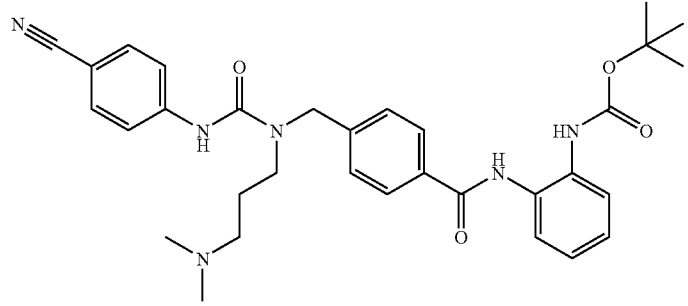 | $^1$H-NMR (500 MHz, CDCl$_3$) δ 1.51 (s, 9H), 1.71 (m, 2H), 2.31 (s, 6H), 2.39 (t, J = 6.0 Hz, 2H), 3.39 (t, J = 5.7 Hz, 2H), 4.62 (s, 2H), 6.69 (s, 1H), 7.19 (dd, J = 7.6, 1.6 Hz, 1H), 7.23-7.28 (m, 2H), 7.43 (d, J = 8.5 Hz, 2H), 7.52-7.54 (m, 4H), 7.82 (d, J = 8.3 Hz, 1H), 7.93 (d, J = 8.5 Hz, 2H), 9.12 (s, 1H), 10.72 (s, 1H) |
| N-(2-t-Butoxycarbonylaminophenyl)-4-[1-(3-dimethylaminopropyl)-3-(pyridin-3-yl)ureidomethyl]benzamide (Reference Compound No. 13-98) 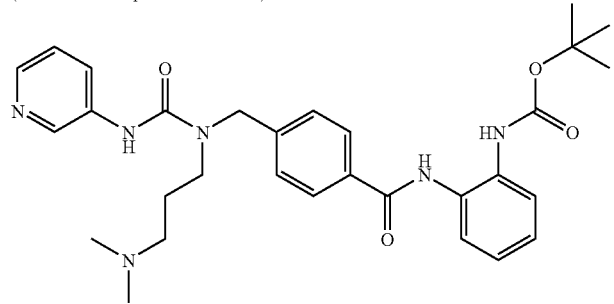 | $^1$H-NMR (500 MHz, CDCl$_3$) δ 1.51 (s, 9H), 1.72 (m, 2H), 2.32 (s, 6H), 2.41 (t, J = 5.9 Hz, 2H), 3.39 (t, J = 5.7 Hz, 2H), 4.63 (s, 2H), 6.92 (s, 1H), 7.15-7.23 (m, 2H), 7.29 (dd, J = 7.7, 1.5 Hz, 1H), 7.43 (d, J = 8.5 Hz, 2H), 7.76 (d, J = 7.0 Hz, 1H), 7.92 (d, J = 8.5 Hz, 2H), 8.08 (m, 1H), 8.16 (ddd, J = 8.3, 2.4, 1.5 Hz, 1H), 8.22 (ddd, J = 7.8, 4.9, 1.5 Hz, 1H), 8.41 (d, J = 2.4 Hz, 1H), 9.32 (s, 1H), 10.56 (s, 1H) |
| N-(2-t-Butoxycarbonylaminophenyl)-4-[3-(4-cyanophenyl)-1-[3-(morpholin-4-yl)propyl]ureidomethyl]benzamide (Reference Compound No. 13-99) 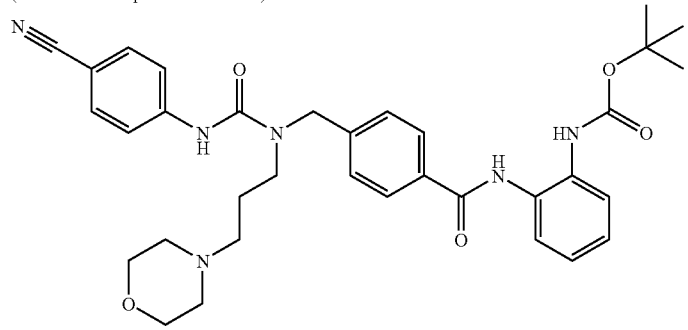 | $^1$H-NMR (500 MHz, CDCl$_3$) δ 1.49 (s, 9H), 1.77 (m, 2H), 2.41-2.50 (m, 6H), 3.38 (t, J = 5.5 Hz, 2H), 3.72 (t, J = 4.6 Hz, 4H), 4.62 (s, 2H), 7.11-7.18 (m, 3H), 7.27 (m, 1H), 7.37 (d, J = 8.2 Hz, 2H), 7.56 (d, J = 8.7 Hz, 2H), 7.63 (d, J = 8.7 Hz, 2H), 7.70 (d, J = 7.6 Hz, 1H), 7.90 (d, J = 8.2 Hz, 2H), 9.04 (br s, 1H), 9.36 (br s, 1H) |
| N-(2-t-Butoxycarbonylaminophenyl)-4-[3-(4-isopropylphenyl)-1-[3-(morpholin-4-yl)propyl]ureidomethyl]benzamide (Reference Compound No. 13-100) 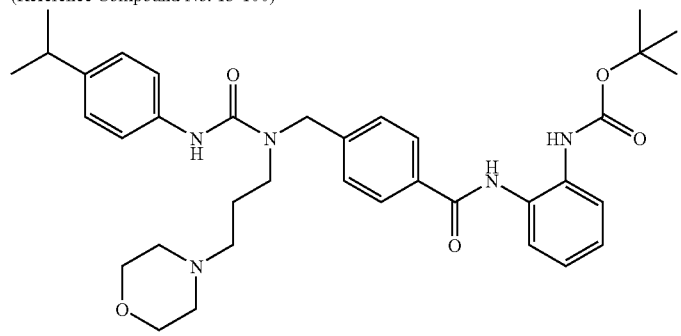 | $^1$H-NMR (500 MHz, CDCl$_3$) δ 1.22 (d, J = 7.0 Hz, 6H), 1.47 (s, 9H), 1.71 (m, 2H), 2.39-2.45 (m, 6H), 2.86 (m, 1H), 3.34 (t, J = 5.7 Hz, 2H), 3.65 (t, J = 4.6 Hz, 4H), 4.59 (s, 2H), 7.10-7.12 (m, 2H), 7.14 (d, J = 8.2 Hz, 2H), 7.31-7.36 (m, 6H), 7.62 (m, 1H), 7.86 (d, J = 8.2 Hz, 2H), 8.73 (br s, 1H), 9.36 (br s, 1H) |

N-(2-t-Butoxycarbonylaminophenyl)-4-[3-(4-chlorophenyl)-1-(3-dimethylaminopropyl)ureidomethyl]benzamide
(Reference Compound No. 13-101)

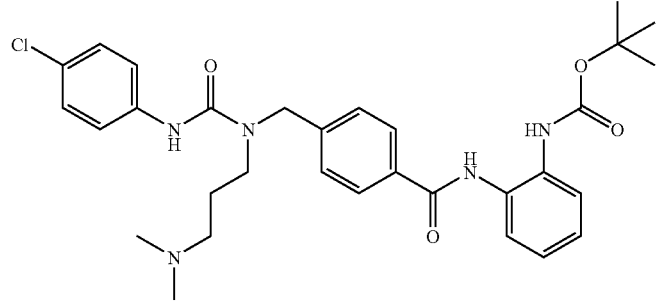

¹H-NMR (500 MHz, CDCl₃)
δ 1.51 (s, 9H), 1.68 (m, 2H), 2.29 (s, 6H), 2.37 (t, J = 6.0 Hz, 2H), 3.38 (t, J = 5.5 Hz, 2H), 4.61 (s, 2H), 6.72 (s, 1H), 7.19 (dd, J = 7.6, 1.6 Hz, 1H), 7.23 (d, J = 8.9 Hz, 2H), 7.21-7.29 (m, 2H), 7.40 (d, J = 8.9 Hz, 2H), 7.44 (dd, J = 8.2 Hz, 2H), 7.81 (d, J = 7.9 Hz, 1H), 7.92 (d, J = 8.2 Hz, 2H), 9.07 (s, 1H), 10.23 (s, 1H)

4-[3-(4-Acetylphenyl)-1-(3-dimethylaminopropyl)ureidomethyl]-N-(2-t-butoxycarbonylaminophenyl)benzamide
(Reference Compound No. 13-102)

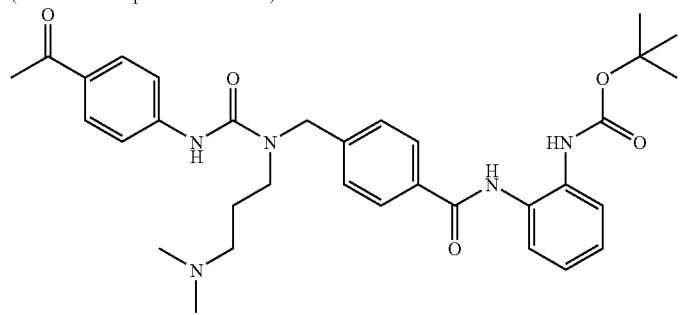

¹H-NMR (500 MHz, CDCl₃)
δ 1.53 (s, 9H), 1.70 (t, J = 5.5 Hz, 2H), 2.32 (s, 6H), 2.39 (t, J = 6.0 Hz, 2H), 2.56 (s, 3H), 3.40 (t, J = 5.7 Hz, 2H), 4.63 (s, 2H), 6.71 (s, 1H), 7.18 (td, J = 7.6, 1.5 Hz, 1H), 7.24-7.27 (m, 2H), 7.45 (d, J = 8.2 Hz, 2H), 7.52 (d, J = 8.9 Hz, 2H), 7.82 (d, J = 7.6 Hz, 1H), 7.91 (d, J = 8.9 Hz, 2H), 7.93 (d, J = 8.2 Hz, 2H), 9.09 (s, 1H), 10.62 (s, 1H)

N-(2-t-Butoxycarbonylaminophenyl)-4-[1-(3-dimethylaminopropyl)-3-(4-nitrophenyl)ureidomethyl]benzamide
(Reference Compound No. 13-103)

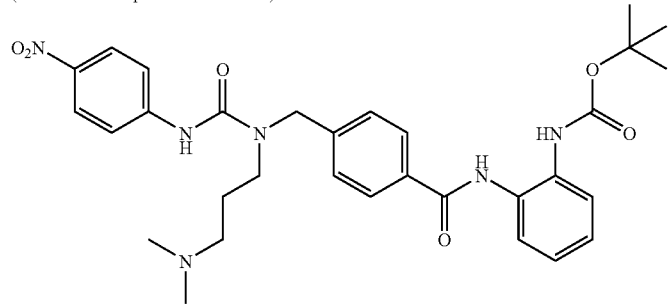

¹H-NMR (500 MHz, CDCl₃)
δ 1.51 (s, 9H), 1.73 (m, 2H), 2.33 (s, 6H), 2.40 (t, J = 6.0 Hz, 2H), 3.41 (t, J = 5.7 Hz, 2H), 4.63 (s, 2H), 6.70 (s, 1H), 7.19 (td, J = 7.6, 1.5 Hz, 1H), 7.24-7.27 (m, 2H), 7.44 (d, J = 8.0 Hz, 2H), 7.56 (d, J = 9.5 Hz, 2H), 7.82 (d, J = 7.6 Hz, 1H), 7.94 (d, J = 8.0 Hz, 2H), 8.17 (d, J = 9.5 Hz, 2H), 9.13 (s, 1H), 10.94 (s, 1H)

N-(2-t-Butoxycarbonylaminophenyl)-4-[3-(4-dimethylaminophenyl)-1-[2-(4-methylpiperazin-1-yl)ethyl]ureidomethyl]benzamide
(Reference Compound No. 13-104)

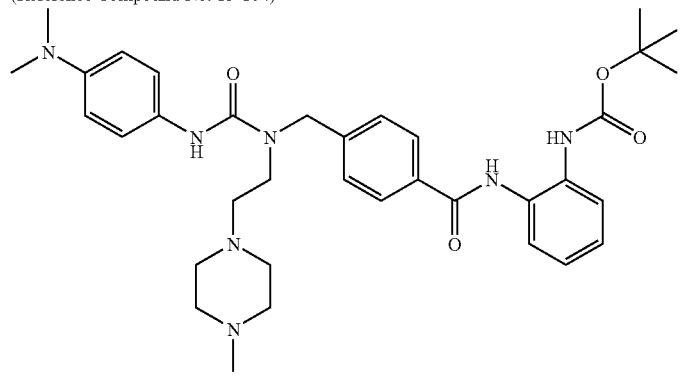

¹H-NMR (400 MHz, CDCl₃)
δ 1.51 (s, 9H), 2.30 (s, 3H), 2.49 (t, J = 4.3 Hz, 2H), 2.49 (br s, 4H), 2.61 (br s, 4H), 2.91 (s, 6H), 3.35 (t, J = 4.3 Hz, 2H), 4.63 (s, 2H), 6.74 (d, J = 9.0 Hz, 2H), 6.82 (s, 1H), 7.15-7.27 (m, 3H), 7.30 (d, J = 9.0 Hz, 2H), 7.42 (d, J = 8.3 Hz, 2H), 7.79 (dd, J = 7.8, 1.0 Hz, 1H), 7.92 (d, J = 8.3 Hz, 2H), 9.13 (br s, 1H), 9.57 (br s, 1H)

N-(2-t-Butoxycarbonylaminophenyl)-4-[3-(3,4-difluorophenyl)-1-[2-(4-methylpiperazin-1-yl)ethyl]ureidomethyl]benzamide
(Reference Compound No. 13-105)

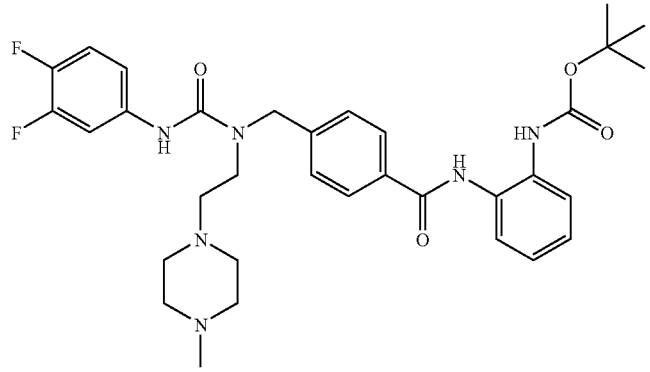

¹H-NMR (400 MHz, CDCl₃)
δ 1.51 (s, 9H), 2.31 (s, 3H), 2.51 (br s, 4H), 2.52 (t, J = 4.3 Hz, 2H), 2.64 (br s, 4H), 3.35 (t, J = 4.3 Hz, 2H), 4.63 (s, 2H), 6.76 (br s, 1H), 7.06-7.25 (m, 5H), 7.41 (d, J = 8.3 Hz, 2H), 7.49 (m, 1H), 7.82 (d, J = 7.6 Hz, 1H), 7.94 (d, J = 8.3 Hz, 2H), 9.17 (br s, 1H), 10.13 (br s, 1H)

4-[3-(Benzo[1,3]dioxol-5-yl)-1-[2-(4-methylpiperazin-1-yl)ethyl]ureidomethyl]-N-(2-t-butoxycarbonylaminophenyl)benzamide
(Reference Compound No. 13-106)

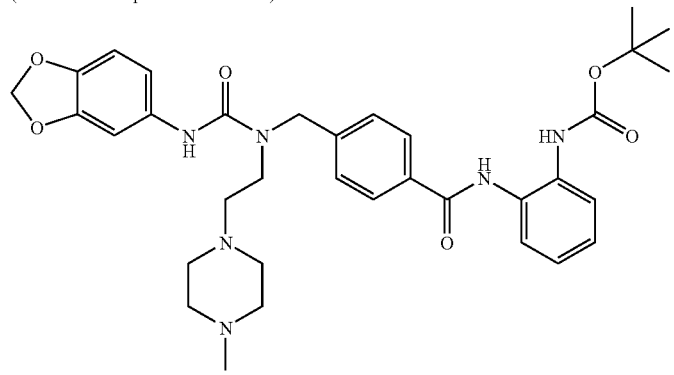

¹H-NMR (400 MHz, CDCl₃)
δ 1.51 (s, 9H), 2.30 (s, 3H), 2.49 (br s, 4H), 2.50 (t, J = 4.3 Hz, 2H), 2.62 (br s, 4H), 3.34 (t, J = 4.3 Hz, 2H), 4.62 (s, 2H), 5.93 (s, 2H), 6.71-6.77 (m, 2H), 6.79 (br s, 1H), 7.13 (m, 1H), 7.15-7.28 (m, 3H), 7.42 (d, J = 8.3 Hz, 2H), 7.80 (d, J = 7.1 Hz, 1H), 7.93 (d, J = 8.3 Hz, 2H), 9.15 (br s, 1H), 9.82 (br s, 1H)

N-(2-t-Butoxycarbonylaminophenyl)-4-[3-(2,3-dihydrobenzo[1,4]dioxin-6-yl)-1-[[2-hydroxy-3-(morpholin-4-yl)]propyl]ureidomethyl]benzamide
(Reference Compound No. 13-107)

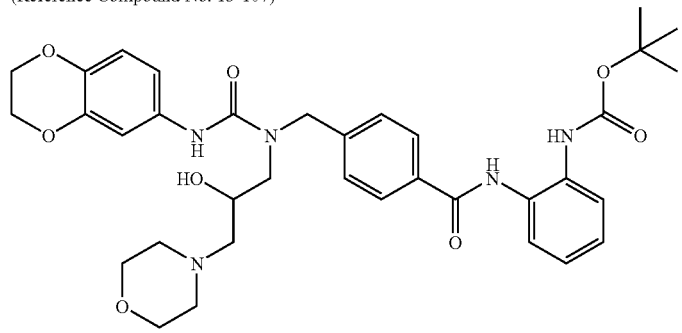

¹H-NMR (500 MHz, CDCl₃)
δ 1.51 (s, 9H), 2.28 (dd, J = 12.2, 4.0 Hz, 1H), 2.31-2.42 (m, 3H), 2.61 (m, 2H), 3.32 (m, 2H), 3.67-3.75 (m, 4H), 3.84 (m, 1H), 4.20-4.25 (m, 4H), 4.51 (d, J = 15.7 Hz, 1H), 4.79 (d, J = 15.7 Hz, 1H), 6.74 (br s, 1H), 6.77 (d, J = 8.6 Hz, 1H), 6.82 (dd, J = 8.6, 2.4 Hz, 1H), 7.00 (d, J = 2.4 Hz, 1H), 7.18 (td, J = 7.9, 1.5 Hz, 1H), 7.23-7.28 (m, 2H), 7.41 (d, J = 8.2 Hz, 2H), 7.82 (d, J = 7.9 Hz, 1H), 7.93 (d, J = 8.2 Hz, 2H), 8.52 (br s, 1H), 9.13 (br s, 1H)

N-(2-t-Butoxycarbonylaminophenyl)-4-[3-(4-dimethylaminophenyl)-1-[2-hydroxy-3-(morpholin-4-yl)]propylureidomethyl]benzamide
(Reference Compound No. 13-108)

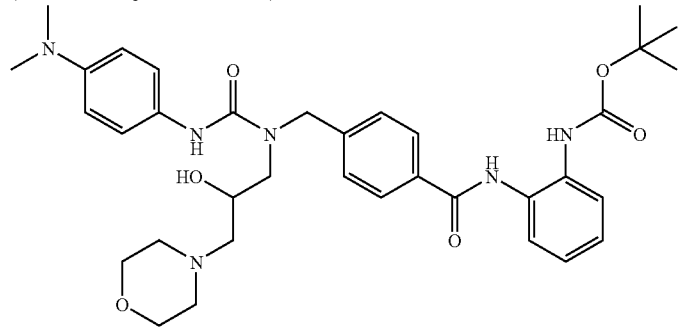

¹H-NMR (500 MHz, CDCl₃)
δ 1.51 (s, 9H), 2.30 (dd, J = 12.2, 4.0 Hz, 1H), 2.33-2.43 (m, 3H), 2.61 (m, 2H), 2.89 (s, 6H), 3.34 (m, 2H), 3.67-3.75 (m, 4H), 3.86 (m, 1H), 4.54 (d, J = 15.9 Hz, 1H), 4.80 (d, J = 15.9 Hz, 1H), 6.71 (d, J = 8.9 Hz, 2H), 6.75 (s, 1H), 7.18 (td, J = 7.6, 1.2 Hz, 1H), 7.23-7.28 (m, 4H), 7.42 (d, J = 8.1 Hz, 2H), 7.81 (d, J = 7.6 Hz, 1H), 7.93 (d, J = 8.1 Hz, 2H), 8.29 (br s, 1H), 9.12 (br s, 1H)

N-(2-t-Butoxycarbonylaminophenyl)-4-[3-(3,4-difluorophenyl)-1-[2-hydroxy-3-(morpholin-4-yl)]propylureidomethyl]benzamide
(Reference Compound No. 13-109)

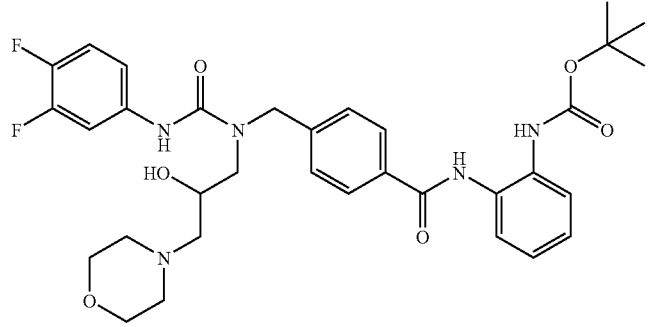

¹H-NMR (400 MHz, CDCl₃)
δ 1.52 (s, 9H), 2.27-2.44 (m, 4H), 2.64 (m, 2H), 3.32 (m, 2H), 3.65-3.76 (m, 4H), 3.85 (m, 1H), 4.34 (br s, 1H), 4.51 (d, J = 15.7 Hz, 1H), 4.78 (d, J = 15.7 Hz, 1H), 6.72 (s, 1H), 6.92-7.12 (m, 2H), 7.18 (td, J = 7.8, 1.7 Hz, 1H), 7.22-7.29 (m, 2H), 7.41 (d, J = 8.3 Hz, 2H), 7.45 (m, 1H), 7.83 (d, J = 7.8 Hz, 1H), 7.94 (d, J = 8.3 Hz, 2H), 8.93 (br s, 1H), 9.18 (br s, 1H)

N-(2-t-Butoxycarbonylaminophenyl)-4-[3-(4-fluorophenyl)-1-[3-(morpholin-4-yl)propyl]ureidomethyl]benzamide
(Reference Compound No. 13-110)

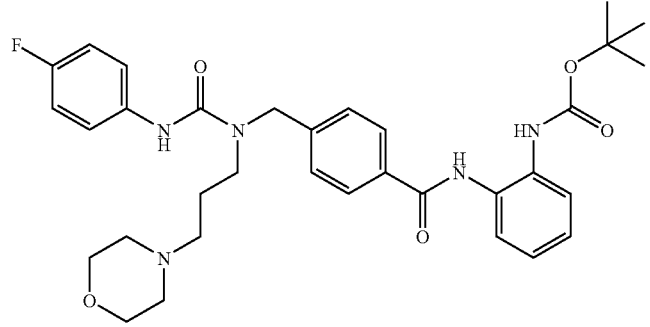

¹H-NMR (400 MHz, CDCl₃)
δ 1.47 (s, 9H), 1.71 (m, 2H), 2.37-2.46 (m, 6H), 3.34 (t, J = 5.6 Hz, 2H), 3.61 (t, J = 4.4 Hz, 4H), 4.58 (s, 2H), 6.97 (t, J = 8.7 Hz, 2H), 7.08-7.13 (m, 2H), 7.30-7.37 (m, 6H), 7.62 (m, 1H), 7.86 (d, J = 8.3 Hz, 2H), 8.93 (br s, 1H), 9.37 (br s, 1H)

4-[3-Benzyl-1-[3-(morpholin-4-yl)propyl]ureidomethyl]-N-(2-t-butoxycarbonylaminophenyl)benzamide
(Reference Compound No. 13-111)

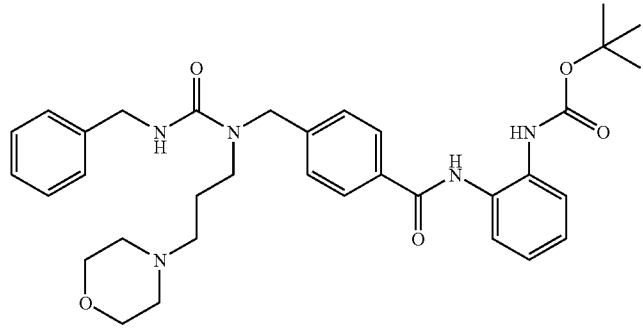

¹H-NMR (400 MHz, CDCl₃)
δ 1.51 (s, 9H), 1.61 (m, 2H), 2.24 (br s, 4H), 2.32 (t, J = 6.0 Hz, 2H), 3.28 (t, J = 5.6 Hz, 2H), 3.41 (br s, 4H), 4.50 (d, J = 5.6 Hz, 2H), 4.62 (s, 2H), 6.88 (br s, 1H), 7.15-7.36 (m, 8H), 7.39 (d, J = 8.3 Hz, 2H), 7.42 (br s, 1H), 7.78 (dd, J = 7.9, 1.3 Hz, 1H), 7.91 (d, J = 8.3 Hz, 2H), 9.14 (br s, 1H)

N-(2-t-Butoxycarbonylaminophenyl)-4-[1-[3-(morpholin-4-yl)propyl]-3-(3-phenylpropyl)ureidomethyl]benzamide
(Reference Compound No. 13-112)

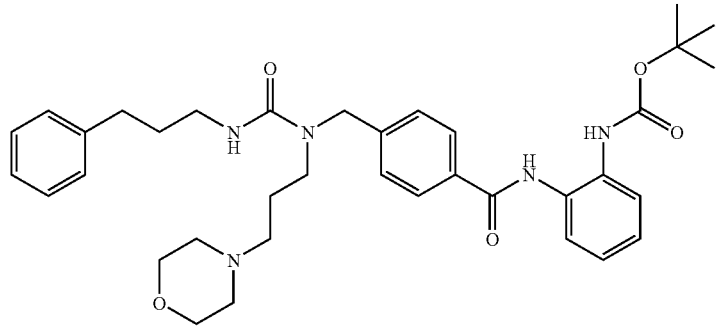

$^1$H-NMR (400 MHz, CDCl$_3$)
δ 1.50 (s, 9H), 1.62 (m, 2H), 1.88 (m, 2H), 2.33 (t, J = 6.1 Hz, 2H), 2.40 (br s, 4H), 2.67 (t, J = 7.6 Hz, 2H), 3.19 (t, J = 5.9 Hz, 2H), 3.27 (q, J = 6.8 Hz, 2H), 3.66 (t, J = 4.4 Hz, 4H), 4.55 (s, 2H), 6.78 (s, 1H), 6.81 (br s, 1H), 7.15-7.30 (m, 8H), 7.36 (d, J = 8.2 Hz, 2H), 7.79 (dd, J = 7.9, 1.1 Hz, 1H), 7.91 (d, J = 8.2 Hz, 2H), 9.10 (br s, 1H)

N-(2-t-Butoxycarbonylaminophenyl)-4-[1-(3-dimethylaminopropyl)-3-(thiophen-2-yl)-ureidomethyl]benzamide
(Reference Compound No. 13-113)

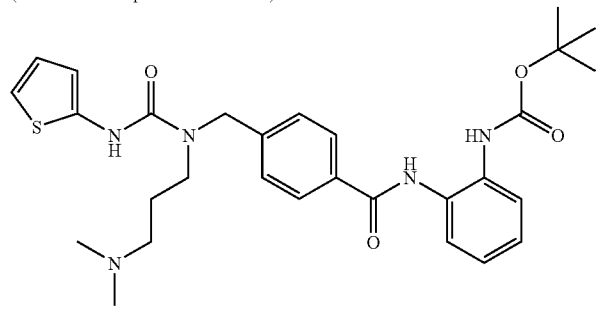

$^1$H-NMR (500 MHz, CDCl$_3$)
δ 1.51 (s, 9H), 1.65 (m, 2H), 2.30 (s, 6H), 2.35 (t, J = 6.0 Hz, 2H), 3.34 (t, J = 5.7 Hz, 2H), 4.64 (s, 2H), 6.44 (dd, J = 3.5, 1.2 Hz, 1H), 6.76 (dd, J = 5.5, 1.2 Hz, 1H), 6.82 (dd, J = 5.5, 3.5 Hz, 1H), 6.85 (s, 1H), 7.17 (td, J = 7.6, 1.5 Hz, 1H), 7.22 (td, J = 7.6, 1.5 Hz, 1H), 7.28 (dd, J = 7.6, 1.5 Hz, 1H), 7.41 (d, J = 8.2 Hz, 2H), 7.78 (d, J = 7.6 Hz, 1H), 7.90 (d, J = 8.2 Hz, 2H), 9.13 (s, 1H), 11.50 (s, 1H)

N-(2-t-Butoxycarbonylaminophenyl)-4-[1-(3-dimethylaminopropyl)-3-(thiophen-3-yl)ureidomethyl]benzamide
(Reference Compound No. 13-114)

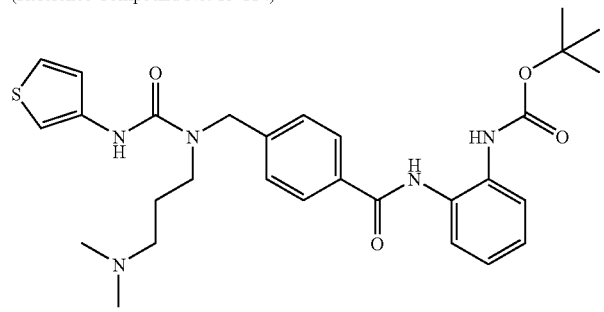

$^1$H-NMR (500 MHz, CDCl$_3$)
δ 1.51 (s, 9H), 1.65 (m, 2H), 2.29 (s, 6H), 2.36 (t, J = 6.0 Hz, 2H), 3.35 (t, J = 5.7 Hz, 2H), 4.62 (s, 2H), 6.81 (s, 1H), 6.92 (dd, J = 5.1, 1.3 Hz, 1H), 7.17 (td, J =7.6, 1.5 Hz, 1H), 7.20 (dd, J = 5.1, 3.2 Hz, 1H), 7.23 (td, J = 7.6, 1.5 Hz, 1H), 7.28 (dd, J = 7.6, 1.5 Hz, 1H), 7.35 (dd, J = 3.2, 1.3 Hz, 1H), 7.42 (d, J = 8.2 Hz, 2H), 7.78 (d, J = 7.6 Hz, 1H), 7.91 (d, J = 8.2 Hz, 2H), 9.09 (s, 1H), 10.53 (s, 1H)

N-(2-t-Butoxycarbonylaminophenyl)-4-[1-(3-dimethylaminopropyl)-3-(4-ethoxyphenyl)ureidomethyl]benzamide
(Reference Compound No. 13-115)

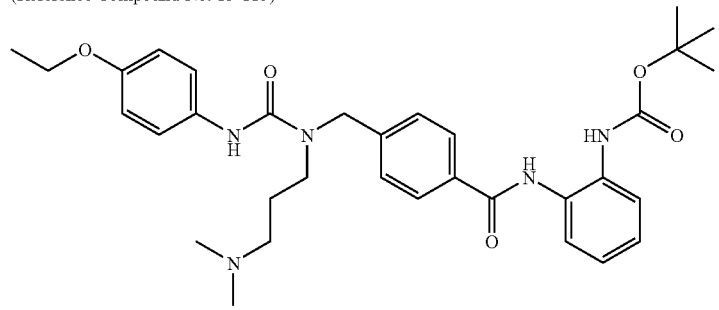

$^1$H-NMR (500 MHz, CDCl$_3$)
δ 1.39 (t, J = 7.0 Hz, 3H), 1.50 (s, 9H), 1.66 (m, 2H), 2.27 (s, 6H), 2.36 (t, J = 6.0 Hz, 2H), 3.36 (t, J = 5.7 Hz, 2H), 4.00 (q, J = 7.0 Hz, 2H), 4.61 (s, 2H), 6.83 (d, J = 9.2 Hz, 2H), 6.89 (s, 1H), 7.16 (td, J = 7.8, 1.5 Hz, 1H), 7.22 (td, J = 7.8, 1.5 Hz, 1H), 7.30 (dd, J = 7.8, 1.5 Hz, 1H), 7.35 (d, J = 9.2 Hz, 2H), 7.42 (d, J = 8.2 Hz, 2H), 7.76 (d, J = 7.8 Hz, 1H), 7.90 (d, J = 8.2 Hz, 2H), 9.11 (s, 1H), 9.87 (s, 1H)

N-(2-t-Butoxycarbonylaminophenyl)-4-[3-cyclopentyl-1-(3-dimethylaminopropyl)ureidomethyl]benzamide
(Reference Compound No. 13-116)

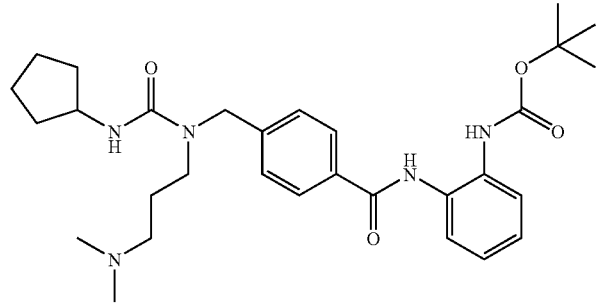

¹H-NMR (500 MHz, CDCl₃)
δ 1.35 (m, 2H), 1.51 (s, 9H), 1.57 (m, 4H), 1.65 (m, 2H), 2.03 (m, 2H), 2.19 (s, 6H), 2.25 (t, J = 6.0 Hz, 2H), 3.21 (t, J = 6.0 Hz, 2H), 4.04 (m, 1H), 4.54 (s, 2H), 6.76 (s, 1H), 7.15 (s, 1H), 7.18 (td, J = 7.9, 1.5 Hz, 1H), 7.24 (td, J = 7.9, 1.5 Hz, 1H), 7.29 (d, J =7.9 Hz, 1H), 7.39 (d, J = 8.2 Hz, 2H), 7.79 (d, J = 7.9 Hz, 1H), 7.90 (d, J = 8.2 Hz, 2H), 9.02 (s, 1H)

N-(2-t-Butoxycarbonylaminophenyl)-4-[3-(3,4-dimethoxyphenyl)-1-(3-dimethylaminopropyl)ureidomethyl]benzamide
(Reference Compound No. 13-117)

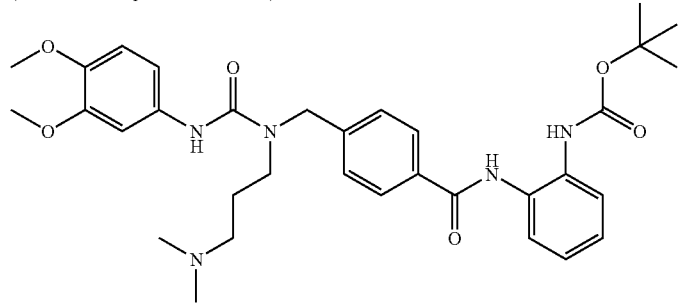

¹H-NMR (500 MHz, CDCl₃)
δ 1.51 (s, 9H), 1.66 (m, 2H), 2.29 (s, 6H), 2.37 (t, J = 6.0 Hz, 2H), 3.38 (t, J = 5.7 Hz, 2H), 3.86 (s, 3H), 3.90 (s, 3H), 4.63 (s, 2H), 6.72 (s, 1H), 6.77 (dd, J = 8.7, 2.3 Hz, 1H), 6.79 (d, J = 8.7 Hz, 1H), 7.18 (td, J = 7.6, 1.5 Hz, 1H), 7.23-7.28 (m, 2), 7.42 (d, J = 2.3 Hz, 1H), 7.44 (d, J = 8.2 Hz, 2H), 7.80 (d, J = 7.6 Hz, 1H), 7.92 (d, J = 8.2 Hz, 2H), 9.05 (s, 1H), 9.98 (s, 1H)

N-(2-t-Butoxycarbonylaminophenyl)-4-[1-(3-dimethylaminopropyl)-3-(furan-2-ylmethyl)ureidomethyl]benzamide
(Reference Compound No. 13-118)

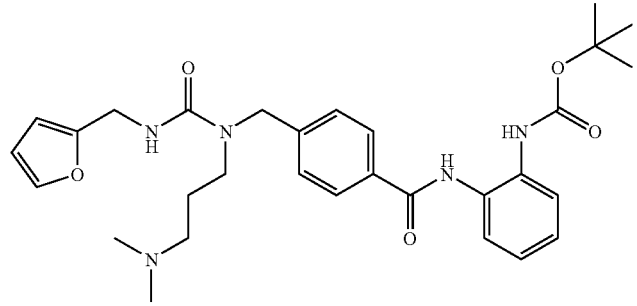

¹H-NMR (500 MHz, CDCl₃)
δ 1.52 (s, 9H), 1.55 (m, 2H), 2.07 (s, 6H), 2.22 (t, J = 6.0 Hz, 2H), 3.24 (t, J = 5.7 Hz, 2H), 4.42 (d, J = 4.9 Hz, 2H), 4.58 (s, 2H), 6.22 (d, J = 3.1 Hz, 1H), 6.32 (dd, J = 3.1, 1.8 Hz, 1H), 6.85 (s, 1H), 7.18 (td, J = 7.8, 1.5 Hz, 1H), 7.23 (td, J = 7.8, 1.5 Hz, 1H), 7.30 (dd, J = 7.8, 1.5 Hz, 1H), 7.35 (m, 1H), 7.38 (d, J = 8.2 Hz, 2H), 7.78 (d, J = 7.8 Hz, 1H), 7.90 (d, J = 8.2 Hz, 2H), 8.18 (s, 1H), 9.07 (s, 1H)

N-(2-t-Butoxycarbonylaminophenyl)-4-[3-(3,5-dimethoxyphenyl)-1-(3-dimethylaminopropyl)ureidomethyl]benzamide
(Reference Compound No. 13-119)

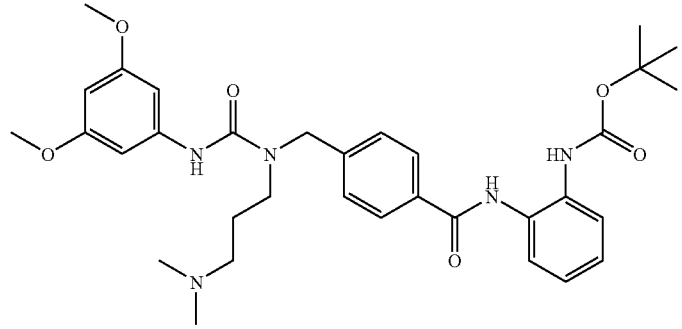

¹H-NMR (500 MHz, CDCl₃)
δ 1.51 (s, 9H), 1.65 (m, 2H), 2.31 (s, 6H), 2.36 (t, J = 6.0 Hz, 2H), 3.38 (t, J = 5.5 Hz, 2H), 3.80 (s, 6H), 4.62 (s, 2H), 6.14 (t, J = 2.1 Hz, 1H), 6.72 (s, 1H), 6.75 (d, J = 2.1 Hz, 2H), 7.18 (td, J = 7.6, 1.6 Hz, 1H), 7.23-7.29 (m, 2H), 7.43 (d, J = 8.2 Hz, 2H), 7.80 (d, J = 7.9 Hz, 1H), 7.92 (d, J = 8.2 Hz, 2H), 9.06 (s, 1H), 10.18 (s, 1H)

N-(2-t-Butoxycarbonylaminophenyl)-4-[3-(2,3-dihydrobenzo[1,4]dioxin-6-yl)-1-[3-(4-methylpiperidin-1-yl)propyl]ureidomethyl]benzamide
(Reference Compound No. 13-120)

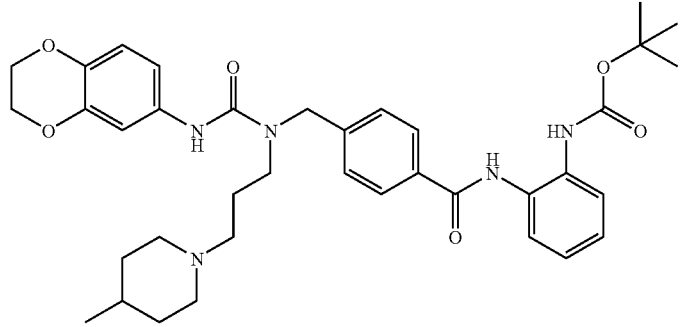

¹H-NMR (400 MHz, CDCl₃)
δ 0.88 (d, J = 6.3 Hz, 3H), 1.13-1.19 (m, 2H), 1.34 (m, 1H), 1.50 (s, 9H), 1.52-1.61 (m, 2H), 1.68 (m, 2H), 1.90 (t, J = 11.1 Hz, 2H), 2.38 (t, J = 5.7 Hz, 2H), 2.84 (d, J = 11.1 Hz, 2H), 3.33 (t, J = 5.7 Hz, 2H), 4.23-4.23 (m, 4H), 4.60 (s, 2H), 6.78 (d, J = 8.6 Hz, 1H), 6.80 (br s, 1H), 6.86 (dd, J = 8.6, 2.4 Hz, 1H), 7.03 (d, J = 2.4 Hz, 1H), 7.15-7.31 (m, 3H), 7.42 (d, J = 8.3 Hz, 2H), 7.77 (dd, J = 7.8, 1.2 Hz, 1H), 7.90 (d, J = 8.3 Hz, 2H), 9.05 (br s, 1H), 9.25 (br s, 1H)

N-(2-t-Butoxycarbonylaminophenyl)-4-[3-(3,4-dimethoxyphenyl)-1-(2-dimethylaminoethyl)ureidomethyl]benzamide
(Reference Compound No. 13-121)

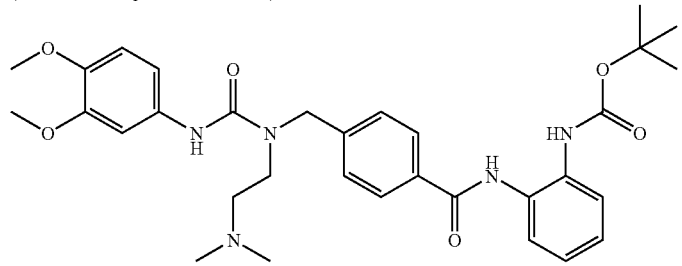

¹H-NMR (400 MHz, CDCl₃)
δ 1.51 (s, 9H), 2.37 (s, 6H), 2.45 (t, J = 4.2 Hz, 2H), 3.33 (t, J = 4.2 Hz, 2H), 3.85 (s, 3H), 3.90 (s, 3H), 4.65 (s, 2H), 6.65 (dd, J = 8.5, 2.4 Hz, 1H), 6.79 (d, J = 8.5 Hz, 1H), 6.82 (s, 1H), 7.17 (td, J = 7.6, 1.7 Hz, 1H), 7.21-7.27 (m, 2H), 7.36 (d, J = 2.4 Hz, 1H), 7.41 (d, J = 8.3 Hz, 2H), 7.80 (d, J = 7.8 Hz, 1H), m7.93 (d, J = 8.3 Hz, 2H), 9.16 (s, 1H), 10.89 (s, 1H)

N-(2-t-Butoxycarbonylaminophenyl)-4-[1-(2-dimthylaminoethyl)-3-(4-methoxyphenyl)ureoidomethyl]benzamide
(Reference Compound No. 13-122)

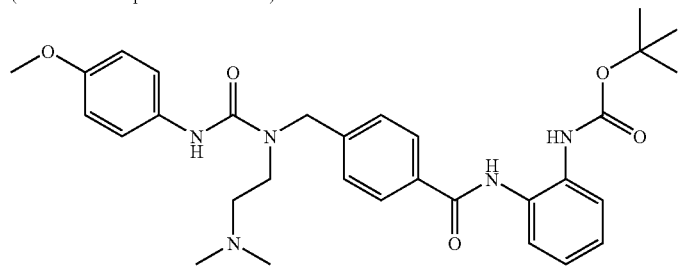

¹H-NMR (400 MHz, CDCl₃)
δ 1.51 (s, 9H), 2.34 (s, 6H), 2.45 (t, J = 4.3 Hz, 2H), 3.32 (t, J = 4.3 Hz, 2H), 3.78 (s, 3H), 4.63 (s, 2H), 6.84 (d, J = 9.0 Hz, 2H), 6.91 (s, 1H), 7.16 (td, J = 7.6, 1.7 Hz, 1H), 7.22 (td, J = 7.6, 1.7 Hz, 1H), 7.27 (m, 1H), 7.28 (d, J = 9.0 Hz, 2H), 7.40 (d, J = 8.3 Hz, 2H), 7.77 (d, J = 7.6 Hz, 1H), 7.92 (d, J = 8.3 Hz, 2H), 9.19 (s, 1H), 10.76 (s, 1H)

N-(2-t-Butoxycarbonylaminophenyl)-4-[1-(2-dimethylaminoethyl)-3-(3-ethoxyphenyl)ureidomethyl]benzamide
(Reference Compound No. 13-123)

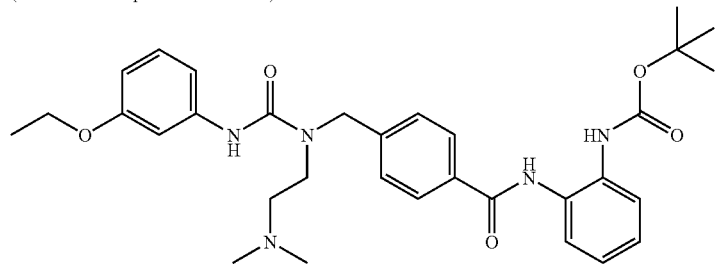

¹H-NMR (400 MHz, CDCl₃)
δ 1.40 (t, J = 7.0 Hz, 3H), 1.52 (s, 9H), 2.38 (s, 6H), 2.46 (t, J = 4.3 Hz, 2H), 3.32 (t, J = 4.3 Hz, 2H), 4.05 (q, J = 7.0 Hz, 2H), 4.65 (s, 2H), 6.54 (ddd, J = 8.3, 2.4, 0.7 Hz, 1H), 6.75 (s, 1H), 6.81 (ddd, J = 7.9, 2.0, 0.7 Hz, 1H), 7.13-7.21 (m, 3H), 7.23-7.27 (m, 2H), 7.42 (d, J = 8.2 Hz, 2H), 7.82 (d, J = 7.9 Hz, 1H), 7.93 (d, J = 8.2 Hz, 2H), 9.13 (s, 1H), 11.02 (s, 1H)

| | |
|---|---|
| N-(2-t-Butoxycarbonylaminophenyl)-4-[1-(2-dimethylaminoethyl)-3-(pyridin-3-yl)ureidomethyl]benzamide (Reference Compound No. 13-124)<br>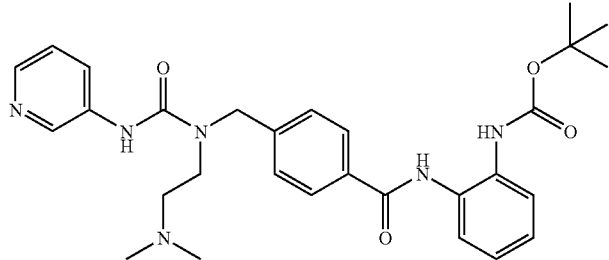 | $^1$H-NMR (400 MHz, CDCl$_3$)<br>δ 1.50 (s, 9H), 2.38 (s, 6H), 2.49 (t, J = 4.3 Hz, 2H), 3.34 (t, J = 4.3 Hz, 2H), 4.64 (s, 2H), 6.97 (s, 1H), 7.17 (td, J = 7.6, 1.5 Hz, 1H), 7.19-7.27 (m, 3H), 7.40 (d, J = 8.3 Hz, 2H), 7.78 (d, J = 8.3 Hz, 1H), 7.93 (d, J = 8.3 Hz, 2H), 8.08 (ddd, J = 8.3, 2.7, 1.5 Hz, 1H), 8.21 (dd, J = 4.6, 1.5 Hz, 1H), 8.32 (dd, J = 2.7, 0.7 Hz, 1H), 9.25 (s, 1H), 11.48 (s, 1H) |
| N-(2-t-Butoxycarbonylaminophenyl)-4-[3-(2,3-dihydrobenzofuran-5-yl)-1-[3-(morpholin-4-yl)propyl]ureidomethyl]benzamide (Reference Compound No. 13-125)<br>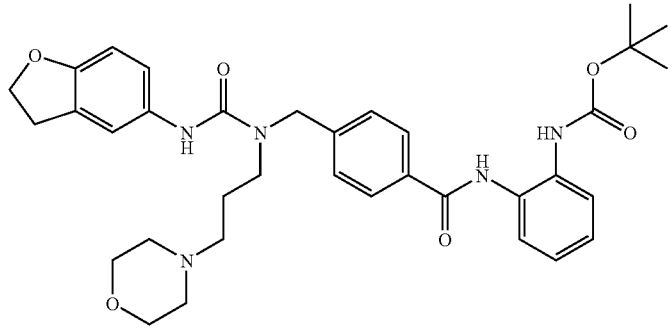 | $^1$H-NMR (500 MHz, CDCl$_3$)<br>δ 1.50 (s, 9H), 1.72 (m, 2H), 2.40-2.48 (m, 6H), 3.20 (t, J = 8.6 Hz, 2H), 3.36 (t, J = 5.7 Hz, 2H), 3.62 (t, J = 4.4 Hz, 4H), 4.56 (t, J = 8.6 Hz, 2H), 4.62 (s, 2H), 6.71 (d, J = 8.2 Hz, 1H), 6.77 (br s, 1H), 6.95 (dd, J = 8.2, 2.0 Hz, 1H), 7.18 (td, J = 7.6, 1.5 Hz, 1H), 7.24 (td, J = 7.6, 1.5 Hz, 6H), 7.28 (dd, J = 7.6, 1.5 Hz, 6H), 7.36 (d, J = 2.0 Hz, 1H), 7.43 (d, J = 8.2 Hz, 2H), 7.79 (d, J = 7.6 Hz, 1H), 7.91 (d, J = 8.2 Hz, 2H), 8.78 (br s, 1H), 9.09 (br s, 1H) |
| N-(2-t-Butoxycarbonylaminophenyl)-4-[1-[3-(morpholin-4-yl)propyl]-3-(thiophen-3-yl)ureidomethyl]benzamide (Reference Compound No. 13-126)<br>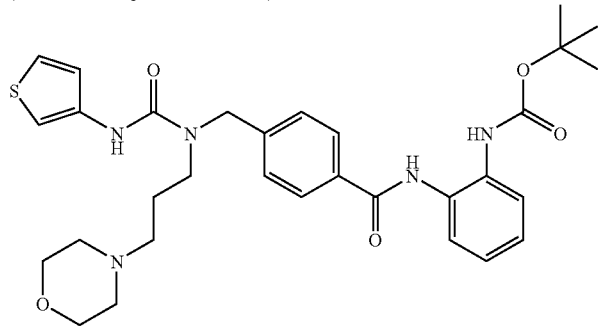 | $^1$H-NMR (400 MHz, CDCl$_3$)<br>δ 1.51 (s, 9H), 1.73 (m, 2H), 2.40-2.49 (m, 6H), 3.35 (t, J = 5.7 Hz, 2H), 3.72 (t, J = 4.6 Hz, 4H), 4.64 (s, 2H), 6.73 (br s, 1H), 7.10 (dd, J = 5.1, 1.5 Hz, 1H), 7.18 (td, J = 8.0, 1.5 Hz, 1H), 7.22-7.29 (m, 3H), 7.32 (dd, J = 3.3, 1.5 Hz, 1H), 7.42 (d, J = 8.2 Hz, 2H), 7.80 (d, J = 8.0 Hz, 1H), 7.91 (d, J = 8.2 Hz, 2H), 9.08 (br s, 2H) |
| N-(2-t-Butoxycarbonylaminophenyl)-4-[3-(4-fluoro-3-methylphenyl)-1-[3-(morpholin-4-yl)propyl]ureidomethyl]benzamide (Reference Compound No. 13-127)<br>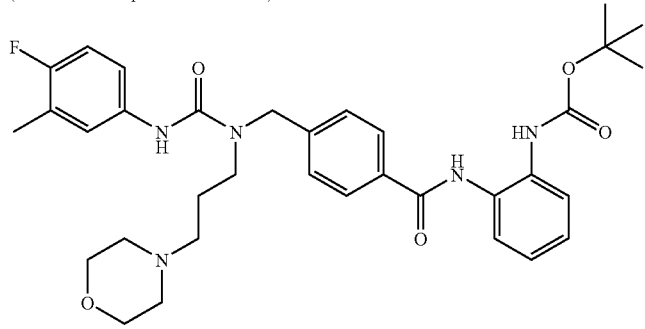 | $^1$H-NMR (400 MHz, CDCl$_3$)<br>δ 1.50 (s, 9H), 1.73 (m, 2H), 2.26 (d, J = 1.7 Hz, 3H), 2.40-2.49 (m, 6H), 3.37 (t, J = 5.6 Hz, 2H), 3.65 (t, J = 4.4 Hz, 4H), 4.63 (s, 2H), 6.74 (s, 1H), 6.94 (t, J = 8.9 Hz, 1H), 7.13 (m, 1H), 7.18 (td, J = 7.7, 1.5 Hz, 1H), 7.22-7.28 (m, 2H), 7.32 (m, 1H), 7.43 (d, J = 8.3 Hz, 2H), 7.80 (d, J = 7.7 Hz, 1H), 7.92 (d, J = 8.3 Hz, 2H), 8.80 (s, 1H), 9.10 (s, 1H) |

N-(2-t-Butoxycarbonylaminophenyl)-4-[3-(3-fluoro-4-methylphenyl)-1-[3-(morpholin-4-yl)propyl]ureidomethyl]benzamide
(Reference Compound No. 13-128)

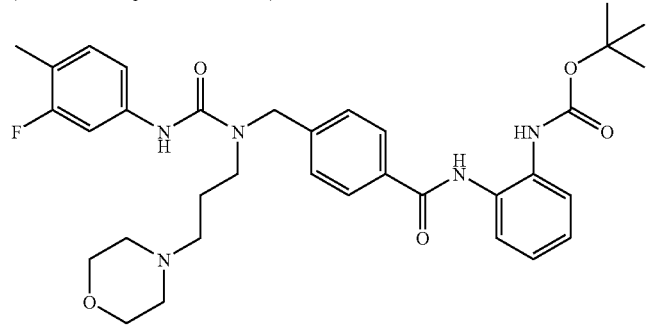

$^1$H-NMR (500 MHz, CDCl$_3$)
δ 1.50 (s, 9H), 1.73 (m, 2H), 2.22 (s, 3H), 2.42-2.47 (m, 6H), 3.36 (t, J = 5.7 Hz, 2H), 3.69 (t, J = 4.3 Hz, 4H), 4.63 (s, 2H), 6.76 (br s, 1H), 7.01 (d, J = 8.2 Hz, 1H), 7.08 (t, J = 8.4 Hz, 1H), 7.17 (t, J = 7.4 Hz, 1H), 7.22-7.28 (m, 2H), 7.33 (m, 1H), 7.42 (d, J = 8.1 Hz, 2H), 7.79 (d, J = 7.4 Hz, 1H), 7.91 (d, J = 8.1 Hz, 2H), 8.79 (br s, 1H), 9.10 (br s, 1H)

N-(2-t-Butoxycarbonylaminophenyl)-4-[3-(3,5-difluorophenyl)-1-[3-(morpholin-4-yl)propyl]ureidomethyl]benzamide
(Reference Compound No. 13-129)

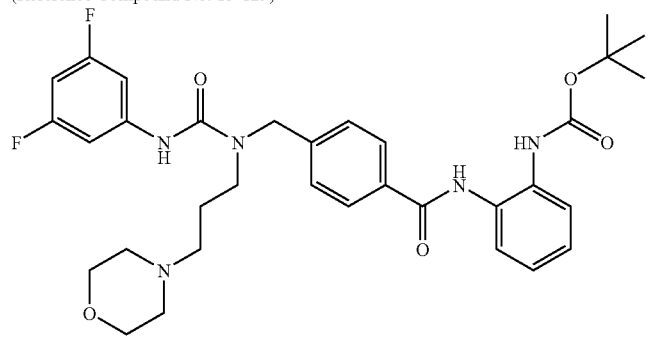

$^1$H-NMR (500 MHz, CDCl$_3$)
δ 1.51 (s, 9H), 1.75 (m, 2H), 2.42-2.51 (m, 6H), 3.36 (t, J = 5.8 Hz, 2H), 3.74 (t, J = 4.6 Hz, 4H), 4.62 (s, 2H), 6.50 (tt, J = 8.9, 2.2 Hz, 1H), 6.72 (s, 1H), 7.11 (m, 2H), 7.18 (td, J = 7.8, 1.6 Hz, 1H), 7.23-7.27 (m, 2H), 7.42 (d, J = 8.2 Hz, 2H), 7.82 (d, J = 7.8 Hz, 1H), 7.93 (d, J = 8.2 Hz, 2H), 8.91 (br s, 1H), 9.13 (br s, 1H)

N-(2-t-Butoxycarbonylaminophenyl)-4-[3-(3-chloro-4-fluorophenyl)-1-[3-(morpholin-4-yl)propyl]ureidomethyl]benzamide
(Reference Compound No. 13-130)

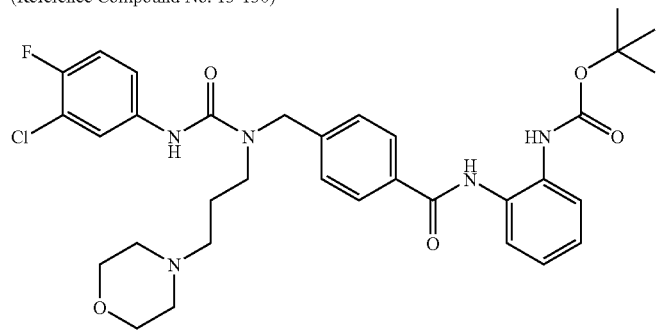

$^1$H-NMR (400 MHz, CDCl$_3$)
δ 1.51 (s, 9H), 1.74 (m, 2H), 2.40-2.49 (m, 6H), 3.37 (t, J = 5.6 Hz, 2H), 3.67 (t, J = 4.6 Hz, 4H), 4.62 (s, 2H), 6.73 (s, 1H), 7.08 (t, J = 8.5 Hz, 1H), 7.18 (td, J = 7.6, 1.7 Hz, 1H), 7.21-7.29 (m, 3H), 7.42 (d, J = 8.4 Hz, 2H), 7.63 (dd, J = 6.7, 2.6 Hz, 1H), 7.81 (d, J = 7.6 Hz, 1H), 7.92 (d, J = 8.4 Hz, 2H), 8.98 (br s, 1), 9.12 (br s, 1H)

N-(2-t-Butoxycarbonylaminophenyl)-4-[3-(4-fluoro-3-trifluoromethylphenyl)-1-[3-(morpholin-4-yl)propyl]ureidomethyl]benzamide
(Reference Compound No. 13-131)

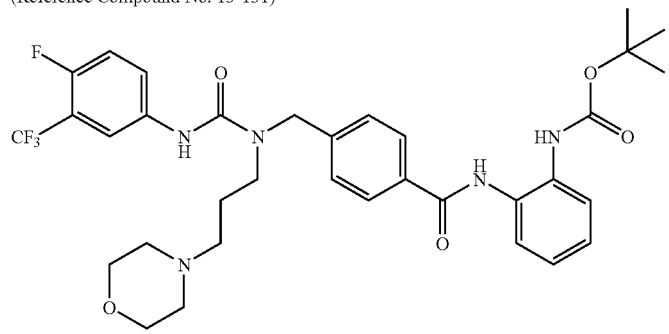

$^1$H-NMR (400 MHz, CDCl$_3$)
δ 1.50 (s, 9H), 1.75 (m, 2H), 2.42-2.51 (m, 6H), 3.38 (t, J = 5.7 Hz, 2H), 3.67 (t, J = 4.6 Hz, 4H), 4.63 (s, 2H), 6.72 (s, 1H), 7.12-7.21 (m, 2H), 7.22-7.28 (m, 2H), 7.42 (d, J = 8.3 Hz, 2H), 7.66 (m, 1H), 7.70 (dd, J = 6.1, 2.4 Hz, 1H), 7.81 (d, J = 7.6 Hz, 1H), 7.93 (d, J = 8.3 Hz, 2H), 9.12 (br s, 2H)

N-(2-t-Butoxycarbonylaminophenyl)-4-[3-(3-fluoro-5-trifluoromethylphenyl)-1-[3-(morpholin-4-yl)propyl]ureidomethyl]benzamide
(Reference Compound No. 13-132)

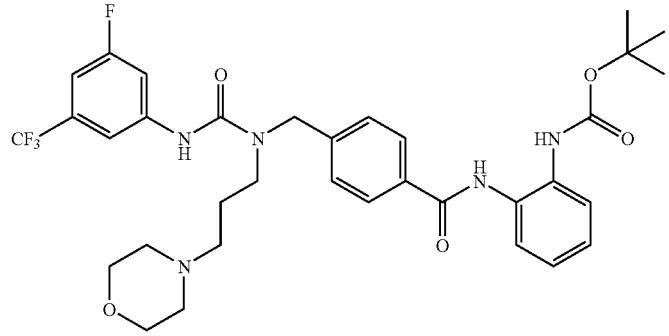

$^1$H-NMR (400 MHz, CDCl$_3$)
δ 1.51 (s, 9H), 1.77 (m, 2H), 2.44-2.51 (m, 6H), 3.38 (t, J = 5.6 Hz, 2H), 3.74 (t, J = 4.6 Hz, 4H), 4.64 (s, 2H), 6.71 (br s, 1H), 7.01 (d, J = 8.1 Hz, 1H), 7.18 (td, J = 7.7, 1.5 Hz, 1H), 7.23-7.28 (m, 2H), 7.42 (d, J = 8.3 Hz, 2H), 7.42 (m, 1H), 7.71 (dt, J = 10.9, 2.1 Hz, 1H), 7.82 (d, J = 7.7 Hz, 1H), 7.93 (d, J = 8.3 Hz, 2H), 9.14 (br s, 2H)

N-(2-t-Butoxycarbonylaminophenyl)-4-[1-(2-dimethylaminoethyl)-3-(4-fluorophenyl)ureidomethyl]benzamide
(Reference Compound No. 13-133)

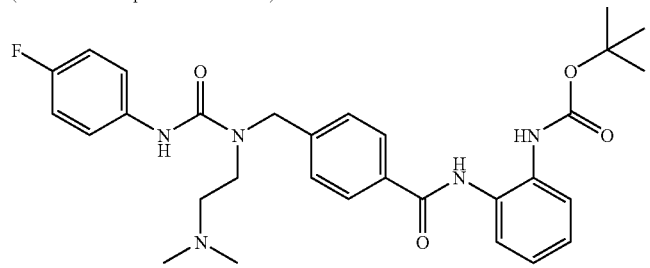

$^1$H-NMR (500 MHz, CDCl$_3$)
δ 1.51 (s, 9H), 2.37 (s, 6H), 2.47 (t, J = 4.3 Hz, 2H), 3.32 (t, J = 4.3 Hz, 2H), 4.64 (s, 2H), 6.75 (s, 1H), 6.98 (t, J = 8.7 Hz, 2H), 7.18 (td, J = 7.6, 1.5 Hz, 1H), 7.23-7.27 (m, 2H), 7.31 (dd, J = 9.0, 4.7 Hz, 2H), 7.42 (d, J = 8.2 Hz, 2H), 7.82 (d, J = 7.6 Hz, 1H), 7.93 (d, J = 8.2 Hz, 2H), 9.13 (s, 1H), 10.99 (s, 1H)

N-(2-t-Butoxycarbonylaminophenyl)-4-[1-(2-dimethylaminoethyl)-3-(3-fluoro-4-methylphenyl)ureidomethyl]benzamide
(Reference Compound No. 13-134)

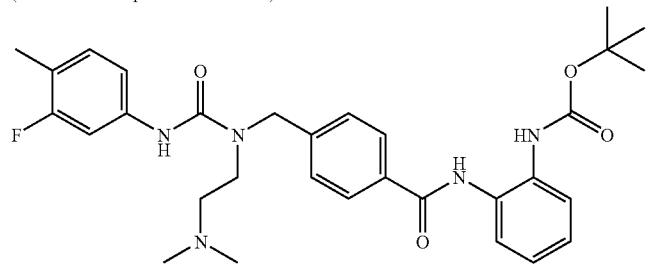

$^1$H-NMR (500 MHz, CDCl$_3$)
δ 1.51 (s, 9H), 2.21 (s, 3H), 2.37 (s, 6H), 2.46 (t, J = 4.3 Hz, 2H), 3.31 (t, J = 4.3 Hz, 2H), 4.63 (s, 2H), 6.73 (s, 1H), 6.93 (dd, J = 7.9, 2.1 Hz, 1H), 7.04 (t, J = 8.4 Hz, 1H), 7.16-7.28 (m, 4H), 7.44 (d, J = 8.2 Hz, 2H), 7.82 (d, J = 7.6 Hz, 1H), 7.93 (d, J = 8.2 Hz, 2H), 9.12 (s, 1H), 11.09 (s, 1H)

N-(2-t-Butoxycarbonylaminophenyl)-4-[1-(2-dimethylaminoethyl)-3-(4-fluoro-3-methylphenyl)ureidomethyl]benzamide
(Reference Compound No. 13-135)

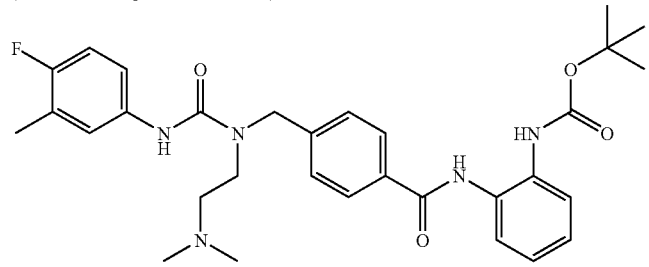

$^1$H-NMR (400 MHz, DMSO-d$_6$)
δ 1.44 (s, 9H), 2.19-2.22 (m, 5H), 2.28 (s, 6H), 3.38 (s, 2H), 4.63 (s, 2H), 7.02 (t, J = 9.5 Hz, 1H), 7.13-7.22 (m, 3H), 7.30 (d, J = 7.1 Hz, 1H), 7.44 (d, J = 8.3 Hz, 2H), 7.51-7.53 (m, 2H), 7.93 (d, J = 8.3 Hz, 2H), 8.67 (s, 1H), 9.81 (s, 1H), 9.97 (s, 1H)

N-(2-t-Butoxycarbonylaminophenyl)-4-[1-(2-dimethylaminoethyl)-3-(thiophen-3-yl)ureidomethyl]benzamide
(Reference Compound No. 13-136)

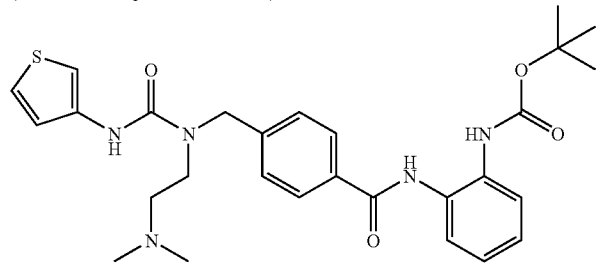

$^1$H-NMR (400 MHz, CDCl$_3$)
δ 1.51 (s, 9H), 2.36 (s, 6H), 2.46 (t, J = 4.2 Hz, 2H), 3.30 (t, J = 4.2 Hz, 2H), 4.65 (s, 2H), 6.79 (s, 1H), 6.87 (dd, J = 5.0, 1.3 Hz, 1H), 7.16-7.27 (m, 4H), 7.31 (dd, J = 3.2, 1.3 Hz, 1H), 7.41 (d, J = 8.1 Hz, 2H), 7.81 (d, J = 8.1 Hz, 1H), 7.92 (d, J = 8.1 Hz, 2H), 9.14 (s, 1H), 11.42 (s, 1H)

N-(2-t-Butoxycarbonylaminophenyl)-4-[3-(4-dimethylaminophenyl)-1-[3-(4-methylpiperidin-1-yl)propyl]ureidomethyl]benzamide
(Reference Compound No. 13-137)

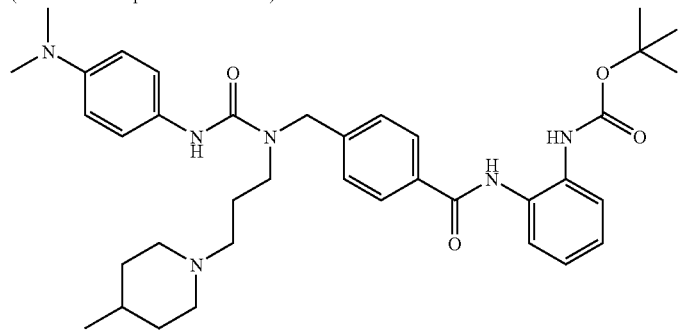

$^1$H-NMR (400 MHz, CDCl$_3$)
δ 0.85 (d, J = 6.6 Hz, 3H), 1.10-1.18 (m, 2H), 1.26-1.31 (m, 1H), 1.50 (s, 9H), 1.50-1.69 (m, 4H), 1.89 (t, J = 11.5 Hz, 2H), 2.39 (t, J = 5.6 Hz, 2H), 2.85 (d, J = 11.5 Hz, 2H), 2.91 (s, 6H), 3.34 (t, J = 5.6 Hz, 2H), 4.62 (s, 2H), 6.72 (d, J = 9.0 Hz, 2H), 6.79 (br s, 1H), 7.15-7.31 (m, 5H), 7.44 (d, J = 8.2 Hz, 2H), 7.77 (d, J = 7.1 Hz, 1H), 7.90 (d, J = 8.2 Hz, 2H), 9.03 (br s, 1H), 9.10 (br s, 1H)

N-(2-t-Butoxycarbonylaminophenyl)-4-[3-(3,4-difluorophenyl)-1-[3-(4-methylpiperidin-1-yl)propyl]ureidomethyl]benzamide
(Reference Compound No. 13-138)

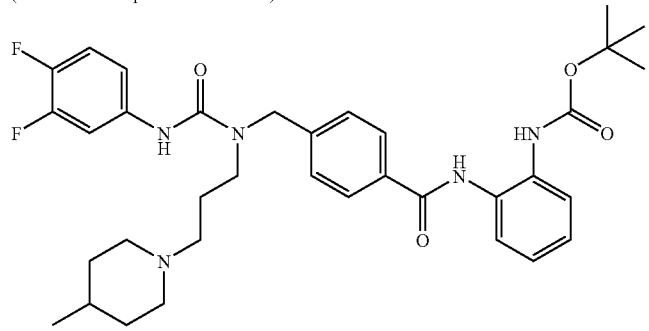

$^1$H-NMR (400 MHz, CDCl$_3$)
δ 0.90 (d, J = 6.6 Hz, 3H), 1.25-1.67 (m, 7H), 1.51 (s, 9H), 1.94-2.01 (m, 2H), 2.40 (t, J = 6.3 Hz, 2H), 2.88 (m, 2H), 3.35 (t, J = 6.3 Hz, 2H), 4.61 (s, 2H), 6.74 (br s, 1H), 7.05-7.27 (m, 6H), 7.42 (d, J = 8.2 Hz, 2H), 7.80 (d, J = 7.6 Hz, 1H), 7.91 (d, J = 8.2 Hz, 2H), 9.08 (br s, 1H), 9.54 (br s, 1H)

N-(2-t-Butoxycarbonylaminophenyl)-4-[3-(3-fluorobenzyl)-1-[3-(morpholin-4-yl)propyl]ureidomethyl]benzamide
(Reference Compound No. 13-139)

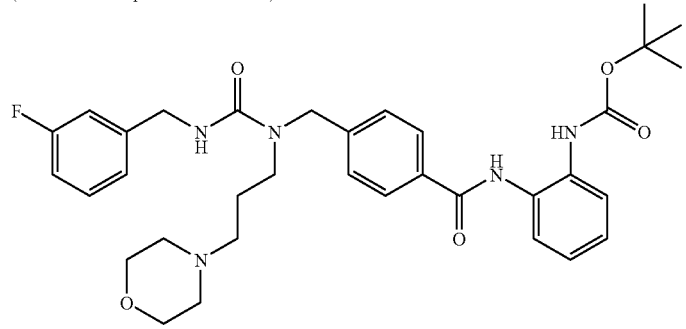

$^1$H-NMR (400 MHz, CDCl$_3$)
δ 1.48 (s, 9H), 1.64 (m, 2H), 2.27 (br s, 4H), 2.32 (t, J = 6.0 Hz, 2H), 3.28 (t, J = 5.5 Hz, 2H), 3.45 (br s, 4H), 4.47 (d, J = 5.6 Hz, 2H), 4.58 (s, 2H), 6.92 (td, J = 8.4, 2.0 Hz, 1H), 7.02-7.16 (m, 4H), 7.26 (m, 1H), 7.30 (d, J = 8.3 Hz, 2H), 7.35 (dd, J = 7.6, 2.0 Hz, 1H), 7.45 (s, 1H), 7.61-7.70 (m, 2H), 7.88 (d, J = 8.3 Hz, 2H), 9.43 (br s, 1H)

N-(2-t-Butoxycarbonylaminophenyl)-4-[3-(2-fluorophenethyl)-1-[3-(morpholin-4-yl)propyl]ureidomethyl]benzamide
(Reference Compound No. 13-140)

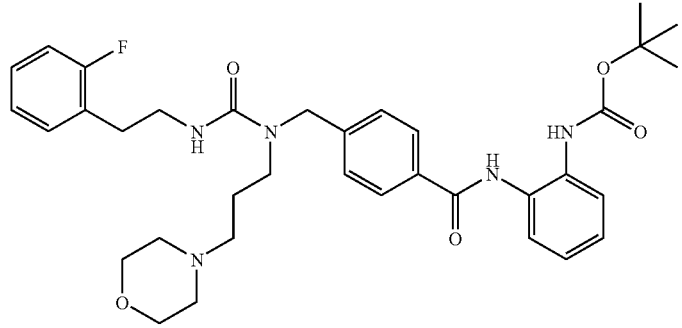

$^1$H-NMR (500 MHz, CDCl$_3$)
δ 1.49 (s, 9H), 1.56 (m, 2H), 2.24-2.33 (m, 6H), 2.89 (t, J = 6.6 Hz, 2H), 3.11 (t, J = 5.7 Hz, 2H), 3.47 (q, J = 6.6 Hz, 2H), 3.54 (br s, 4H), 4.52 (s, 2H), 7.01 (dd, J = 10.1, 8.9 Hz, 1H), 7.04-7.22 (m, 6H), 7.24 (d, J = 8.2 Hz, 2H), 7.36 (dd, J = 7.6, 1.8 Hz, 1H), 7.50 (s, 1H), 7.69 (dd, J = 7.8, 1.4 Hz, 1H), 7.88 (d, J = 8.2 Hz, 2H), 9.45 (br s, 1H)

N-(2-t-Butoxycarbonylaminophenyl)-4-[3-(2-fluorobenzyl)-1-[3-(morpholin-4-yl)propyl]ureidomethyl]benzamide
(Reference Compound No. 13-141)

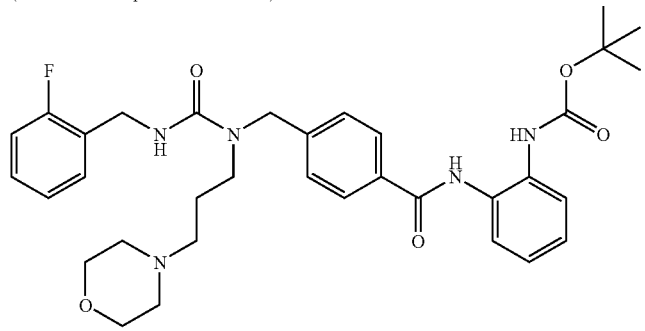

$^1$H-NMR (400 MHz, CDCl$_3$)
δ 1.48 (s, 9H), 1.61 (m, 2H), 2.27-2.36 (m, 6H), 3.24 (t, J = 5.6 Hz, 2H), 3.54 (br s, 4H), 4.52 (d, J = 5.6 Hz, 2H), 4.56 (s, 2H), 7.02 (m, 1H), 7.07-7.15 (m, 3H), 7.22 (m, 1H), 7.27 (d, J = 8.3 Hz, 2H), 7.34 (dd, J = 7.6, 1.8 Hz, 1H), 7.41 (td, J = 7.6, 1.8 Hz, 1H), 7.47 (br s, 1H), 7.52 (br s, 1H), 7.67 (dd, J = 7.6, 1.8 Hz, 1H), 7.86 (d, J = 8.3 Hz, 2H), 9.41 (br s, 1H)

N-(2-t-Butoxycarbonylaminophenyl)-4-[3-(3-fluorophenyl)-1-[3-(4-methylpiperidin-1-yl)propyl]ureidomethyl]benzamide
(Reference Compound No. 13-142)

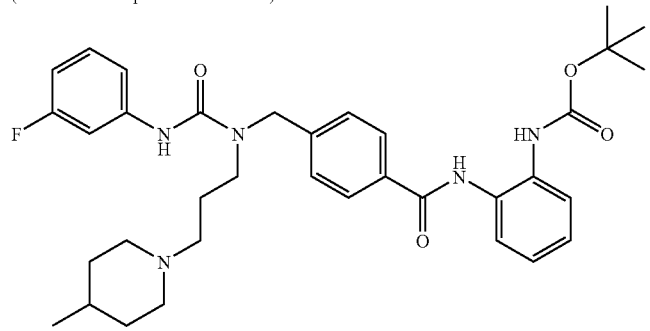

$^1$H-NMR (500 MHz, CDCl$_3$)
δ 0.92 (d, J = 6.4 Hz, 3H), 1.21-1.27 (m, 2H), 1.40 (m, 1H), 1.50 (s, 9H), 1.60 (m, 2H), 1.72 (m, 2H), 1.93 (td, J = 11.9, 2.1 Hz, 2H), 2.39 (t, J = 6.0 Hz, 2H), 2.88 (d, J = 11.9 Hz, 2H), 3.36 (t, J = 6.0 Hz, 2H), 4.62 (s, 2H), 6.73-6.76 (m, 2H), 7.16-7.29 (m, 5H), 7.40 (m, 1H), 7.43 (d, J = 8.2 Hz, 2H), 7.80 (d, J = 7.3 Hz, 1H), 7.91 (d, J = 8.2 Hz, 2H), 9.06 (s, 1H), 9.44 (s, 1H)

N-(2-t-Butoxycarbonylaminophenyl)-4-[3-(4-fluoro-3-nitrophenyl)-1-[3-(4-methylpiperidin-1-yl)propyl]ureidomethyl]benzamide
(Reference Compound No. 13-143)

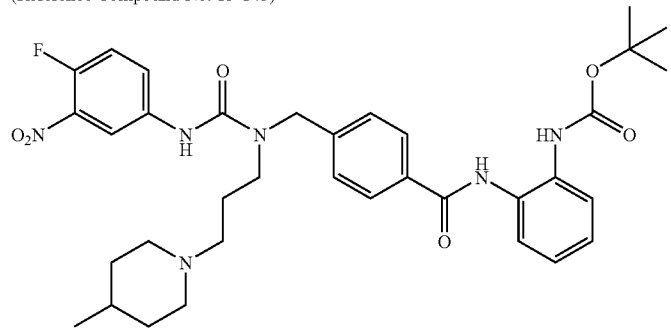

$^1$H-NMR (500 MHz, CDCl$_3$)
δ 0.92 (d, J = 6.4 Hz, 3H), 1.12-1.18 (m, 2H), 1.41 (m, 1H), 1.51 (s, 9H), 1.62-1.64 (m, 2H), 1.73 (m, 2H), 1.96 (t, J = 11.6 Hz, 2H), 2.41 (t, J = 6.0 Hz, 2H), 2.88 (d, J = 11.6 Hz, 2H), 3.37 (t, J = 6.0 Hz, 2H), 4.62 (s, 2H), 6.70 (br s, 1H), 7.16-7.26 (m, 4H), 7.42 (d, J = 8.2 Hz, 2H), 7.81 (d, J = 7.3 Hz, 1H), 7.92 (d, J = 8.2 Hz, 2H), 7.95 (m, 1H), 8.11 (dd, J = 6.6, 2.6 Hz, 1H), 9.10 (br s, 1H), 9.96 (br s, 1H)

N-(2-t-Butoxycarbonylaminophenyl)-4-[3-(3-ethoxyphenyl)-1-[3-(4-methylpiperidin-1-yl)propyl]ureidomethyl]benzamide
(Reference Compound No. 13-144)

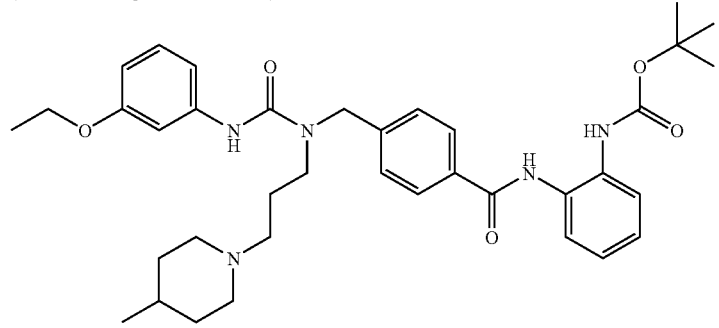

¹H-NMR (400 MHz, CDCl₃)
δ 0.91 (d, J = 6.3 Hz, 1H), 1.26-1.30 (m, 2H), 1.39 (t, J = 7.0 Hz, 3H), 1.40 (m, 1H), 1.50 (s, 9H), 1.59 (m, 2H), 1.70 (m, 2H), 1.91 (td, J = 12.0, 2.2 Hz, 2H), 2.38 (t, J = 6.0 Hz, 2H), 2.87 (d, J = 12.0 Hz, 2H), 3.35 (t, J = 6.0 Hz, 2H), 4.04 (q, J = 7.0 Hz, 2H), 4.62 (s, 2H), 6.60 (dd, J = 8.1, 2.5 Hz, 1H), 6.77 (br s, 1H), 6.99 (d, J = 8.1 Hz, 1H), 7.15-7.29 (m, 5H), 7.42 (d, J = 8.3 Hz, 2H), 7.78 (d, J = 8.1 Hz, 1H), 7.90 (d, J = 8.3 Hz, 2H), 9.06 (br s, 1H), 9.23 (br s, 1H)

N-(2-t-Butoxycarbonylaminophenyl)-4-[3-(4-fluorobenzyl)-1-[3-(morpholin-4-yl)propyl]ureidomethyl]benzamide
(Reference Compound No. 13-145)

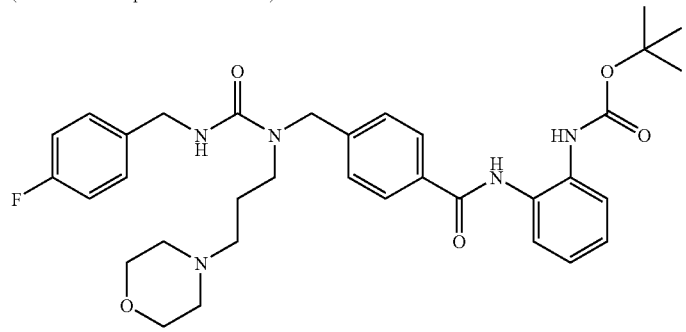

¹H-NMR (400 MHz, CDCl₃)
δ 1.48 (s, 9H), 1.62 (m, 2H), 2.25 (br s, 4H), 2.31 (t, J = 6.0 Hz, 2H), 3.26 (t, J = 5.6 Hz, 2H), 3.45 (br s, 4H), 4.44 (d, J = 5.6 Hz, 2H), 4.57 (s, 2H), 6.99 (t, J = 8.5 Hz, 2H), 7.11 (m, 2H), 7.25-7.28 (m, 2H), 7.29 (d, J = 8.1 Hz, 2H), 7.36 (dd, J = 7.1, 2.1 Hz, 1H), 7.49 (br s, 1H), 7.58 (br s, 1H), 7.67 (dd, J = 7.1, 2.1 Hz, 1H), 7.88 (d, J = 8.1 Hz, 2H), 9.46 (br s, 1H)

N-(2-t-Butoxycarbonylaminophenyl)-4-[3-(4-fluorophenethyl)-1-[3-(morpholin-4-yl)-propyl]ureidomethyl]benzamide
(Reference Compound No. 13-146)

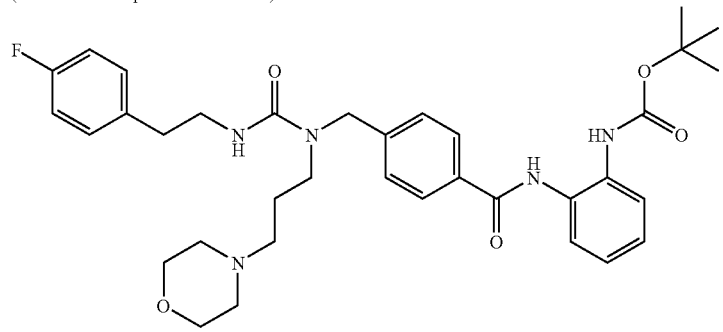

¹H-NMR (400 MHz, CDCl₃)
δ 1.49 (s, 9H), 1.57 (m, 2H), 2.20-2.36 (m, 6H), 2.80 (t, J = 6.5 Hz, 2H), 3.13 (t, J = 5.7 Hz, 2H), 3.42 (q, J = 6.5 Hz, 2H), 3.55 (br s, 4H), 4.52 (s, 2H), 6.96 (t, J = 8.7 Hz, 2H), 6.97 (m, 1H), 7.08-7.17 (m, 4H), 7.26 (d, J = 8.2 Hz, 2H), 7.35 (dd, J = 7.6, 2.0 Hz, 1H), 7.45 (br s, 1H), 7.69 (dd, J = 7.4, 1.8 Hz, 1H), 7.89 (d, J = 8.2 Hz, 2H), 9.43 (br s, 1H)

N-(2-t-Butoxycarbonylaminophenyl)-4-[3-(3-chlorophenyl)-1-(3-dimethylaminopropyl)ureidomethyl]benzamide
(Reference Compound No. 13-147)

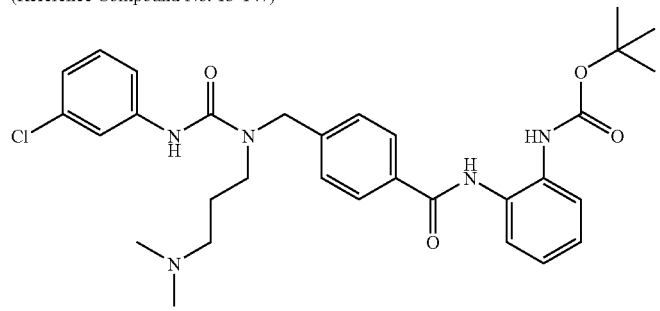

¹H-NMR (500 MHz, CDCl₃)
δ 1.51 (s, 9H), 1.69 (m, 2H), 2.30 (s, 6H), 2.37 (t, J = 6.0 Hz, 2H), 3.38 (t, J = 5.5 Hz, 2H), 4.61 (s, 2H), 6.71 (s, 1H), 6.94 (ddd, J = 7.9, 2.1, 0.9 Hz, 1H), 7.16 (m, 1H), 7.18 (t, J = 7.9 Hz, 1H), 7.22-7.28 (m, 3H), 7.45 (d, J = 8.2 Hz, 2H), 7.58 (t, J = 2.1 Hz, 1H), 7.81 (d, J = 7.9 Hz, 1H), 7.93 (d, J = 8.2 Hz, 2H), 9.07 (s, 1H), 10.31 (s, 1H)

N-(2-t-Butoxycarbonylaminophenyl)-4-[3-(3-chlorophenyl)-1-(2-dimthylaminoethyl)ureidomethyl]benzamide
(Reference Compound No. 13-148)

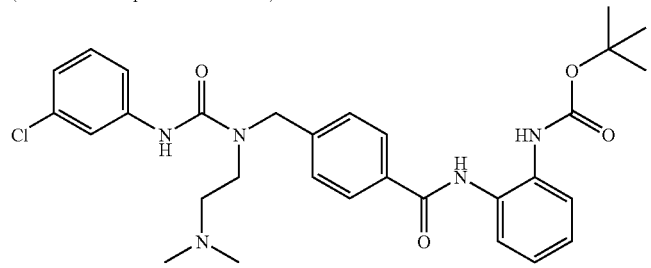

$^1$H-NMR (500 MHz, CDCl$_3$)
δ 1.51 (s, 9H), 2.38 (s, 6H), 2.47 (t, J = 4.3 Hz, 2H), 3.32 (t, J = 4.3 Hz, 2H), 4.64 (s, 2H), 6.73 (s, 1H), 6.96 (m, 1H), 7.15-7.20 (m, 3H), 7.23-7.27 (m, 2H), 7.42 (d, J = 8.2 Hz, 2H), 7.48 (m, 1H), 7.82 (d, J = 7.6 Hz, 1H), 7.93 (d, J = 8.2 Hz, 2H), 9.13 (s, 1H), 11.23 (s, 1H)

N-(2-t-Butoxycarbonylaminophenyl)-4-[3-(3-fluorophenyl)-1-[2-(4-methylpiperazin-1-yl)ethyl]ureidomethyl]benzamide
(Reference Compound No. 13-149)

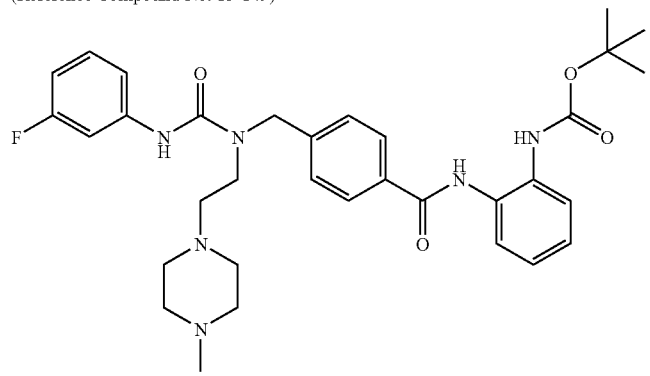

$^1$H-NMR (400 MHz, CDCl$_3$)
δ 1.55 (s, 9H), 2.36 (s, 3H), 2.55-2.57 (m, 6H), 2.68 (br s, 4H), 3.40 (t, J = 4.4 Hz, 2H), 4.67 (s, 2H), 6.75 (m, 1H), 6.79 (br s, 1H), 7.19-7.30 (m, 5H), 7.42 (m, 1H), 7.46 (d, J = 8.3 Hz, 2H), 7.85 (d, J = 7.8 Hz, 1H), 7.97 (d, J = 8.3 Hz, 2H), 9.20 (br s, 1H), 10.13 (br s, 1H)

N-(2-t-Butoxycarbonylaminophenyl)-4-[3-(4-fluoro-3-methylphenyl)-1-[2-(4-methylpiperazin-1-yl)ethyl]ureidomethyl]benzamide
(Reference Compound No. 13-150)

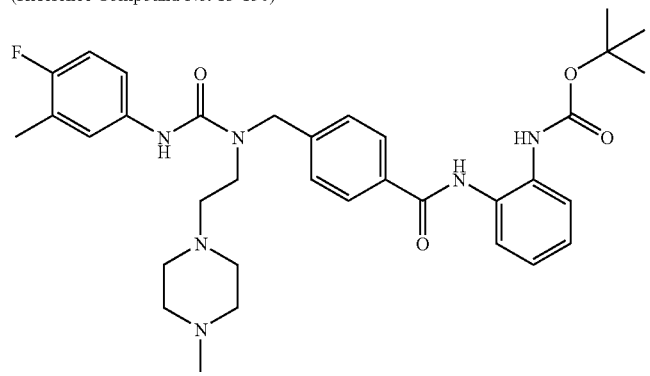

$^1$H-NMR (400 MHz, CDCl$_3$)
δ 1.55 (s, 9H), 2.31 (d, J = 1.7 Hz, 3H), 2.34 (s, 3H), 2.53-2.56 (m, 6H), 2.66 (br s, 4H), 3.39 (t, J = 4.2 Hz, 2H), 4.67 (s, 2H), 6.79 (br s, 1H), 6.97 (t, J = 9.0 Hz, 1H), 7.19-7.30 (m, 4H), 7.36 (dd, J = 6.8, 2.4 Hz, 1H), 7.46 (d, J = 8.3 Hz, 2H), 7.85 (d, J = 8.1 Hz, 1H), 7.97 (d, J = 8.3 Hz, 2H), 9.18 (br s, 1H), 9.91 (br s, 1H)

N-(2-t-Butoxycarbonylaminophenyl)-4-[3-(4-fluoro-4-nitrophenyl)-1-[2-(4-methylpiperazin-1-yl)ethyl]ureidomethyl]benzamide
(Reference Compound No. 13-151)

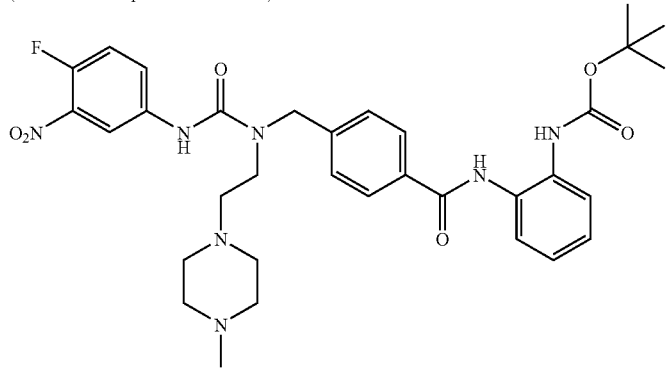

$^1$H-NMR (500 MHz, CDCl$_3$)
δ 1.52 (s, 9H), 2.36 (s, 3H), 2.54-2.57 (m, 6H), 2.66 (br s, 4H), 3.38 (t, J = 4.1 Hz, 2H), 4.64 (s, 2H), 6.72 (br s, 1H), 7.16-7.27 (m, 4H), 7.42-(d, J = 8.2 Hz, 2H), 7.83 (d, J = 7.6 Hz, 1H), 7.95 (d, J = 8.2 Hz, 2H), 7.99 (td, J = 6.3, 3.1 Hz, 1H), 8.12 (dd, J = 6.3, 3.1 Hz, 1H), 9.19 (br s, 1H), 10.68 (br s, 1H)

N-(2-t-Butoxycarbonylaminophenyl)-4-[1-[3-(morpholin-4-yl)propyl]-3-(quinolin-6-yl)ureidomethyl]benzamide
(Reference Compound No. 13-152)

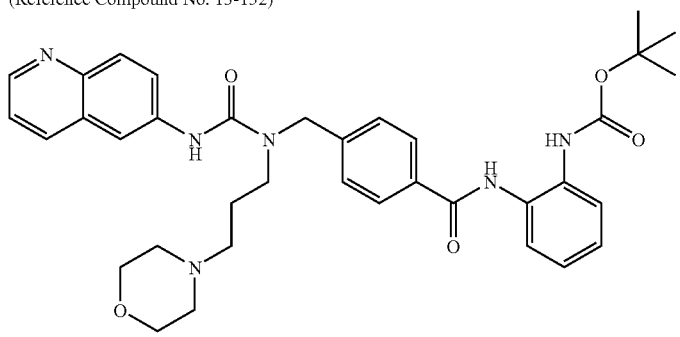

$^1$H-NMR (400 MHz, CDCl$_3$)
δ 1.49 (s, 9H), 1.79 (m, 2H), 2.42-2.53 (m, 6H), 3.45 (t, J = 5.7 Hz, 2H), 3.74 (t, J = 4.6 Hz, 4H), 4.69 (s, 2H), 6.77 (s, 1H), 7.17 (td, J = 7.7, 1.5 Hz, 1H), 7.21-7.30 (m, 2H), 7.37 (dd, J = 8.2, 4.3 Hz, 1H), 7.45 (d, J = 8.4 Hz, 2H), 7.68 (dd, J = 9.0, 2.3 Hz, 1H), 7.80 (d, J = 7.7 Hz, 1H), 7.94 (d, J = 8.4 Hz, 2H), 8.04 (d, J = 9.0 Hz, 1H), 8.09 (dd, J = 8.2, 1.6 Hz, 1H), 8.18 (d, J = 2.3 Hz, 1H), 8.81 (dd, J = 4.3, 1.6 Hz, 1H), 9.02 (br s, 1H), 9.13 (br s, 1H)

N-(2-t-Butoxycarbonylaminophenyl)-4-[3-(3-dimethylaminophenyl)-1-[3-(4-hydroxypiperidin-1-yl)propyl]ureidomethyl]benzamide
(Reference Compound No. 13-153)

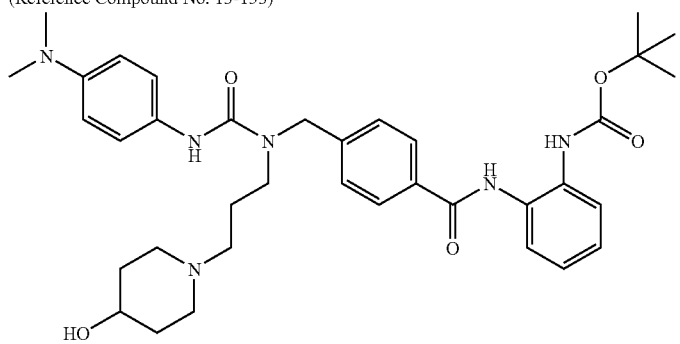

$^1$H-NMR (400 MHz, CDCl$_3$)
δ 1.50 (s, 9H), 1.62-1.68 (m, 4H), 1.78 (m, 2H), 2.14 (m, 2H), 2.42 (t, J = 6.0 Hz, 2H), 2.73 (m, 2H), 2.90 (s, 6H), 3.34 (t, J = 5.6 Hz, 2H), 3.68 (m, 1H), 4.61 (s, 2H), 6.70 (d, J = 9.0 Hz, 2H), 6.95 (s, 1H), 7.16 (td, J = 7.6, 1.7 Hz, 1H), 7.20 (m, 1H), 7.22 (d, J = 9.0 Hz, 2H), 7.32 (dd, J = 7.6, 1.7 Hz, 1H), 7.41 (d, J = 8.3 Hz, 2H), 7.73 (dd, J = 7.6, 1.7 Hz, 1H), 7.89 (d, J = 8.3 Hz, 2H), 8.89 (s, 1H), 9.14 (s, 1H)

N-(2-t-Butoxycarbonylaminophenyl)-4-[3-(3,4-difluorophenyl)-1-[3-(4-hydroxypiperidin-1-yl)propyl]ureidomethyl]benzamide
(Reference Compound No. 13-154)

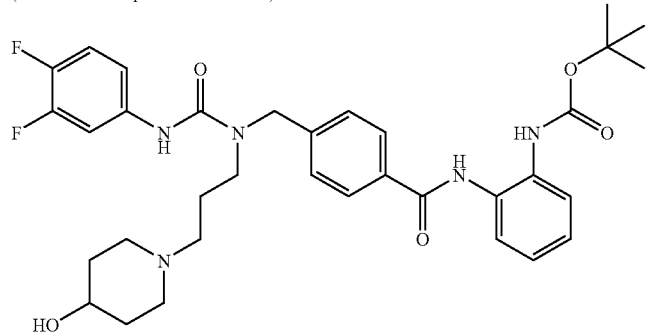

¹H-NMR (400 MHz, CDCl₃)
δ 1.51 (s, 9H), 1.61 (m, 4H), 1.72 (m, 2H), 1.82 (m, 2H), 2.43 (t, J = 5.9 Hz, 2H), 2.74 (m, 2H), 3.36 (t, J = 5.6 Hz, 2H), 3.78 (m, 1H), 4.61 (m, 2H), 6.79 (s, 1H), 7.02 (m, 1H), 7.08 (m, 1H), 7.17 (td, J = 7.6, 1.5 Hz, 1H), 7.23 (td, J = 7.6, 1.5 Hz, 1H), 7.26 (m, 1H), 7.41 (d, J = 8.2 Hz, 2H), 7.50 (ddd, J = 12.3, 7.2, 2.6, 1H), 7.79 (d, J = 7.6 Hz, 1H), 7.92 (d, J = 8.2 Hz, 2H), 9.12 (s, 1H), 9.25 (s, 1H)

N-(2-t-Butoxycarbonylaminophenyl)-4-[3-(2,3-dihydrobenzo[1,4]dioxin-6-yl)-1-[3-(4-hydroxypiperidin-1-yl)propyl]ureidomethyl]benzamide
(Reference Compound No. 13-155)

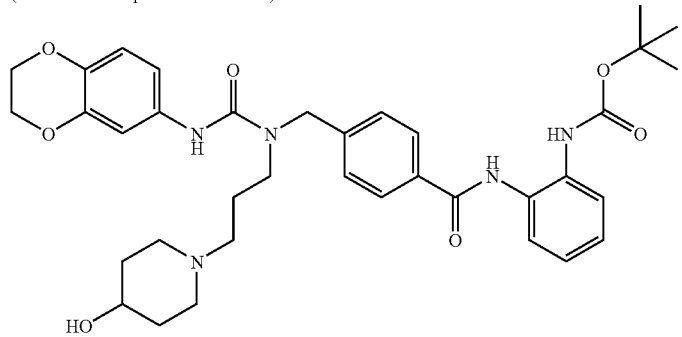

¹H-NMR (400 MHz, CDCl₃)
δ 1.51 (s, 9H), 1.60-1.72 (m, 6H), 1.80 (m, 2H), 2.37 (m, 2H), 2.72 (m, 2H), 3.32 (m, 2H), 3.71 (m, 1H), 4.20-4.26 (m, 4H), 4.59 (s, 2H), 6.76-6.83 (m, 3H), 6.99 (m, 1H), 7.17 (dd, J = 7.6, 1.6 Hz, 1H), 7.22 (dd, J = 7.6, 1.6 Hz, 1H), 7.30 (dd, J = 7.6, 1.6 Hz, 1H), 7.41 (d, J = 8.4 Hz, 2H), 7.76 (d, J = 7.6 Hz, 1H), 7.90 (d, J = 8.4 Hz, 2H), 9.11 (s, 1H), 10.67 (s, 1H)

N-(2-t-Butoxycarbonylaminophenyl)-4-[3-(4-dimethylaminophenyl)-1-[3-(pyrrolidin-1-yl)propyl]ureidomethyl]benzamide
(Reference Compound No. 13-156)

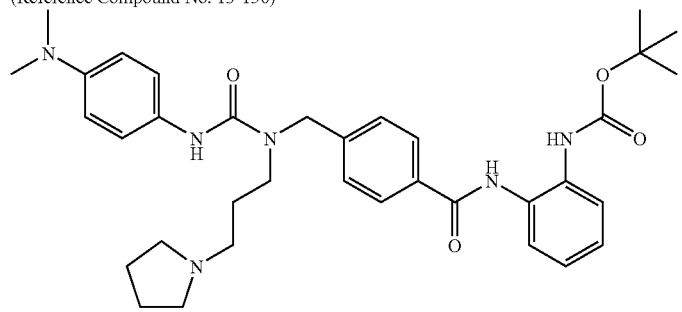

¹H-NMR (500 MHz, CDCl₃)
δ 1.50 (s, 9H), 1.63 (m, 2H), 1.91 (m, 4H), 2.63 (m, 2H), 2.68 (m, 4H), 2.89 (s, 6H), 3.49 (s, 2H), 4.63 (s, 2H), 6.70 (d, J = 8.9 Hz, 2H), 6.94 (s, 1H), 7.17 (td, J = 7.6, 1.5 Hz, 1H), 7.21 (td, J = 7.6, 1.5 Hz, 1H), 7.27 (d, J = 8.9 Hz, 2H), 7.32 (d, J = 7.9 Hz, 1H), 7.41 (d, J = 8.2 Hz, 2H), 7.76 (d, J = 7.6 Hz, 1H), 7.92 (d, J = 8.2 Hz, 2H), 9.19 (s, 1H)

N-(2-t-Butoxycarbonylaminophenyl)-4-[3-(3,4-difluorophenyl)-1-[3-(pyrrolidin-1-yl)-propyl]ureidomethyl]benzamide
(Reference Compound No. 13-157)

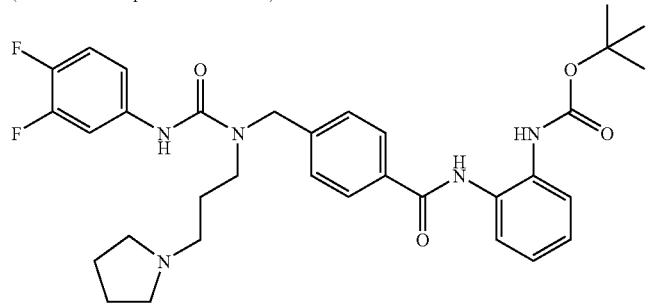

$^1$H-NMR (500 MHz, CDCl$_3$)
δ 1.50 (s, 9H), 1.83 (m, 2H), 1.95 (m, 4H), 2.64 (m, 2H), 2.70 (m, 4H), 3.54 (s, 2H), 4.61 (s, 2H), 7.02 (m, 1H), 7.03 (m, 1H), 7.15 (m, 1H), 7.17 (td, J = 7.6, 1.5 Hz, 1H), 7.21 (td, J = 7.6, 1.5 Hz, 1H), 7.30 (dd, J = 7.6, 1.5 Hz, 1H), 7.37 (d, J = 8.1 Hz, 2H), 7.57 (s, 1H), 7.76 (d, J = 7.6 Hz, 1H), 7.90 (d, J = 8.1 Hz, 2H), 9.27 (s, 1H)

N-(2-t-Butoxycarbonylaminophenyl)-4-[3-(2,3-dihydrobenzo[1,4]dioxin-6-yl)-1-[3-(pyrrolidin-1-yl)propyl]ureidomethyl]benzamide
(Reference Compound No. 13-158)

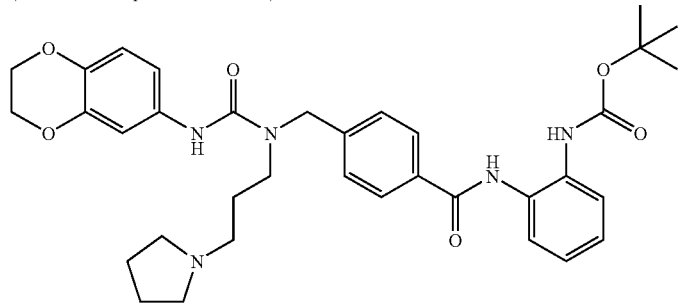

$^1$H-NMR (500 MHz, CDCl$_3$)
δ 1.50 (s, 9H), 1.88 (m, 2H), 1.95 (m, 4H), 2.63 (m, 2H), 2.70 (m, 4H), 3.50 (s, 2H), 4.21 (m, 4H), 4.61 (s, 2H), 6.75 (d, J = 8.6 Hz, 1H), 6.86 (dd, J = 8.6, 2.4 Hz, 1H), 7.01 (m, 1H), 7.02 (d, J = 2.4 Hz, 1H), 7.17 (td, J = 7.6, 1.5 Hz, 1H), 7.21 (td, J = 7.6, 1.5 Hz, 1H), 7.32 (dd, J = 7.6, 1.5 Hz, 1H), 7.38 (d, J = 7.9 Hz, 2H), 7.75 (d, J = 7.6 Hz, 1H), 7.91 (d, J = 7.9 Hz, 2H), 9.24 (s, 1H)

Reference Example 14

4-[3-(3-Benzyloxyphenyl)-1-(3-dimethylaminopropyl)ureidomethyl]-N-(2-t-butoxycarbonylaminophenyl)benzamide (Reference Compound No. 14-1)

1-Benzyloxy-3-(phenoxycarbonylamino)benzene (Reference Compound No. 5-1, 3.7 g, 12 mmol) was added to a solution of the mixture containing N-(2-t-butoxycarbonylaminophenyl)-4-(3-dimethylaminopropylaminomethyl)benzamide (Reference Compound No. 4-5, 10 g, 24 mmol) in DMSO (30 mL), and then the reaction mixture was stirred at room temperature for 15 hours. Water (300 mL) was added thereto, the whole was extracted with ethyl acetate (250 mL) twice, and then the organic layer was washed with brine (250 mL) twice. The organic layer was dried over anhydrous magnesium sulfate, and then the solvent was evaporated under reduced pressure. The residue was purified by silica gel column chromatography (chloroform-methanol) to give 1.1 g of the title reference compound as a white amorphous product. (Yield 15%)

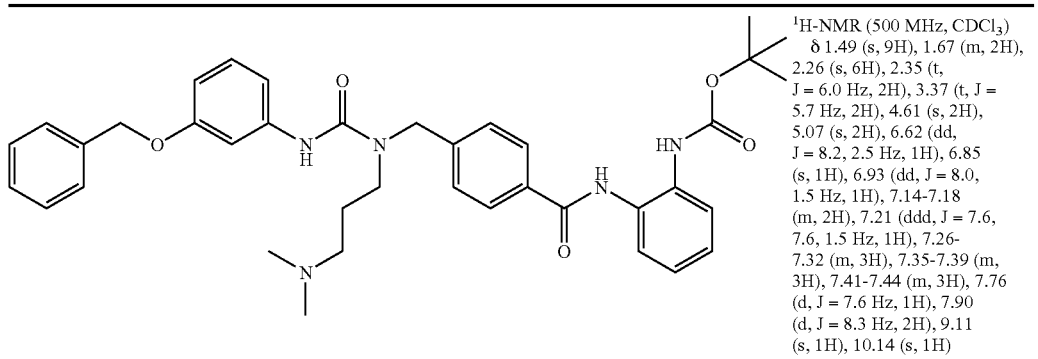

$^1$H-NMR (500 MHz, CDCl$_3$)
δ 1.49 (s, 9H), 1.67 (m, 2H), 2.26 (s, 6H), 2.35 (t, J = 6.0 Hz, 2H), 3.37 (t, J = 5.7 Hz, 2H), 4.61 (s, 2H), 5.07 (s, 2H), 6.62 (dd, J = 8.2, 2.5 Hz, 1H), 6.85 (s, 1H), 6.93 (dd, J = 8.0, 1.5 Hz, 1H), 7.14-7.18 (m, 2H), 7.21 (ddd, J = 7.6, 7.6, 1.5 Hz, 1H), 7.26-7.32 (m, 3H), 7.35-7.39 (m, 3H), 7.41-7.44 (m, 3H), 7.76 (d, J = 7.6 Hz, 1H), 7.90 (d, J = 8.3 Hz, 2H), 9.11 (s, 1H), 10.14 (s, 1H)

By using any compounds selected from Reference Compound No. 4-5, 4-11, 5-2 to 5-4, commercially available compounds, and known compounds, the following Reference Compounds No. 14-2 to 14-4 were obtained by a method similar to that of Reference Compound No. 14-1.

4-[3-(4-Benzyloxyphenyl)-1-(3-dimethylaminopropyl)ureidomethyl]-N-(2-t-butoxycarbonylaminophenyl)benzamide (Reference Compound No. 14-2)

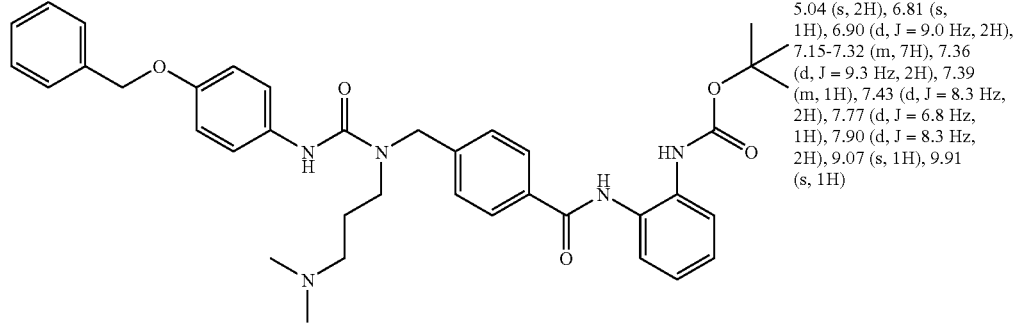

$^1$H-NMR (400 MHz, CDCl$_3$)
δ 1.50 (s, 9H), 1.66 (m, 2H), 2.27 (s, 6H), 2.34 (t, J = 5.9 Hz, 2H), 3.37 (t, J = 5.4 Hz, 2H), 4.61 (s, 2H), 5.04 (s, 2H), 6.81 (s, 1H), 6.90 (d, J = 9.0 Hz, 2H), 7.15-7.32 (m, 7H), 7.36 (d, J = 9.3 Hz, 2H), 7.39 (m, 1H), 7.43 (d, J = 8.3 Hz, 2H), 7.77 (d, J = 6.8 Hz, 1H), 7.90 (d, J = 8.3 Hz, 2H), 9.07 (s, 1H), 9.91 (s, 1H)

N-(2-t-Butoxycarbonylamino phenyl)-4-[1-(3-dimethyl-aminopropyl)-3-[4-(4-methyl-piperazin-1-yl)phenyl]ureidomethyl]benzamide (Reference Compound No. 14-3)

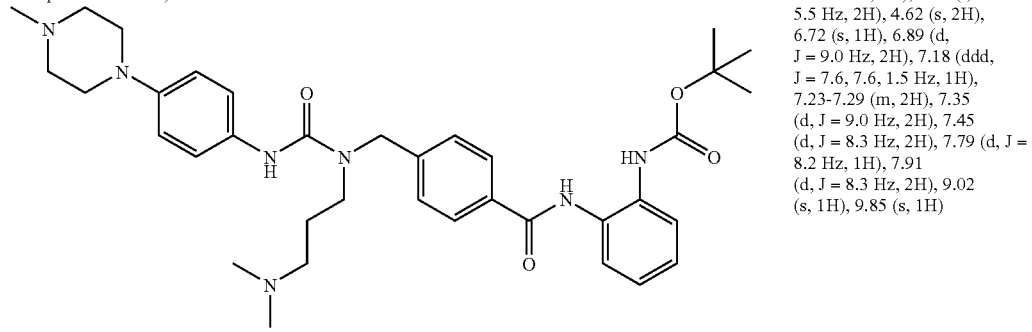

$^1$H-NMR (500 MHz, CDCl$_3$)
δ 1.51 (s, 9H), 1.65 (m, 2H), 2.27 (s, 6H), 2.35 (s, 3H), 2.37 (m, 2H), 2.59 (t, J = 4.9 Hz, 4H), 3.14 (t, J = 4.9 Hz, 4H), 3.36 (t, J = 5.5 Hz, 2H), 4.62 (s, 2H), 6.72 (s, 1H), 6.89 (d, J = 9.0 Hz, 2H), 7.18 (ddd, J = 7.6, 7.6, 1.5 Hz, 1H), 7.23-7.29 (m, 2H), 7.35 (d, J = 9.0 Hz, 2H), 7.45 (d, J = 8.3 Hz, 2H), 7.79 (d, J = 8.2 Hz, 1H), 7.91 (d, J = 8.3 Hz, 2H), 9.02 (s, 1H), 9.85 (s, 1H)

N-(2-t-Butoxycarbonylamino phenyl)-4-[3-(3-dimethyl-aminophenyl)-1-[3-(morpholin-4-yl)propyl]ureidomethyl]benzamide (Reference Compound No. 14-4)

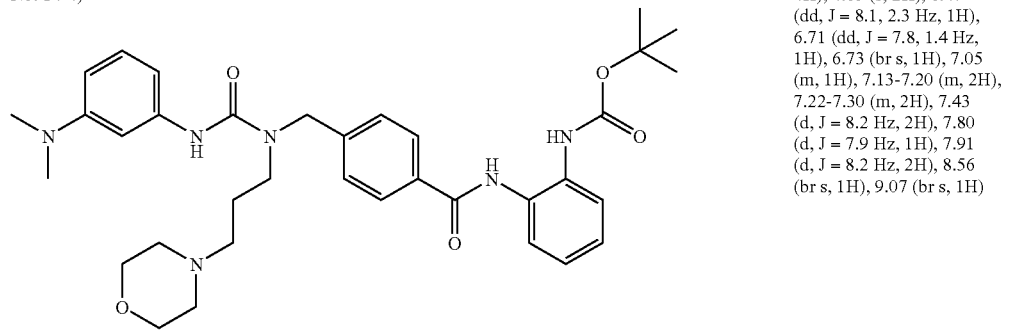

$^1$H-NMR (500 MHz, CDCl$_3$)
δ 1.50 (s, 9H), 1.73 (m, 2H), 2.40-2.49 (m, 6H), 2.96 (s, 6H), 3.38 (t, J = 5.8 Hz, 2H), 3.72 (t, J = 4.7 Hz, 4H), 4.65 (s, 2H), 6.47 (dd, J = 8.1, 2.3 Hz, 1H), 6.71 (dd, J = 7.8, 1.4 Hz, 1H), 6.73 (br s, 1H), 7.05 (m, 1H), 7.13-7.20 (m, 2H), 7.22-7.30 (m, 2H), 7.43 (d, J = 8.2 Hz, 2H), 7.80 (d, J = 7.9 Hz, 1H), 7.91 (d, J = 8.2 Hz, 2H), 8.56 (br s, 1H), 9.07 (br s, 1H)

Reference Example 15

4-[3-(4-Aminophenyl)-1-[3-(morpholin-4-yl)propyl] ureidomethyl]-N-(2-t-butoxycarbonylaminophenyl) benzamide (Reference Compound No. 15-1)

5% Palladium on carbon (10 mg) was added to a solution of N-(2-t-butoxycarbonylaminophenyl)-4-[1-[3-(morpholin-4-yl)propyl]-3-(4-nitrophenyl)ureidomethyl]benzamide (Reference Compound No. 13-62, 80 mg, 0.13 mmol) in methanol (2.0 mL), and then the reaction mixture was stirred under a hydrogen atmosphere at room temperature for 18 hours. The insoluble was filtered off, and then the solvent was evaporated under reduced pressure. The residue was purified by silica gel column chromatography (chloroform-methanol) to give 45 mg of the title reference compound as pale yellow oil. (Yield 60%)

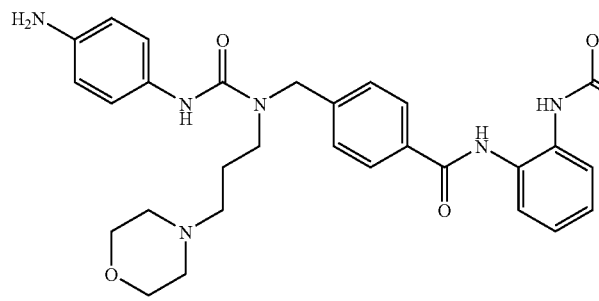

$^1$H-NMR (400 MHz, CDCl$_3$)
δ 1.50 (s, 9H), 1.71 (m, 2H), 2.36-2.49 (m, 6H), 3.36 (t, J = 5.7 Hz, 2H), 3.59 (br s, 2H), 3.61 (t, J = 4.4 Hz, 4H), 4.62 (s, 2H), 6.65 (d, J = 8.7 Hz, 2H), 6.78 (br s, 1H), 7.14-7.31 (m, 3H), 7.16 (d, J = 8.7 Hz, 2H), 7.43 (d, J = 8.2 Hz, 2H), 7.78 (dd, J = 8.1, 1.2 Hz, 1H), 7.91 (d, J = 8.2 Hz, 2H), 8.71 (br s, 1H), 9.08 (br s, 1H)

Reference Example 16

N-(2-t-Butoxycarbonylamino-5-methoxyphenyl)-4-[1-(2-dimethylaminoethyl)-3-(indan-5-yl)ureidomethyl]benzamide (Reference Compound No. 16-1)

HATU (130 mg, 0.33 mmol) was added to a solution of benzoic acid (Reference Compound No. 10-1, 120 mg, 0.30 mmol), 2-amino-4-methoxyphenylcarbamic acid t-butyl ester (Reference Compound No. 12-1, 80 mg, 0.33 mmol) and N,N-diisopropylethylamine (0.12 mL, 0.66 mmol) in DMF (3.0 mL), and then the reaction mixture was stirred at room temperature for 18 hours. Water (30 mL) was added thereto, the whole was extracted with ethyl acetate (30 mL) twice, and then the organic layer was washed with brine (40 mL) twice. The organic layer was dried over anhydrous magnesium sulfate, and then the solvent was evaporated under reduced pressure. The residue was purified by silica gel column chromatography (chloroform-methanol) to give 43 mg of the title reference compound as a colorless amorphous product. (Yield 24%)

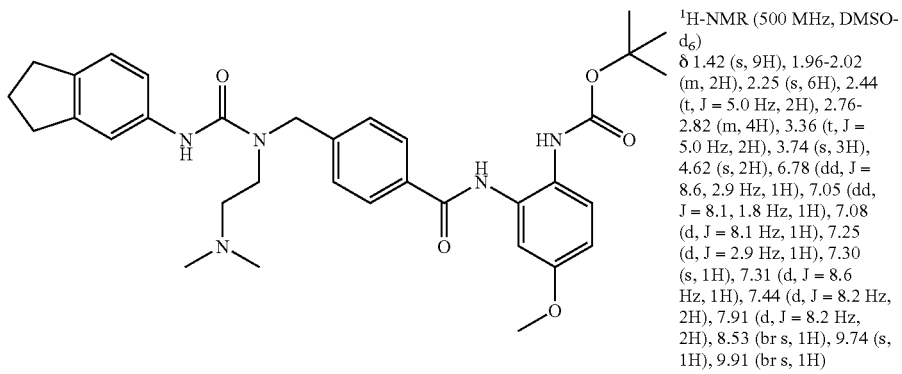

$^1$H-NMR (500 MHz, DMSO-d$_6$)
δ 1.42 (s, 9H), 1.96-2.02 (m, 2H), 2.25 (s, 6H), 2.44 (t, J = 5.0 Hz, 2H), 2.76-2.82 (m, 4H), 3.36 (t, J = 5.0 Hz, 2H), 3.74 (s, 3H), 4.62 (s, 2H), 6.78 (dd, J = 8.6, 2.9 Hz, 1H), 7.05 (dd, J = 8.1, 1.8 Hz, 1H), 7.08 (d, J = 8.1 Hz, 1H), 7.25 (d, J = 2.9 Hz, 1H), 7.30 (s, 1H), 7.31 (d, J = 8.6 Hz, 1H), 7.44 (d, J = 8.2 Hz, 2H), 7.91 (d, J = 8.2 Hz, 2H), 8.53 (br s, 1H), 9.74 (s, 1H), 9.91 (br s, 1H)

By using any compounds selected from Reference Compound No. 10-1, commercially available compounds, and known compounds, the following Reference Compounds No. 16-2 was obtained by a method similar to that of Reference Compound No. 16-1.

| | |
|---|---|
| N-(5-Bromo-2-t-butoxy-carbonylaminophenyl)-4-[1-(2-dimethylaminoethyl)-3-(indan-5-yl)ureidomethyl]benz-amide (Reference Compound No. 16-2) 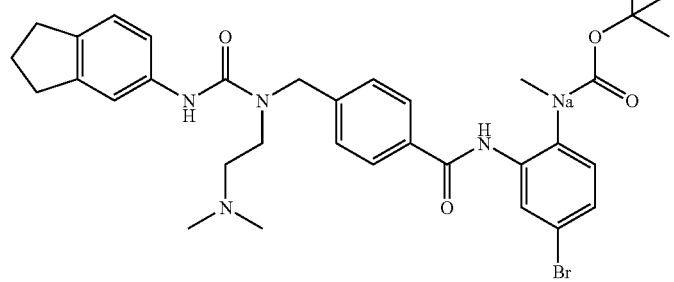 | $^1$H-NMR (500 MHz, CDCl$_3$) δ 1.50 (s, 9H), 2.06 (m, 2H), 2.44 (s, 6H), 2.57 (br s, 2H), 2.83-2.90 (m, 4H), 3.40 (br s, 2H), 4.71 (s, 2H), 7.00 (d, J = 8.1 Hz, 2H), 7.08-7.16 (m, 2H), 7.36-7.42 (m, 2H), 7.56 (d, J = 8.3 Hz, 2H), 7.90 (d, J = 8.3 Hz, 1H), 8.26 (d, J = 8.3 Hz, 2H), 8.47 (dd, J = 8.3, 1.3 Hz, 1H), 8.74 (dd, J = 4.5, 1.3 Hz, 1H) |

Reference Example 17

N-(2-t-Butoxycarbonylaminophenyl)-4-[1-[3-(morpholin-4-yl)propyl]-3-(thiazol-2-yl)ureidomethyl] benzamide (Reference Compound No. 17-1)

Under ice cooling, 2-aminothiazole (65 mg, 0.64 mmol) was added to a solution of N,N'-carbonyldiimidazole (110 mg, 0.68 mmol) in THF (3.0 mL), and then the reaction mixture was stirred for 6 hours. N-(2-t-butoxycarbonylaminophenyl)-4-[3-(morpholin-4-yl) propylaminomethyl]benzamide (Reference Compound No. 4-11, 110 mg, 0.23 mmol) was added thereto, and then the reaction mixture was stirred at 60° C. for 16 hours. Water (100 mL) was added thereto, the whole was extracted with ethyl acetate (100 mL), and then the organic layer was washed with brine (100 mL). The organic layer was dried over anhydrous sodium sulfate, and then the solvent was evaporated under reduced pressure. The residue was purified by silica gel column chromatography (chloroform-methanol) to give 90 mg of the title reference compound as a colorless amorphous product. (Yield 65%)

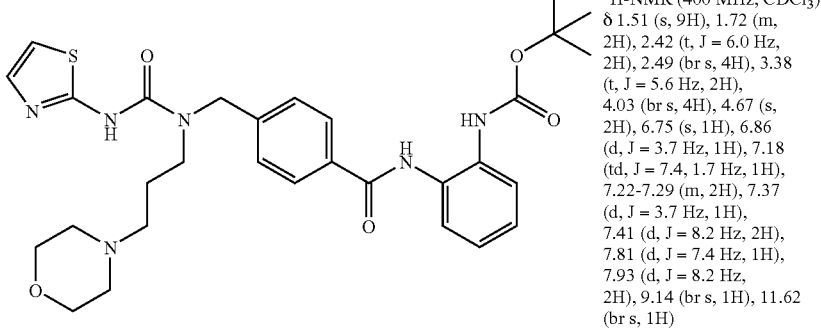

$^1$H-NMR (400 MHz, CDCl$_3$) δ 1.51 (s, 9H), 1.72 (m, 2H), 2.42 (t, J = 6.0 Hz, 2H), 2.49 (br s, 4H), 3.38 (t, J = 5.6 Hz, 2H), 4.03 (br s, 4H), 4.67 (s, 2H), 6.75 (s, 1H), 6.86 (d, J = 3.7 Hz, 1H), 7.18 (td, J = 7.4, 1.7 Hz, 1H), 7.22-7.29 (m, 2H), 7.37 (d, J = 3.7 Hz, 1H), 7.41 (d, J = 8.2 Hz, 2H), 7.81 (d, J = 7.4 Hz, 1H), 7.93 (d, J = 8.2 Hz, 2H), 9.14 (br s, 1H), 11.62 (br s, 1H)

By using any compounds selected from Reference Compound 4-11, the following Reference Compounds No. 17-2 to 17-6 were obtained by a method similar to that of Reference Compound No. 17-1.

---

N-(2-t-Butoxycarbonylaminophenyl)-4-[3-(3-methylisoxazol-5-yl)-1-[3-(morpholin-4-yl)propyl]ureidomethyl]benzamide (Reference Compound No. 17-2)

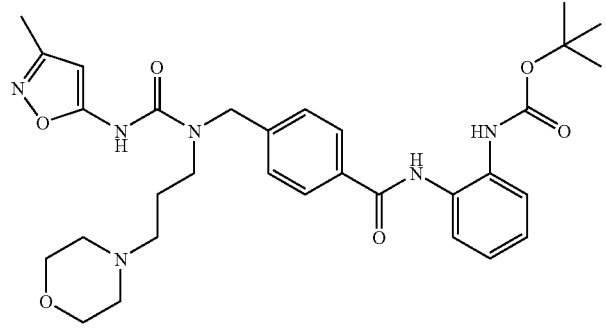

$^1$H-NMR (500 MHz, CDCl$_3$) δ 1.51 (s, 9H), 1.72 (m, 2H), 2.37 (d, J = 0.9 Hz, 3H), 2.42 (t, J = 6.0 Hz, 2H), 2.49 (br s, 4H), 3.37 (t, J = 5.5 Hz, 2H), 3.95 (t, J = 4.4 Hz, 4H), 4.62 (s, 2H), 6.60 (d, J = 0.9 Hz, 1H), 6.71 (s, 1H), 7.18 (td, J = 7.6, 2.1 Hz, 1H), 7.24-7.27 (m, 2H), 7.41 (d, J = 8.2 Hz, 2H), 7.82 (d, J = 7.6 Hz, 1H), 7.93 (d, J = 8.2 Hz, 2H), 9.10 (br s, 1H), 10.43 (br s, 1H)

---

4-[3-(Benzimidazol-2-yl)-1-[3-(morpholino-4-yl)propyl]ureidomethyl]-N-(2-t-butoxycarbonylaminophenyl)benzamide (Reference Compound No. 17-3)

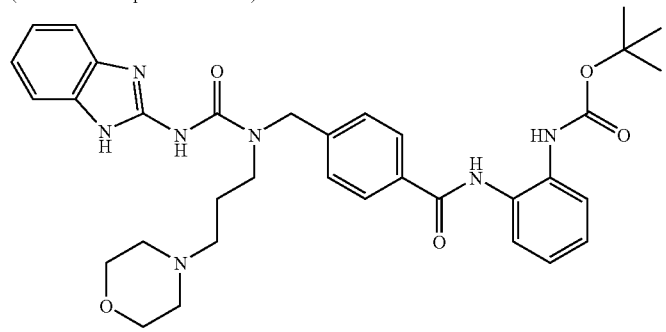

$^1$H-NMR (400 MHz, CDCl$_3$) δ 1.50 (s, 9H), 1.78 (m, 2H), 2.45 (t, J = 6.1 Hz, 2H), 2.51 (br s, 4H), 3.44 (t, J = 5.6 Hz, 2H), 4.09 (br s, 4H), 4.67 (s, 2H), 6.76 (s, 1H), 7.11-7.20 (m, 3H), 7.21-7.28 (m, 3H), 7.33 (br s, 1H), 7.41 (d, J = 8.2 Hz, 2H), 7.50 (br s, 1H), 7.82 (d, J = 7.8 Hz, 1H), 7.95 (d, J = 8.2 Hz, 2H), 9.17 (br s, 1H), 10.97 (br s, 1H)

| | |
|---|---|
| N-(2-t-butoxycarbonylamino-phenyl)-4-[3-[4-(morpholin-4-yl)phenyl]-1-[3-(morpholin-4-yl)propyl]ureidomethyl]benz-amide (Reference Compound No. 17-4)<br>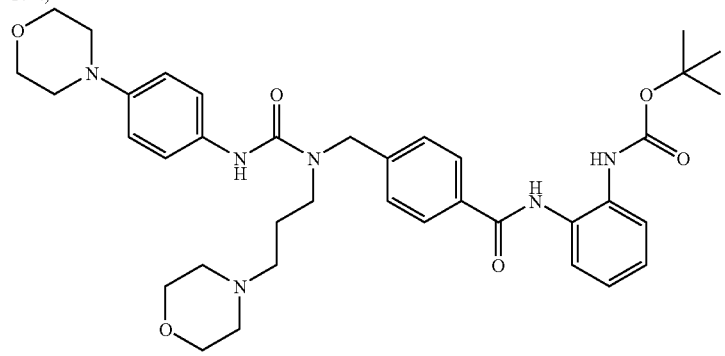 | $^1$H-NMR (500 MHz, DMSO-d$_6$) δ 1.44 (s, 9H), 1.68 (m, 2H), 2.25-2.34 (m, 6H), 3.02 (t, J = 4.8 Hz, 4H), 3.31 (m, 2H), 3.53 (t, J = 4.4 Hz, 4H), 3.73 (t, J = 4.8 Hz, 4H), 4.63 (s, 2H), 6.86 (d, J = 9.2 Hz, 2H), 7.15 (td, J =7.6, 1.4 Hz, 1H), 7.20 (td, J = 7.6, 1.7 Hz, 1H), 7.31 (d, J = 9.2 Hz, 2H), 7.42 (d, J = 8.2 Hz, 2H), 7.51-7.57 (m, 2H), 7.93 (d, J = 8.2 Hz, 2H), 8.42 (s, 1H), 8.66 (br s, 1H), 9.81 (s, 1H) |
| N-(2-t-Butoxycarbonylamino-phenyl)-4-[1-[3-(morpholin-4-yl)propyl]-3-(5-nitrothiazol-2-yl)ureidomethyl]benzamide (Reference Compound No. 17-5)<br>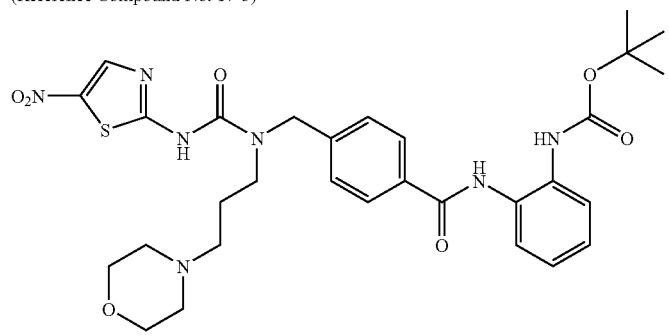 | $^1$H-NMR (400 MHz, CDCl$_3$) δ 1.52 (s, 9H), 1.77 (m, 2H), 2.45 (t, J = 6.0 Hz, 2H), 2.53 (br s, 4H), 3.39 (t, J = 5.6 Hz, 2H), 4.01 (br s, 4H), 4.66 (s, 2H), 6.69 (s, 1H), 7.16-7.31 (m, 4H), 7.42 (d, J = 8.3 Hz, 2H), 7.85 (d, J = 7.8 Hz, 1H), 7.95 (d, J = 8.3 Hz, 2H), 8.27 (s, 1H), 9.23 (br s, 1H) |
| N-(2-t-Butoxycarbonylamino-phenyl)-4-[1-[3-(morpholin-4-yl)propyl]-3-(4,5,6,7-tetrahydro-benzothiazol-2-yl)ureido-methyl]benzamide (Reference Compound No. 17-6)<br>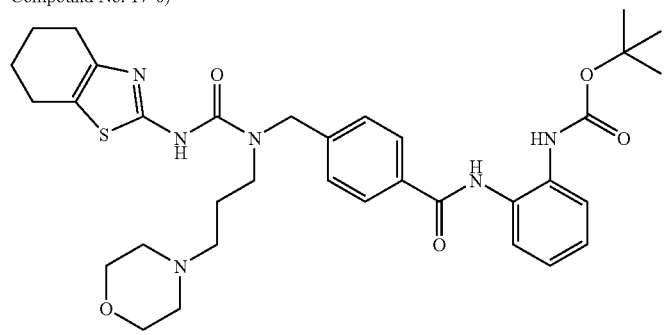 | $^1$H-NMR (400 MHz, CDCl$_3$) δ 1.51 (s, 9H), 1.70 (m, 2H), 1.78-1.87 (m, 4H), 2.40 (t, J = 6.0 Hz, 2H), 2.48 (br s, 4H), 2.52-2.69 (m, 4H), 3.35 (t, J = 5.5 Hz, 2H), 4.00 (br s, 4H), 4.65 (s, 2H), 6.75 (s, 1H), 7.17 (td, J = 7.8, 1.5 Hz, 1H), 7.22-7.29 (m, 2H), 7.40 (d, J = 8.3 Hz, 2H), 7.81 (d, J = 7.8 Hz, 1H), 7.92 (d, J = 8.3 Hz, 2H), 9.12 (br s, 1H), 11.21 (br s, 1H) |

Reference Example 18

N-(2-t-Butoxycarbonylaminophenyl)-4-[3-(4-dimethylamino phenyl)-1-[3-(N-ethyl-N-methylamino)propyl]ureidomethyl]benzamide (Reference Compound No. 18-1)

Under ice cooling, methanesulfonyl chloride (0.30 mL, 3.9 mmol) was added to a solution of N-(2-t-butoxycarbonylaminophenyl)-4-[3-(4-dimethylamino phenyl)-1-(3-hydroxypropyl)ureidomethyl]benzamide (Reference Compound No. 13-79, 200 mg, 0.36 mmol) and triethylamine (0.68 mL, 4.9 mmol) in anhydrous dichloromethane (5.0 mL), and then the reaction mixture was stirred for 7 hours. Water (100 mL) was added thereto, the whole was extracted with ethyl acetate (100 mL), and then the organic layer was washed with brine (100 mL). The organic layer was dried over anhydrous sodium sulfate, and then the solvent was evaporated under reduced pressure. Anhydrous dichloromethane (1.0 mL) and ethylmethylamine (0.03 mL, 0.35 mmol) were added to the residue, and then the mixture was stirred at room temperature for 5 hours. Water (50 mL) was added thereto, the whole was extracted with ethyl acetate (50 mL) and then the organic layer was washed with brine (50 mL). After the organic layer was dried over anhydrous sodium sulfate, the solvent was evaporated under reduced pressure. The residue was purified by silica gel column chromatography (chloroform-methanol) to give 9.0 mg of the title reference compound as colorless oil. (Yield 4%)

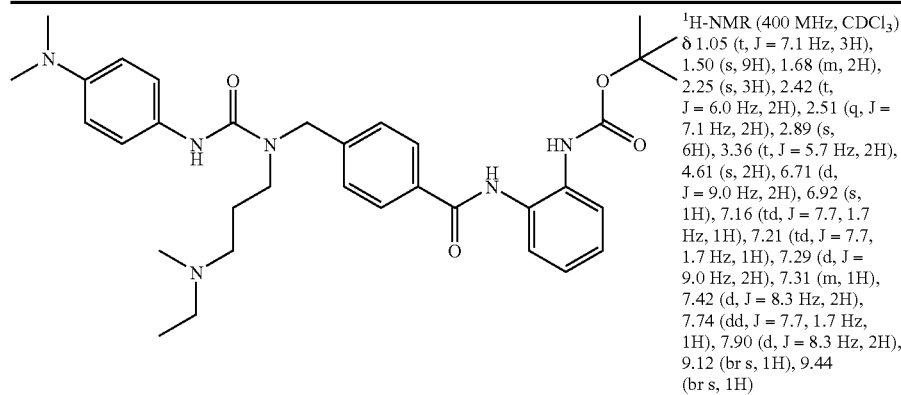

$^1$H-NMR (400 MHz, CDCl$_3$) δ 1.05 (t, J = 7.1 Hz, 3H), 1.50 (s, 9H), 1.68 (m, 2H), 2.25 (s, 3H), 2.42 (t, J = 6.0 Hz, 2H), 2.51 (q, J = 7.1 Hz, 2H), 2.89 (s, 6H), 3.36 (t, J = 5.7 Hz, 2H), 4.61 (s, 2H), 6.71 (d, J = 9.0 Hz, 2H), 6.92 (s, 1H), 7.16 (td, J = 7.7, 1.7 Hz, 1H), 7.21 (td, J = 7.7, 1.7 Hz, 1H), 7.29 (d, J = 9.0 Hz, 2H), 7.31 (m, 1H), 7.42 (d, J = 8.3 Hz, 2H), 7.74 (dd, J = 7.7, 1.7 Hz, 1H), 7.90 (d, J = 8.3 Hz, 2H), 9.12 (br s, 1H), 9.44 (br s, 1H)

Example 1

N-(2-Aminophenyl)-4-[3-(2,3-dihydrobenzo[1,4]dioxin-6-yl)-1-[3-(4-methylpiperazin-1-yl)propyl]ureidomethyl]benzamide (Compound No. 1-1)

4.0 M hydrogen chloride ethyl acetate solution (10 mL) was added to a solution of N-(2-t-butoxycarbonylaminophenyl)-4-[3-(2,3-dihydrobenz o[1,4]dioxin-6-yl)-1-[3-(4-methylpiperazine-1-yl)propyl]ureidomethyl]benzamide (Reference Compound No. 13-1, 450 mg, 0.68 mmol) in a mixed solvent (ethyl acetate (10 mL) and methanol (10 mL)), and then the mixture was stirred at room temperature for 2.5 hours. Saturated aqueous sodium hydrogen carbonate solution (150 mL) was added thereto, the whole was extracted with chloroform (150 mL), and then the organic layer was washed with brine (150 mL). The organic layer was dried over anhydrous sodium sulfate, and then the solvent was evaporated under reduced pressure. The residue was purified by silica gel column chromatography (NH-modified silica gel, chloroform-methanol) to give 310 mg of the title compound as a colorless amorphous product. (Yield 82%)

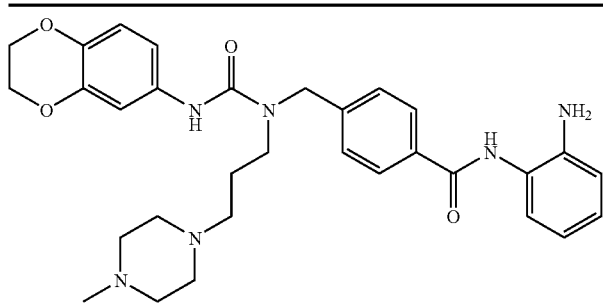

$^1$H-NMR (400 MHz, CDCl$_3$) δ 1.72 (m, 2H), 2.25 (s, 3H), 2.41 (br s, 8H), 2.44 (t, J = 6.0 Hz, 2H), 3.34 (t, J = 5.4 Hz, 2H), 3.87 (br s, 2H), 4.20-4.27 (m, 4H), 4.61 (s, 2H), 6.79 (d, J = 8.5 Hz, 1H), 6.83-6.88 (m, 3H), 7.04 (d, J = 2.4 Hz, 1H), 7.10 (td, J = 7.6, 1.3 Hz, 1H), 7.33 (d, J = 7.6 Hz, 1H), 7.45 (d, J = 8.1 Hz, 2H), 7.82-7.87 (m, 3H), 8.91 (br s, 1H)

By using any compounds selected from Reference Compounds No. 13-2 to 13-158, Reference Compounds No. 14-1 to 14-4, Reference Compound No. 15-1, Reference Compounds No. 16-1 to 16-2, Reference Compounds No. 17-1 to 17-6, Reference Compound No. 18-1, commercially available compounds, and known compounds, the following Compounds No. 1-2 to 1-172 were obtained by a method similar to that of Compound No. 1-1.

N-(2-Aminophenyl)-4-[1-(2-dimethylaminoerthyl)-3-phenyl-ureidomethyl]benzamide (Compound No. 1-2)

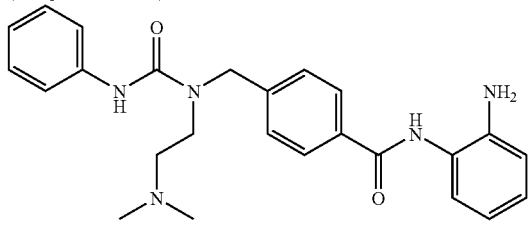

$^1$H-NMR (500 MHz, DMSO-d$_6$) δ 2.28 (s, 6H), 2.46 (t, J = 4.9 Hz, 2H), 3.38 (t, J = 4.9 Hz, 2H), 4.62 (s, 2H), 4.88 (s, 2H), 6.60 (t, J = 7.6 Hz, 1H), 6.78 (d, J = 7.6 Hz, 1H), 6.93 (t, J = 7.6 Hz, 1H), 7.00 (m, 1H), 7.16 (d, J = 7.6 Hz, 1H), 7.25 (t, J = 7.6 Hz, 2H), 7.38 (d, J = 7.6 Hz, 2H), 7.42 (d, J = 8.1 Hz, 2H), 7.96 (d, J = 8.1 Hz, 2H), 9.63 (s, 1H), 10.18 (br s, 1H)

N-(2-Aminophenyl)-4-[3-(4-chlorophenyl)-1-(2-dimethyl-aminoethyl)ureidomethyl]-benzamide (Compound No. 1-3)

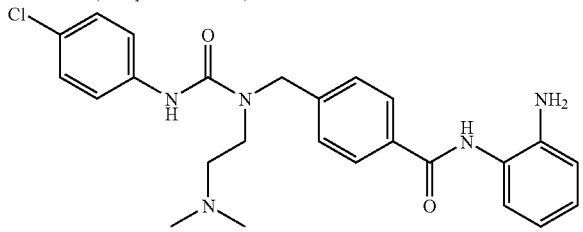

$^1$H-NMR (500 MHz, DMSO-d$_6$) δ 2.27 (s, 6H), 2.52-2.57 (m, 2H), 3.39 (br s, 2H), 4.63 (s, 2H), 4.88 (s, 2H), 6.60 (t, J = 7.6 Hz, 1H), 6.78 (dd, J = 7.6, 1.2 Hz, 1H), 6.97 (td, J = 7.6, 1.2 Hz, 1H), 7.16 (d, J = 7.6 Hz, 1H), 7.29 (d, J = 9.2 Hz, 2H), 7.40-7.44 (m, 4H), 7.96 (d, J = 8.2 Hz, 2H), 9.63 (s, 1H), 10.33 (br s, 1H)

N-(2-Aminophenyl)-4-[1-(2-dimethylaminoethyl)-3-phenethylureidomethyl]benz-amide (Compound No. 1-4)

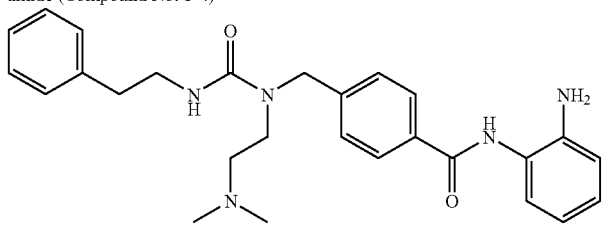

$^1$H-NMR (400 MHz, DMSO-d$_6$) δ 2.07 (s, 6H), 2.27 (t, J = 6.3 Hz, 2H), 2.74 (t, J = 7.2 Hz, 2H), 3.17 (m, 2H), 3.30 (m, 2H), 4.51 (s, 2H), 4.89 (s, 2H), 6.60 (t, J = 7.5 Hz, 1H), 6.78 (d, J = 8.1 Hz, 1H), 6.91 (br s, 1H), 6.97 (m, 1H), 7.15-7.21 (m, 4H), 7.28 (d, J = 7.6 Hz, 2H), 7.30 (d, J = 8.1 Hz, 2H), 7.93 (d, J = 8.1 Hz, 2H), 9.63 (s, 1H)

| Compound | NMR |
|---|---|
| N-(2-Aminophenyl)-4-[3-benzyl-1-(2-dimethylaminoethyl)ureidomethyl]benzamide (Compound No. 1-5)<br />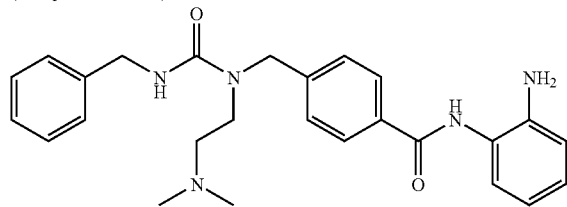 | $^1$H-NMR (400 MHz, DMSO-d$_6$) δ 2.11 (s, 6H), 2.36 (t, J = 6.5 Hz, 2H), 3.27 (t, J = 6.5 Hz, 2H), 4.27 (d, J = 5.4 Hz, 2H), 4.57 (s, 2H), 4.89 (s, 2H), 6.60 (t, J = 7.6 Hz, 1H), 6.78 (d, J = 7.6 Hz, 1H), 6.97 (t, J = 7.6 Hz, 1H), 7.15-7.25 (m, 4H), 7.30 (d, J = 7.1 Hz, 2H), 7.34 (d, J = 8.2 Hz, 2H), 7.43 (br s, 1H), 7.94 (d, J = 8.2 Hz, 2H), 9.63 (s, 1H) |
| N-(2-Aminophenyl)-4-[3-(3,5-dimethoxybenzyl)-1-(2-dimethylaminoethyl)ureidomethyl]benzamide (Compound No. 1-6)<br />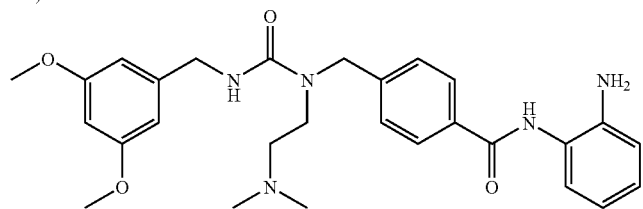 | $^1$H-NMR (400 MHz, DMSO-d$_6$) δ 2.13 (s, 6H), 2.37 (m, 2H), 3.29 (m, 2H), 3.71 (s, 6H), 4.21 (d, J = 5.4 Hz, 2H), 4.57 (s, 2H), 4.89 (s, 2H), 6.34 (t, J = 2.2 Hz, 1H), 6.42 (d, J = 2.2 Hz, 2H), 6.60 (t, J = 7.6 Hz, 1H), 6.78 (dd, J = 7.6, 1.5 Hz, 1H), 6.97 (td, J = 7.6, 1.5 Hz, 1H), 7.16 (d, J = 7.6 Hz, 1H), 7.35 (d, J = 8.2 Hz, 2H), 7.36 (s, 1H), 7.94 (d, J = 8.2 Hz, 2H), 9.63 (s, 1H) |
| N-(2-Aminophenyl)-4-[3-cyclopentyl-1-(2-dimethylaminoethyl)ureidomethyl]benzamide (Compound No. 1-7)<br />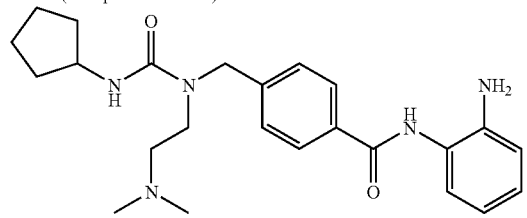 | $^1$H-NMR (400 MHz, DMSO-d$_6$) δ 1.37 (m, 2H), 1.50 (m, 2H), 1.62 (m, 2H), 1.79 (m, 2H), 2.15 (s, 6H), 2.32 (t, J = 5.6 Hz, 2H), 3.19 (t, J = 5.6 Hz, 2H), 3.93 (m, 1H), 4.50 (s, 2H), 4.89 (s, 2H), 6.60 (t, J = 7.6 Hz, 1H), 6.78 (d, J = 7.6 Hz, 1H), 6.97 (td, J = 7.6, 1.2 Hz, 1H), 7.13 (br s, 1H), 7.16 (d, J = 7.6 Hz, 1H), 7.33 (d, J = 8.3 Hz, 2H), 7.93 (d, J = 8.3 Hz, 2H), 9.62 (s, 1H) |
| N-(2-(Aminophenyl)-4-[3-(benzo[1,3]dioxol-5-yl)-1-(2-dimethylaminoethyl)ureidomethyl]benzamide (Compound No. 1-8)<br />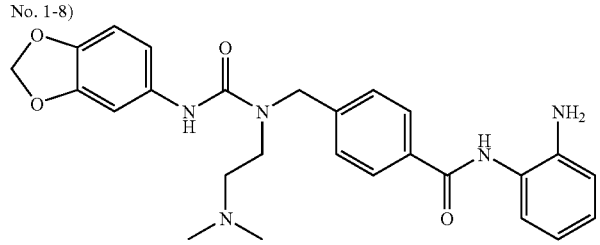 | $^1$H-NMR (400 MHz, DMSO-d$_6$) δ 2.25 (s, 6H), 2.44 (t, J = 5.2 Hz, 2H), 3.33 (m, 2H), 4.60 (s, 2H), 4.89 (s, 2H), 5.95 (s, 2H), 6.60 (t, J = 7.6 Hz, 1H), 6.70 (dd, J = 8.3, 2.2 Hz, 1H), 6.78 (d, J = 7.6 Hz, 2H), 6.80 (d, J = 8.3 Hz, 1H), 6.97 (td, J = 7.6, 1.2 Hz, 1H), 7.13 (d, J = 2.2 Hz, 1H), 7.16 (d, J = 7.6 Hz, 1H), 7.40 (d, J = 8.2 Hz, 2H), 7.95 (d, J = 8.2 Hz, 2H), 9.63 (s, 1H), 9.96 (br s, 1H) |

| | |
|---|---|
| N-(2-Aminophenyl)-4-[1-(2-dimethylaminoethyl)-3-(5,6,7,8-tetrahydronaphthalen-1-yl)ureidomethyl]benzamide (Compound No. 1-9)<br />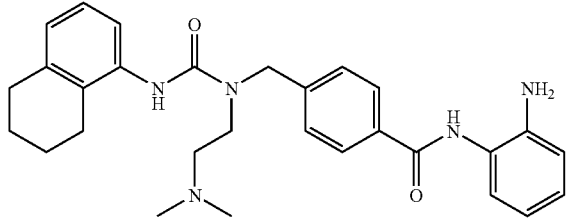 | $^1$H-NMR (400 MHz, DMSO-d$_6$) δ 1.68-1.73 (m, 4H), 2.22 (s, 6H), 2.46 (t, J = 5.4 Hz, 2H), 2.72 (t, J = 5.5 Hz, 2H), 3.17 (d, J = 5.1 Hz, 2H), 3.38 (t, J = 5.4 Hz, 2H), 4.61 (s, 2H), 4.90 (s, 2H), 6.60 (t, J = 7.6 Hz, 1H), 6.78 (dd, J = 7.8, 1.2 Hz, 1H), 6.81 (d, J = 7.6 Hz, 1H), 6.97 (m, 1H), 7.02 (t, J = 7.8 Hz, 1H), 7.11 (d, J = 7.8 Hz, 1H), 7.17 (d, J = 7.3 Hz, 1H), 7.43 (d, J = 8.1 Hz, 2H), 7.97 (d, J = 8.1 Hz, 2H), 8.90 (br s, 1H), 9.65 (s, 1H) |
| N-(2-Aminophenyl)-4-[1-(2-hydroxyethyl)-3-phenyl-ureidomethyl]benzamide (Compound No. 1-10)<br />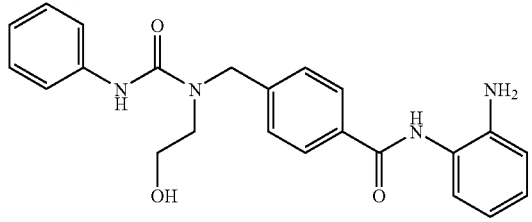 | $^1$H-NMR (500 MHz, DMSO-d$_6$) δ 3.42 (t, J = 5.3 Hz, 2H), 3.59 (m, 2H), 4.67 (s, 2H), 4.88 (s, 2H), 5.32 (br s, 1H), 6.60 (t, J = 7.6 Hz, 1H), 6.78 (dd, J = 7.6, 1.2 Hz, 1H), 6.92-6.98 (m, 2H), 7.16 (d, J = 7.6 Hz, 1H), 7.24 (t, J = 7.6 Hz, 2H), 7.41 (d, J = 8.2 Hz, 2H), 7.42 (dd, J = 7.6, 1.8 Hz, 2H), 7.96 (d, J = 8.2 Hz, 2H), 8.74 (br s, 1H), 9.62 (br s, 1H) |
| N-(2-Aminophenyl)-4-[3-(benzo[1,3]dioxol-5-yl)-1-(2-hydroxyethyl)ureidomethyl]benzamide (Compound No. 1-11)<br />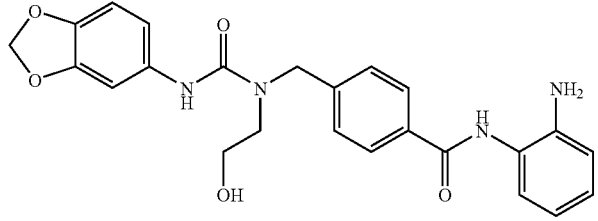 | $^1$H-NMR (500 MHz, DMSO-d$_6$) δ 3.38 (t, J = 5.3 Hz, 2H), 3.57 (m, 2H), 4.65 (s, 2H), 4.88 (s, 2H), 5.23 (br s, 1H), 5.95 (s, 2H), 6.60 (td, J = 7.6, 1.2 Hz, 1H), 6.75-6.80 (m, 3H), 6.97 (td, J = 2.1 Hz, 1H), 7.16 (d, J = 7.6 Hz, 1H), 7.39 (d, J = 8.1 Hz, 2H), 7.95 (d, J = 8.1 Hz, 2H), 8.59 (s, 1H), 9.62 (s, 1H) |
| N-(2-Aminophenyl)-4-[1-(2-methoxyethyl)-3-phenylureido-methyl]benzamide (Compound No. 1-12)<br />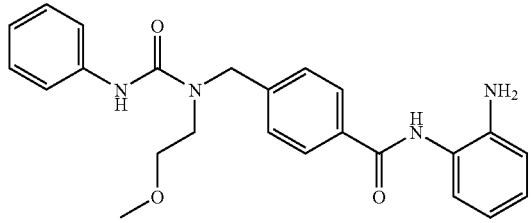 | $^1$H-NMR (400 MHz, CDCl$_3$) δ 3.47 (s, 3H), 3.48-3.54 (m, 4H), 3.88 (br s, 2H), 4.68 (s, 2H), 6.84-6.88 (m, 2H), 7.01 (m, 1H), 7.10 (td, J = 7.7, 1.4 Hz, 1H), 7.26-7.38 (m, 5H), 7.46 (d, J = 8.2 Hz, 2H), 7.83 (br s, 1H), 7.88 (d, J = 8.2 Hz, 2H), 8.34 (br s, 1H) |

| | |
|---|---|
| N-(2-Aminophenyl)-4-[3-(indan-5-yl)-1-(2-methoxyethyl)ureidomethyl]benzamide (Compound No. 1-13) 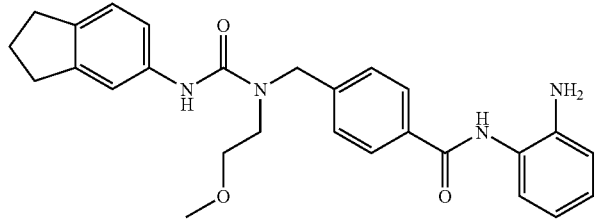 | $^1$H-NMR (400 MHz, CDCl$_3$) δ 2.06 (m, 2H), 2.82-2.92 (m, 4H), 3.46 (s, 3H), 3.48-3.52 (m, 4H), 3.87 (br s, 2H), 4.67 (s, 2H), 6.84-6.89 (m, 2H), 7.01 (dd, J = 7.7, 2.1 Hz, 1H), 7.08-7.14 (m, 2H), 7.32-7.37 (m, 2H), 7.46 (d, J = 8.1 Hz, 2H), 7.81 (br s, 1H), 7.88 (d, J = 8.1 Hz, 2H), 8.18 (br s, 1H) |
| N-(2-Aminophenyl)-4-[3-(3,4-benzo[1,3]dioxol-5-yl)-1-(2-methoxyethyl)ureidomethyl]benzamide (Compound No. 1-14) 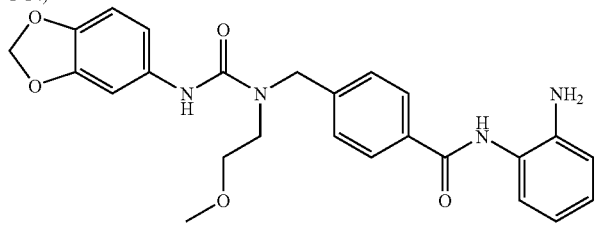 | $^1$H-NMR (400 MHz, CDCl$_3$) δ 3.45 (s, 3H), 3.46-3.53 (m, 4H), 3.88 (br s, 2H), 4.66 (s, 2H), 5.92 (s, 2H), 6.64 (dd, J = 8.2, 2.2 Hz, 1H), 6.72 (d, J = 8.2 Hz, 1H), 6.83-6.89 (m, 2H), 7.07-7.13 (m, 2H), 7.35 (d, J = 8.1 Hz, 1H), 7.45 (d, J = 8.1 Hz, 2H), 7.83 (br s, 1H), 7.88 (d, J = 8.1 Hz, 2H), 8.18 (br s, 1H) |
| N-(2-Aminophenyl)-4-[1-(3-hydroxypropyl)-3-(indan-5-yl)ureidomethyl]benzamide (Compound No. 1-15) 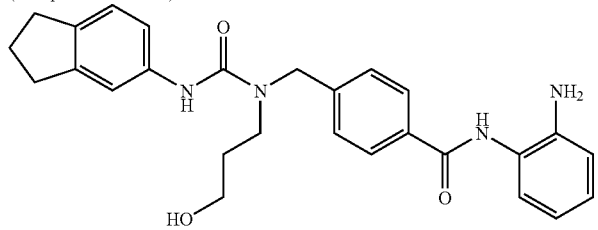 | $^1$H-NMR (500 MHz, CD$_3$OD) δ 1.79 (m, 2H), 2.05 (m, 2H), 2.81-2.88 (m, 4H), 3.48 (t, J = 6.7 Hz, 2H), 3.64 (t, J = 5.9 Hz, 2H), 4.68 (s, 2H), 6.76 (dd, J = 7.8, 1.2 Hz, 1H), 6.89 (dd, J = 7.8, 1.2 Hz, 1H), 7.05-7.09 (m, 3H), 7.18 (dd, J = 7.8, 1.2 Hz, 1H), 7.24 (s, 1H), 7.46 (d, J = 8.3 Hz, 2H), 7.96 (d, J = 8.3 Hz, 2H) |
| N-(2-Aminophenyl)-4-[1-(2,3-dihydroxypropyl)-3-(indan-5-yl)ureidomethyl]benzamide (Compound No. 1-16) 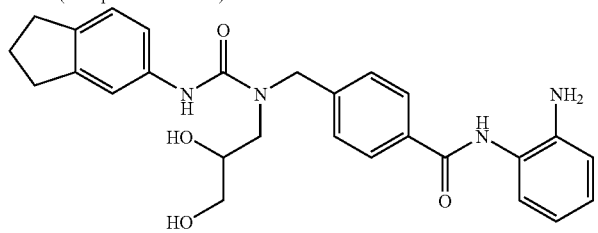 | $^1$H-NMR (500 MHz, CD$_3$OD) δ 2.05 (m, 2H), 2.82-2.88 (m, 4H), 3.47 (m, 2H), 3.57 (m, 2H), 3.85 (m, 1H), 4.74 (s, 2H), 6.77 (td, J = 7.6, 1.2 Hz, 1H), 6.90 (dd, J = 8.0, 1.2 Hz, 1H), 7.02-7.10 (m, 3H), 7.17-7.22 (m, 2H), 7.47 (d, J = 8.3 Hz, 2H), 7.97 (d, J = 8.3 Hz, 2H) |
| N-(2-Aminophenyl)-4-[1-(3-dimethylaminopropyl)-3-(indan-5-yl)ureidomethyl]benzamide (Compound No. 1-17) 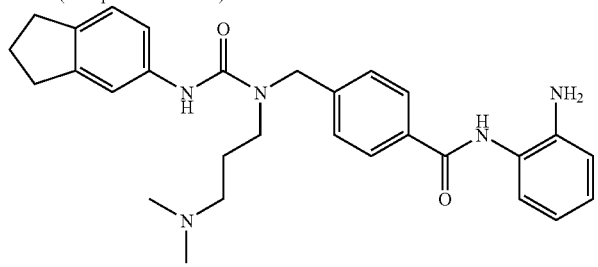 | $^1$H-NMR (500 MHz, CD$_3$OD) δ 1.78 (m, 2H), 2.05 (m, 2H), 2.28 (s, 6H), 2.38 (t, J = 6.8 Hz, 2H), 2.82-2.89 (m, 4H), 3.43 (t, J = 6.8 Hz, 2H), 4.67 (s, 2H), 6.75 (td, J = 7.8, 1.2 Hz,1H), 6.90 (dd, J = 8.0, 1.2 Hz, 1H), 7.05-7.08 (m, 2H), 7.10 (d, J = 8.0 Hz, 1H), 7.18 (dd, J = 7.8, 1.2 Hz, 1H), 7.18 (s, 1H), 7.47 (d, J = 8.3 Hz, 2H), 7.97 (d, J = 8.3 Hz, 2H) |

| | |
|---|---|
| 4-[1-(2-Aminoethyl)-3-phenyl-ureidomethyl]-N-(2-amino phenyl)benzamide (Compound No. 1-18)<br>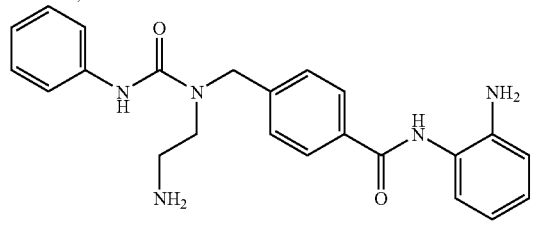 | $^1$H-NMR (400 MHz, CDCl$_3$) δ 2.89 (m 2H), 3.39 (m, 2H), 3.88 (br s, 2H), 4.64 (s, 2H), 6.83-6.88 (m, 2H), 6.98 (tt, J = 7.3, 1.1 Hz, 1H), 7.10 (td, J = 7.6, 1.5 Hz, 1H), 7.27 (m, 2H), 7.34 (d, J = 7.6 Hz, 1H), 7.42 (m, 2H), 7.46 (d, J = 8.3 Hz, 2H), 7.84-7.90 (m, 3H), 10.21 (br s, 1H) |
| 4-[1-(2-Aminoethyl)-3-(indan-5-yl)ureidomethyl]-N-(2-aminophenyl)benzamide (Compound No. 1-19)<br>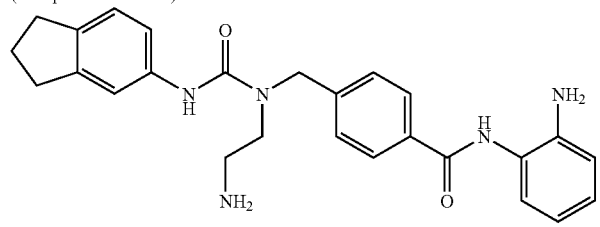 | $^1$H-NMR (400 MHz, CDCl$_3$) δ 2.05 (m, 2H), 2.81-2.91 (m, 6H), 3.37 (t, J = 4.5 Hz, 2H), 3.88 (br s, 2H), 4.63 (s, 2H), 6.82-6.88 (m, 2H), 7.06-7.12 (m, 3H), 7.34 (d, J = 7.6 Hz, 1H), 7.37 (s, 1H), 7.44 (d, J = 8.1 Hz, 2H), 7.86 (d, J = 8.1 Hz, 2H), 7.91 (br s, 1H), 9.94 (br s, 1H) |
| 4-[1-(2-Aminoethyl)-3-(4-dimethylaminophenyl)ureido-methyl]-N-(2-aminophenyl)benzamide (Compound No. 1-20)<br>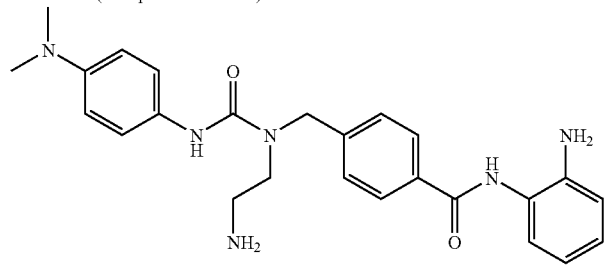 | $^1$H-NMR (400 MHz, CDCl$_3$) δ 2.88 (m, 2H), 2.88 (s, 6H), 3.37 (t, J = 4.8 Hz, 2H), 3.89 (br s, 2H), 4.63 (s, 2H), 6.72 (d, J = 9.0 Hz, 2H), 6.83-6.88 (m, 2H), 7.10 (td, J = 8.1, 1.4 Hz, 1H), 7.28 (m, 2H), 7.34 (d, J = 8.1 Hz, 1H), 7.45 (d, J = 8.2 Hz, 2H), 7.86 (d, J = 8.2 Hz, 2H), 7.88 (br s, 1H), 9.55 (br s, 1H) |
| N-(2-Aminophenyl)-4-[3-(indan-5-yl)-1-(2-methylamino ethyl)ureidomethyl]benz-amide (Compound No. 1-21)<br>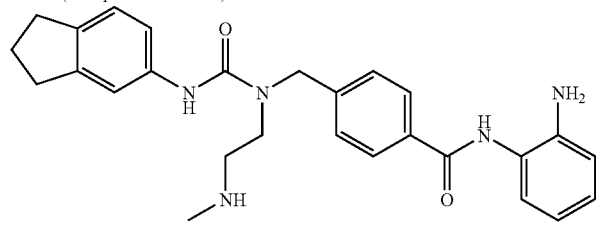 | $^1$H-NMR (500 MHz, CDCl$_3$) δ 2.05 (m, 2H), 2.51 (s, 3H), 2.76 (m, 2H), 2.82-2.90 (m, 4H), 3.36 (m, 2H), 3.87 (br s, 2H), 4.64 (s, 2H), 6.83-6.88 (m, 2H), 7.03-7.12 (m, 3H), 7.35 (d, J = 7.9 Hz, 1H), 7.39 (s, 1H), 7.46 (d, J = 7.9 Hz, 2H), 7.85 (br s, 1H), 7.87 (d, J = 7.9 Hz, 2H), 10.33 (br s, 1H) |
| N-(2-Aminophenyl)-4-[3-cyclo-pentyl-1-(2-methylamino-ethyl)ureidomethyl]benz-amide (Compound No. 1-22)<br>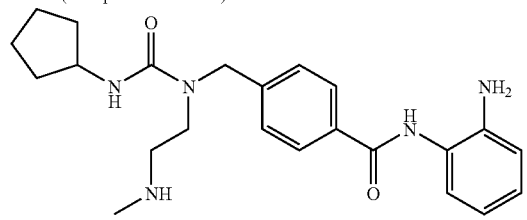 | $^1$H-NMR (500 MHz, CDCl$_3$) δ 1.39 (m, 2H), 1.50-1.69 (m, 4H), 1.95 (m, 2H), 2.41 (s, 3H), 2.67 (t, J = 5.0 Hz, 2H), 3.25 (t, J = 5.0 Hz, 2H), 3.88 (br s, 2H), 4.10 (m, 1H), 4.56 (s, 2H), 6.83-6.88 (m, 2H), 6.93 (br s, 1H), 7.10 (t, J = 7.8 Hz, 1H), 7.34 (d, J = 7.8 Hz, 1H), 7.39 (d, J = 7.9 Hz, 2H), 7.86 (d, J = 7.9 Hz, 2H), 7.89 (br s, 1H) |

| | |
|---|---|
| N-(2-Aminophenyl)-4-[3-(2,3-dihydrobenzo[1,4]dioxin-6-yl)-1-(2-methylamino-ethyl)ureidomethyl]benzamide (Compound No. 1-23)<br>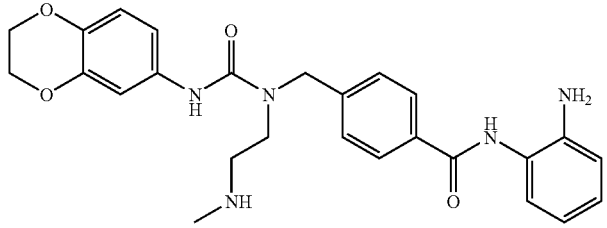 | $^1$H-NMR (500 MHz, CDCl$_3$) δ 2.50 (s, 3H), 2.75 (m, 2H), 3.34 (m, 2H), 3.87 (br s, 2H), 4.20-4.25 (m, 4H), 4.63 (s, 2H), 6.77 (d, J = 8.6 Hz, 1H), 6.83-6.88 (m, 3H), 6.98 (d, J = 1.8 Hz, 1H), 7.10 (t, J = 7.6 Hz, 1H), 7.35 (d, J = 7.6 Hz, 1H), 7.45 (d, J = 7.9 Hz, 2H), 7.84 (br s, 1H), 7.86 (d, J = 7.9 Hz, 2H), 10.36 (br s, 1H) |
| N-(2-Aminophenyl)-4-[1-(2-diethylaminoethyl)-3-(indan-5-yl)ureidomthyl]benzamide (Compound No. 1-24)<br>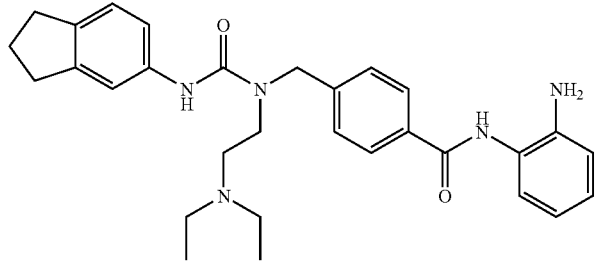 | $^1$H-NMR (400 MHz, CD$_3$OD) δ 1.08 (t, J = 7.2 Hz, 6H), 2.06 (m, 2H), 2.59-2.64 (m, 6H), 2.82-2.89 (m, 4H), 3.44 (t, J = 4.9 Hz, 2H), 4.67 (s, 2H), 6.77 (ddd, J = 7.9, 7.2, 1.2 Hz, 1H), 6.90 (dd, J = 7.9, 1.2 Hz, 1H), 6.99 (dd, J = 7.9, 2.2 Hz, 1H), 7.05-7.12 (m, 2H), 7.18-7.21 (m, 2H), 7.48 (d, J = 8.1 Hz, 2H), 7.97 (d, J = 8.1 Hz, 2H) |
| N-(2-Aminophenyl)-4-[1-(3-dimethylamino-2,2-dimethyl propyl)-3-(indan-5-yl)-ureidomethyl]benzamide (Compound No. 1-25)<br>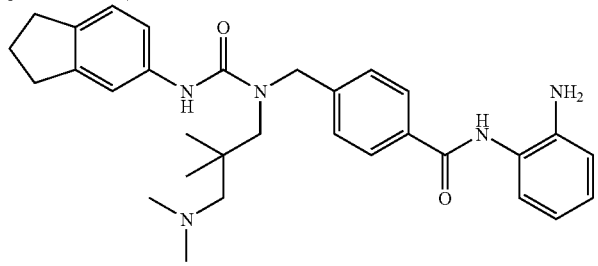 | $^1$H-NMR (400 MHz, CD$_3$OD) δ 1.05 (s, 6H), 2.05 (m, 2H), 2.32 (s, 2H), 2.35 (s, 6H), 2.81-2.88 (m, 4H), 3.36 (s, 2H), 4.85 (s, 2H), 6.77 (m, 1H), 6.89 (dd, J = 7.9, 1.3 Hz, 1H), 7.03-7.11 (m, 3H), 7.18 (dd, J = 7.9, 1.3 Hz, 1H), 7.26 (s, 1H), 7.41 (d, J = 8.3 Hz, 2H), 7.94 (d, J = 8.3 Hz, 2H) |
| N-(2-Aminophenyl)-4-[1-[2-(2-hydroxyethoxy)ethyl]-3-(indan-5-yl)ureidomethyl]benzamide (Compound No. 1-26)<br>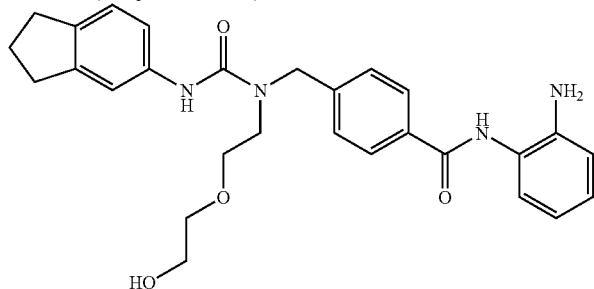 | $^1$H-NMR (400 MHz, CD$_3$OD) δ 2.05 (m, 2H), 2.81-2.88 (m, 4H), 3.58-3.61 (m, 4H), 3.66 (t, J = 4.7 Hz, 2H), 3.72 (m, 2H), 4.74 (s, 2H), 6.77 (ddd, J = 7.8, 7.1, 1.2 Hz, 1H), 6.90 (dd, J = 7.8, 1.2 Hz, 1H), 7.04-7.11 (m, 3H), 7.18 (dd, J = 7.8, 1.2 Hz, 1H), 7.24 (s, 1H), 7.47 (d, J = 8.1 Hz, 2H), 7.97 (d, J = 8.1 Hz, 2H) |

N-(2-Aminophenyl)-4-[3-(2,3-dihydrobenzo[1,4]dioxin-6-yl)-1-(3-dimethylaminopropyl)ureidomethyl]benzamide (Compound No. 1-27)

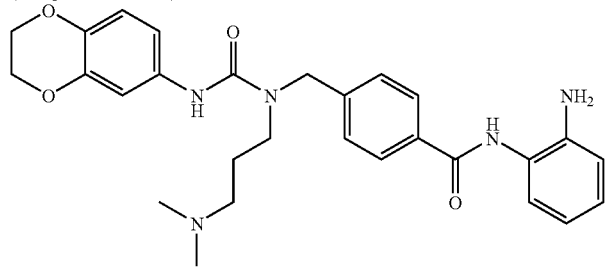

$^1$H-NMR (400 MHz, CD$_3$OD) δ 1.64 (m, 2H), 2.24 (s, 6H), 2.34 (t, J = 6.7 Hz, 2H), 3.39 (t, J = 6.7 Hz, 2H), 4.16-4.21 (m, 4H), 4.64 (s, 2H), 6.71-6.78 (m, 3H), 6.89 (dd, J = 8.0, 1.5 Hz, 1H), 6.97 (d, J = 2.0 Hz, 1H), 7.06 (ddd, J = 8.0, 7.7, 1.5 Hz, 1H), 7.17 (dd, J = 7.7, 1.2 Hz, 1H), 7.44 (d, J = 8.3 Hz, 2H), 7.95 (d, J = 8.3 Hz, 2H)

N-(2-Aminophenyl)-4-[1-(3-dimethylaminopropyl)-3-phenylethylureidomethyl]benzamide (Compound No. 1-28)

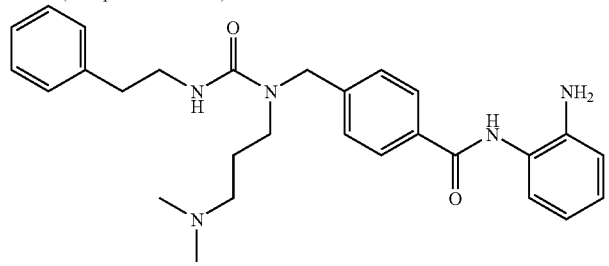

$^1$H-NMR (400 MHz, CD$_3$OD) δ 1.64 (m, 2H), 2.17 (s, 6H), 2.27 (t, J = 7.1 Hz, 2H), 2.81 (t, J = 7.0 Hz, 2H), 3.21 (t, J = 7.0 Hz, 2H), 3.43 (t, J = 7.1 Hz, 2H), 4.57 (s, 2H), 6.77 (ddd, J = 7.1, 6.9, 1.2 Hz, 1H), 6.90 (dd, J = 7.1, 1.2 Hz, 1H), 7.07 (ddd, J = 7.3, 6.9, 1.5 Hz, 1H), 7.17-7.22 (m, 4H), 7.24-7.31 (m, 2H), 7.34 (d, J = 8.3 Hz, 2H), 7.94 (d, J = 8.3 Hz, 2H)

N-(2-Aminophenyl)-4-[3-(indan-5-yl)-1-[3-(morpholin-4-yl)propyl]ureidomethyl]benzamide (Compound No. 1-29)

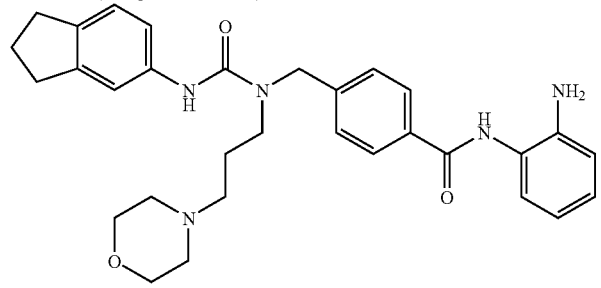

$^1$H-NMR (400 MHz, CDCl$_3$) δ 1.74 (m, 2H), 2.06 (m, 2H), 2.41-2.49 (m, 6H), 2.84-2.91 (m, 4H), 3.38 (t, J = 5.6 Hz, 2H), 3.68 (t, J = 4.6 Hz, 4H), 3.86 (br s, 2H), 4.64 (s, 2H), 6.84-6.87 (m, 2H), 7.06-7.15 (m, 3H), 7.34 (d, J = 8.3 Hz, 1H), 7.41 (s, 1H), 7.46 (d, J = 8.2 Hz, 2H), 7.79 (br s, 1H), 7.86 (d, J = 8.2 Hz, 2H), 8.70 (br s, 1H)

N-(2-Aminophenyl)-4-[3-cyclopentyl-1-[3-(morpholin-4-yl)propyl]ureidomethyl]benzamide (Compound No. 1-30)

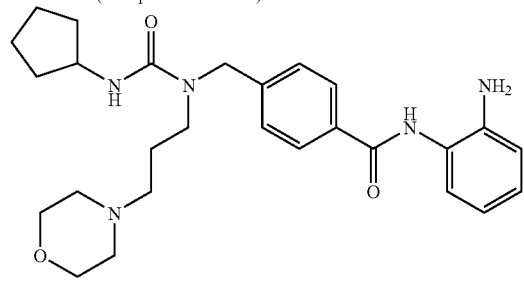

$^1$H-NMR (400 MHz, CDCl$_3$) δ 1.28-1.38 (m, 2H), 1.50-1.71 (m, 6H), 2.00-2.09 (m, 2H), 2.35 (t, J = 6.2 Hz, 2H), 2.43 (t, J = 4.5 Hz, 4H), 3.23 (t, J = 6.1 Hz, 2H), 3.73 (t, J = 4.5 Hz, 4H), 3.87 (s, 2H), 4.11 (m, 1H), 4.55 (s, 2H), 5.64 (m, 1H), 6.84-6.88 (m, 2H), 7.10 (td, J = 7.5, 1.5 Hz, 1H), 7.34 (d, J = 7.5 Hz, 1H), 7.40 (d, J = 8.1 Hz, 2H), 7.79 (br s, 1H), 7.86 (d, J = 8.1 Hz, 2H)

| | |
|---|---|
| N-(2-Aminophenyl)-4-[3-(4-dimethylaminophenyl)-1-[3-(morpholin-4-yl)propyl]ureidomethyl]benzamide (Compound No. 1-31)<br>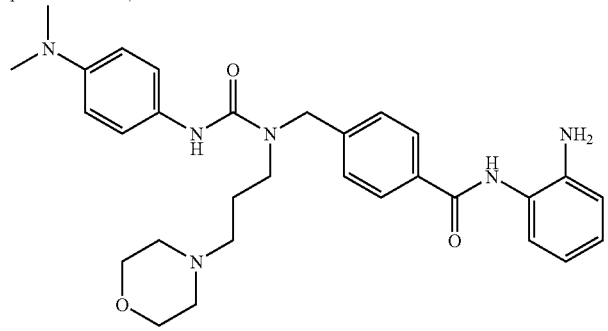 | $^1$H-NMR (400 MHz, CDCl$_3$) δ 1.73 (m, 2H), 2.40-2.49 (m, 6H), 2.91 (s, 6H), 3.37 (t, J = 5.7 Hz, 2H), 3.63 (t, J = 4.5 Hz, 4H), 3.87 (br s, 2H), 4.63 (s, 2H), 6.72 (d, J = 9.0 Hz, 2H), 6.84-6.87 (m, 2H), 7.10 (td, J = 7.7, 1.3 Hz, 1H), 7.26 (m, 2H), 7.34 (d, J = 7.7 Hz, 1H), 7.47 (d, J = 7.9 Hz, 2H), 7.81 (br s, 1H), 7.85 (d, J = 7.9 Hz, 2H), 8.74 (br s, 1H) |
| N-(2-Aminophenyl)-4-[3-(indan-5-yl)-1-(piperidin-4-ylmethyl)ureidomethyl]benzamide (Compound No. 1-32)<br>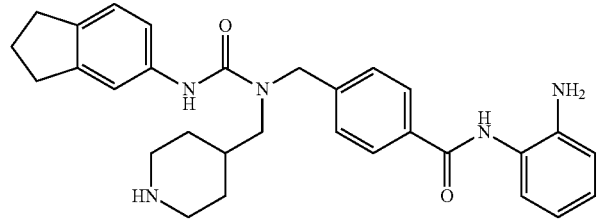 | $^1$H-NMR (500 MHz, CDCl$_3$) δ 1.21 (m, 2H), 1.75 (m, 2H), 1.87 (m, 1H), 2.04 (m, 2H), 2.59 (m, 2H), 2.81-2.89 (m, 4H), 3.11 (m, 2H), 3.24 (d, J = 7.3 Hz, 2H), 3.86 (br s, 2H), 4.67 (s, 2H), 6.23 (s, 1H), 6.84-6.88 (m, 2H), 6.95 (d, J = 7.9 Hz, 1H), 7.08-7.13 (m, 2H), 7.29 (s, 1H), 7.35 (d, J = 7.9 Hz, 1H), 7.42 (d, J = 7.9 Hz, 2H), 7.83 (s, 1H), 7.90 (d, J = 7.9 Hz, 2H) |
| N-(2-Aminophenyl)-4-[3-cyclopentyl-1-(piperidin-4-yl methyl)ureidomethyl]benzamide (Compound No. 1-33)<br>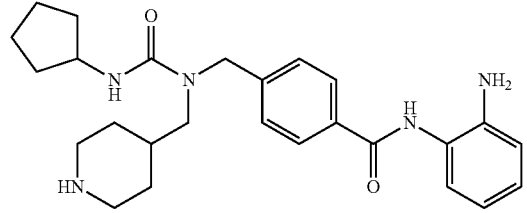 | $^1$H-NMR (500 MHz, CDCl$_3$) δ 1.10-1.19 (m, 2H), 1.24-1.32 (m, 2H), 1.53-1.61 (m, 4H), 1.66-1.72 (m, 2H), 1.76 (m, 1H), 1.92-1.99 (m, 2H), 2.53-2.60 (m, 2H), 3.06-3.14 (m, 4H), 3.86 (br s, 2H), 4.12 (m, 1H), 4.23 (d, J = 7.0 Hz, 1H), 4.55 (s, 2H), 6.84-6.89 (m, 2H), 7.11 (td, J = 7.6, 1.5 Hz, 1H), 7.33-7.38 (m, 3H), 7.83 (br s, 1H), 7.88 (d, J = 7.9 Hz, 2H) |
| N-(2-Aminophenyl)-4-[3-(4-chlorophenyl)-1-(piperidin-4-ylmethyl)ureidomethyl]benzamide (Compound No. 1-34)<br>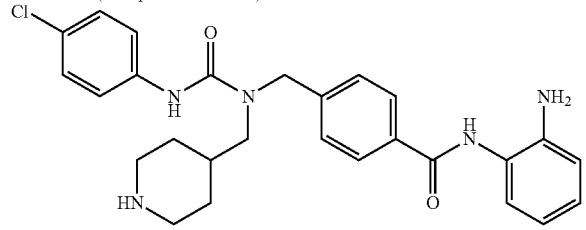 | $^1$H-NMR (500 MHz, DMSO-d$_6$) δ 1.01-1.11 (m, 2H), 1.49-1.55 (m, 2H), 1.73 (m, 1H), 2.35-2.42 (m, 2H), 2.87-2.93 (m, 2H), 3.22 (d, J = 7.3 Hz, 2H), 4.67 (s, 2H), 4.88 (s, 2H), 6.59 (t, mJ = 7.6 Hz, 1H), 6.77 (d, J = 7.6 Hz, 1H), 6.96 (td, J = 7.6, 1.4 Hz, 1H), 7.15 (d, J = 7.6 Hz, 1H), 7.28 (d, J = 8.9 Hz, 2H), 7.36 (d, J = 8.2 Hz, 2H), 7.50 (d, J = 8.9 Hz, 2H), 7.95 (d, J = 8.2 Hz, 2H), 8.52 (s, 1H), 9.61 (s, 1H) |

| | |
|---|---|
| N-(2-Aminophenyl)-4-[1-(3-dimethylamino-2,2-dimethylpropyl)-3-(4-nitrophenyl)ureidomethyl]benzamide (Compound No. 1-35)<br>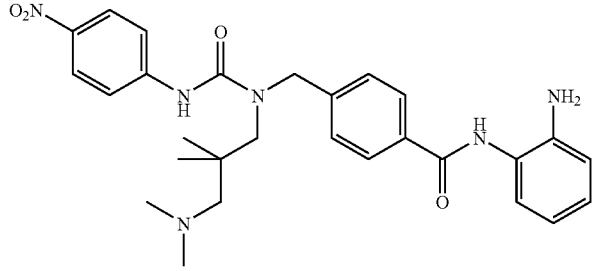 | $^1$H-NMR (400 MHz, CDCl$_3$) δ 1.07 (s, 6H), 2.36 (s, 2H), 2.41 (s, 6H), 3.29 (s, 2H), 3.85 (s, 2H), 4.76 (s, 2H), 6.84-6.88 (m, 2H), 7.10 (ddd, J = 7.6, 7.6, 1.5 Hz, 1H), 7.34 (d, J = 7.6 Hz, 1H), 7.38 (d, J = 8.3 Hz, 2H), 7.60 (d, J = 8.4 Hz, 2H), 7.80 (s, 1H), 7.88 (d, J = 8.3 Hz, 2H), 8.17 (d, J = 8.4 Hz, 2H), 11.49 (s, 1H) |
| N-(2-Aminophenyl)-4-[3-(3,4-dimethoxyphenyl)-1-(3-dimethylamino-2,2-dimethylpropyl)ureidomethyl]benzamide (Compound No. 1-36)<br>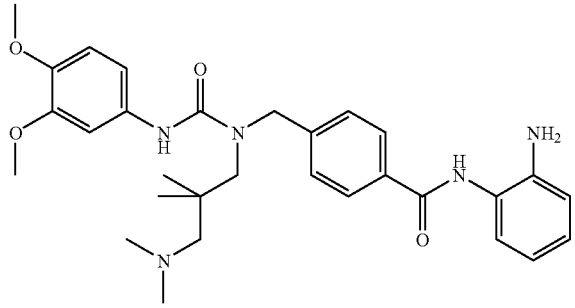 | $^1$H-NMR (500 MHz, CD$_3$OS) δ 1.06 (s, 6H), 2.31 (s, 2H), 2.36 (s, 6H), 3.37 (s, 2H), 3.79 (s, 3H), 3.82 (s, 3H), 4.77 (s, 2H), 6.77 (dd, J = 8.3, 7.6 Hz, 1H), 6.82 (dd, J = 8.3, 2.5 Hz, 1H), 6.86-6.92 (m, 2H), 7.08 (ddd, J = 7.6, 7.6, 1.5 Hz, 1H), 7.13 (s, 1H), 7.18 (d, J = 7.6 Hz, 1H), 7.40 (d, J = 8.3 Hz, 2H), 7.96 (d, J = 8.3 Hz, 2H) |
| N-(2-Aminophenyl)-4-[1-(3-dimethylamino-2,2-dimethylpropyl)-3-(4-fluorophenyl)ureidomethyl]benzamide (Compound No. 1-37)<br>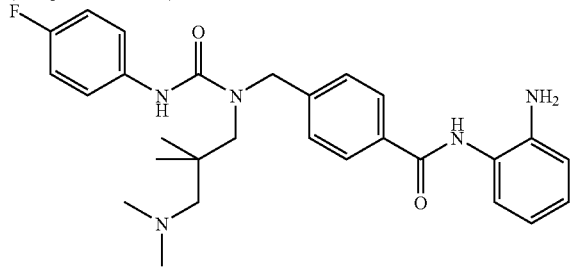 | $^1$H-NMR (400 MHz, CDCl$_3$) δ 1.04 (s, 6H), 2.29 (s, 2H), 2.35 (s, 6H), 3.24 (s, 2H), 3.89 (s, 2H), 4.70 (s, 2H), 6.83 (d, J = 7.8 Hz, 2H), 6.92-6.99 (m, 2H), 7.08 (ddd, J = 7.8, 7.8, 1.5 Hz, 1H), 7.28-7.36 (m, 3H), 7.40-7.43 (m, 2H), 7.82 (s, J = 8.3 Hz, 2H), 7.97 (s, 1H), 10.64 (s, 1H) |
| N-(2-Aminophenyl)-4-[3-(4-cyanomethylphenyl)-1-(3-dimethylamino-2,2-dimethylpropyl)ureidomethyl]benzamide (Compound No. 1-38)<br>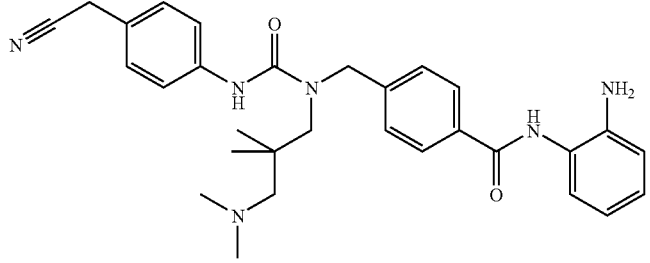 | $^1$H-NMR (400 MHz, CDCl$_3$) δ 1.04 (s, 6H), 2.30 (s, 2H), 2.37 (s, 6H), 3.25 (s, 2H), 3.48 (s, 2H), 3.75 (s, 2H), 4.72 (s, 2H), 6.81-6.84 (m, 2H), 7.04-7.12 (m, 3H), 7.31 (d, J = 7.8 Hz, 1H), 7.36 (s, J = 8.1 Hz, 2H), 7.46 (d, J = 8.5 Hz, 2H), 7.83 (d, J = 8.1 Hz, 2H), 7.97 (s, 1H), 10.69 (s, 1H) |

-continued

N-(2-Aminophenyl)-4-[1-(3-aminopropyl)-3-(2,3-dihydrobenzo[1,4]dioxin-6-yl)ureidomethyl]benzamide (Compound No. 1-39)

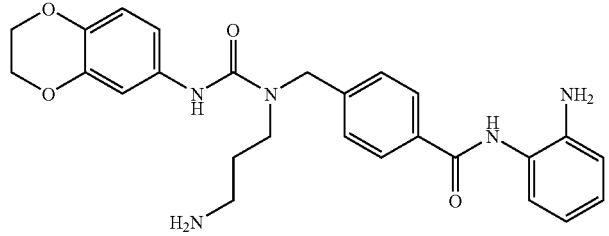

$^1$H-NMR (500 MHz, CDCl$_3$) δ 1.63 (m, 2H), 2.84 (t, J = 5.7 Hz, 2H), 3.46 (t, J = 5.7 Hz, 2H), 3.88 (br s, 2H), 4.20-4.25 (m, 4H), 4.60 (s, 2H), 6.76 (d, J = 8.7 Hz, 1H), 6.83-6.87 (m, 2H), 6.96 (dd, J = 8.7, 2.4 Hz, 1H), 7.05 (d, J = 2.4 Hz, 1H), 7.09 (td, J = 7.6, 1.5 Hz, 1H), 7.34 (d, J = 7.6 Hz, 1H), 7.44 (d, J = 7.9 Hz, 2H), 7.84 (d, J = 7.9 Hz, 2H), 7.88 (br s, 1H), 9.85 (br s, 1H)

N-(2-Aminophenyl)-4-[1-(3-aminopropyl)-3-(4-dimethyl aminophenyl)ureidomethyl]benzamide (Compound No. 1-40)

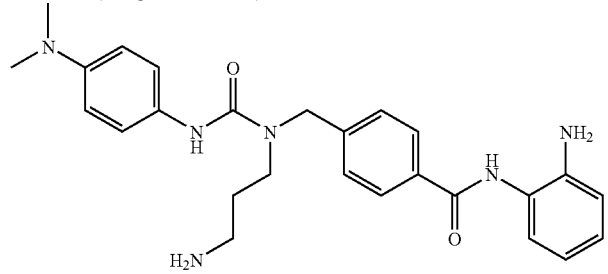

$^1$H-NMR (400 MHz, CDCl$_3$) δ 1.63 (m, 2H), 2.85 (t, J = 5.9 Hz, 2H), 2.88 (s, 6H), 3.47 (t, J = 5.7 Hz, 2H), 3.88 (br s, 2H), 4.62 (s, 2H), 6.72 (d, J = 9.3 Hz, 2H), 6.82-6.87 (m, 2H), 7.10 (td, J = 7.6, 1.4 Hz, 1H), 7.31-7.37 (m, 3H), 7.46 (d, J = 8.3 Hz, 2H), 7.85 (d, J = 8.3 Hz, 2H), 7.88 (br s, 1H), 9.60 (br s, 1H)

N-(2-Aminophenyl)-4-[1-(3-aminopropyl)-3-phenethyl-ureidomethyl]benzamide (Compound No. 1-41)

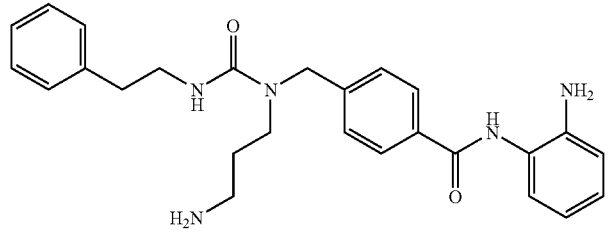

$^1$H-NMR (500 MHz, CDCl$_3$) δ 1.44 (m, 2H), 2.53 (t, J = 6.0 Hz, 2H), 2.86 (t, J = 6.7 Hz, 2H), 3.24 (t, J = 6.1 Hz, 2H), 3.52 (m, 2H), 3.88 (br s, 2H), 4.54 (s, 2H), 6.83-6.88 (m, 2H), 7.08 (br s, 1H), 7.10 (td, J = 8.0, 1.4 Hz, 1H), 7.19-7.24 (m, 3H), 7.25-7.31 (m, 2H), 7.35 (d, J = 8.0 Hz, 1H), 7.37 (d, J = 8.1 Hz, 2H), 7.85 (d, J = 8.1 Hz, 2H), 7.86 (br s, 1H)

N-(2-Aminophenyl)-4-[3-(2,3-dihydrobenzo[1,4]dioxin-6-yl)-1-[3-(pyrrolidin-2-on-1-yl)propyl]ureidomethyl]benzamide (Compound No. 1-42)

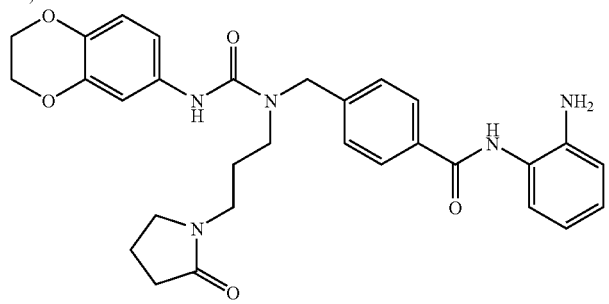

$^1$H-NMR (500 MHz, DMSO-d$_6$) δ 1.68 (m, 2H), 1.89 (m, 2H), 2.19 (t, J = 8.1 Hz, 2H), 3.17 (t, J = 6.9 Hz, 2H), 3.22-3.30 (m, 4H), 4.15-4.22 (m, 4H), 4.64 (s, 2H), 4.89 (br s, 2H), 6.59 (m, 1H), 6.72 (d, J = 8.9 Hz, 1H), 6.78 (dd, J = 7.9, 1.2 Hz, 1H), 6.90 (dd, J = 8.9, 2.4 Hz, 1H), 6.97 (m, 1H), 7.06 (d, J = 2.4 Hz, 1H), 7.16 (d, J = 7.3 Hz, 1H), 7.37 (d, J = 8.1 Hz, 2H), 7.96 (d, J = 8.1 Hz, 2H), 8.30 (s, 1H), 9.63 (s, 1H)

| | |
|---|---|
| N-(2-Aminophenyl)-4-[3-(4-dimethylaminophenyl)-1-[3-(pyrrolidin-2-on-1-yl)propyl]ureidomethyl]benzamide (Compound No. 1-43)<br>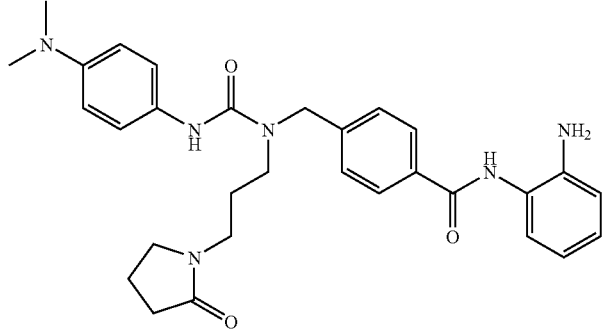 | $^1$H-NMR (400 MHz, DMSO-d$_6$) δ 1.69 (m, 2H), 1.89 (m, 2H), 2.19 (t, J = 8.1 Hz, 2H), 2.82 (s, 6H), 3.18 (t, J = 7.0 Hz, 2H), 3.22-3.31 (m, 4H), 4.64 (s, 2H), 4.89 (br s, 2H), 6.59 (m, 1H), 6.66 (d, J = 9.0 Hz, 2H), 6.78 (dd, J = 8.1, 1.2 Hz, 1H), 6.97 (m, 1H), 7.16 (d, J = 6.8 Hz, 1H), 7.25 (d, J = 9.0 Hz, 2H), 7.38 (d, J = 8.2 Hz, 2H), 7.96 (d, J = 8.2 Hz, 2H), 8.19 (s, 1H), 9.63 (s, 1H) |
| N-(2-Aminophenyl)-4-[3-phenethyl-1-[3-(pyrrolidin-2-on-1-yl)propyl]ureidomethyl]benzamide (Compound No. 1-44)<br>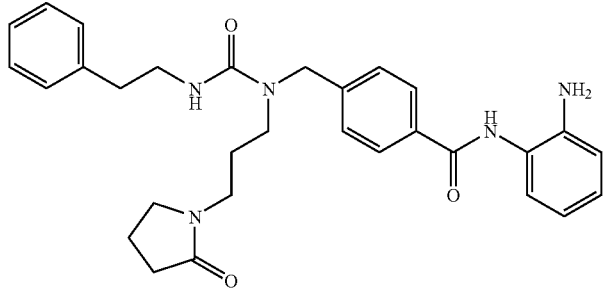 | $^1$H-NMR (500 MHz, DMSO-d$_6$) δ 1.58 (m, 2H), 1.88 (m, 2H), 2.18 (t, J = 8.1 Hz, 2H), 2.75 (t, J = 7.3 Hz, 2H), 3.07 (t, J = 7.5 Hz, 2H), 3.11 (t, J = 7.0 Hz, 2H), 3.23 (t, J = 7.0 Hz, 2H), 3.29 (m, 2H), 4.50 (s, 2H), 4.89 (s, 2H), 6.56 (t, J = 5.5 Hz, 1H), 6.60 (m, 1H), 6.78 (dd, J = 8.2, 1.2 Hz, 1H), 6.97 (m, 1H), 7.15-7.21 (m, 4H), 7.26-7.31 (m, 4H), 7.93 (d, J = 7.9 Hz, 2H), 9.63 (s, 1H) |
| N-(2-Aminophenyl)-4-[1-(3-dimethylaminopropyl)-3-(4-methylphenyl)ureidomethyl]benzamide (Compound No. 1-45)<br>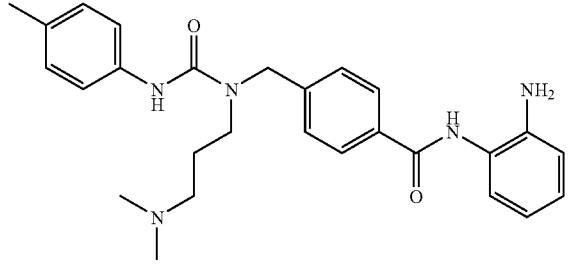 | $^1$H-NMR (400 MHz, CD$_3$OD) δ 2.00 (m, 2H), 2.29 (s, 6H), 2.87 (s, 3H), 3.13 (t, J = 7.5 Hz, 2H), 3.51 (t, J = 6.7 Hz, 2H), 4.79 (s, 2H), 6.78 (m, 1H), 6.91 (dd, J = 7.7, 1.2 Hz, 1H), 7.06-7.11 (m, 3H), 7.18 (d, J = 7.7, 1.2 Hz, 1H), 7.24 (dd, J = 6.7, 1.8 Hz, 2H), 7.47 (d, J = 8.3 Hz, 2H), 8.01 (d, J = 8.3 Hz, 2H) |
| N-(2-Aminophenyl)-4-[1-(3-dimethylaminopropyl)-3-(4-methoxycarbonylphenyl)ureidomethyl]benzamide (Compound No. 1-46)<br>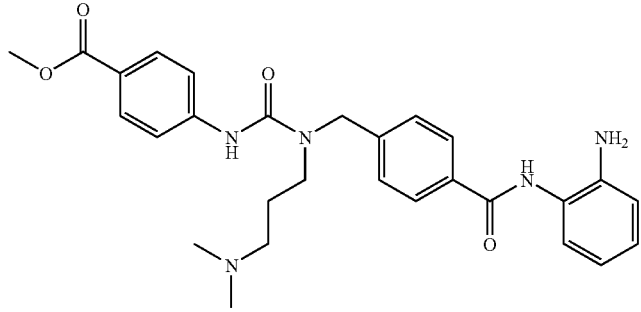 | $^1$H-NMR (500 MHz, CD$_3$OD) δ 1.80 (m, 2H), 2.31 (s, 6H), 2.39 (t, J = 6.4 Hz, 2H), 3.46 (t, J = 6.3 Hz, 2H), 3.87 (s, 3H), 4.69 (s, 2H), 6.76 (m, 1H), 6.90 (dd, J = 8.2, 1.2 Hz, 1H), 7.07 (m, 1H), 7.18 (d, J = 7.9, 1.2 Hz, 1H), 7.48 (d, J = 8.3 Hz, 2H), 7.52 (d, J = 8.8 Hz, 2H), 7.93 (d, J = 8.8 Hz, 2H), 7.97 (d, J = 8.3 Hz, 2H) |

| | |
|---|---|
| N-(2-Aminophenyl)-4-[3-(4-dimethylaminophenyl)-1-(2-hydroxyethyol)ureidomethyl]benzamide (Compound Ni. 1-47)<br>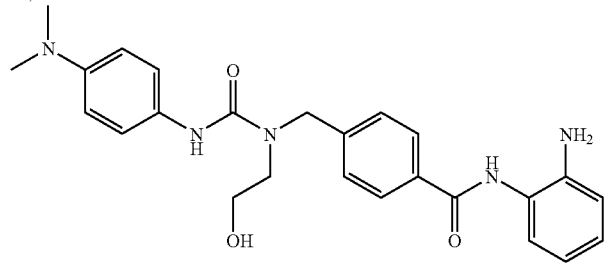 | $^1$H-HNMR (400 MHz, DMSO-d$_6$) δ 2.82 (s, 6H), 3.37 (m, 2H), 3.57 (m, 2H), 4.65 (s, 2H), 4.89 (br s, 2H), 5.20 (br s, 1H), 6.59 (t, J = 7.5 Hz, 1H), 6.67 (d, J = 8.9 Hz, 2H), 6.78 (d, J = 7.5 Hz, 1H), 6.97 (t, J = 7.5 Hz, 1H), 7.16 (d, J = 7.5 Hz, 1H), 7.21 (d, J = 8.9 Hz, 2H), 7.39 (d, J = 8.0 Hz, 2H), 7.95 (d, J = 8.0 Hz, 2H), 8.38 (br s, 1H), 9.63 (br s, 1H) |
| N-(2-Aminophenyl)-4-[3-(3,4-difluorophenyl)-1-(2-hydroxyethyl)ureidomethyl]benzamide (Compound No. 1-48)<br>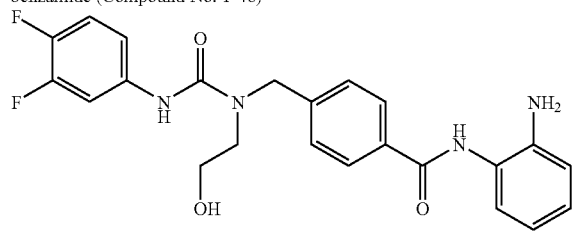 | $^1$H-NMR (400 MHz, DMSO-d$_6$) δ 3.41 (t, J = 5.4 Hz, 2H), 3.58 (m, 2H), 4.68 (s, 2H), 4.89 (br s, 2H), 5.22 (br s, 1H), 6.60 (t, J = 7.6 Hz, 1H), 6.78 (dd, J = 7.6, 1.3 Hz, 1H), 6.97 (td, J = 7.6, 1.3 Hz, 1H), 7.15-7.19 (m, 2H), 7.31 (m, 1H), 7.39 (d, J = 8.2 Hz, 2H), 7.64 (m, 1H), 7.96 (d, J = 8.2 Hz, 2H), 8.87 (br s, 1H), 9.63 (br s, 1H) |
| N-(2-Aminophenyl)-4-[1-(2-hydroxyethyl)-3-phenylethyl-ureidomethyl]benzamide (Compound No. 1-49)<br>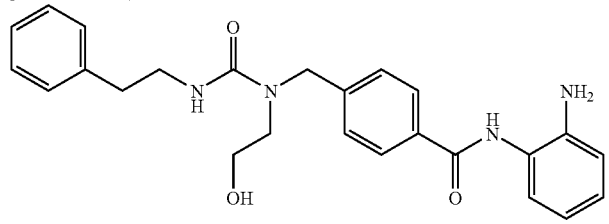 | $^1$H-NMR (400 MHz, DMSO-d$_6$) δ 2.73 (t, J = 7.4 Hz, 2H), 3.20 (t, J = 5.6 Hz, 2H), 3.28 (m, 2H), 3.45 (t, J = 5.6 Hz, 2H), 4.55 (s, 2H), 4.83 (t, J = 5.0 Hz, 1H), 4.89 (br s, 2H), 6.52-6.62 (m, 2H), 6.78 (dd, J = 7.9, 1.2 Hz, 1H), 6.97 (td, J = 7.9, 1.2 Hz, 1H), 7.16-7.21 (m, 4H), 7.27-7.31 (m, 4H), 7.93 (d, J = 8.3 Hz, 2H), 9.63 (br s, 1H) |
| N-(2-Aminophenyl)-4-[3-(2,3-dihydrobenzo[1,4]dioxin-6-yl)-1-(1-ethylpyrrolidin-2-ylmethyl)ureidomethyl]benzamide (Compound No. 1-50)<br>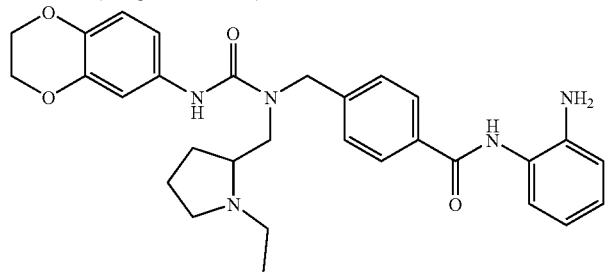 | $^1$H-NMR (400 MHz, CDCl$_3$) δ 1.09 (t, J = 7.3 Hz, 3H), 1.51 (m, 1H), 1.73-1.92 (m, 3H), 2.46 (m, 2H), 2.82 (m, 2H), 3.16-3.35 (m, 3H), 3.89 (br s, 2H), 4.20-4.25 (m, 4H), 4.48 (d, J = 15.5 Hz, 1H), 4.75 (d, J = 15.5 Hz, 1H), 6.76 (d, J = 8.5 Hz, 1H), 6.81-6.86 (m, 3H), 6.97 (d, J = 2.4 Hz, 1H), 7.09 (td, J = 7.8, 1.4 Hz, 1H), 7.33 (d, J = 7.8 Hz, 1H), 7.42 (d, J = 8.2 Hz, 2H), 7.86 (d, J = 8.2 Hz, 2H), 7.96 (br s, 1H), 11.14 (br s, 1H) |

| | |
|---|---|
| N-(2-Aminophenyl)-4-[3-(4-dimethylaminophenyl)-1-(1-ethylpyrrolidin-2-ylmethyl)ureidomethyl]benzamide (Compound No. 1-51)<br>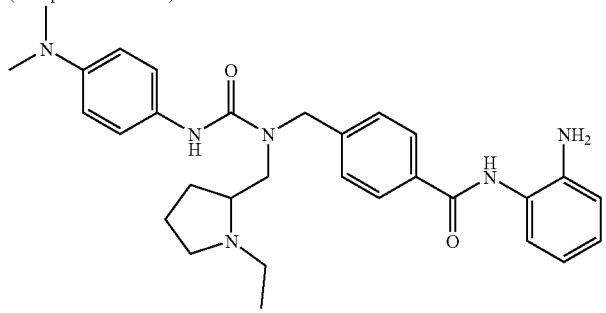 | ¹H-NMR (400 MHz, CDCl₃) δ 1.09 (t, J = 7.2 Hz, 3H), 1.54 (m, 1H), 1.75-1.92 (m, 3H), 2.44 (m, 2), 2.85 (m, 2H), 2.88 (s, 6H), 3.19-3.35 (m, 3H), 3.89 (br s, 2H), 4.47 (d, J = 15.5 Hz, 1H), 4.78 (d, J = 15.5 Hz, 1H), 6.73 (d, J = 9.0 Hz, 2H), 6.82-6.87 (m, 2H), 7.09 (td, J = 7.6, 1.4 Hz, 1H), 7.27 (d, J = 9.0 Hz, 2H), 7.33 (d, J = 7.6 Hz, 1H), 7.44 (d, J = 8.2 Hz, 2H), 7.86 (d, J = 8.2 Hz, 2H), 7.93 (br s, 1H), 10.96 (br s, 1H) |
| N-(2-Aminophenyl)-4-[3-(3,4-difluorophenyl)-1-(1-ethylpyrrolidin-2-ylmethyl)ureidomethyl]benzamide (Compound No. 1-52)<br>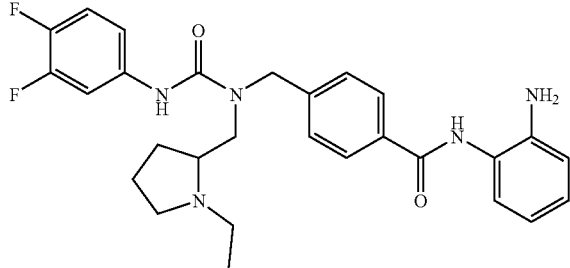 | ¹H-NMR (400 MHz, CDCl₃) δ 1.09 (t, J = 7.2 Hz, 3H), 1.52 (m, 1H), 1.75-1.95 (m, 3H), 2.51 (m, 2H), 2.83 (m, 2H), 3.21 (m, 2H), 3.34 (m, 1H), 3.88 (br s, 2H), 4.49 (d, J = 15.4 Hz, 1H), 4.75 (d, J = 15.4 Hz, 1H), 6.82-6.88 (m, 2H), 6.93 (m, 1H), 7.03 (m, 1H), 7.10 (td, J = 7.9, 1.3 Hz, 1H), 7.34 (d, J = 7.9 Hz, 1H), 7.40-7.47 (m, 3H), 7.87 (d, J = 8.1 Hz, 2H), 7.91 (br s, 1H), 11.61 (br s, 1H) |
| N-(2-Aminophenyl)-4-[1-(4-dimethylaminobutyl)-3-(4-dimethylaminoiphenyl)ureidomethyl]benzamide (Compound No. 1-53)<br>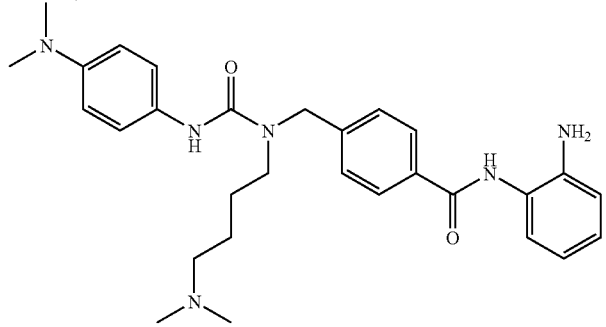 | ¹H-NMR (400 MHz, CDCl₃) δ 1.49 (m, 2H), 1.65 (m, 2H), 2.19 (s, 6H), 2.32 (t, J = 6.7 Hz, 2H), 2.90 (s, 6H), 3.26 (t, J = 8.2 Hz, 2H), 3.88 (br s, 2H), 4.65 (s, 2H), 6.70 (d, J = 9.0 Hz, 2H), 6.82-6.87 (m, 2H), 7.09 (td, J = 7.9, 1.3 Hz, 1H), 7.17 (d, J = 9.0 Hz, 2H), 7.34 (d, J = 7.9 Hz, 1H), 7.44 (d, J = 8.2 Hz, 2H), 7.50 (br s, 1H), 7.87 (d, J = 8.2 Hz, 2H), 7.92 (br s, 1H) |

| | |
|---|---|
| N-(2-Aminophenyl)-4-[3-(4-cyanomethylphenyl)-1-(4-dimethylaminobutyl)ureidomethyl]benzamide (Compound No. 1-54)<br>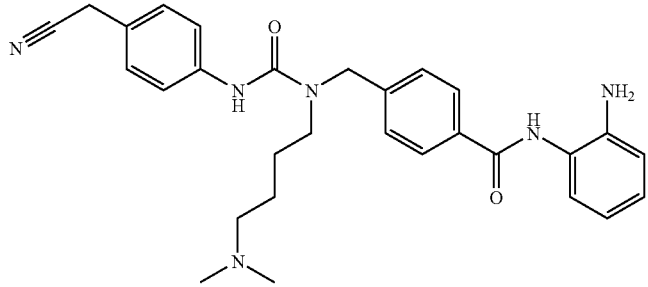 | $^1$H-NMR (500 MHz, CDCl$_3$) δ 1.54 (m, 2H), 1.70 (m, 2H), 2.23 (s, 6H), 2.35 (t, J = 6.6 Hz, 2H), 3.28 (t, J = 8.4 Hz, 2H), 3.71 (s, 2H), 3.86 (br s, 2H), 4.67 (s, 2H), 6.84-6.89 (m, 2H), 7.11 (td, J = 7.7, 1.3 Hz, 1H), 7.23-7.27 (m, 2H), 7.34-7.39 (m, 3H), 7.46 (d, J = 8.1 Hz, 2H), 7.73 (br s, 1H), 7.81 (br s, 1H), 7.89 (d, J = 8.1 Hz, 2H) |
| N-(2-Aminophenyl)-4-[1-[3-(morpholin-4-yl)propyl]]-3-phenethylureidomethyl]benzamide (Compound No. 1-55)<br>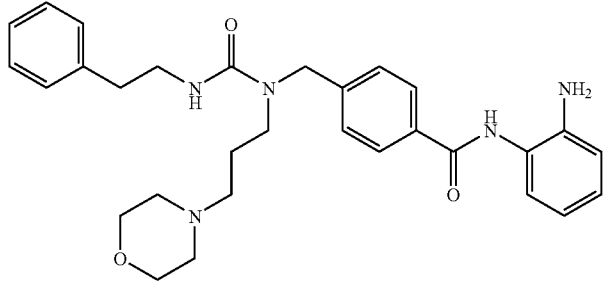 | $^1$H-NMR (400 MHz, CDCl$_3$) δ 1.58 (m, 2H), 2.23-2.32 (m, 6H), 2.85 (t, J = 6.8 Hz, 2H), 3.16 (t, J = 5.9 Hz, 2H), 3.44-3.57 (m, 6H), 3.88 (br s, 2H), 4.56 (s, 2H), 6.83-6.88 (m, 2H), 6.94 (br s, 1H), 7.10 (td, J = 7.7, 1.4 Hz, 1H), 7.18-7.37 (m, 6H), 7.36 (d, J = 8.1 Hz, 2H), 7.86 (d, J = 8.1 Hz, 2H), 7.92 (br s, 1H) |
| N-(2-Aminophenyl)-4-[3-(4-methoxyphenyl)-1-[3-(morpholin-4-yl)propyl]ureidomethyl]benzamide (Compound No. 1-56)<br>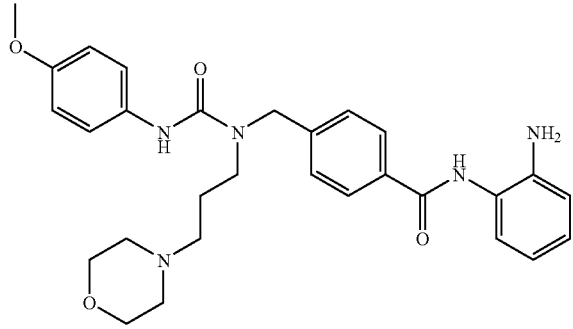 | $^1$H-NMR (400 MHz, CDCl$_3$) δ 1.74 (m, 2H), 2.40-2.50 (m, 6H), 3.38 (t, J = 5.7 Hz, 2H), 3.63 (t, J = 4.6 Hz, 4H), 3.79 (s, 3H), 3.87 (br s, 2H), 4.63 (s, 2H), 6.83-6.89 (m, 2H), 6.86 (d, J = 9.0 Hz, 2H), 7.10 (t, J = 7.7 Hz, 1H), 7.32 (m, 1H), 7.32 (d, J = 9.0 Hz, 2H), 7.46 (d, J = 8.2 Hz, 2H), 7.82 (br s, 1H), 7.86 (d, J = 8.2 Hz, 2H), 8.85 (br s, 1H) |
| N-(2-Aminophenyl)-4-[3-(2-methoxyphenyl)-1-[3-(morpholin-4-yl)propyl]ureidomethyl]benzamide (Compound No. 1-57)<br>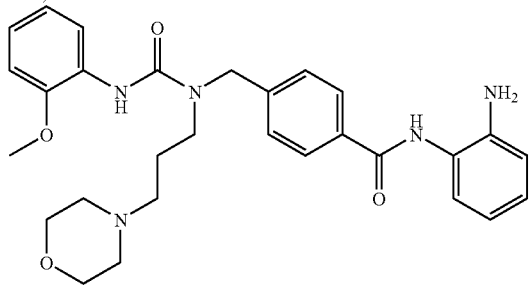 | $^1$H-NMR (400 MHz, CDCl$_3$) δ 1.81 (m, 2H), 2.37-2.45 (m, 6H), 3.44 (t, J = 6.7 Hz, 2H), 3.63 (t, J = 4.6 Hz, 4H), 3.80 (s, 3H), 3.87 (br s, 2H), 4.66 (s, 2H), 6.82-6.88 (m, 3H), 6.95 (td, J = 7.7, 1.5 Hz, 1H), 7.01 (td, J = 7.7, 1.7 Hz, 1H), 7.10 (td, J = 7.6, 1.5 Hz, 1H), 7.34 (d, J = 7.6 Hz, 1H), 7.45 (d, J = 8.1 Hz, 2H), 7.82 (br s, 1H), 7.87 (br s, 1H), 7.88 (d, J = 8.1 Hz, 2H), 8.01 (dd, J = 7.7 1.7 Hz, 1H) |

| | |
|---|---|
| N-(2-Aminophenyl)-4-[3-(3-methoxyphenyl)-1-[3-(morpholin-4-yl)propyl]ureidomethyl]benzamide (Compound No. 1-58) 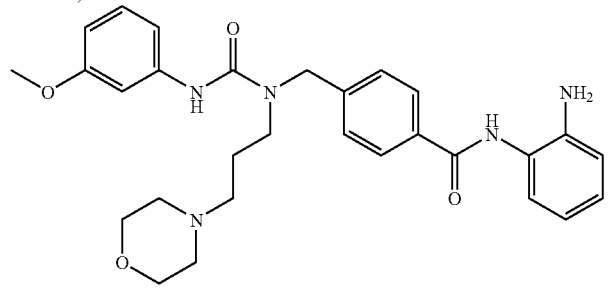 | ¹H-NMR (400 MHz, CDCl₃) δ 1.75 (m, 2H), 2.40-2.50 (m, 6H), 3.38 (t, J = 5.7 Hz, 2H), 3.71 (t, J = 4.6 Hz, 4H), 3.81 (s, 3H), 3.82 (br s, 2H), 4.63 (s, 2H), 6.63 (ddd, J = 8.2, 2.2, 1.0 Hz, 1H), 6.82-6.87 (m, 2H), 6.96 (ddd, J = 8.2, 2.2, 1.0 Hz, 1H), 7.09 (td, J = 7.8, 1.3 Hz, 1H), 7.20 (t, J = 8.2 Hz, 1H), 7.23 (t, J = 2.2 Hz, 1H), 7.33 (d, J = 7.8 Hz, 1H), 7.43 (d, J = 8.1 Hz, 2H), 7.85 (d, J = 8.1 Hz, 2H), 7.88 (br s, 1H), 8.75 (br s, 1H) |
| N-(2-Aminophenyl)-4-[3-[2-(benzo[1,3]dioxol-5-yl)ethyl]-1-[3-(morpholin-4-yl)propyl]ureidomethyl]benzamide (Compound No. 1-59) 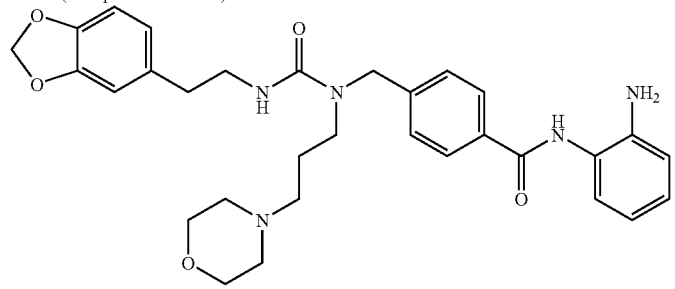 | ¹H-NMR (400 MHz, CDCl₃) δ 1.60 (m, 2H), 2.26-2.37 (m, 6H), 2.76 (t, J = 6.8 Hz, 2H), 3.18 (t, J = 5.9 Hz, 2H), 3.42 (m, 2H), 3.60 (br s, 4H), 3.89 (br s, 2H), 4.54 (s, 2H), 5.92 (s, 2H), 6.63 (dd, J = 7.8, 1.6 Hz, 1H), 6.68 (d, J = 1.6 Hz, 1H), 6.73 (d, J = 7.8 Hz, 1H), 6.76-6.89 (m, 3H), 7.10 (td, J = 7.6, 1.4 Hz, 1H), 7.33 (d, J = 8.1 Hz, 2H), 7.34 (m, 1H), 7.86 (d, J = 8.1 Hz, 2H), 7.96 (br s, 1H) |
| N-(2-Aminophenyl)-4-[3-(4-difluoromethoxyphenyl)-1-[3-(morpholin-4-yl)propyl]ureidomethyl]benzamide (Compound No. 1-60) 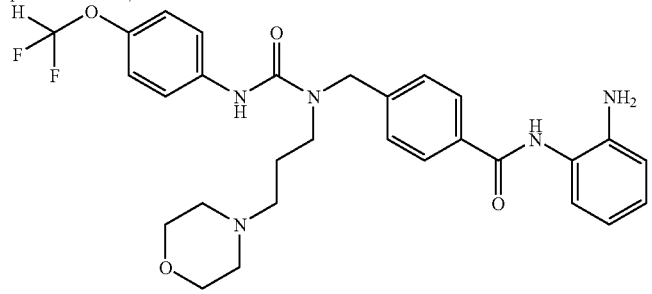 | ¹H-NMR (400 MHz, CDCl₃) δ 1.75 (m, 2H), 2.41-2.49 (m, 6H), 3.38 (t, J = 5.7 Hz, 2H), 3.66 (t, J = 4.5 Hz, 4H), 3.84 (br s, 2H), 4.62 (s, 2H), 6.46 (t, J = 7.41 Hz, 1H), 6.82-6.87 (m, 2H), 7.08 (d, J = 9.0 Hz, 2H), 7.09 (m, 1H), 7.33 (d, J = 8.1 Hz, 1H), 7.41-7.46 (m, 4H), 7.85 (d, J = 8.1 Hz, 2H), 7.89 (br s, 1H), 8.93 (br s, 1H) |
| N-(2-Aminophenyl)-4-[3-(3,4-dimethoxyphenyl)-1-[3-(morpholin-4-yl)propyl]ureidomethyl]benzamide (Compound No. 1-61) 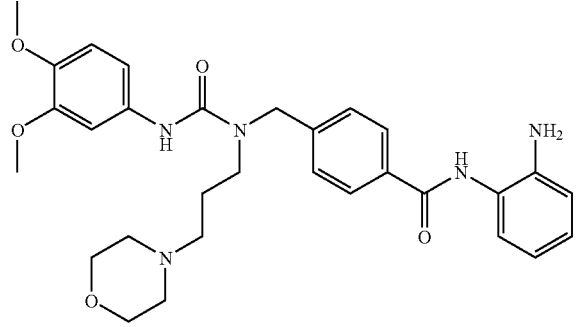 | ¹H-NMR (500 MHz, CDCl₃) δ 1.74 (m, 2H), 2.41-2.49 (m, 6H), 3.38 (t, J = 5.7 Hz, 2H), 3.66 (t, J = 4.6 Hz, 4H), 3.86 (s, 3H), 3.89 (s, 3H), 4.63 (s, 2H), 6.79-6.82 (m, 2H), 6.83-6.87 (m, 2H), 7.09 (td, J = 7.8, 1.4 Hz, 1H), 7.24 (s, 1H), 7.33 (d, J = 7.8 Hz, 1H), 7.44 (d, J = 8.1 Hz, 2H), 7.85 (d, J = 8.1 Hz, 2H), 7.89 (br s, 1H), 8.86 (br s, 1H) |

| | |
|---|---|
| N-(2-Aminophenyl)-4-[3-(3,4-difluorophenyl)-1-[3-(morpholino-4-yl)propyl]ureidomethyl]benzamide (Compound No. 1-62)<br>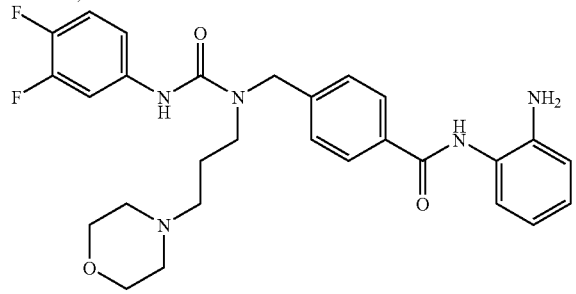 | $^1$H-NMR (400 MHz, CDCl$_3$) δ 1.75 (m, 2H), 2.40-2.50 (m, 6H), 3.37 (t, J = 5.7 Hz, 2H), 3.67 (t, J = 4.6 Hz, 4H), 3.86 (br s, 2H), 4.62 (s, 2H), 6.83-6.88 (m, 2H), 7.01-7.13 (m, 3H), 7.33 (d, J = 7.6 Hz, 1H), 7.43 (d, J = 8.1 Hz, 2H), 7.52 (m, 1H), 7.86 (m, 1H), 7.86 (d, J = 8.1 Hz, 2H), 9.00 (br s, 1H) |
| N-(2-Aminophenyl)-4-[3-(3-dimethylaminophenyl)-1-[3-(morpholin-4-yl)propyl]ureidomethyl]benzamide (Compound No. 1-63)<br>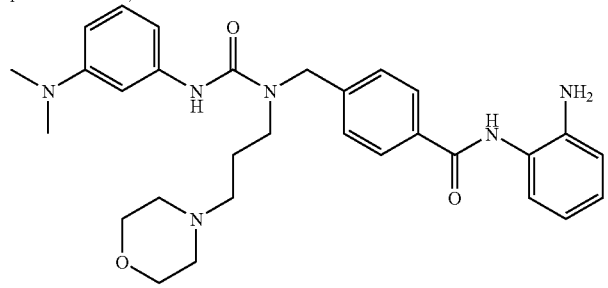 | $^1$H-NMR (500 MHz, CDCl$_3$) δ 1.74 (m, 2H), 2.41-2.49 (m, 6H), 2.95 (s, 6H), 3.38 (t, J = 5.8 Hz, 2H), 3.71 (t, J = 4.7 Hz, 4H), 3.86 (br s, 2H), 4.63 (s, 2H), 6.47 (dd, J = 8.0, 2.2 Hz, 1H), 6.71 (d, J = 8.0 Hz, 1H), 6.81-6.87 (m, 2H), 7.05 (t, J = 2.2 Hz, 1H), 7.09 (td, J = 7.8, 1.5 Hz, 1H), 7.15 (t, J = 8.0 Hz, 1H), 7.33 (d, J = 7.8 Hz, 1H), 7.43 (d, J = 8.1 Hz, 2H), 7.84 (d, J = 8.1 Hz, 2H), 7.90 (br s, 1H), 8.61 (br s, 1H) |
| N-(2-Aminophenyl)-4-[1-[3-(morpholin-4-yl)propyl]-3-(4-nitrophenyl)ureidomethyl]benzamide (Compound No. 1-64)<br>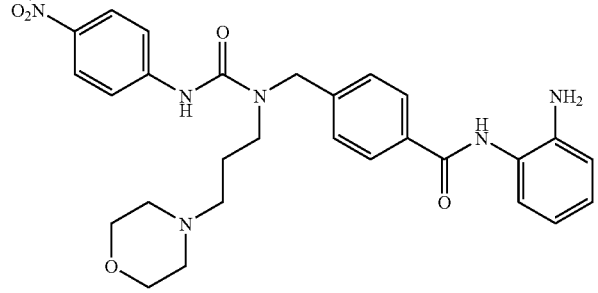 | $^1$H-NMR (500 MHz, CDCl$_3$) δ 1.80 (m, 2H), 2.46-2.53 (m, 6H), 3.42 (t, J = 5.7 Hz, 2H), 3.76 (t, J = 4.7 Hz, 4H), 3.86 (br s, 2H), 4.65 (s, 2H), 6.84-6.88 (m, 2H), 7.10 (td, J = 7.5, 1.3 Hz, 1H), 7.35 (d, J = 7.5 Hz, 1H), 7.45 (d, J = 8.1 Hz, 2H), 7.70 (d, J = 9.2 Hz, 2H), 7.82 (br s, 1H), 7.88 (d, J = 8.1 Hz, 2H), 8.20 (d, J = 9.2 Hz, 2H), 9.19 (br s, 1H) |
| N-(2-Aminophenyl)-4-[1-[3-(morpholin-4-yl)propyl]-3-(pyridin-3-yl)ureidomethyl]benzamide (Compound No. 1-65)<br>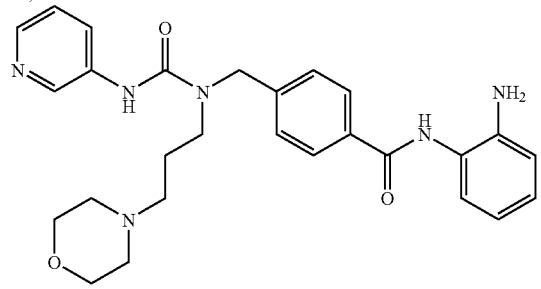 | $^1$H-NMR (500 MHz, CDCl$_3$) δ 1.77 (m, 2H), 2.42-2.51 (m, 6H), 3.41 (t, J = 5.7 Hz, 2H), 3.69 (t, J = 4.6 Hz, 4H), 3.87 (br s, 2H), 4.64 (s, 2H), 6.83-6.88 (m, 2H), 7.10 (td, J = 8.1, 1.2 Hz, 1H), 7.26 (m, 1H), 7.34 (d, J = 8.1 Hz, 1H), 7.44 (d, J = 8.2 Hz, 2H), 7.84-7.89 (m, 3H), 8.05 (ddd, J = 7.9, 2.3, 1.4 Hz, 1H), 8.32 (dd, J = 4.6, 1.4 Hz, 1H), 8.57 (d, J = 2.3 Hz, 1H), 9.08 (br s, 1H) |

| | |
|---|---|
| N-(2-Aminophenyl)-4-[3-(4-aminophenyl)-1-[3-(morpholin-4-yl)propyl]ureidomethyl]benzamide (Compound No. 1-66)<br />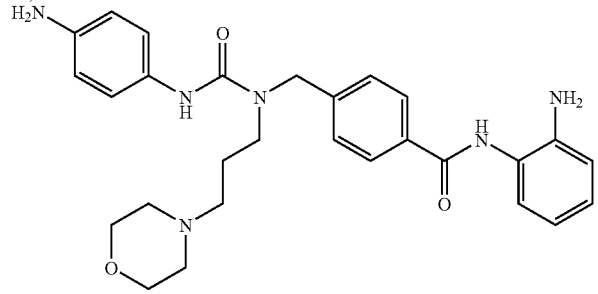 | $^1$H-NMR (500 MHz, CDCl$_3$) δ 1.72 (m, 2H), 2.38-2.47 (m, 6H), 3.36 (t, J = 5.7 Hz, 2H), 3.61 (t, J = 4.3 Hz, 4H), 3.75 (br s, 4H), 4.60 (s, 2H), 6.64 (d, J = 8.7 Hz, 2H), 6.82-6.86 (m, 2H), 7.09 (td, J = 7.8, 1.3 Hz, 1H), 7.16 (d, J = 8.7 Hz, 2H), 7.33 (d, J = 7.8 Hz, 1H), 7.43 (d, J = 8.1 Hz, 2H), 7.84 (d, J = 8.1 Hz, 2H), 7.93 (br s, 1H), 8.73 (br s, 1H) |
| N-(2-Aminophenyl)-4-[3-(3-ethoxyphenyl)-1-[3-(morpholin-4-yl)propyl]ureidomethyl]benzamide (Compound No. 1-67)<br />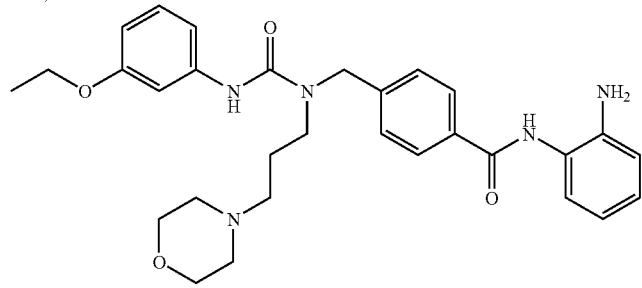 | $^1$H-NMR (400 MHz, CDCl$_3$) δ 1.40 (t, J = 7.0 Hz, 3H), 1.75 (m, 2H), 2.43-2.48 (m, 6H), 3.38 (t, J = 5.9 Hz, 2H), 3.71 (t, J = 4.6 Hz, 4H), 3.88 (br s, 2H), 4.04 (q, J = 7.0 Hz, 2H), 4.64 (s, 2H), 6.62 (ddd, J = 8.2, 2.2, 0.6 Hz, 1H), 6.82-6.88 (m, 2H), 6.92 (ddd, J = 8.2, 2.2, 0.6 Hz, 1H), 7.10 (td, J = 7.6, 1.5 Hz, 1H), 7.18 (t, J = 8.2 Hz, 1H), 7.23 (t, J = 2.2 Hz, 1H), 7.34 (d, J = 7.6 Hz, 1H), 7.44 (d, J = 8.3 Hz, 2H), 7.83-7.88 (m, 3H), 8.70 (br s, 1H) |
| N-(2-Aminophenyl)-4-[3-(3,5-dimethoxyphenyl)-1-[3-(morpholin-4-yl)propyl]ureidomethyl]benzamide (Compound No. 1-68)<br />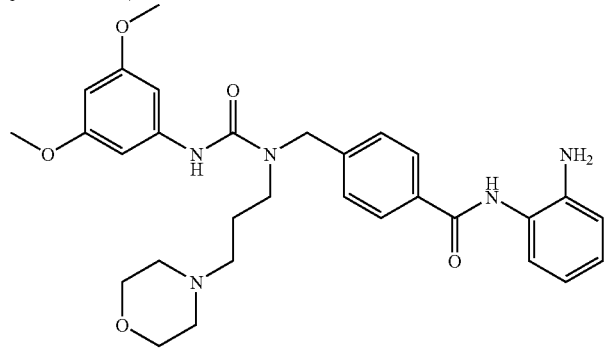 | $^1$H-NMR (400 MHz, CDCl$_3$) δ 1.74 (m, 2H), 2.42-2.49 (m, 6H), 3.37 (t, J = 5.7 Hz, 2H), 3.74 (t, J = 4.8 Hz, 4H), 3.78 (s, 6H), 3.81 (br s, 2H), 4.63 (s, 2H), 6.20 (t, J = 2.2 Hz, 1H), 6.74 (d, J = 2.2 Hz, 2H), 6.82-6.87 (m, 2H), 7.09 (td, J = 7.9, 1.5 Hz, 1H), 7.33 (d, J = 7.9 Hz, 1H), 7.43 (d, J = 8.1 Hz, 2H), 7.85 (d, J = 8.1 Hz, 2H), 7.88 (br s, 1H), 8.71 (br s, 1H) |
| N-(2-Aminophenyl)-4-[3-(2,3-dihydrobenzo[1,4]dioxin-6-yl)-1-(pyridin-4-ylmethyl)-ureidomethyl]benzamide (Compound No. 1-69)<br />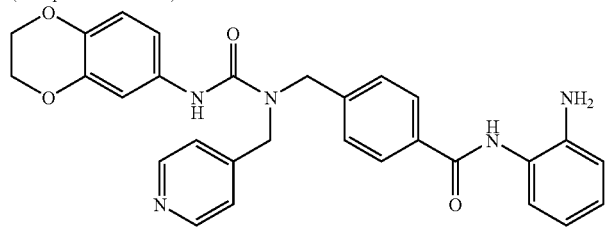 | $^1$H-NMR (400 MHz, CDCl$_3$) δ 3.85 (br s, 2H), 4.19-4.23 (m, 4H), 4.61 (s, 2H), 4.63 (s, 2H), 6.15 (s, 1H), 6.65 (dd, J = 8.7, 2.6 Hz, 1H), 6.75 (d, J = 8.7 Hz, 1H), 6.84-6.89 (m, 3H), 7.11 (td, J = 7.6, 1.4 Hz, 1H), 7.22 (d, J = 4.4 Hz, 2H), 7.36 (d, J = 7.6 Hz, 1H), 7.40 (d, J = 8.3 Hz, 2H), 7.87-7.95 (m, 3H), 8.60 (dd, J = 4.4, 1.5 Hz, 2H) |

| | |
|---|---|
| N-(2-Aminophenyl)-4-[3-(4-dimethylaminophenyl)-1-(pyridin-4-ylmethyl)ureido-methyl]benzamide (Compound No. 1-70) 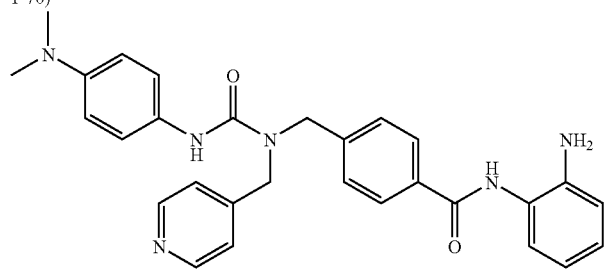 | $^1$H-NMR (400 MHz, CDCl$_3$) δ 2.89 (s, 6H), 3.89 (br s, 2H), 4.62 (s, 2H), 4.65 (s, 2H), 6.08 (br s, 1H), 6.67 (d, J = 9.3 Hz, 2H), 6.84-6.90 (m, 2H), 7.08-7.13 (m, 3H), 7.24 (dd, J = 4.4, 1.6 Hz, 2H), 7.36 (d, J = 7.3 Hz, 1H), 7.43 (d, J = 8.1 Hz, 2H), 7.86 (br s, 1H), 7.92 (d, J = 8.1 Hz, 2H), 8.60 (dd, J = 4.4, 1.6 Hz, 2H) |
| N-(2-Aminophenyl)-4-[3-(3,4-difluorophenyl)-1-(pyridn-4-ylmethyl)ureidomethyl]benzamide (Compound No. 1-71) 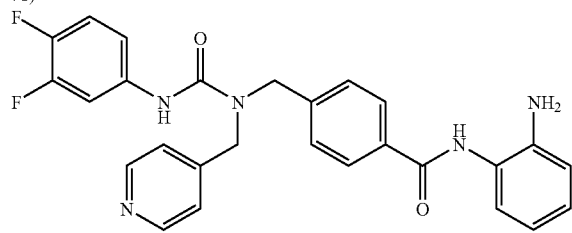 | $^1$H-NMR (400 MHz, CDCl$_3$) δ 3.49 (br s, 2H), 4.64 (s, 2H), 4.66 (s, 2H), 6.24 (s, 1H), 6.78 (m, 1H), 6.84-6.91 (m, 2H), 7.03 (m, 1H), 7.12 (t, J = 7.6 Hz, 1H), 7.20-7.46 (m, 6H), 7.84 (br s, 1H), 7.94 (d, J = 7.6 Hz, 2H), 8.63 (d, J = 5.9 Hz, 2H) |
| N-(2-Aminophenyl)-4-[3-[2-(benzo[1,3]dioxol-5-yl)ethyl]-1-[2-(pyridin-4-yl)ethyl]ureidomethyl]benzamide (Compound No. 1-72) 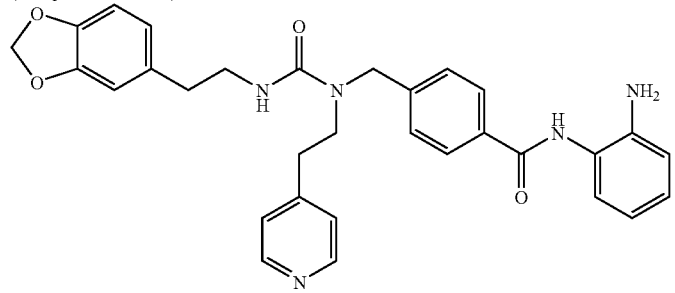 | $^1$H-NMR (400 MHz, CDCl$_3$) δ 2.69 (t, J = 6.5 Hz, 2H), 2.84 (t, J = 7.4 Hz, 2H), 3.45 (m, 2H), 3.55 (t, J = 7.4 Hz, 2H), 3.95 (br s, 2H), 4.19 (t, J = 5.5 Hz, 1H), 4.33 (s, 2H), 5.90 (s, 2H), 6.51-6.55 (m, 2H), 6.67 (dd, J = 7.2, 1.1 Hz, 1H), 6.84-6.89 (m, 2H), 7.06 (dd, J = 4.4, 1.5 Hz, 2H), 7.11 (td, J = 7.6, 1.5 Hz, 1H), 7.17 (d, J = 8.2 Hz, 2H), 7.38 (d, J = 7.6 Hz, 1H), 7.80 (d, J = 8.2 Hz, 2H), 7.93 (br s, 1H), 8.49 (dd, J = 4.4, 1.5 Hz, 2H) |
| N-(2-Aminophenyl)-4-[3-(4-dimethylaminophenyl)-1-[2-(pyridin-4-yl)ethyl]ureido methyl]benzamide (Compound No. 1-73) 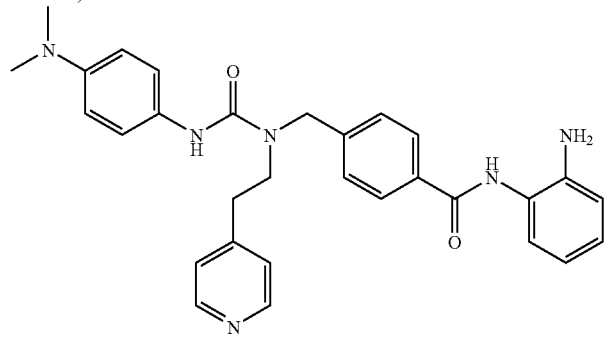 | $^1$H-NMR (400 MHz, CDCl$_3$) δ 2.89 (s, 6H), 2.96 (t, J = 7.1 Hz, 2H), 3.67 (t, J = 7.1 Hz, 2H), 3.80 (br s, 2H), 4.54 (s, 2H), 5.96 (s, 1H), 6.67 (d, J = 9.0 Hz, 2H), 6.83-6.89 (m, 2H), 7.05 (d, J = 9.0 Hz, 2H), 7.10 (m, 1H), 7.14 (d, J = 5.9 Hz, 2H), 7.33-7.41 (m, 3H), 7.88 (d, J = 7.8 Hz, 2H), 7.94 (br s, 1H), 8.51 (d, J = 5.9 Hz, 2H) |

| | |
|---|---|
| N-(2-Aminophenyl)-4-[3-(3,4-difluorophenyl)-1-[2-(pyridin-4-yl)ethyl]ureidomethyl]benzamide (Compound No. 1-74)<br>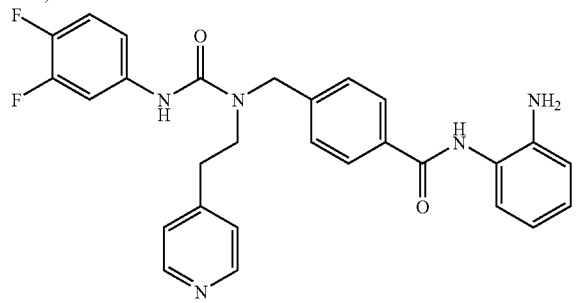 | $^1$H-NMR (400 MHz, CDCl$_3$) δ 2.96 (t, J = 7.1 Hz, 2H), 3.68 (t, J = 7.1 Hz, 2H), 3.92 (br s, 2H), 4.54 (s, 2H), 6.15 (s, 1H), 6.70 (m, 1H), 6.83-6.90 (m, 2H), 7.01 (m, 1H), 7.11 (td, J = 7.7, 1.4 Hz, 1H), 7.14 (dd, J = 4.4, 1.6 Hz, 2H), 7.28-7.41 (m, 2H), 7.34 (d, J = 8.1 Hz, 2H), 7.89 (d, J = 8.1 Hz, 2H), 7.94 (br s, 1H), 8.53 (dd, J = 4.4, 1.6 Hz, 2H) |
| N-(2-Aminophenyl)-4-[3-(2,3-dihydrobenzo[1,4]dioxin-6-yl)-1-[2-(pyridin-4-yl)ethyl]ureidomethyl]benzamide (Compound No. 1-75)<br>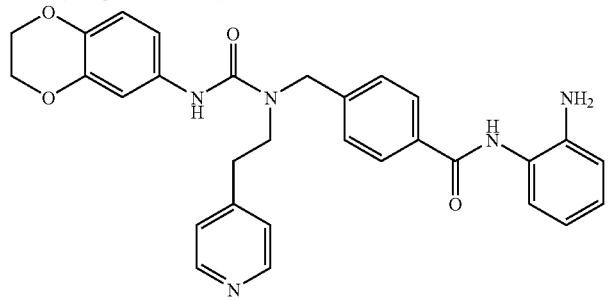 | $^1$H-NMR (400 MHz, CDCl$_3$) δ 2.95 (t, J = 7.3 Hz, 2H), 3.66 (t, J = 7.3 Hz, 2H), 3.93 (br s, 2H), 4.19-4.23 (m, 4H), 4.52 (s, 2H), 6.00 (s, 1H), 6.60 (dd, J = 8.6, 2.5 Hz, 1H), 6.75 (d, J = 8.6 Hz, 1H), 6.82 (d, J = 2.5 Hz, 1H), 6.83-6.89 (m, 2H), 7.08-7.15 (m, 3H), 7.34 (d, J = 8.2 Hz, 2H), 7.38 (d, J = 8.2 Hz, 2H), 7.96 (br s, 1H), 8.51 (dd, J = 4.4, 1.7 Hz, 2H) |
| N-(2-Aminophenyl)-4-[3-(3-benzyloxyphenyl)-1-(3-dimethylaminophenyl)-1-(3-dimethylaminopropyl)ureidomethyl]benzamide (Comnpound No. 1-76)<br>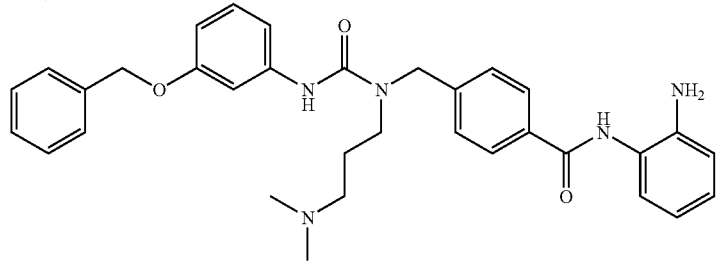 | $^1$H-NMR (500 MHz, CDCl$_3$) δ 1.68 (m, 2H), 2.27 (s, 6H), 2.37 (t, J = 5.8 Hz, 2H), 3.38 (t, J = 5.8 Hz, 2H), 3.86 (s, 2H), 4.62 (s, 2H), 5.08 (s, 2H), 6.62 (dd, J = 7.9, 2.1 Hz, 1H), 6.84-6.89 (m, 2H), 6.93 (dd, J = 8.9, 1.4 Hz, 1H), 7.09 (m, 1H), 7.16 (dd, J = 8.1, 7.9 Hz, 1H), 7.29-7.38 (m, 5H), 7.43-7.47 (m, 4H), 7.82 (s, 1H), 7.86 (d, J = 7.9 Hz, 2H), 10.16 (s, 1H) |

| | |
|---|---|
| N-(2-Aminophenyl)-4-[3-(4-dimethylaminophenyl)-1-[2-(morpholin-4-yl)ethyl]ureidomethyl]benzamide (Compound No. 1-77)<br>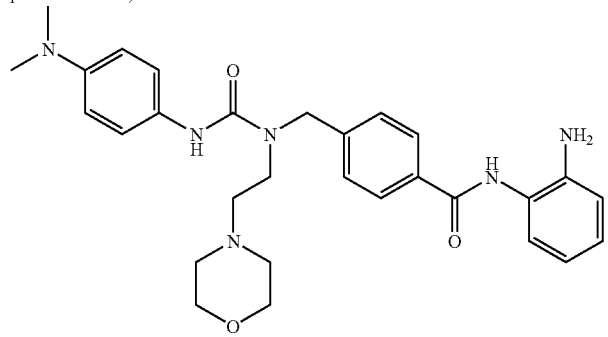 | $^1$H-NMR (500 MHz, CDCl$_3$) δ 2.52 (t, J = 4.4 Hz, 2H), 2.58 (m, 4H), 2.91 (s, 6H), 3.38 (t, J = 4.4 Hz, 2H), 3.76 (t, J = 4.8 Hz, 4H), 3.87 (s, 2H), 4.64 (s, 2H), 6.74 (d, J = 8.9 Hz, 2H), 6.83-6.88 (m, 2H), 7.10 (m, 1H), 7.28 (d, J = 8.9 Hz, 2H), 7.34 (d, J = 8.0 Hz, 1H), 7.46 (d, J = 8.1 Hz, 2H), 7.81 (s, 1H), 7.87 (d, J = 8.1 Hz, 2H), 9.36 (s, 1H) |
| N-(2-Aminophenyl)-4-[3-(2,3-dihydrobenzo[1,4]dioxin-6-yl)-1-[2-(morpholin-4-yl)ethyl]ureidomethyl]benzamide (Compound No. 1-78)<br>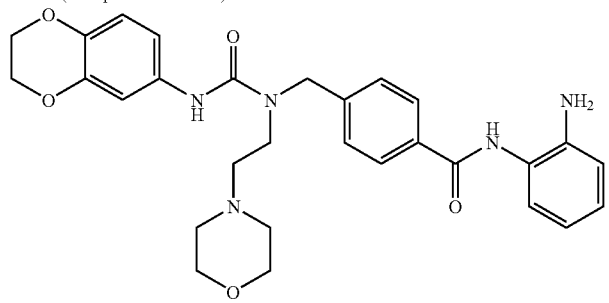 | $^1$H-NMR (500 MHz, CDCl$_3$) δ 2.52 (t, J = 4.4 Hz, 2H), 2.58 (m, 4H), 3.37 (t, J = 4.4 Hz, 2H), 3.76 (t, J = 4.8 Hz, 4H), 3.87 (s, 2H), 4.21-4.26 (m, 4H), 4.62 (s, 2H), 6.78 (d, J = 8.9 Hz, 1H), 6.83-6.88 (m, 3H), 7.00 (d, J = 2.4 Hz, 1H), 7.10 (ddd, J = 7.7, 7.6, 1.5 Hz, 1H), 7.34 (d, J = 7.7 Hz, 1H), 7.45 (d, J = 8.1 Hz, 2H), 7.85 (s, 1H), 7.87 (d, J = 8.1 Hz, 2H), 9.50 (s, 1H) |
| N-(2-Aminophenyl)-4-[1-(2-dimthylaminoethyl)-3-(4-dimethylaminophenyl)ureidomethyl]benzamide (Compound No. 1-79)<br>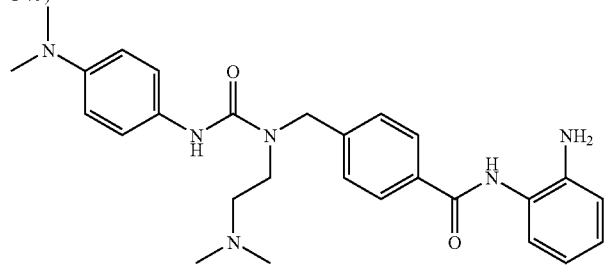 | $^1$H-NMR (400 MHz, CDCl$_3$) δ 2.36 (s, 6H), 2.46 (t, J = 4.1 Hz, 2H), 2.89 (s 6H), 3.32 (t, J = 4.1 Hz, 2H), 3.87 (s, 2H), 4.64 (s, 2H), 6.74 (d, J = 9.0 Hz, 2H), 6.84-6.87 (m, 2H), 7.10 (ddd, J = 8.2, 7.1 1.5 Hz, 1H), 7.23-7.28 (m, 2H), 7.35 (d, J = 7.6 Hz, 1H), 7.45 (d, J = 8.2 Hz, 2H), 7.82 (s, 1H), 7.86 (d, J = 8.2 Hz, 2H), 10.53 (s, 1H) |
| N-(2-Aminophenyl)-4-[3-(2,3-dihydrobenzo[1,4]dioxin-6-yl)-1-(2-dimethylaminoethyl)ureidomethyl]benzamide (Compound No. 1-80)<br>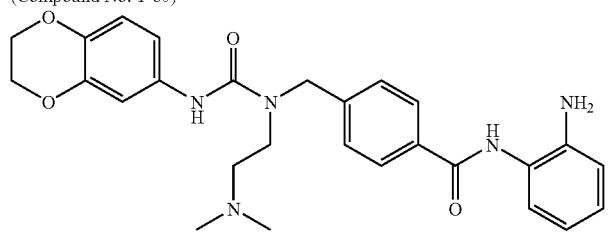 | $^1$H-NMR (500 MHz, CDCl$_3$) δ 2.24 (s, 6H), 2.43 (t, J = 4.3 Hz, 2H), 3.34 (t, J = 4.3 Hz, 2H), 4.17 (m, 2H), 4.20 (m, 2H), 4.60 (s, 2H), 4.88 (s, 2H), 6.59 (dd, J = 7.7, 7.3 Hz, 1H), 6.71-6.78 (m, 3H), 6.97 (m, 1H), 7.01 (d, J = 2.5 Hz, 1H), 7.16 (d, J = 7.0 Hz, 1H), 7.39 (d, J = 8.0 Hz, 2H), 7.95 (d, J = 8.0 Hz, 2H), 9.62 (s, 1H), 9.81 (s, 1H) |

| | |
|---|---|
| N-(2-Aminophenyl)-4-[3-(4-benzyloxyphenyl)-1-(3-dimethylaminopropyl)ureidomethyl]benzamide (Compound No. 1-81)<br>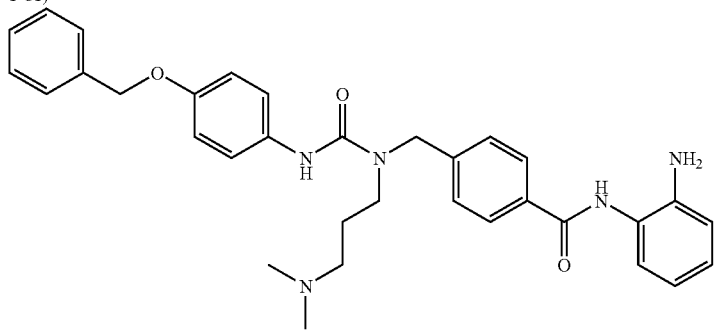 | $^1$H-NMR (400 MHz, CDCl$_3$) δ 1.68 (m, 2H), 2.28 (s, 6H), 2.37 (t, J = 5.9 Hz, 2H), 3.37 (m, 2H), 3.87 (s, 2H), 4.61 (s, 2H), 5.04 (s, 2H), 6.84-6.87 (m, 2H), 6.91 (d, J = 9.0 Hz, 2H), 7.09 (m, 1H), 7.29-7.47 (m, 10 H), 7.82 (s, 1H), 7.86 (d, J = 8.0 Hz, 2H), 9.92 (s, 1H) |
| N-(2-Aminophenyl)-4-[3-(4-dimethylaminophenyl)-1-[3-(4-methylpiperazin-1-yl)propyl]ureidomethyl]benzamide (Compound No. 1-82)<br>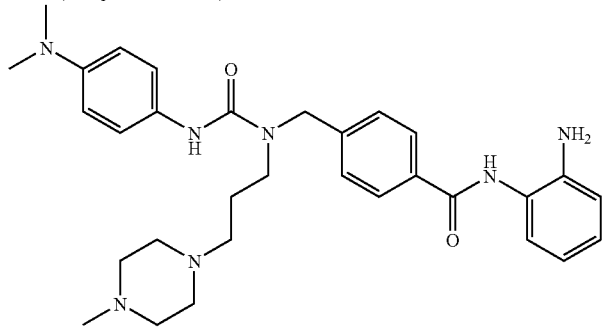 | $^1$H-NMR (500 MHz, CDCl$_3$) δ 1.71 (m, 2H), 2.22 (s, 3H), 2.40 (br s, 8H), 2.45 (t, J = 6.0 Hz, 2H), 2.91 (s, 6H), 3.35 (t, J = 5.7 Hz, 2H), 3.86 (br s, 2H), 4.61 (s, 2H), 6.72 (d, J = 9.2 Hz, 2H), 6.83-6.87 (m, 2H), 7.09 (td, J = 7.6, 1.2 Hz, 1H), 7.26 (d, J = 9.2 Hz, 2H), 7.34 (d, J = 7.6 Hz, 1H), 7.46 (d, J = 7.9 Hz, 2H), 7.82-7.87 (m, 3H), 8.80 (br s, 1H) |
| N-(2-Aminophenyl)-4-[3-(3,4-difluorophenyl)-1-[3-(4-methylpiperazin-1-yl)propyl]ureidomethyl]benzamide (Compound No. 1-83)<br>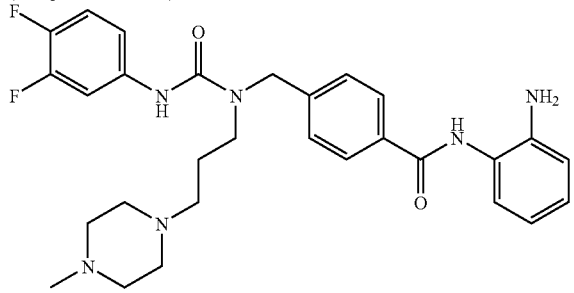 | $^1$H-NMR (400 MHz, CDCl$_3$) δ 1.74 (m, 2H), 2.27 (s, 3H), 2.33-2.57 (m, 8H), 2.45 (t, J = 6.0 Hz, 2H), 3.36 (t, J = 5.7 Hz, 2H), 3.86 (br s, 2H), 4.61 (s, 2H), 6.83-6.88 (m, 2H), 7.06-7.14 (m, 3H), 7.34 (d, J = 7.6 Hz, 1H), 7.44 (d, J = 8.2 Hz, 2H), 7.49 (m, 1H), 7.84 (br s, 1H), 7.86 (d, J = 8.2 Hz, 2H), 9.20 (br s, 1H) |

| | |
|---|---|
| N-(2-Aminophenyl)-4-[1-(3-dimethylaminopropyl)-3-[4-(4-methylpiperazin-1-yl)phenyl]ureidomethyl]benzamide (Compound No. 1-84) 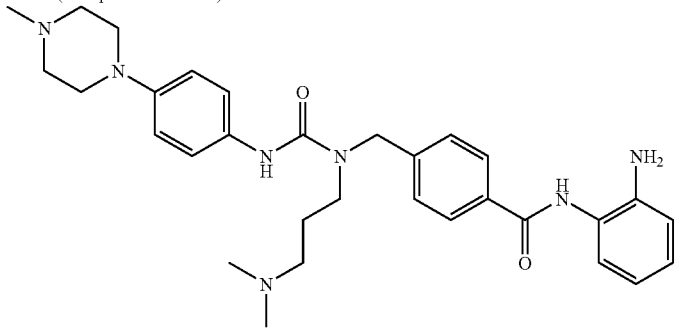 | ¹H-NMR (400 MHz, CDCl₃) δ 1.67 (m, 2H), 2.27 (s, 6H), 2.35 (s, 3H), 2.37 (t, J = 6.3 Hz, 2H), 2.59 (t, J = 4.9 Hz, 4H), 3.14 (t, J = 4.9 Hz, 4H), 3.36 (m, 2H), 3.87 (s, 2H), 4.61 (s, 2H), 6.84-6.89 (m, 2H), 6.89 (d, J = 9.0 Hz, 2H), 7.08 (dd, J = 7.8, 7.6 Hz, 1H), 7.28 (m, 1H), 7.34 (d, J = 9.0 Hz, 2H), 7.46 (d, J = 8.0 Hz, 2H), 7.80 (s, 1H), 7.85 (d, J = 8.0 Hz, 2H), 9.89 (s, 1H) |
| N-(2-Aminophenyl)-4-[3-(4-dimethylaminophenyl)-1-(3-hydroxypropyl)ureidomethyl]benzamide (Compound No. 1-85) 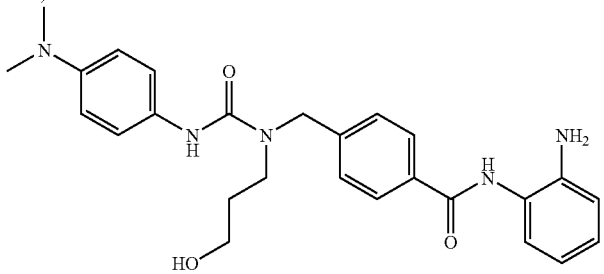 | ¹H-NMR (400 MHz, CDCl₃) δ 1.74 (m, 2H), 2.88 (s, 6H), 3.05 (br s, 1H), 3.55 (t, J = 5.7 Hz, 2H), 3.71 (t, J = 5.2 Hz, 2H), 3.92 (br s, 2H), 4.61 (s, 2H), 6.68 (d, J = 8.9 Hz, 2H), 6.83-6.89 (m, 2H), 7.10 (td, J = 7.5, 1.2 Hz, 1H), 7.11 (br s, 1H), 7.20 (d, J = 8.9 Hz, 2H), 7.36 (d, J = 7.5 Hz, 1H), 7.42 (d, J = 8.0 Hz, 2H), 7.88 (d, J = 8.0 Hz, 2H), 7.94 (br s, 1H) |
| N-(2-Aminophenyl)-4-[3-(3,4-difluorophenyl)-1-[2-(morpholin-4-yl)ethyl]ureidomethyl]benzamide (Compound No. 1-86) 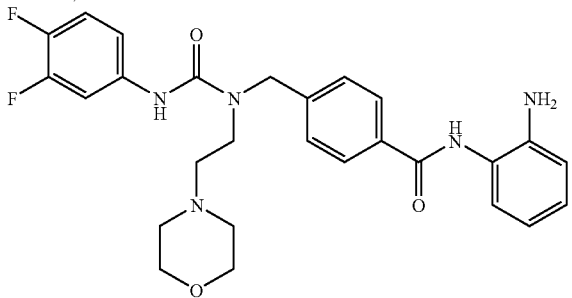 | ¹H-NMR (500 MHz, DMSO-d₆) δ 2.41 (m, 2H), 2.47 (m, 4H), 3.44 (t, J = 6.1 Hz, 2H), 3.55 (t, J = 4.5 Hz, 4H), 4.68 (s, 2H), 4.88 (s, 2H), 6.60 (dd, J = 7.9, 7.7 Hz, 1H), 6.78 (dd, J = 7.9, 1.2 Hz, 1H), 6.95 (ddd, J = 7.7, 7.7, 1.2 Hz, 1H), 7.16 (d, J = 7.7 Hz, 1H), 7.21 (m, 1H), 7.32 (dd, J = 19.8, 9.2 Hz, 1H), 7.40 (d, J = 8.3 Hz, 2H), 7.66 (m, 1H), 7.96 (d, J = 8.3 Hz, 2H), 9.06 (s, 1H), 9.63 (s, 1H) |
| N-(2-Aminophenyl)-4-[3-(3,4-difluorophenyl)-1-(2-dimethylaminoethyl)ureidomethyl]benzamide (Compound No. 1-87) 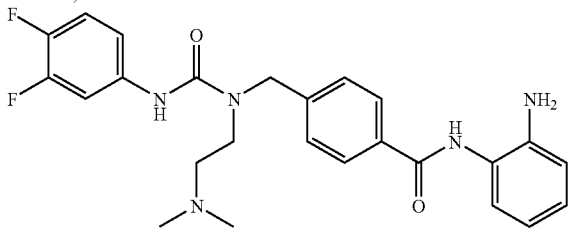 | ¹H-NMR (500 MHz, DMSO-d₆) δ 2.26 (s, 6H), 2.52 (m, 2H), 3.38 (t, J = 5.3 Hz, 2H), 4.62 (s, 2H), 4.89 (s, 2H), 6.60 (dd, J = 7.9, 7.7 Hz, 1H), 6.78 (dd, J = 7.9, 1.2 Hz, 1H), 6.97 (ddd, J = 7.7, 7.7, 1.2 Hz, 1H), 7.05 (m, 1H), 7.16 (d, J = 7.7 Hz, 1H), 7.30 (dd, J = 19.6, 9.2 Hz, 1H), 7.41 (d, J = 8.1 Hz, 2H), 7.61 (m, 1H), 7.95 (d, J = 8.1 Hz, 2H), 8.32 (s, 1H), 9.63 (s, 1H) |

N-(2-Aminophenyl)-4-[3-(2,3-dihydrobenzo[1,4]dioxin-6-yl)-1-[3-(morpholin-4-yl)propyl]ureidomethyl]benzamide (Compound No. 1-88)

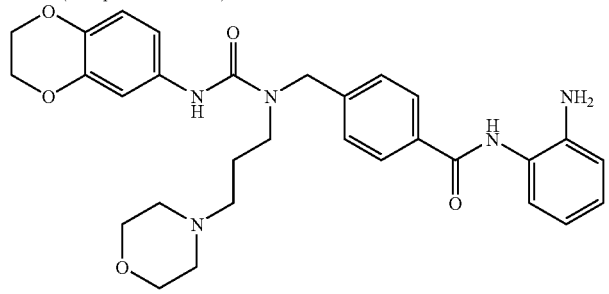

¹H-NMR (500 MHz, CDCl₃) δ 1.73 (m, 2H), 2.39-2.45 (m, 6H), 3.35 (t, J = 5.7 Hz, 2H), 3.64 (t, J = 4.6 Hz, 4H), 3.87 (s, 2H), 4.23 (s, 4H), 4.61 (s, 2H), 6.78-6.87 (m, 4H), 7.00 (d, J = 2.4 Hz, 1H), 7.09 (dd, J = 7.6, 1.2 Hz, 1H), 7.33 (d, J = 8.0 Hz, 1H), 7.45 (d, J = 8.0 Hz, 2H), 7.84 (s, 1H), 7.85 (d, J = 8.0 Hz, 2H), 8.88 (s, 1H)

N-(2-Aminophenyl)-4-[3-(4-dimethylaminophenyl)-1-(3-dimethylaminopropyl)ureidomethyl]benzamide (Compound No. 1-89)

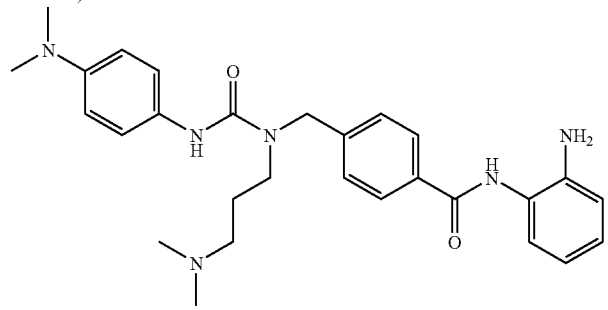

¹H-NMR (500 MHz, CDCl₃) δ 1.67 (m, 2H), 2.27 (s, 6H), 2.37 (br s, 2H), 2.89 (s, 6H), 3.37 (br s, 2H), 3.87 (s, 2H), 4.61 (s, 2H), 6.73 (d, J = 9.0 Hz, 2H), 6.83-6.86 (m, 2H), 7.09 (ddd, J = 8.0, 7.6, 1.2 Hz, 1H), 7.32 (d, J = 9.0 H 2H), 7.35 (m, 1H), 7.46 (d, J = 8.1 Hz, 2H), 7.82 (s, 1H), 7.85 (d, J = 8.1 Hz, 2H), 9.75 (s, 1H)

N-(2-Aminophenyl)-4-[3-(3,4-difluorophenyl)-1-(3-dimethylamino-2,2-dimethylpropyl)ureidomethyl]benzamide (Compound No. 1-90)

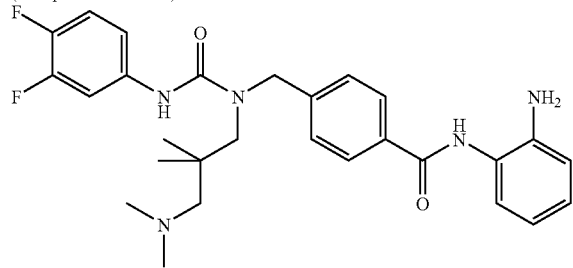

¹H-NMR (500 MHz, CDCl₃) δ 1.03 (s, 6H), 2.30 (s, 2H), 2.36 (s, 6H), 3.23 (s, 2H), 3.87 (s, 2H), 4.70 (s, 2H), 6.81-6.84 (m, 2H), 6.99-7.04 (m, 2H), 7.08 (ddd, J = 7.6, 7.6, 1.2 Hz, 1H), 7.31 (m, 1H), 7.33 (d, J = 8.3 Hz, 2H), 7.56 (m, 1H), 7.83 (d, J = 8.3 Hz, 2H), 7.96 (s, 1H), 10.87 (s, 1H)

N-(2-Aminophenyl)-4-[3-(2,3-dihydrobenzo[1,4]dioxin-6-yl)-1-(3-dimethylamino-2,2-dimethylpropyl)ureidomethyl]benzamide (Compound No. 1-91)

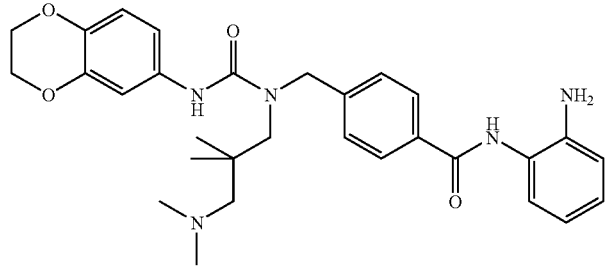

¹H-NMR (500 MHz, CDCl₃) δ 1.03 (s, 6H), 2.28 (s, 2H), 2.35 (s, 6H), 3.21 (s, 2H), 3.86 (s, 2H), 4.21-4.25 (m, 4H), 4.72 (s, 2H), 6.77 (d, J = 8.5 Hz, 1H), 6.84-6.86 (m, 2H), 6.90 (dd, J = 8.8, 2.4 Hz, 1H), 7.07-7.10 (m, 2H), 7.33 (d, J = 8.5 Hz, 1H), 7.39 (d, J = 8.1 Hz, 2H), 7.79 (s, 1H), 7.84 (d, J = 8.1 Hz, 2H), 10.42 (s, 1H)

N-(2-Aminophenyl)-4-[3-(4-cyanomethylphenyl)-1-[3-(morpholin-4-yl)propyl]ureidomethyl]benzamide (Compound No. 1-92)

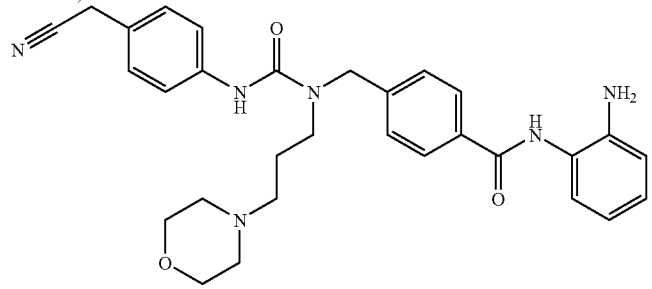

$^1$H-NMR (400 MHz, CDCl$_3$) δ 1.76 (m, 2H), 2.40-2.48 (m, 6H), 3.39 (m, 2H), 3.67-3.70 (m, 4H), 3.71 (s, 2H), 3.87 (br s, 2H), 4.63 (s, 2H), 6.85 (d, J = 8.2 Hz, 2H), 7.10 (dd, J = 7.5, 6.3 Hz, 1H), 7.24-7.28 (m, 2H), 7.31 (d, J = 8.5 Hz, 1H), 7.43 (d, J = 8.1 Hz, 2H), 7.48 (d, J = 8.2 Hz, 2H), 7.85 (d, J = 8.1 Hz, 2H), 7.92 (s, 1H), 8.90 (s, 1H)

N-(2-Aminophenyl)-4-[1-(3-dimethylamino-2,2-dimethyl propyl)-3-(4-dimethylamino phenyl)ureidomethyl]benzamide (Compound No. 1-93)

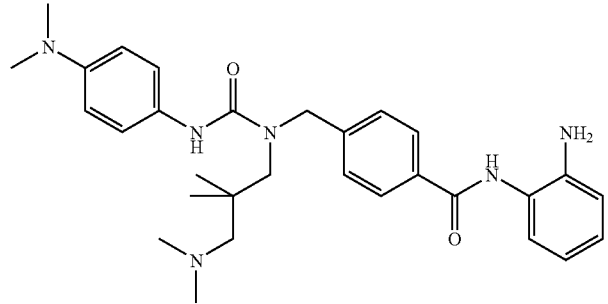

$^1$H-NMR (400 MHz, CDCl$_3$) δ 1.03 (s, 6H), 2.27 (s, 2H), 2.34 (s, 6H), 2.89 (s, 6H), 3.22 (s, 2H), 3.88 (s, 2H), 4.72 (s, 2H), 6.72 (dd, J = 7.0, 2.2 Hz, 2H), 6.82-6.85 (m, 2H), 7.09 (m, 1H), 7.31-7.39 (m, 5H), 7.83 (d, J = 8.1 Hz, 2H), 7.89 (s, 1H), 10.25 (s, 1H)

N-(2-Aminophenyl)-4-[3-(2,3-dihydrobenzo[1,4]dioxin-6-yl)-1-[2-(4-methylpiperazin-1-yl)ethyl]ureidomethyl]benzamide (Compound No. 1-94)

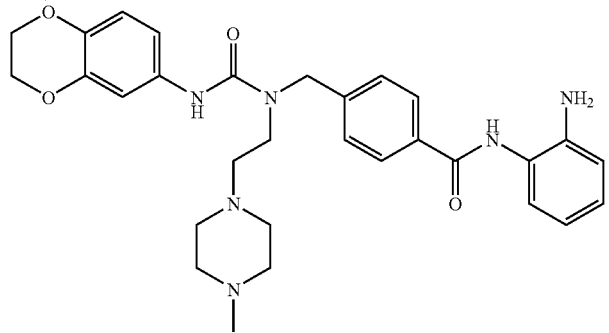

$^1$H-NMR (400 MHz, DMSO-d$_6$) δ 2.14 (s, 3H), 2.33 (br s, 8H), 2.45 (t, J = 5.6 Hz, 2H), 3.38 (t, J = 5.6 Hz, 2H), 4.17-4.21 (m, 4H), 4.62 (s, 2H), 4.89 (br s, 2H), 6.60 (t, J = 7.6 Hz, 1H), 6.73 (d, J = 8.8 Hz, 1H), 6.78 (dd, J = 7.6, 1.4 Hz, 1H), 6.86 (dd, J = 8.8, 2.4 Hz, 1H), 6.97 (td, J = 7.6, 1.4 Hz, 1H), 7.04 (d, J = 2.4 Hz, 1H), 7.16 (d, J = 7.6 Hz, 1H), 7.39 (d, J = 8.3 Hz, 2H), 7.95 (d, J = 8.3 Hz, 2H), 8.95 (br s, 1H), 9.63 (br s, 1H)

| | |
|---|---|
| N-(2-Aminophenyl)-4-[3-(2,3-dihydrobenzo[1,4]dioxin-6-yl)-1-[2-(1-methylpyrrolidin-2-yl)ethyl]ureidomethyl]benzamide (Compound No. 1-95)<br>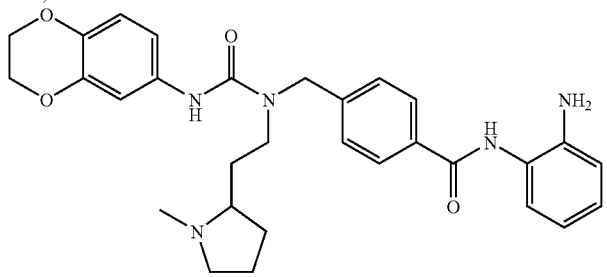 | $^1$H-NMR (400 MHz, CDCl$_3$) δ 1.54-1.78 (m, 4H), 1.82-1.94 (m, 2H), 2.27-2.43 (m, 5H), 3.15-3.45 (m, 3H), 3.88 (br s, 2H), 4.20-4.25 (m, 4H), 4.52 (d, J = 15.7 Hz, 1H), 4.70 (d, J = 15.7 Hz, 1H), 6.77 (d, J = 8.8 Hz, 1H), 6.82-6.88 (m, 3H), 7.01 (d, J = 2.4 Hz, 1H), 7.10 (td, J = 7.8, 1.4 Hz, 1H), 7.34 (d, J = 7.8 Hz, 1H), 7.46 (d, J = 7.9 Hz, 2H), 7.86 (br s, 1H), 7.86 (d, J = 7.9 Hz, 2H), 9.51 (br s, 1H) |
| N-(2-Aminophenyl)-4-[3-(4-dimethylaminophenyl)-1-[2-(1-methylpyrrolidin-2-yl)-ethyl]ureidomethyl]benzamide (Compound No. 1-96)<br>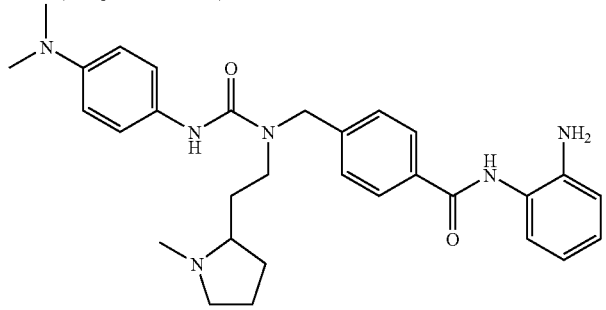 | $^1$H-NMR (500 MHz, CDCl$_3$) δ 1.56-1.80 (m, 4H), 1.84-1.94 (m, 2H), 2.26-2.41 (m, 5H), 2.89 (s, 6H), 3.14-3.45 (m, 3H), 3.88 (br s, 2H), 4.55 (d, J = 15.7 Hz, 1H), 4.70 (d, J = 15.7 Hz, 1H), 6.73 (d, J = 9.0 Hz, 2H), 6.83-6.87 (m, 2H), 7.09 (td, J = 7.8, 1.3 Hz, 1H), 7.28 (d, J = 9.0 Hz, 2H), 7.34 (d, J = 7.8 Hz, 1H), 7.46 (d, J = 8.1 Hz, 2H), 7.87 (d, J = 8.1 Hz, 2H), 7.88 (br s, 1H), 9.15 (br s, 1H) |
| N-(2-Aminophenyl)-4-[3-(3,4-difluorophenyl)-1-[2-(1-methylpyrrolidin-2-yl)-ethyl]ureidomethyl]benzamide (Compound 1-97)<br>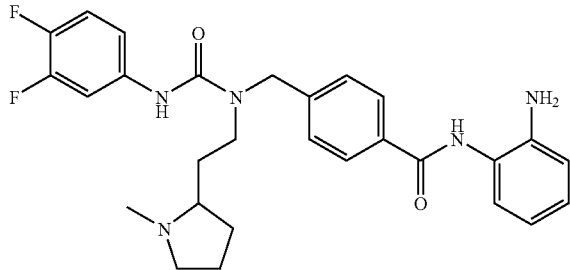 | $^1$H-NMR (400 MHz, CDCl$_3$) δ 1.55-1.79 (m, 4H), 1.84-1.96 (m, 2H), 2.32-2.50 (m, 5H), 3.16 (m, 1H), 3.28 (m, 1H), 3.43 (m, 1H), 3.87 (br s, 2H), 4.52 (d, J = 15.5 Hz, 1H), 4.72 (d, J = 15.5 Hz, 1H), 6.83-6.89 (m, 2H), 6.95-7.06 (m, 2H), 7.10 (td, J = 8.0, 1.5 Hz, 1H), 7.34 (d, J = 8.0 Hz, 1H), 7.46 (d, J = 8.2 Hz, 2H), 7.50 (m, 1H), 7.84 (br s, 1H), 7.88 (d, J = 8.2 Hz, 2H), 10.11 (br s, 1H) |
| N-(2-Aminophenyl-4-[3-(4-methoxycarbonylphenyl)-1-[3-(morpholin-4-yl)propyl]ureidomethyl]benzamide (Compound No. 1-98)<br>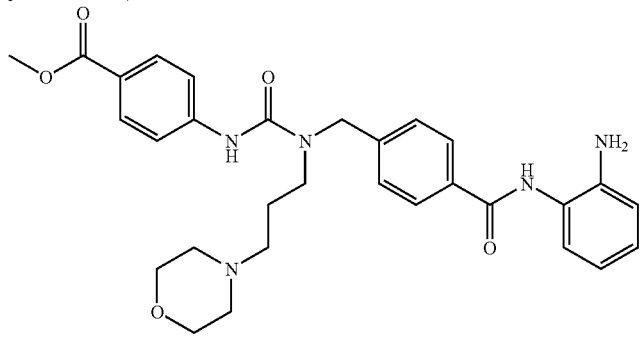 | $^1$H-NMR (500 MHz, CDCl$_3$) δ 1.78 (m, 2H), 2.44-2.52 (m, 6H), 3.40 (t, J = 5.8 Hz, 2H), 3.74 (t, J = 4.7 Hz, 4H), 3.86 (br s, 2H), 3.90 (s, 3H), 4.64 (s, 2H), 6.83-6.88 (m, 2H), 7.10 (td, J = 7.8, 1.3 Hz, 1H), 7.34 (d, J = 7.8 Hz, 1H), 7.45 (d, J = 7.9 Hz, 2H), 7.59 (d, J = 8.9 Hz, 2H), 7.85 (br s, 1H), 7.87 (d, J = 7.9 Hz, 2H), 8.00 (d, J = 8.9 Hz, 2H), 8.93 (br s, 1H) |

N-(2-Aminophenyl)-4-[3-(benzo[1,3]dioxol-5-yl)-1-[3-(morpholin-4-yl)propyl]-ureidomethyl]benzamide (Compound No. 1-99)

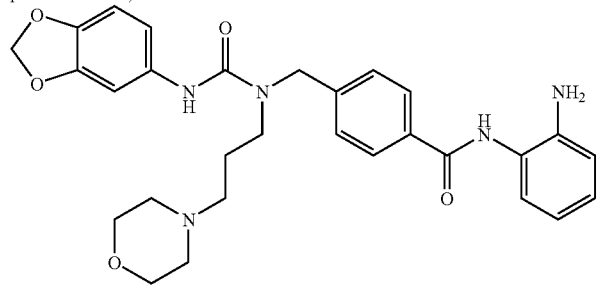

$^1$H-NMR (500 MHz, CDCl$_3$) δ 1.73 (m, 2H), 2.38-2.49 (m, 6H), 3.36 (t, J = 5.8 Hz, 2H), 3.64 (t, J = 4.4 Hz, 4H), 3.87 (br s, 2H), 4.62 (s, 2H), 5.94 (s, 2H), 6.71 (dd, J = 8.2, 1.8 Hz, 1H), 6.75 (d, J = 8.2 Hz, 1H), 6.83-6.88 (m, 2H), 7.08-7.12 (m, 2H), 7.34 (d, J = 7.6 Hz, 1H), 7.46 (d, J = 7.9 Hz, 2H), 7.83 (br s, 1H), 7.86 (d, J = 7.9 Hz, 2H), 8.90 (br s, 1H)

N-(2-Aminophenyl)-4-[3-(4-methylphenyl)-1-[3-(morpholin-4-yl)propyl]ureidomethyl]benzamide (Compound No. 1-100)

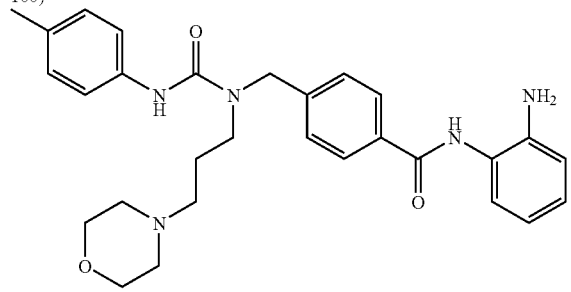

$^1$H-NMR (500 MHz, CDCl$_3$) δ 1.74 (m, 2H), 2.31 (s, 3H), 2.40-2.49 (m, 6H), 3.38 (t, J = 5.8 Hz, 2H), 3.67 (t, J = 4.7 Hz, 4H), 3.87 (br s, 2H), 4.63 (s, 2H), 6.83-6.88 (m, 2H), 7.08-7.13 (m, 3H), 7.30-7.36 (m, 3H), 7.45 (d, J = 8.1 Hz, 2H), 7.85 (br s, 1H), 7.85 (d, J = 8.1 Hz, 2H), 8.73 (br s, 1H)

N-(2-Aminophenyl)-4-[1-(3-dimethylaminopropyl)-3-(3-ethoxyphenyl)ureidomethyl]benzamide (Compound No. 1-101)

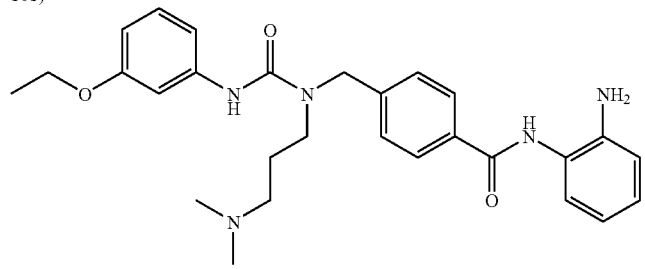

$^1$H-NMR (500 MHz, CDCl$_3$) δ 1.40 (t, J = 7.0 Hz, 3H), 1.68 (m, 2H), 2.30 (s, 6H), 2.37 (t, J = 5.8 Hz, 2H), 3.38 (t, J = 5.5 Hz, 2H), 3.87 (s, 2H), 4.04 (q, J = 7.0 Hz, 2H), 4.62 (s, 2H), 6.53 (ddd, J = 7.9, 2.4, 0.9 Hz, 1H), 6.84-6.87 (m, 2H), 6.89 (ddd, J = 7.9, 1.9, 0.9 Hz, 1H), 7.09 (m, 1H), 7.15 (dd, J = 7.9, 7.9 Hz, 1H), 7.27 (m, 1H), 7.34 (d, J = 7.9 Hz, 1H), 7.46 (d, J = 8.2 Hz, 2H), 7.82 (s, 1H), 7.86 (d, J = 8.2 Hz, 2H), 10.13 (s, 1H)

N-(2-Aminophenyl)-4-[1-(3-dimethylaminopropyl)-3-(4-fluoro-3-nitrophenyl)ureidomethyl]benzamide (Compound No. 1-102)

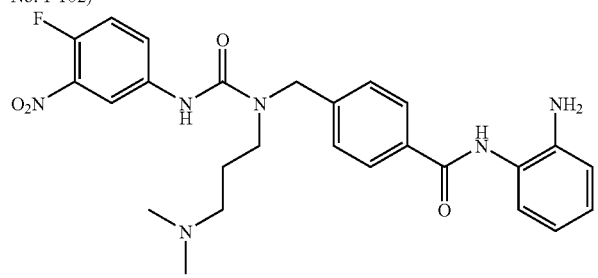

$^1$H-NMR (500 MHz, CDCl$_3$) δ 1.73 (m, 2H), 2.33 (s, 6H), 2.41 (t, J = 5.8 Hz, 2H), 3.40 (t, J = 5.5 Hz, 2H), 3.86 (s, 2H), 4.62 (s, 2H), 6.85-6.86 (m, 2H), 7.10 (ddd, J = 7.8, 7.6, 1.5 Hz, 1H), 7.19 (m, 1H), 7.35 (d, J = 7.8 Hz, 1H), 7.46 (d, J = 8.2 Hz, 2H), 7.81 (s, 1H), 7.85-7.89 (m, 3H), 8.05 (dd, J = 6.2, 2.5 Hz, 1H), 10.73 (s, 1H)

| | |
|---|---|
| N-(2-Aminophenyl)-4-[3-(4-cyanophenyl)-1-(3-dimethylaminopropyl)ureidomethyl]benzamide (Compound 1-103)<br>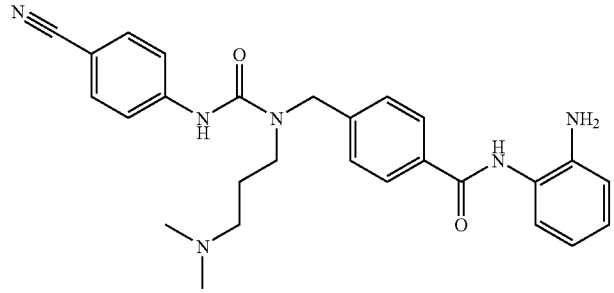 | ¹H-NMR (500 MHz, CDCl₃) δ 1.73 (m, 2H), 2.32 (s, 6H), 2.40 (t, J = 6.5 Hz, 2H), 3.40 (t, J = 5.5 Hz, 2H), 3.86 (s, 2H), 4.62 (s, 2H), 6.85-6.88 (m, 2H), 7.10 (ddd, J = 7.6, 7.6, 1.5 Hz, 1H), 7.35 (d, J = 7.7 Hz, 1H), 7.46 (d, J = 8.0 Hz, 2H), 7.52-7.55 (m, 4H), 7.80 (s, 1H), 7.88 (d, J = 8.0 Hz, 2H), 10.73 (s, 1H) |
| N-(2-Aminophenyl)-4-[1-(3-dimethylaminopropyl)-3-(pyridin-3-yl)ureidomethyl]-benzamide (Compound No. 1-104)<br>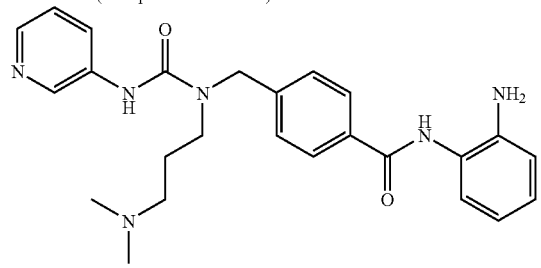 | ¹H-NMR (500 MHz, CDCl₃) δ 1.72 (m, 2), 2.31 (s, 6H), 2.40 (t, J = 6.0 Hz, 2H), 3.41 (t, J = 5.7 Hz, 2H), 3.87 (s, 2H), 4.62 (s, 2H), 6.82-6.87 (m, 2H), 7.10 (ddd, J = 7.6, 7.6, 1.2 Hz, 1H), 7.22 (dd, J = 8.5, 5.5 Hz, 1H), 7.34 (d, J = 7.6 Hz, 1H), 7.46 (d, J = 7.9 Hz, 2H), 7.85 (m, 1H), 7.87 (d, J = 7.9 Hz, 2H), 8.19-8.22 (m, 2H), 8.39 (d, J = 2.1 Hz, 1H), 10.51 (s, 1H) |
| N-(2-Aminophenyl)-4-[3-(4-cyanophenyl)-1-[3-(morpholin-4-yl)propyl]ureidomethyl]benzamide (Compound No. 1-105)<br>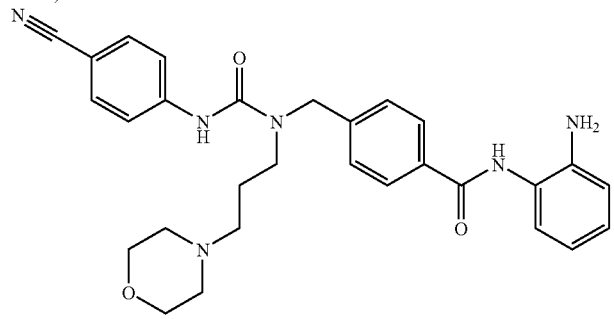 | ¹H-NMR (500 MHz, CDCl₃) δ 1.79 (m, 2H), 2.45-2.52 (m, 6H), 3.40 (t, J = 5.8 Hz, 2H), 3.74 (t, J = 4.6 Hz, 4H), 3.86 (br s, 2H), 4.64 (s, 2H), 6.84-6.88 (m, 2H), 7.10 (td, J = 7.8, 1.3 Hz, 1H), 7.34 (d, J = 7.8 Hz, 1H), 7.44 (d, J = 8.1 Hz, 2H), 7.59 (d, J = 8.9 Hz, 2H), 7.65 (d, J = 8.9 Hz, 2H), 7.83 (br s, 1H), 7.87 (d, J = 8.1 Hz, 2H), 9.05 (br s, 1H) |
| N-(2-Aminophenyl)-4-[3-(4-isopropylphenyl)-1-[3-(morpholin-4-yl)propyl]ureidomethyl]benzamide (Compound No. 1-106)<br>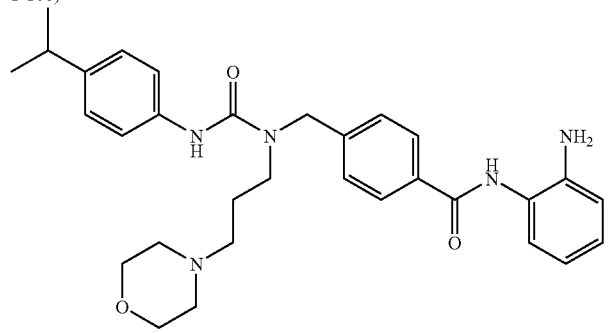 | ¹H-NMR (500 MHz, CDCl₃) δ 1.23 (d, J = 7.0 Hz, 6H), 1.74 (m, 2H), 2.42-2.49 (m, 6H), 2.87 (m, 1H), 3.38 (t, J = 5.7 Hz, 2H), 3.68 (t, J = 4.7 Hz, 4H), 3.87 (br s, 2H), 4.63 (s, 2H), 6.83-6.87 (m, 2H), 7.10 (td, J = 7.6, 1.5 Hz, 1H), 7.17 (d, J = 8.2 Hz, 2H), 7.37-7.36 (m, 3H), 7.45 (d, J = 7.9 Hz, 2H), 7.85 (br s, 1H), 7.85 (d, J = 7.9 Hz, 2H), 8.72 (br s, 1H) |

N-(2-Amino-5-methoxyphenyl)-4-[1-(2-dimethylamino-ethyl)-3-(indan-5-yl)ureod-methyl]benzamide (Compound No. 1-107)

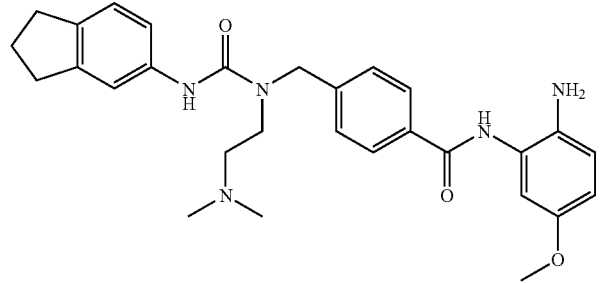

$^1$H-NMR (500 MHz, DMSO-d$_6$) δ 1.99 (m, 2H), 2.26 (s, 6H), 2.45 (t, J = 5.2 Hz, 2H), 2.76-2.82 (m, 4H), 3.36 (t, J = 5.2 Hz, 2H), 3.65 (s, 3H), 4.50 (br s, 2H), 4.61 (s, 2H), 6.63 (dd, J = 8.6, 2.7 Hz, 1H), 6.74 (d, J = 8.6 Hz, 1H), 6.91 (d, J = 2.7 Hz, 1H), 7.05 (dd, J = 8.2, 2.0 Hz, 1H), 7.08 (d, J = 8.2 Hz, 1H), 7.31 (s, 1H), 7.41 (d, J = 8.2 Hz, 2H), 7.95 (d, J = 8.2 Hz, 2H), 9.65 (s, 1H), 9.92 (br s, 1H)

N-(2-Amino-5-bromophenyl)-4-[1-(2-dimethylamino-ethyl)-3-(indan-5-yl)ureido-methyl]benzamide (Compound No. 1-108)

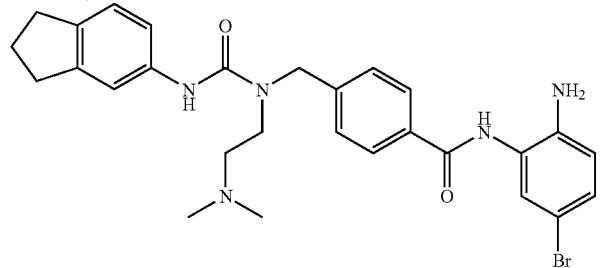

$^1$H-NMR (500 MHz, CD$_3$OD) δ 2.06 (m, 2H), 2.35 (s, 6H), 2.55 (t, J = 5.3 Hz, 2H), 2.82-2.88 (m, 4H), 3.45 (t, J = 5.3 Hz, 2H), 4.68 (s, 2H), 6.80 (d, J = 8.6 Hz, 1H), 7.00 (dd, J = 7.9, 2.1 Hz, 1H), 7.10 (d, J = 7.9 Hz, 1H), 7.16 (dd, J = 8.6, 2.4 Hz, 1H), 7.21 (s, 1H), 7.37 (d, J = 2.1 Hz, 1H), 7.45 (d, J = 8.2 Hz, 2H), 7.97 (d, J = 8.2 Hz, 2H)

N-(2-Aminophenyl)-4-[3-(4-chlorophenyl)-1-(3-dimethyl-aminopropyl)ureidomethyl]benzamide (Compound No. 1-109)

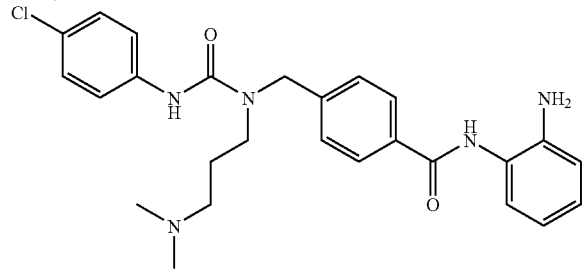

$^1$H-NMR (400 MHz, CDCl$_3$) δ 1.70 (m, 2H), 2.29 (s, 6H), 2.38 (t, J = 6.0 Hz, 2H), 3.38 (t, J = 5.6 Hz 2H), 3.87 (s, 2H), 4.60 (s, 2H), 6.83-6.87 (m, 2H), 7.10 (td, J = 7.6, 1.4 Hz, 1H), 7.22 (d, J = 9.0 Hz, 2H), 7.34 (d, J = 7.3 Hz, 1H), 7.40 (d, J = 9.0 Hz, 2H), 7.45 (d, J = 7.9 Hz, 2H), 7.86 (d, J = 7.9 Hz, 2H), 7.87 (m, 1H), 10.26 (s, 1H)

4-[3-(4-Acetylphenyl)-1-(3-dimethylaminopropyl)ureido-methyl]-N-(2-aminophenyl)benzamide (Compound No. 1-110)

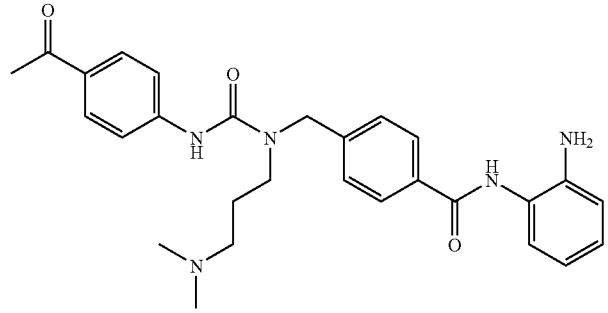

$^1$H-NMR (400 MHz, CDCl$_3$) δ 1.72 (m, 2H), 2.32 (s, 6H), 2.40 (t, J = 5.9 Hz, 2H), 2.56 (s, 3H), 3.41 (t, J = 5.5 Hz, 2H), 3.87 (s, 2H), 4.63 (s, 2H), 6.86 (t, J = 7.8 Hz, 1H), 6.87 (dd, J = 7.8, 1.5 Hz, 1H), 7.10 (td, J = 7.8, 1.4 Hz, 1H), 7.34 (d, J = 7.8 Hz, 1H), 7.47 (d, J = 8.2 Hz, 2H), 7.53 (d, J = 8.8 Hz, 2H), 7.83 (s, 1H), 7.88 (d, J = 8.2 Hz, 2H), 7.91 (d, J = 8.8 Hz, 2H), 10.65 (s, 1H)

N-(2-Aminophenyl)-4-[1-(3-dimthylaminopropyl)-3-(4-nitrophenyl)ureidomethyl]-benzamide (Compound No. 1-111)

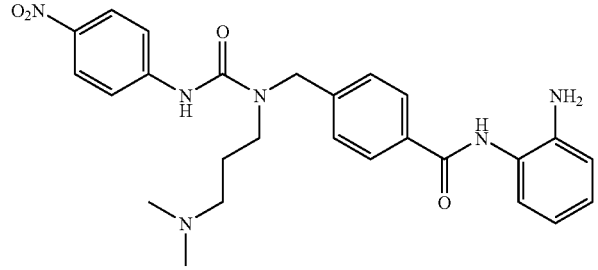

$^1$H-NMR (400 MHz, CDCl$_3$) δ 1.74 (m, 2H), 2.34 (s, 6H), 2.41 (t, J = 6.0 Hz, 2H), 3.42 (t, J = 5.6 Hz, 2H), 3.87 (s, 2H), 4.62 (s, 2H), 6.85 (t, J = 7.8 Hz, 1H), 6.86 (dd, J = 7.8, 1.5 Hz, 1H), 7.10 (td, J = 7.8, 1.5 Hz, 1H), 7.34 (d, J = 7.8 Hz, 1H), 7.46 (d, J = 8.2 Hz, 2H), 7.55 (d, J = 9.3 Hz, 2H), 7.87 (m, 1H), 7.88 (d, J = 8.2 Hz, 2H), 8.16 (d, J = 9.3 Hz, 2H), 10.97 (s, 1H)

N-(2-Aminophenyl)-4-[3-(4-dimethylaminophenyl)-1-[2-(4-methylpiperazin-1-yl)-ethyl]ureidomethyl]benzamide (Compound No. 1-112)

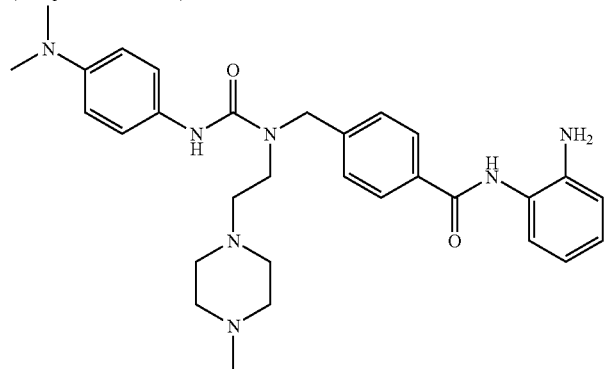

$^1$H-NMR (400 MHz, DMSO-d$_6$) δ 2.14 (s, 3H), 2.33 (br s, 4H), 2.44 (br s, 4H), 2.46 (t, J = 5.5 Hz, 2H), 2.83 (s, 6H), 3.37 (t, J = 5.5 Hz, 2H), 4.62 (s, 2H), 4.89 (br s, 2H), 6.60 (t, J = 7.6 Hz, 1H), 6.68 (d, J = 9.0 Hz, 2H), 6.78 (dd, J = 7.6, 1.3 Hz, 1H), 6.97 (td, J = 7.6, 1.3 Hz, 1H), 7.16 (d, J = 7.6 Hz, 1H), 7.24 (d, J = 9.0 Hz, 2H), 7.40 (d, J = 8.3 Hz, 2H), 7.95 (d, J = 8.3 Hz, 2H), 8.85 (br s, 1H), 9.63 (br s, 1H)

N-(2-Aminophenyl)-4-[3-(3,4-difluorophenyl)-1-[2-(4-methylpiperazin-1-yl)ethyl]-ureidomethyl]benzamide (Compound No. 1-113)

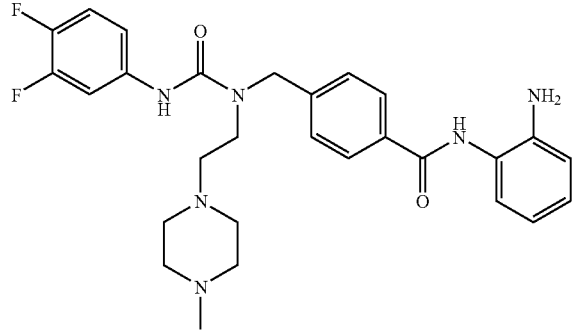

$^1$H-NMR (400 MHz, DMSO-d$_6$) δ 2.13 (s, 3H), 2.30 (br s, 4H), 2.45 (br s, 4H), 2.47 (t, J = 5.6 Hz, 2H), 3.41 (t, J = 5.6 Hz, 2H), 4.66 (s, 2H), 4.89 (br s, 2H), 6.60 (t, J = 7.6 Hz, 1H), 6.78 (d, J = 7.6 Hz, 1H), 6.97 (t, J = 7.6 Hz, 1H), 7.16 (d, J = 7.6 Hz, 1H), 7.22 (m, 1H), 7.33 (m, 1H), 7.40 (d, J = 8.1 Hz, 2H), 7.65 (m, 1H), 7.96 (d, J = 8.1 Hz, 2H), 9.26 (br s, 1H), 9.64 (br s, 1H)

| | |
|---|---|
| N-(2-Aminophenyl)-4-[3-(2,3-dihydrobenzo[1,4]dioxin-6-yl)-1-[2-hydroxy-3-(morpholin-4-yl)propyl]ureidomethyl]benzamide (Compound No. 1-114)<br>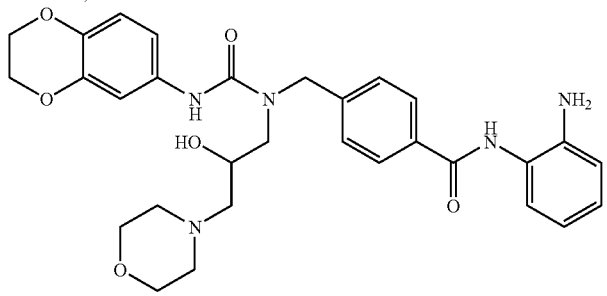 | $^1$H-NMR (500 MHz, CDCl$_3$) δ 2.28-2.43 (m, 4H), 2.62 (m, 2H), 3.33 (m, 2H), 3.67-3.76 (m, 4H), 3.87 (m, 1H), 4.20-4.25 (m, 4H), 4.51 (d, J = 15.9 Hz, 1H), 4.76 (d, J = 15.9 Hz, 1H), 6.76 (d, J = 8.7 Hz, 1H), 6.82 (dd, J = 8.7, 2.4 Hz, 1H), 6.83-6.88 (m, 2H), 7.00 (d, J = 2.4 Hz, 1H), 7.10 (td, J = 7.7, 1.3 Hz, 1H), 7.34 (d, J = 7.7 Hz, 1H), 7.42 (d, J = 8.2 Hz, 2H), 7.86 (d, J = 8.2 Hz, 2H), 7.91 (br s, 1H), 8.55 (br s, 1H) |
| N-(2-Aminophenyl)-4-[3-(4-dimethylaminophenyl)-1-[2-hydroxy-3-(morpholin-4-yl)propyl]ureidomethyl]benzamide (Compound No. 1-115)<br>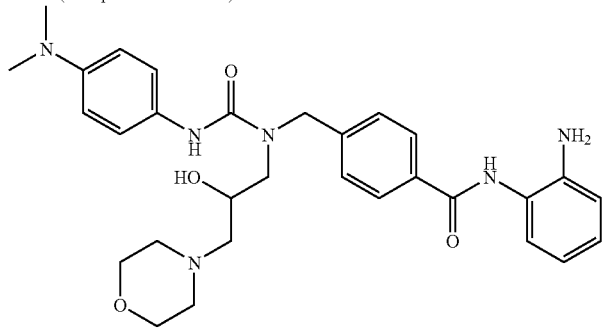 | $^1$H-NMR (500 MHz, CDCl$_3$) δ 2.29-2.43 (m, 4H), 2.62 (m, 2H), 2.89 (s, 6H), 3.35 (m, 2H), 3.67-3.75 (m, 4H), 3.88 (m, 1H), 4.53 (d, J = 15.9 Hz, 1H), 4.78 (d, J = 15.9 Hz, 1H), 6.71 (d, J = 9.0 Hz, 2H), 6.83-6.88 (m, 2H), 7.10 (td, J = 7.6, 1.4 Hz, 1H), 7.25 (d, J = 9.0 Hz, 2H), 7.34 (d, J = 7.6 Hz, 1H), 7.43 (d, J = 7.9 Hz, 2H), 7.86 (d, J = 7.9 Hz, 2H), 7.91 (br s, 1H), 8.34 (br s, 1H) |
| N-(2-Aminophenyl)-4-[3-(3,4-difluorophenyl)-1-[2-hydroxy-3-(morpholin-4-yl)-propyl]ureidomethyl]benzamide (Compound No. 1-116)<br>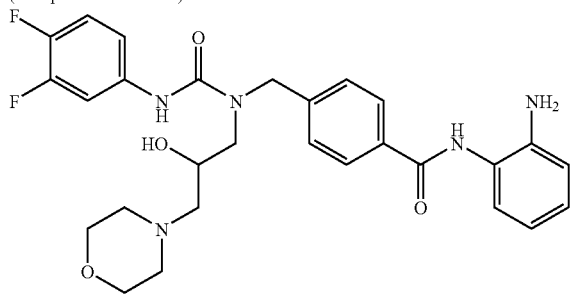 | $^1$H-NMR (400 MHz, CDCl$_3$) δ 2.29-2.45 (m, 4H), 2.65 (m, 2H), 3.33 (m, 2H), 3.65-3.78 (m, 4H), 3.88 (m, 1H), 4.52 (d, J = 15.7 Hz, 1H), 4.77 (d, J = 15.7 Hz, 1H), 6.85-6.88 (m, 2H), 6.97-7.13 (m, 3H), 7.35 (d, J = 8.3 Hz, 1H), 7.41-7.48 (m, 3H), 7.84 (br s, 1H), 7.89 (d, J = 8.1 Hz, 2H), 8.96 (br s, 1H) |

| | |
|---|---|
| N-(2-Aminophenyl)-4-[3-(4-fluorophenyl)-1-[3-(morpholin-4-yl)propyl]ureido-methyl]benzamide (Compound No. 1-117)<br>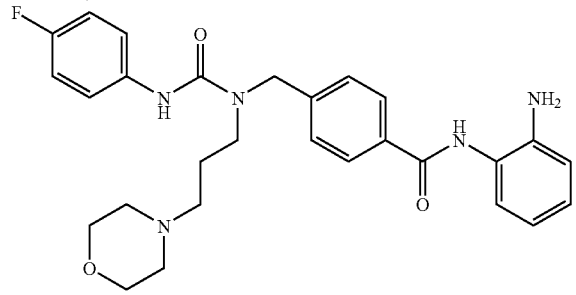 | $^1$H-NMR (500 MHz, CDCl$_3$) δ 1.75 (m, 2H), 2.44 (br s, 4H), 2.47 (t, J = 6.0 Hz, 2H), 3.38 (t, J = 5.7 Hz, 2H), 3.64 (t, J = 4.6 Hz, 4H), 3.86 (br s, 2H), 4.63 (s, 2H), 6.86 (t, J = 7.7 Hz, 1H), 6.86 (dd, J = 7.7, 1.4 Hz, 1H), 7.01 (t, J = 8.8 Hz, 2H), 7.10 (td, J = 7.7, 1.4 Hz, 1H), 7.34 (d, J = 7.7 Hz, 1H), 7.39 (dd, J = 8.8, 4.7 Hz, 2H), 7.45 (d, J = 7.9 Hz, 2H), 7.84 (br s, 1H), 7.86 (d, J = 7.9 Hz, 2H), 8.92 (br s, 1H) |
| N-(2-Aminophenyl)-4-[3-benzyl-1-[3-(morpholin-4-yl)-propyl]ureidomethyl]benz-amide (Compound No. 1-118)<br>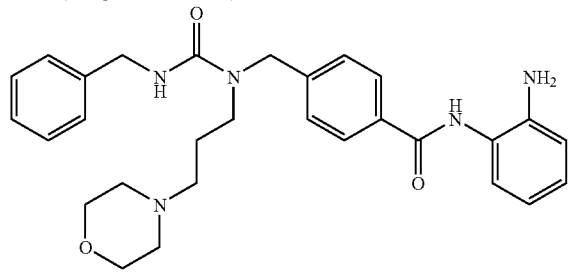 | $^1$H-NMR (500 MHz, CDCl$_3$) δ 1.64 (m, 2H), 2.25 (br s, 4H), 2.33 (t, J = 6.1 Hz, 2H), 3.30 (t, J = 5.7 Hz, 2H), 3.41 (br s, 4H), 3.89 (br s, 2H), 4.49 (d, J = 5.8 Hz, 2H), 4.62 (s, 2H), 6.86 (t, J = 7.6 Hz, 1H), 6.86 (dd, J = 7.6, 1.3 Hz, 1H), 7.10 (td, J = 7.6, 1.3 Hz, 1H), 7.26 (m, 1H), 7.30-7.36 (m, 5H), 7.41 (br s, 1H), 7.43 (d, J = 7.9 Hz, 2H), 7.85 (br s, 1H), 7.87 (d, J = 7.9 Hz, 2H) |
| N-(2-Aminophenyl)-4-[1-[3-(morpholin-4-yl)propyl]-3-(3-phenylpropyl)]ureido-methyl]benzamide (Compound No. 1-119)<br>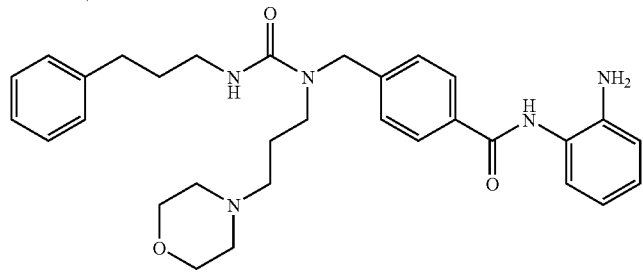 | $^1$H-NMR (500 MHz, CDCl$_3$) δ 1.62 (m, 2H), 1.88 (m, 2H), 2.34 (t, J = 6.1 Hz, 2H), 2.40 (br s, 4H), 2.66 (t, J = 7.6 Hz, 2H), 3.19 (t, J = 5.8 Hz, 2H), 3.26 (td, J = 7.6, 6.4 Hz, 2H), 3.66 (br s, 4H), 3.86 (br s, 2H), 4.55 (s, 2H), 6.79-6.88 (m, 3H), 7.10 (td, J = 7.8, 1.2 Hz, 1H), 7.16-7.20 (m, 3H), 7.25-7.29 (m, 2H), 7.33 (d, J = 7.8 Hz, 1H), 7.38 (d, J = 7.9 Hz, 2H), 7.86 (d, J = 7.9 Hz, 2H), 7.90 (br s, 1H) |
| N-(2-Aminophenyl)-4-[1-(3-dimethylaminopropyl)-3-(thiophen-2-yl)ureidomethyl]-benzamide (Compound No. 1-120)<br>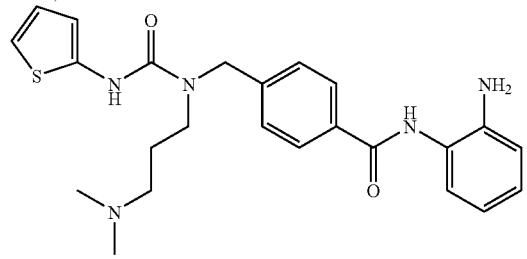 | $^1$H-NMR (500 MHz, CDCl$_3$) δ 1.68 (m, 2H), 2.29 (s, 6H), 2.37 (t, J = 5.8 Hz, 2H), 3.36 (t, J = 5.5 Hz, 2H), 3.87 (s, 2H), 4.63 (s, 2H), 6.26 (s, 1H), 6.50 (d, J = 4.0 Hz, 1H), 6.83-6.86 (m, 3H), 7.09 (t, J = 7.6 Hz, 1H), 7.34 (d, J = 7.6 Hz, 1H), 7.43 (d, J = 7.9 Hz, 2H), 7.85 (d, J = 7.9 Hz, 2H), 7.93 (s, 1H), 11.22 (s, 1H) |

| | |
|---|---|
| N-(2-Aminophenyl)-4-[1-(3-dimethylaminopropyl)-3-(thiophen-3-yl)ureidomethyl]benzamide (Compound No. 1-121)<br>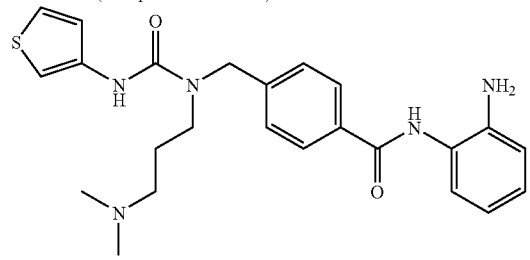 | $^1$H-NMR (500 MHz, CDCl$_3$) δ 1.68 (m, 2H), 2.29 (s, 6H), 2.37 (t, J = 5.8 Hz, 2H), 3.36 (t, J = 5.5 Hz, 2H), 3.87 (s, 2H), 4.63 (s, 2H), 6.84-6.86 (m, 2H), 6.92 (d, J = 5.1 Hz, 1H), 7.10 (t, J = 7.6 Hz, 1H), 7.20 (dd, J = 5.1, 3.4 Hz, 1H), 7.34 (s, 1H), 7.35 (d, J = 3.4 Hz, 1H), 7.45 (d, J = 7.9 Hz, 2H), 7.82 (s, 1H), 7.86 (d, J = 7.9 Hz, 2H), 10.52 (s, 1H) |
| N-(2-Aminophenyl)-4-[3-(4-ethoxyphenyl)-1-(3-dimethyl-aminopropyl)ureidomethyl]benzamide (Compound No. 1-122)<br>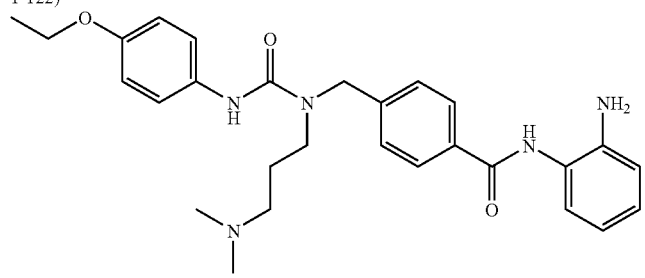 | $^1$H-NMR (500 MHz, CDCl$_3$) δ 1.39 (t, J = 7.0 Hz, 3H), 1.65 (m, 2H), 2.27 (s, 6H), 2.36 (t, J = 6.0 Hz, 2H), 3.37 (t, J = 5.7 Hz, 2H), 3.89 (s, 2H), 4.00 (q, J = 7.0 Hz, 2H), 4.59 (s, 2H), 6.82 (d, J = 9.1 Hz, 2H), 6.83 (t, J = 7.7 Hz, 1H), 6.84 (m, 1H), 7.08 (td, J = 7.7, 1.4 Hz, 1H), 7.32 (m, 1H), 7.34 (d, J = 9.1 Hz, 2H), 7.43 (d, J = 7.9 Hz, 2H), 7.85 (d, J = 7.9 Hz, 2H), 7.99 (s, 1H), 9.88 (s, 1H) |
| N-(2-Aminophenyl)-4-[3-cyclopentyl-1-(3-dimethyl-aminopropyl)ureidomethyl]benzamide (Compound No. 1-123)<br>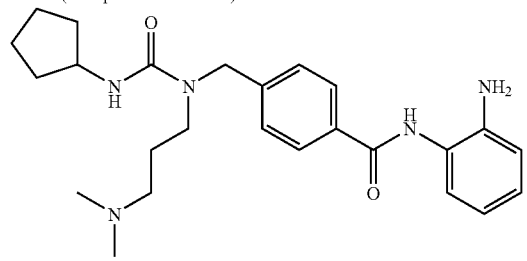 | $^1$H-NMR (500 MHz, CDCl$_3$) δ 1.34 (m, 2H), 1.55-1.69 (m, 6H), 2.03 (m, 2H), 2.19 (s, 6H), 2.26 (t, J = 6.1 Hz, 2H), 3.21 (t, J = 6.0 Hz, 2H), 3.88 (s, 2H), 4.03 (m, 1H), 4.53 (s, 2H), 6.85 (dd, J = 7.6, 1.4 Hz, 1H), 6.85 (t, J = 7.6 Hz, 1H), 7.09 (td, J = 7.6, 1.4 Hz, 1H), 7.18 (s, 1H), 7.34 (d, J = 7.6 Hz, 1H), 7.40 (d, J = 8.0 Hz, 2H), 7.85 (d, J = 8.0 Hz, 2H), 7.90 (s, 1H) |
| N-(2-Aminophenyl)-4-[3-(3,4-dimethoxyphenyl)-1-(3-di methylaminopropyl)ureido-methyl]benzamide (Compound No. 1-124)<br>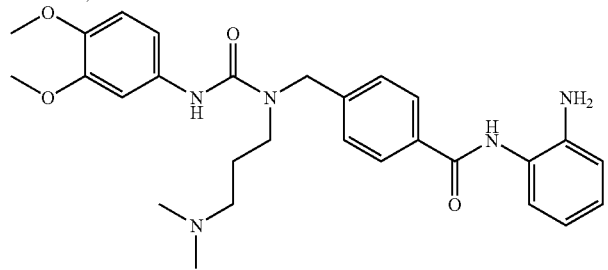 | $^1$H-NMR (400 MHz, CDCl$_3$) δ 1.66 (m, 2H), 2.29 (s, 6H), 2.38 (t, J = 6.0 Hz, 2H), 2.38 (t, J = 6.0 Hz, 2H), 3.38 (t, J = 5.6 Hz, 2H), 3.85 (s, 3H), 3.87 (m, 2H), 3.89 (s, 3H), 4.62 (s, 2H), 6.75-6.78 (m, 2H), 6.81-6.86 (m, 2H), 7.09 (td, J = 7.6, 1.5 Hz, 1H), 7.33 (d, J = 7.6 Hz, 1H), 7.40 (d, J = 2.0 Hz, 1H), 7.44 (d, J = 8.2 Hz, 2H), 7.86 (d, J = 8.2 Hz, 2H), 7.92 (s, 1H), 9.99 (s, 1H) |

| | -continued | |
|---|---|---|
| N-(2-Aminophenyl)-4-[1-(3-dimethylaminopropyl)-3-(furan-2-ylmethyl)ureodmethyl]benzamide (Compound No. 1-125) 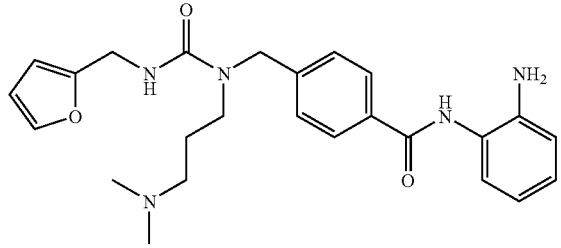 | | $^1$H-NMR (400 MHz, CDCl$_3$) δ 1.59 (m, 2H), 2.02 (s, 6H), 2.24 (t, J = 6.1 Hz, 2H), 3.25 (t, J = 5.7 Hz, 2H), 3.90 (s, 2H), 4.40 (d, J = 4.9 Hz, 2H), 4.56 (s, 2H), 6.22 (dd, J = 3.2, 0.8 Hz, 1H), 6.32 (dd, J = 3.2, 1.7 Hz, 1H), 6.85 (t, J = 7.6 Hz, 1H), 6.86 (dd, J = 7.6, 1.4 Hz, 1H), 7.09 (td, J = 7.6, 1.4 Hz, 1H), 7.34 (m, 1H), 7.35 (dd, J = 1.7, 0.8 Hz, 1H), 7.39 (d, J = 8.2 Hz, 2H), 7.84 (d, J = 8.2 Hz, 2H), 7.98 (s, 1H), 8.19 (s, 1H) |
| N-(2-Aminophenyl)-4-[3-(3,5-dimethoxyphenyl)-1-(3-dimethylaminopropyl)ureidomethyl]benzamide (Compound No. 1-126) 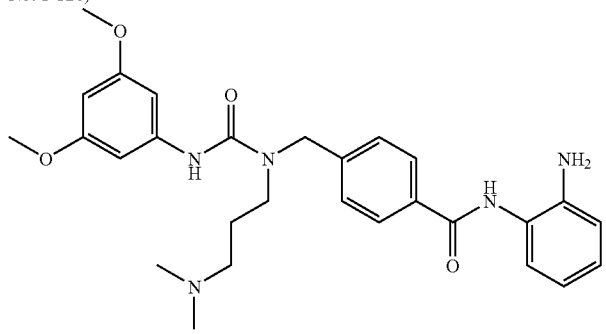 | | $^1$H-NMR (500 MHz, CDCl$_3$) δ 1.68 (m, 2H), 2.29 (s, 6H), 2.37 (t, J = 6.0 Hz, 2H), 3.37 (t, J = 5.7 Hz, 2H), 3.78 (s, 6H), 3.79 (s, 2H), 4.60 (s, 2H), 6.14 (t, J = 2.1 Hz, 1H), 6.74 (d, J = 2.1 Hz, 2H), 6.83 (t, J = 7.9 Hz, 1H), 6.85 (d, J = 7.9 Hz, 1H), 7.09 (td, J = 7.9, 1.3 Hz, 1H), 7.33 (d, J = 7.9 Hz, 1H), 7.43 (d, J = 7.9 Hz, 2H), 7.85 (d, J = 7.9 Hz, 2H), 7.96 (s, 1H), 10.18 (s, 1H) |
| N-(2-Aminophenyl)-4-[3-(benzo[1,3]dioxol-5-yl)-1-[2-(4-methylpiperazin-1-yl)ethyl]ureidomethyl]benzamide (Compound No. 1-127) 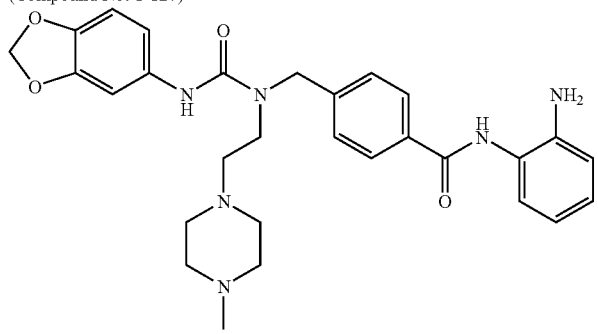 | | $^1$H-NMR (500 MHz, DMSO-d$_6$) δ 2.14 (s, 3H), 2.31 (br s, 4H), 2.45 (br s, 4H), 2.46 (t, J = 5.6 Hz, 2H), 3.38 (t, J = 5.6 Hz, 2H), 4.63 (s, 2H), 4.88 (br s, 2H), 5.95 (s, 2H), 6.60 (td, J = 7.6, 1.2 Hz, 1H), 6.78 (dd, J = 7.9, 1.2 Hz, 1H), 6.81-6.82 (m, 2H), 6.97 (td, J = 7.6, 1.2 Hz, 1H), 7.14 (m, 1H), 7.16 (d, J = 7.6 Hz, 1H), 7.39 (d, J = 8.1 Hz, 2H), 7.96 (d, J = 8.1 Hz, 2H), 9.02 (br s, 1H), 9.63 (br s, 1H) |

| | |
|---|---|
| N-(2-Aminophenyl)-4-[3-(2,3-dihydrobenzo[1,4]dioxin-6-yl)-1-[3-(4-methylpiperidin-1-yl)propyl]ureidomethyl]benzamide (Compound No. 1-128)<br>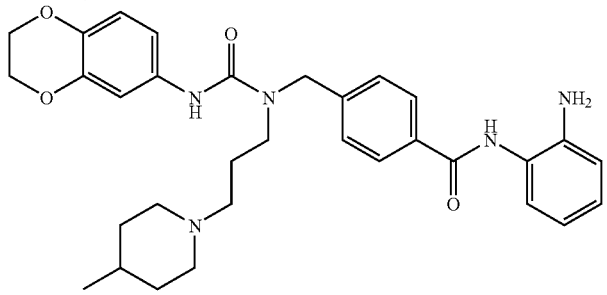 | $^1$H-NMR (400 MHz, DMSO-d$_6$) δ 0.86 (d, J = 6.6 Hz, 3H), 1.08-1.17 (m, 2H), 1.23 (m, 1H), 1.53 (d, J = 11.2 Hz, 2H), 1.67 (t, J = 6.5 Hz, 2H), 1.82 (br s, 2H), 2.26 (br s, 2H), 2.78 (d, J = 11.2 Hz, 2H), 3.29 (t, J = 6.5 Hz, 2H), 4.17-4.19 (m, 4H), 4.60 (s, 2H), 4.89 (s, 2H), 6.59 (td, J = 7.6, 1.2 Hz, 1H), 6.73 (d, J = 8.8 Hz, 1H), 6.78 (dd, J = 7.6, 1.2 Hz, 1H), 6.87 (dd, J = 8.8, 2.4 Hz, 1H), 6.97 (td, J = 7.6, 1.2 Hz, 1H), 7.06 (d, J = 2.4 Hz, 1H), 7.16 (d, J = 7.6 Hz, 1H), 7.38 (d, J = 8.2 Hz, 2H), 7.95 (d, J = 8.2 Hz, 2H), 8.62 (s, 1H), 9.63 (s, 1H) |
| N-(2-Aminophenyl)-4-[3-(3,4-dimethoxyphenyl)-1-(2-dimethylaminoethyl)ureidomethyl]benzamide (Compound No. 1-129)<br>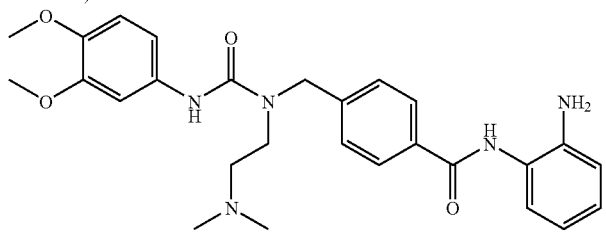 | $^1$H-NMR (500 MHz, CDCl$_3$) δ 2.38 (s, 6H), 2.48 (t, J = 4.2 Hz, 2H), 3.34 (t, J = 4.2 Hz, 2H), 3.86 (s, 3H), 3.87 (s, 2H), 3.89 (s, 3H), 4.65 (s, 2H), 6.65 (dd, J = 8.6, 2.4 Hz, 1H), 6.79 (d, J = 8.6 Hz, 1H), 6.85 (t, J = 7.6 Hz, 1H), 6.86 (dd, J = 7.6, 1.4 Hz, 1H), 7.10 (td, J = 7.6, 1.4 Hz, 1H), 7.33 (m, 1H), 7.35 (d, J = 2.4 Hz, 1H), 7.44 (d, J = 8.0 Hz, 2H), 7.88 (d, J = 8.0 Hz, 2H), 7.90 (s, 1H), 10.88 (s, 1H) |
| N-(2-Aminophenyl)-4-[1-(2-dimethylaminoethyl)-3-(4-methoxyphenyl)ureidomethyl]benzamide (Compound No. 1-130)<br>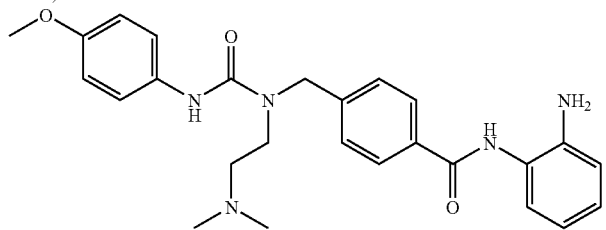 | $^1$H-NMR (400 MHz, CDCl$_3$) δ 2.37 (s, 6H), 2.47 (t, J = 4.3 Hz, 2H), 3.32 (t, J = 4.3 Hz, 2H), 3.78 (s, 3H), 3.88 (s, 2H), 4.63 (s, 2H), 6.83-6.86 (m, 2H), 6.84 (d, J = 9.0 Hz, 2H), 7.10 (m, 1H), 7.28 (d, J = 9.0 Hz, 2H), 7.34 (d, J = 8.3 Hz, 1H), 7.44 (d, J = 8.3 Hz, 2H), 7.87 (d, J = 8.3 Hz, 2H), 7.93 (s, 1H), 10.76 (s, 1H) |
| N-(2-Aminophenyl)-4-[1-(2-dimethylaminoethyl)-3-(3-ethoxyphenyl)ureidomethyl]benzamide (Compound No. 1-131)<br>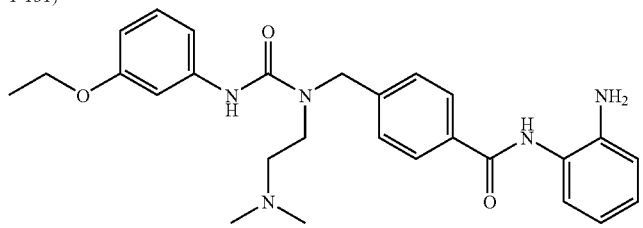 | $^1$H-NMR (500 MHz, CDCl$_3$) δ 1.39 (t, J = 6.9 Hz, 3H), 2.38 (s, 6H), 2.47 (t, J = 4.3 Hz, 2H), 3.33 (m, 2H), 3.89 (s, 2H), 4.04 (q, J = 6.9 Hz, 2H), 4.63 (s, 2H), 6.54 (m, 1H), 6.81 (dd, J = 7.6, 1.3 Hz, 1H), 6.83-6.86 (m, 2H), 7.10 (td, J = 7.6, 1.3 Hz, 1H), 7.13-7.17 (m, 2H), 7.34 (d, J = 7.6 Hz, 1H), 7.43 (d, J = 8.2 Hz, 2H), 7.87 (d, J = 8.2 Hz, 2H), 7.93 (s, 1H), 11.01 (s, 1H) |

| | |
|---|---|
| N-(2-Aminophenyl)-4-[1-(2-dimethylaminoethyl)-3-(pyridin-3-yl)ureidomethyl]-benzamide (Compound No. 1-132)<br />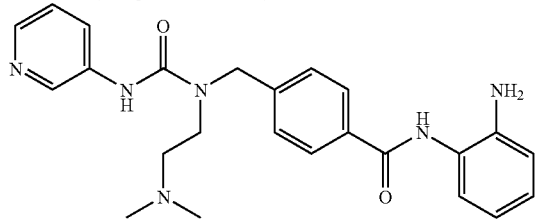 | $^1$H-NMR (400 MHz, CDCl$_3$) δ 2.40 (s, 6H), 2.51 (t, J = 4.3 Hz, 2H), 3.35 (t, J = 4.3 Hz, 2H), 3.88 (s, 2H), 4.64 (s, 2H), 6.83-6.86 (m, 2H), 7.10 (m, 1H), 7.22 (dd, J = 8.3, 4.9 Hz, 1H), 7.33 (d, J = 7.6 Hz, 1H), 7.43 (d, J = 8.2 Hz, 2H), 7.88 (d, J = 8.2 Hz, 2H), 7.97 (s, 1H), 8.09 (ddd, J = 8.3, 2.7, 1.5 Hz, 1H), 8.21 (dd, J = 4.9, 1.5 Hz, 1H), 8.31 (d, J = 2.7 Hz, 1H), 11.48 (s, 1H) |
| N-(2-Aminophenyl)-4-[3-(2,3-dihydrobenzofuran-5-yl)-1-[3-morpholin-4-yl)-propyl]ureidomethyl]benzamide (Compound No. 1-133)<br />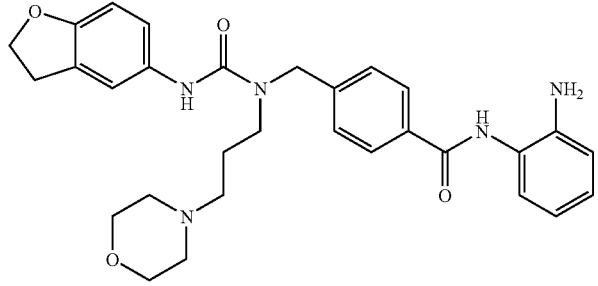 | $^1$H-NMR (500 MHz, CDCl$_3$) δ 1.73 (m, 2H), 2.43 (br s, 4H), 2.46 (t, J = 6.1 Hz, 2H), 3.20 (t, J = 8.6 Hz, 2H), 3.37 (t, J = 5.7 Hz, 2H), 3.62 (t, J = 4.4 Hz, 4H), 3.87 (br s, 2H), 4.56 (t, J = 8.6 Hz, 2H), 4.62 (s, 2H), 6.71 (s, J = 8.2 Hz, 1H), 6.83-6.88 (m, 2H), 6.95 (dd, J = 8.0, 2.3 Hz, 1H), 7.10 (td, J = 8.0, 1.5 Hz, 1H), 7.34 (d, J = 8.2 Hz, 1H), 7.37 (s, 1H), 7.46 (d, J = 8.1 Hz, 2H), 7.84 (br s, 1H), 7.86 (d, J = 8.1 Hz, 2H), 8.83 (br s, 1H) |
| N-(2-Aminophenyl)-4-[1-(3-(morpholin-4-yl)propyl]-3-(thiophen-3-yl)ureido-methyl]benzamide (Compound No. 1-134)<br />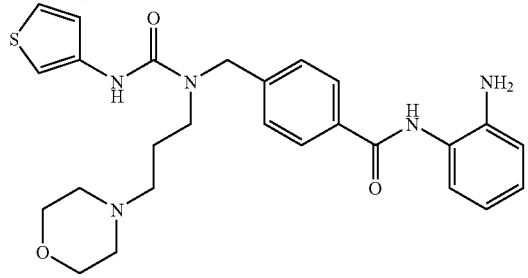 | $^1$H-NMR (500 MHz, CDCl$_3$) δ 1.74 (m, 2H), 2.39-2.50 (m, 6H), 3.36 (t, J = 5.7 Hz, 2H), 3.72 (t, J = 4.6 Hz, 4H), 3.86 (br s, 2H), 4.64 (s, 2H), 6.83-6.88 (m, 2H), 7.08-7.12 (m, 2H), 7.23 (dd, J = 5.0, 3.2 Hz, 1H), 7.31-7.37 (m, 2H), 7.45 (d, J = 8.1 Hz, 2H), 7.81 (br s, 1H), 7.86 (d, J = 8.1 Hz, 2H), 9.11 (br s, 1H) |
| N-(2-Aminophenyl)-4-[3-(4-fluoro-3-methylphenyl)-1-[3-morpholin-4-yl)propyl]ureidomethyl]benzamide (Compound No. 1-135)<br />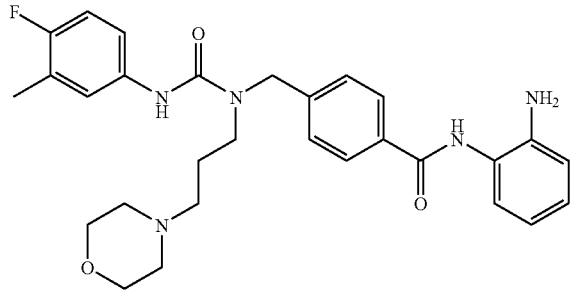 | $^1$H-NMR (500 MHz, CDCl$_3$) δ 1.70 (m, 2H), 2.22 (d, J = 1.8 Hz, 3H), 2.38-2.44 (m, 6H), 3.33 (t, J = 5.8 Hz, 2H), 3.47 (br s, 2H), 3.61 (t, J = 4.4 Hz, 4H), 4.54 (s, 2H), 6.74-6.79 (m, 2H), 6.89 (t, J = 9.0 Hz, 1H), 7.04 (td, J = 7.6, 1.3 Hz, 1H), 7.09 (m, 1H), 7.21-7.27 (m, 2H), 7.30 (d, J = 7.9 Hz, 2H), 7.78 (d, J = 7.9 Hz, 2H), 8.38 (br s, 1H), 8.84 (br s, 1H) |

| | |
|---|---|
| N-(2-Aminophenyl)-4-[3-(3-fluoro-4-methylphenyl)-1-[3-(morpholin-4-yl)propyl]ureidomethyl]benzamide (Compound No. 1-136)<br />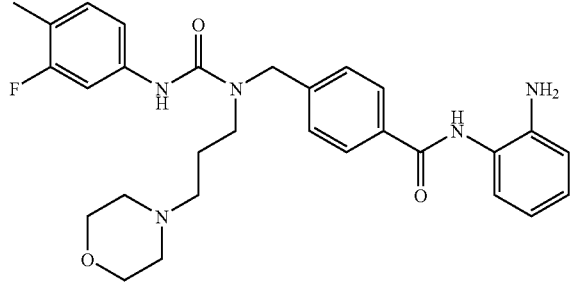 | $^1$H-NMR (500 MHz, CDCl$_3$) δ 1.71 (m, 2H), 2.21 (d, J = 1.2 Hz, 3H), 2.38-2.46 (m, 6H), 3.33 (t, J = 5.7 Hz, 2H), 3.51 (br s, 2H), 3.66 (t, J = 4.7 Hz, 4H), 4.55 (s, 2H), 6.75-6.80 (m, 2H), 6.99 (dd, J = 8.1, 2.0 Hz, 1H), 7.02-7.07 (m, 2H), 7.23-7.30 (m, 2H), 7.31 (d, J = 7.9 Hz, 2H), 7.77 (d, J = 7.9 Hz, 2H), 8.30 (br s, 1H), 8.83 (br s, 1H) |
| N-(2-Aminophenyl)-4-[3-(3,5-difluorophenyl)-1-[3-(morpholin-4-yl)propyl]ureidomethyl]benzamide (Compound No. 1-137)<br />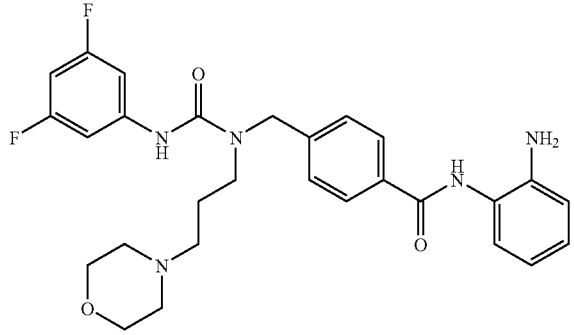 | $^1$H-NMR (500 MHz, CDCl$_3$) δ 1.73 (m, 2H), 2.39-2.47 (m, 6H), 3.33 (t, J = 5.8 Hz, 2H), 3.52 (br s, 2H), 3.71 (t, J = 4.6 Hz, 4H), 4.55 (s, 2H), 6.48 (tt, J = 9.0, 2.3 Hz, 1H), 6.75-6.80 (m, 2H), 7.04 (td, J = 7.6, 1.1 Hz, 1H), 7.08 (m, 2H), 7.25 (d, J = 7.6 Hz, 1H), 7.30 (d, J = 7.9 Hz, 2H), 7.77 (d, J = 7.9 Hz, 2H), 8.28 (br s, 2H), 8.93 (br s, 1H) |
| N-(2-Aminophenyl)-4-[3-(3-chloro-4-fluorophenyl)-1-[3-(morpholin-4-yl)propyl]ureidomethyl]benzamide (Compound No. 1-138)<br />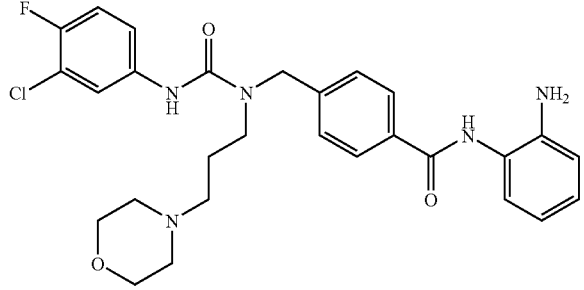 | $^1$H-NMR (400 MHz, CDCl$_3$) δ 1.76 (m, 2H), 2.41-2.49 (m, 6H), 3.38 (t, J = 5.6 Hz, 2H), 3.68 (t, J = 4.5 Hz, 4H), 3.86 (br s, 2H), 4.62 (s, 2H), 6.83-6.89 (m, 2H), 7.06-7.13 (m, 2H), 7.27 (m, 1H), 7.34 (d, J = 7.6 Hz, 1H), 7.44 (d, J = 8.2 Hz, 2H), 7.63 (dd, J = 6.6, 2.7 Hz, 1H), 7.83 (br s, 1H), 7.87 (d, J = 8.2 Hz, 2H), 9.02 (br s, 1H) |
| N-(2-Aminophenyl)-4-[3-(4-fluoro-3-trifluoromethylphenyl)-1-[3-(morpholin-4-yl)propyl]ureidomethyl]benzamide (Compound No. 1-139)<br />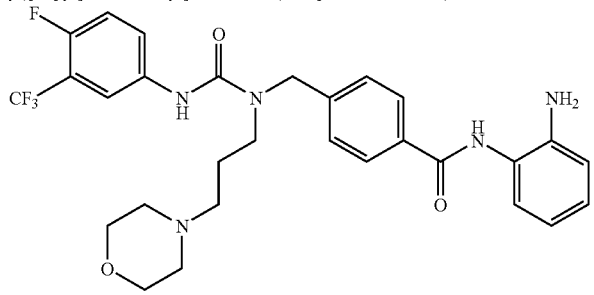 | $^1$H-NMR (500 MHz, CDCl$_3$) δ 1.77 (m, 2H), 2.43-2.50 (m, 6H), 3.39 (t, J = 5.7 Hz, 2H), 3.67 (t, J = 4.6 Hz, 4H), 3.86 (br s, 2H), 4.63 (s, 2H), 6.84-6.88 (m, 2H), 7.10 (td, J = 7.6, 1.5 Hz, 1H), 7.15 (t, J = 9.3 Hz, 1H), 7.34 (d, J = 7.6 Hz, 1H), 7.44 (d, J = 8.1 Hz, 2H), 7.65-7.71 (m, 2H), 7.83 (br s, 1H), 7.87 (d, J = 8.1 Hz, 2H), 9.14 (br s, 1H) |

| | |
|---|---|
| N-(2-Aminophenyl)-4-[3-(3-fluoro-5-trifluoromethyl-phenyl)-1-[3-(morpholin-4-yl)propyl]ureidomethyl]-benzamide (Compound No. 1-140)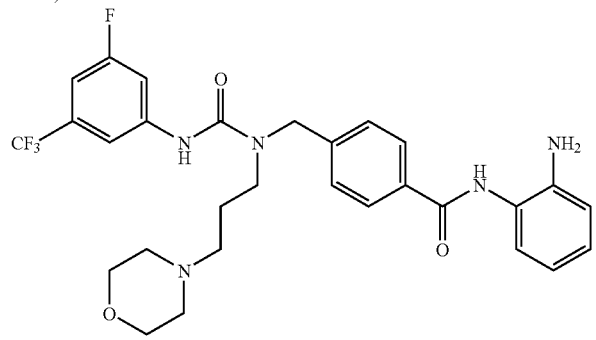 | $^1$H-NMR (400 MHz, CDCl$_3$) δ 1.78 (m, 2H), 2.45-2.52 (m, 6H), 3.39 (t, J = 5.6 Hz, 2H), 3.74 (t, J = 4.6 Hz, 4H), 3.85 (br s, 2H), 4.64 (s, 2H), 6.86 (t, J = 7.8 Hz, 1H), 6.86 (dd, J = 7.8, 1.4 Hz, 1H), 7.01 (d, J = 9.0 Hz, 1H), 7.10 (td, J = 7.8, 1.4 Hz, 1H), 7.35 (d, J = 7.8 Hz, 1H), 7.44 (m, 1H), 7.44 (d, J = 8.2 Hz, 2H), 7.72 (dt, J = 10.7, 2.2 Hz, 1H), 7.82 (br s, 1H), 7.88 (d, J = 8.2 Hz, 2H), 9.18 (br s, 1H) |
| N-(2-Aminophenyl)-4-[1-(2-dimethylaminoethyl)-3-(4-fluorophenyl)ureidomethyl]-benzamide (Compound No. 1-141)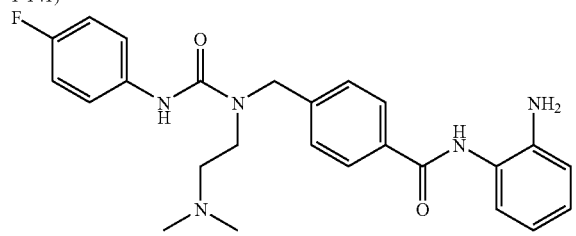 | $^1$H-NMR (500 MHz, CDCl$_3$) δ 2.38 (s, 6H), 2.49 (t, J = 4.1 Hz, 2H), 3.33 (t, J = 4.1 Hz, 2H), 3.87 (s, 2H), 4.64 (s, 2H), 6.83-6.86 (m, 2H), 6.98 (t, J = 8.8 Hz, 2H), 7.10 (td, J = 7.7, 1.3 Hz, 1H), 7.31 (dd, J = 8.8, 4.7 Hz, 2H), 7.34 (d, J = 7.7 Hz, 1H), 7.45 (d, J = 7.9 Hz, 2H), 7.87 (m, 1H), 7.88 (d, J = 7.9 Hz, 2H), 10.99 (s, 1H) |
| N-(2-Aminophenyl)-4-[1-(2-dimethylaminoethyl)-3-(3-fluoro-4-methylphenyl)ureido-methyl]benzamide (Compound No. 1-142)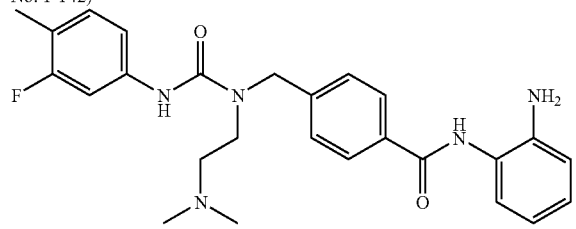 | $^1$H-NMR (500 MHz, CDCl$_3$) δ 2.21 (d, J = 1.2 Hz, 3H), 2.38 (s, 6H), 2.48 (t, J = 4.3 Hz, 2), 3.32 (t, J = 4.3 Hz, 2H), 3.88 (s, 2H), 4.62 (s, 2H), 6.85 (dd, J = 7.8, 1.5 Hz, 1H), 6.85 (t, J = 7.8 Hz, 1H), 6.93 (dd, J = 8.4, 2.1 Hz, 1H), 7.04 (t, J = 8.4 Hz, 1H), 7.10 (td, J = 7.8, 1.5 Hz, 1H), 7.21 (dd, J = 12.1, 2.1 Hz, 1H), 7.34 (d, J = 7.8 Hz, 1H), 7.43 (d, J = 7.9 Hz, 2H), 7.87 (d, J = 7.9 Hz, 2H), 7.91 (s, 1H), 11.10 (s, 1H) |
| N-(2-Aminophenyl)-4-[1-(2-dimethylaminoethyl)-3-(thiophen-3-yl)ureidomethyl] benzamide (Compound No. 1-143)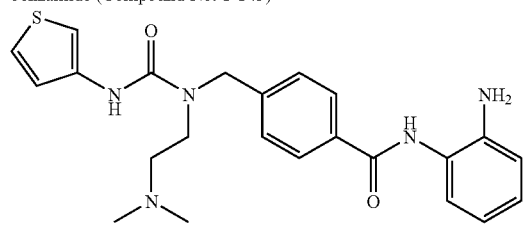 | $^1$H-NMR (500 MHz, CDCl$_3$) δ 2.37 (s, 6H), 2.48 (t, J = 4.2 Hz, 2H), 3.31 (t, J = 4.2 Hz, 2H), 3.87 (s, 2H), 4.65 (s, 2H), 6.86 (dd, J = 7.8, 1.4 Hz, 1H), 6.86 (t, J = 7.8 Hz, 1H), 6.87 (dd, J = 5.1, 1.4 Hz, 1H), 7.10 (td, J = 7.8, 1.4 Hz, 1H), 7.20 (dd, J = 5.1, 3.2, Hz, 1H), 7.30 (dd, J = 3.2, 1.4 Hz, 1H), 7.35 (d, J = 7.8 Hz, 1H), 7.44 (d, J = 8.1 Hz, 2H), 7.83 (s, 1H), 7.87 (d, J = 8.1 Hz, 2H), 11.41 (s, 1H) |

| | |
|---|---|
| N-(2-Aminophenyl)-4-[1-(2-dimethylaminoethyl)-3-(4-fluoro-3-methylphenyl)ureido-methyl]benzamide (Compound No. 1-144) 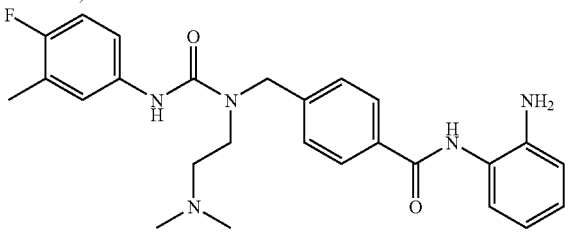 | $^1$H-NMR (500 MHz, CD$_3$OD) δ 2.24 (s, 3H), 2.38 (s, 6H), 2.57 (t, J = 5.3 Hz, 2H), 3.47 (t, J = 5.3 Hz, 2H), 4.69 (s, 2H), 6.77 (t, J = 7.5 Hz, 1H), 6.89-6.96 (m, 2H), 7.06-7.11 (m, 2H), 7.18-7.27 (m, 2H), 7.47 (d, J = 8.2 Hz, 2H), 7.98 (d, J = 8.2 Hz, 2H) |
| N-(2-Aminophenyl)-4-[3-(4-dimethylaminophenyl)-1-[3-(4-methylpiperidin-1-yl)-propyl]ureidomethyl]benz-amide (Compound No. 1-145) 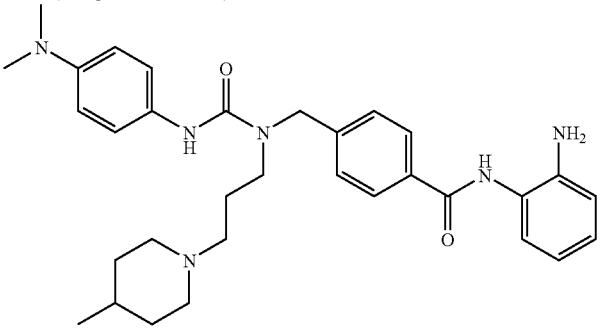 | $^1$H-NMR (400 MHz, DMSO-d$_6$) δ 0.85 (d, J = 6.6 Hz, 3H), 1.01-1.11 (m, 2H), 1.33 (m, 1H), 1.52 (d, J = 11.8 Hz, 2H), 1.67 (t, J = 6.5 Hz, 2H), 1.81 (m, 2H), 2.27 (m, 2H), 2.78 (d, J = 11.8 Hz, 2H), 2.83 (s, 6H), 3.29 (m, 2H), 4.59 (s, 2H), 4.89 (s, 2H), 6.59 (td, J = 7.8, 1.4 Hz, 1H), 6.67 (d, J = 9.0 Hz, 2H), 6.78 (dd, J = 7.8, 1.4 Hz, 1H), 6.97 (td, J = 7.8, 1.4 Hz, 1H), 7.16 (d, J = 7.8 Hz, 1H), 7.23 (d, J = 9.0 Hz, 2H), 7.39 (d, J = 8.1 Hz, 2H), 7.95 (d, J = 8.1 Hz, 2H), 8.55 (s, 1H), 9.63 (s, 1H) |
| N-(2-Aminophenyl)-4-[3-(3,4-difluorophenyl)-1-[3-(4-methylpiperidin-1-yl)-propyl]ureidomethyl]benzamide (Compound No. 1-146) 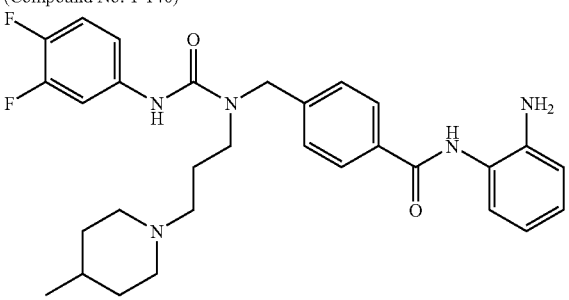 | $^1$H-NMR (500 MHz, DMSO-d$_6$) δ 0.86 (d, J = 6.4 Hz, 3H), 1.08 (m, 2H), 1.29 (m, 1H), 1.54 (d, J = 11.3 Hz, 2H), 1.68 (m, 2H), 1.80 (t, J = 11.3 Hz, 2H), 2.25 (t, J = 6.6 Hz, 2H), 2.77 (d, J = 11.3 Hz, 2), 3.31 (m, 2H), 4.63 (s, 2H), 4.88 (s, 2H), 6.60 (td, J = 7.6, 1.2 Hz, 1H), 6.78 (dd, J = 7.6, 1.2 Hz, 1H), 6.97 (td, J = 7.6, 1.2 Hz, 1H), 7.16 (d, J = 7.6 Hz, 1H), 7.25 (m, 1H), 7.32 (m, 1H), 7.39 (d, J = 8.0 Hz, 2H), 7.66 (m, 1H), 7.96 (d, J = 8.0 Hz, 2H), 8.91 (s, 1H), 9.63 (s, 1H |
| N-(2-Aminophenyl)-4-[3-(3-fluorobenzyl)-1-[3-(mor-pholin-4-yl)propyl]uriedo-methyl]benzamide (Compound No. 1-147) 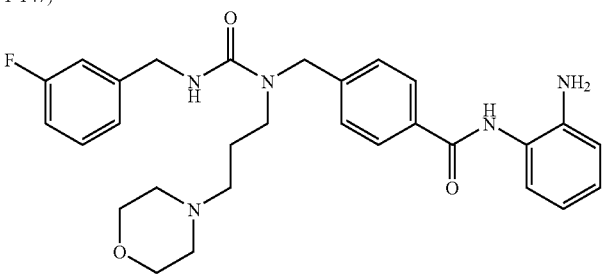 | $^1$H-NMR (400 MHz, CDCl$_3$) δ 1.63 (m, 2H), 2.27 (br s, 4H), 2.32 (t, J = 6.0 Hz, 2H), 3.28 (t, J = 5.6 Hz, 2H), 3.44 (br s, 4H), 3.53 (br s, 2H), 4.42 (d, J = 5.6 Hz, 2H), 4.55 (s, 2H), 6.75-6.83 (m, 2H), 6.92 (td, J = 8.2, 2.0 Hz, 1H), 6.98-7.09 (m, 3H), 7.22-7.29 (m, 2H), 7.31 (d, J = 8.2 Hz, 2H), 7.60 (br s, 1H), 7.83 (d, J = 8.2 Hz, 2H), 8.42 (br s, 1H) |

| | |
|---|---|
| N-(2-Aminophenyl)-4-[3-(2-fluorophenethyl)-1-[3-(morpholin-4-yl)propyl]ureidomethyl]benzamide (Compound No. 1-148)<br>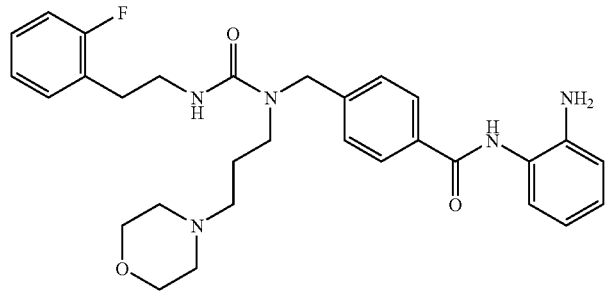 | ¹H-NMR (400 MHz, CDCl₃) δ 1.56 (m, 2H), 2.21-2.33 (m, 6H), 2.86 (t, J = 6.6 Hz, 2H), 3.12 (t, J = 5.6 Hz, 2H), 3.44 (q, J = 6.6 Hz, 2H), 3.54 (br s, 4H), 3.62 (br s, 2H), 4.50 (s, 2H), 6.77-6.83 (m, 2H), 6.98-7.09 (m, 3H), 7.14-7.22 (m, 3H), 7.26 (d, J = 8.2 Hz, 2H), 7.30 (d, J = 7.8 Hz, 1H), 7.85 (d, J = 8.2 Hz, 2H), 8.46 (br s, 1H) |
| N-(2-Aminophenyl)-4-[3-(2-fluorobenzyl)-1-[3-(morpholin-4-yl)propyl]ureidomethyl]benzamide (Compound No. 1-149)<br>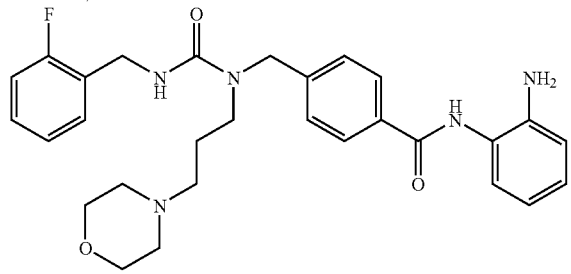 | ¹H-NMR (400 MHz, CDCl₃) δ 1.62 (m, 2H), 2.25-2.39 (m, 6H), 3.25 (t, J = 5.7 Hz, 2H), 3.54 (br s, 4H), 3.62 (br s, 2H), 4.49 (d, J = 5.4 Hz, 2H), 4.55 (s, 2H), 6.77-6.83 (m, 2H), 6.99-7.12 (m, 3H), 7.23 (m, 1H), 7.30 (m, 1H), 7.31 (d, J = 8.1 Hz, 2H), 7.39 (t, J = 7.6 Hz, 1H), 7.49 (br s, 1H), 7.82 (d, J = 8.1 Hz, 2H), 8.24 (br s, 1H) |
| N-(2-Aminophenyl)-4-[3-(3-fluorophenyl)-1-[3-(4-methylpiperidin-1-yl)propyl]-ureidomethyl]benzamide (Compound No. 1-150)<br>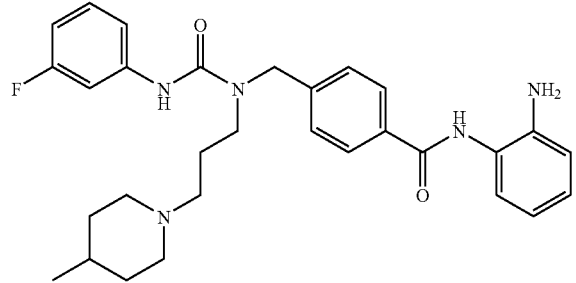 | ¹H-NMR (400 MHz, DMSO-d₆) δ 0.87 (d, J = 6.3 Hz, 3H), 1.06-1.15 (m, 2H), 1.28 (m, 1H), 1.54 (d, J = 11.2 Hz, 2H), 1.69 (m, 2H), 1.81 (t, J = 11.2 Hz, 2H), 2.26 (t, J = 6.6 Hz, 2H), 2.78 (d, J = 11.2 Hz, 2H), 3.33 (m, 2H), 4.64 (s, 2H), 4.88 (s, 2H), 6.60 (t, J = 7.6 Hz, 1H), 6.74-6.79 (m, 2H), 6.97 (m, 1H), 7.16 (d, J = 7.6 Hz, 1H), 7.24-7.31 (m, 2H), 7.39 (d, J = 8.2 Hz, 2H), 7.48 (m, 1H), 7.96 (d, J = 8.2 Hz, 2H), 8.90 (s, 1H), 9.63 (s, 1H) |
| N-(2-Aminophenyl)-4-[3-(4-fluoro-3-nitrophenyl)-1-[3-(4-methylpiperidin-1-yl)-propyl]ureidomethyl]benzamide (Compound No. 1-151)<br>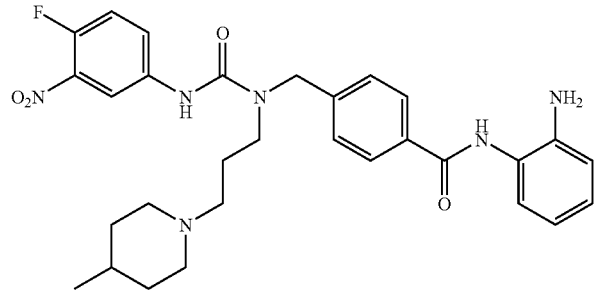 | ¹H-NMR (400 MHz, DMSO-d₆) δ 0.87 (d, J = 6.6 Hz, 3H), 1.07-1.12 (m, 2H), 1.29 (m, 1H), 1.54 (d, J = 10.7 Hz, 2H), 1.70 (m, 2H), 1.81 (t, J = 10.7 Hz, 2H), 2.26 (t, J = 6.5 Hz, 2H), 2.77 (d, J = 10.7 Hz, 2H), 3.35 (m, 2H), 4.66 (s, 2H), 4.88 (s, 2H), 6.59 (td, J = 7.5, 1.2 Hz, 1H), 6.78 (dd, J = 7.5, 1.2 Hz, 1H), 6.97 (td, J = 7.5, 1.2 Hz, 1H), 7.16 (d, J = 7.5 Hz, 1H), 7.40 (d, J = 8.3 Hz, 2H), 7.50 (dd, J = 11.0, 9.2 Hz, 1H), 7.92 (m, 1H), 7.96 (d, J = 8.3 Hz, 2H), 8.39 (dd, J = 6.8, 2.9 Hz, 1H), 9.14 (s, 1H), 9.63 (s, 1H) |

| | |
|---|---|
| N-(2-Aminophenyl)-4-[3-(3-ethoxyphenyl)-1-[3-(4-methylpiperidin-1-yl)propyl]-ureidomethyl]benzamide (Compound No. 1-152) 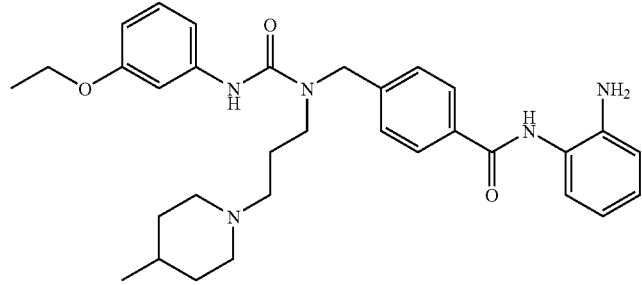 | ¹H-NMR (400 MHz, DMSO-d₆) δ 0.87 (d, J = 6.3 Hz, 3H), 1.07-1.15 (m, 2H), 1.28 (m, 1H), 1.31 (t, J = 7.0 Hz, 3H), 1.54 (d, J = 11.0 Hz, 2H), 1.68 (m, 2H), 1.81 (t, J = 11.0 Hz, 2H), 2.26 (t, J = 6.2 Hz, 2H), 2.79 (d, J = 11.0 Hz, 2H), 3.32 (m, 2H), 3.98 (q, J = 7.0 Hz, 2H), 4.63 (s, 2H), 4.88 (s, 2H), 6.53 (dd, J = 8.1, 1.2 Hz, 1H), 6.60 (t, J = 7.5 Hz, 1H), 6.78 (dd, J = 8.1, 1.2 Hz, 1H), 6.97 (t, J = 7.5 Hz, 1H), 7.05 (d, J = 8.1 Hz, 1H), 7.13 (t, J = 8.1 Hz, 1H), 7.16-7.17 (m, 2H), 7.39 (d, J = 8.1 Hz, 2H), 7.96 (d, J = 8.1 Hz, 2H), 8.69 (s, 1H), 9.63 (s, 1H) |
| N-(2-Aminophenyl)-4-[3-(4-fluorobenzyl)-1-[3-(morpholin-4-yl)propyl]ureidomethyl]benzamide (Compound No. 1-153) 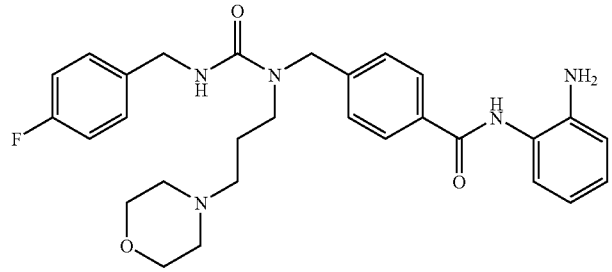 | ¹H-NMR (500 MHz, CDCl₃) δ 1.64 (m, 2H), 2.27 (br s, 4H), 2.33 (t, J = 6.0 Hz, 2H), 3.29 (t, J = 5.8 Hz, 2H), 3.46 (br s, 4H), 3.89 (br s, 2H), 4.45 (d, J = 5.8 Hz, 2H), 4.61 (s, 2H), 6.83-6.88 (m, 2H), 7.01 (t, J = 8.6 Hz, 2H), 7.10 (td, J = 7.7, 1.4 Hz, 1H), 7.30 (dd, J = 8.6, 5.5 Hz, 2H), 7.34 (d, J = 7.7 Hz, 1H), 7.41 (d, J = 7.9 Hz, 2H), 7.51 (br s, 1H), 7.86 (d, J = 7.9 Hz, 2H), 7.90 (br s, 1H) |
| N-(2-Aminophenyl)-4-[3-(4-fluorophenethyl)-1-[3-(morpholin-4-yl)propyl]ureidomethyl]benzamide (Compound No. 1-154) 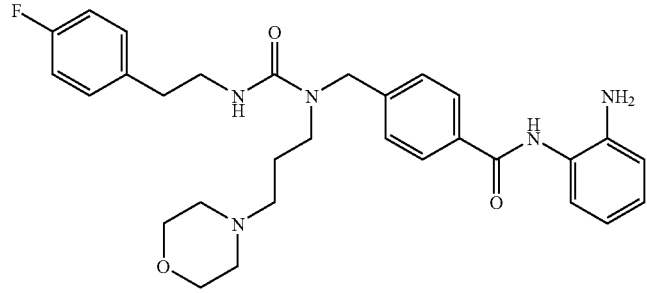 | ¹H-NMR (500 MHz, CDCl₃) δ 1.59 (m, 2H), 2.26-2.35 (m, 6H), 2.81 (t, J = 6.7 Hz, 2H), 3.15 (t, J = 5.8 Hz, 2H), 3.43 (q, J = 6.7 Hz, 2H), 3.57 (br s, 4H), 3.83 (br s, 2H), 4.53 (s, 2H), 6.82-6.86 (m, 2H), 6.96 (m, 1H), 6.98 (t, J = 8.6 Hz, 2H), 7.09 (td, J = 7.7, 1.3 Hz, 1H), 7.14 (dd, J = 8.6, 5.5 Hz, 2H), 7.32 (d, J = 8.1 Hz, 2H), 7.32 (m, 1H), 7.86 (d, J = 8.1 Hz, 2H), 8.08 (br s, 1H) |
| N-(2-Aminophenyl)-4-[3-(3-chlorophenyl)-1-(3-dimethylaminopropyl)ureidomethyl]benzamide (Compound No. 1-155) 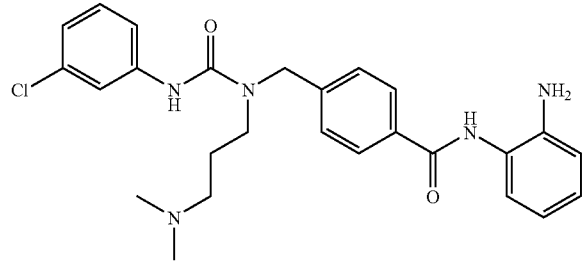 | ¹H-NMR (400 MHz, CDCl₃) δ 1.70 (m, 2H), 2.31 (s, 6H), 2.38 (t, J = 5.9 Hz, 2H), 3.38 (t, J = 5.7 Hz, 2H), 3.87 (s, 2H), 4.61 (s, 2H), 6.85 (t, J = 7.8 Hz, 1H), 6.85 (dd, J = 7.8, 1.5 Hz, 1H), 6.94 (ddd, J = 7.9, 2.1, 1.1 Hz, 1H), 7.10 (td, J = 7.8, 1.5 Hz, 1H), 7.18 (t, J = 7.9 Hz, 1H), 7.28 (ddd, J = 7.9, 2.1, 1.1 Hz, 1H), 7.34 (d, J = 7.8 Hz, 2H), 7.45 (d, J = 8.2 Hz, 2H), 7.58 (t, J = 2.1 Hz, 1H), 7.85 (m, 1H), 7.86 (d, J = 8.2 Hz, 2H), 10.32 (s, 1H) |

| | |
|---|---|
| N-(2-Aminophenyl)-4-[3-(3-chlorophenyl)-1-(2-dimethylaminoethyl)ureidomethyl]benzamide (Compound No. 1-156) 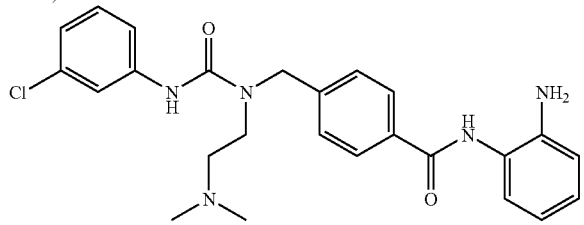 | $^1$H-NMR (400 MHz, CDCl$_3$) δ 2.39 (s, 6H), 2.49 (t, J = 4.3 Hz, 2H), 3.33 (t, J = 4.3 Hz, 2H), 3.89 (s, 2H), 4.62 (s, 2H), 6.83-6.86 (m, 2H), 6.95 (m, 1H), 7.10 (td, J = 7.6, 1.4 Hz, 1H), 7.16-7.20 (m, 2H), 7.34 (d, J = 8.5 Hz, 1H), 7.42 (d, J = 8.2 Hz, 2H), 7.48 (m, 1H), 7.87 (d, J = 8.2 Hz, 2H), 7.94 (s, 1H), 11.25 (s, 1H) |
| N-(2-Aminophenyl)-4-[3-(3-fluorophenyl)-1-[2-(4-methylpiperazin-1-yl)ethyl]ureidomethyl]benzamide (Compound No. 1-157) 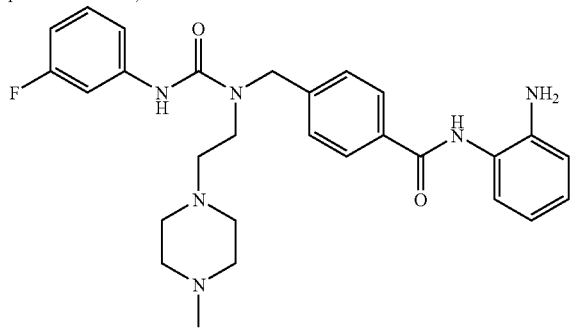 | $^1$H-NMR (500 MHz, CDCl$_3$) δ 2.14 (s, 3H), 2.32 (br s, 4H), 2.46-2.52 (m, 6H), 3.42 (t, J = 5.7 Hz, 2H), 4.66 (s, 2H), 4.88 (s, 2H), 6.60 (t, J = 7.6 Hz, 1H), 6.74-6.79 (m, 2H), 6.97 (td, J = 7.6, 1.5 Hz, 1H), 7.16 (d, J = 7.6 Hz, 1H), 7.23-7.30 (m, 2H), 7.40 (d, J = 8.0 Hz, 2H), 7.46 (dt, J = 12.2, 2.1 Hz, 1H), 7.96 (d, J = 8.0 Hz, 2H), 9.30 (s, 1H), 9.63 (s, 1H) |
| N-(2-Aminophenyl)-4-[3-(4-fluoro-3-methylphenyl)-1-[2-(4-methylpiperazin-1-yl)ethyl]ureidomethyl]benzamide (Compound No. 1-158) 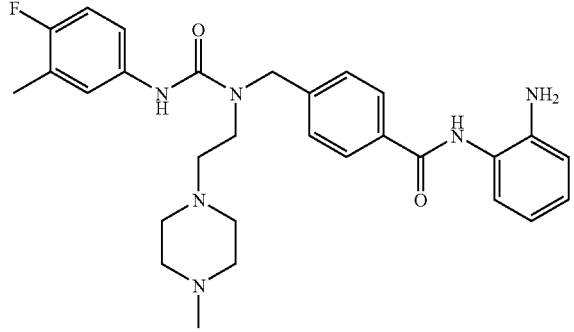 | $^1$H-NMR (500 MHz, CDCl$_3$) δ 2.14 (s, 3H), 2.20 (d, J = 1.5 Hz, 3H), 2.32 (br s, 4H), 2.46-2.52 (m, 6H), 3.40 (t, J = 5.7 Hz, 2H), 4.64 (s, 2H), 4.89 (s, 2H), 6.60 (t, J = 7.6 Hz, 1H), 6.78 (dd, J = 7.6, 1.5 Hz, 1H), 6.97 (td, J = 7.6, 1.5 Hz, 1H), 7.03 (t, J = 9.2 Hz, 1H), 7.16 (d, J = 7.6 Hz, 1H), 7.28 (m, 1H), 7.35 (dd, J = 6.9, 2.6 Hz, 1H), 7.40 (d, J = 7.9 Hz, 2H), 7.96 (d, J = 7.9 Hz, 2H), 9.12 (s, 1H), 9.63 (s, 1H) |

| | |
|---|---|
| N-(2-Aminophenyl)-4-[3-(4-fluoro-3-nitrophenyl)-1-[2-(4-methylpiperazin-1-yl)-ethyl]ureidomethyl]benzamide (Compound No. 1-159) 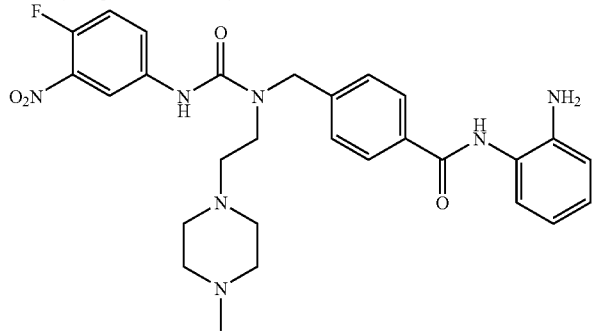 | $^1$H-NMR (400 MHz, DMSO-d$_6$) δ 2.14 (s, 3H), 2.31 (br s, 4H), 2.46-2.51 (m, 6H), 3.44 (t, J = 5.9 Hz, 2H), 4.68 (s, 2H), 4.89 (s, 2H), 6.60 (td, J = 7.6, 1.2 Hz, 1H), 6.78 (dd, J = 7.6, 1.2 Hz, 1H), 6.97 (td, J = 7.6, 1.2 Hz, 1H), 7.16 (d, J = 7.6 Hz, 1H), 7.41 (d, J = 8.3 Hz, 2H), 7.51 (dd, J = 11.2, 9.3 Hz, 1H), 7.89 (m, 1H), 7.96 (d, J = 8.3 Hz, 2H), 8.36 (dd, J = 6.8, 2.9 Hz, 1H), 9.53 (s, 1H), 9.64 (s, 1H) |
| N-(2-Aminophenyl)-4-[1-(3-(morpholin-4-yl)propyl]-3-(thiazol-2-yl)ureido-methyl]benzamide (Compound No. 1-160) 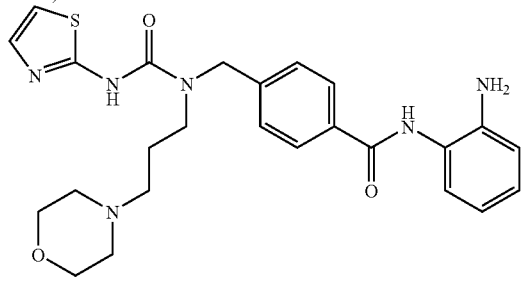 | $^1$H-NMR (500 MHz, CDCl$_3$) δ 1.74 (m, 2H), 2.43 (t, J = 6.1 Hz, 2H), 2.50 (br s, 4H), 3.39 (t, J = 5.7 Hz, 2H), 3.86 (br s, 2H), 4.03 (br s, 4H), 4.67 (s, 2H), 6.84-6.88 (m, 2H), 6.86 (d, J = 3.5 Hz, 1H), 7.10 (td, J = 7.8, 1.3 Hz, 1H), 7.35 (d, J = 7.8 Hz, 1H), 7.37 (d, J = 3.5 Hz, 1H), 7.44 (d, J = 7.9 Hz, 2H), 7.81 (br s, 1H), 7.87 (d, J = 7.9 Hz, 2H), 11.61 (br s, 1H) |
| N-(2-Aminophenyl)-4-[1-(3-(morpholin-4-yl)propyl]-3-(quinolin-6-yl)ureido-methyl]benzamide (Compound No. 1-161) 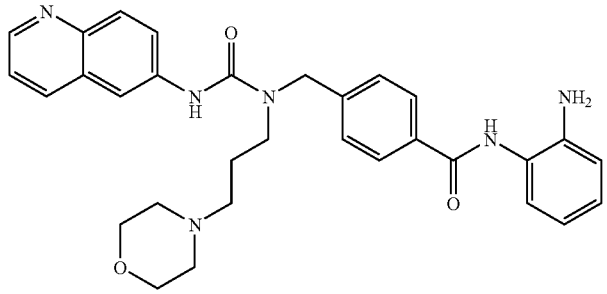 | $^1$H-NMR (400 MHz, CDCl$_3$) δ 1.81 (m, 2H), 2.45-2.54 (m, 6H), 3.46 (t, J = 5.7 Hz, 2H), 3.74 (t, J = 4.8 Hz, 4H), 3.87 (br s, 2H), 4.69 (s, 2H), 6.86 (t, J = 7.9 Hz, 1H), 6.86 (dd, J = 7.9, 1.4 Hz, 1H), 7.10 (td, J = 7.9, 1.4 Hz, 1H), 7.34 (d, J = 7.9 Hz, 1H), 7.37 (dd, J = 8.4, 4.2 Hz, 1H), 7.48 (d, J = 8.2 Hz, 2H), 7.68 (dd, J = 9.0, 2.4 Hz, 1H), 7.85 (br s, 1H), 7.88 (d, J = 8.2 Hz, 2H), 8.05 (d, J = 9.0 Hz, 1H), 8.10 (dd, J = 8.4, 1.6 Hz, 1H), 8.19 (d, J = 2.4 Hz, 1H), 8.82 (dd, J = 4.2, 1.6 Hz, 1H), 9.07 (br s, 1H) |

| | |
|---|---|
| N-(2-Aminophenyl)-4-[3-(3-methylisoxazol-5-yl)-1-[3-(morpholin-4-yl)propyl]-ureidomethyl]benzamide (Compound No. 1-162)<br>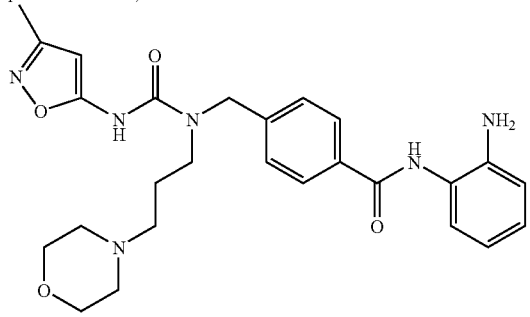 | $^1$H-NMR (400 MHz, CDCl$_3$) δ 1.73 (m, 2H), 2.37 (d, J = 0.9 Hz, 3H), 2.43 (t, J = 6.0 Hz, 2H), 2.49 (br s, 4H), 3.37 (t, J = 5.6 Hz, 2H), 3.87 (br s, 2H), 3.95 (t, J = 4.4 Hz, 4H), 4.62 (s, 2H), 6.60 (d, J = 0.9 Hz, 1H), 6.86 (t, J = 7.7 Hz, 1H), 6.86 (dd, J = 7.7, 1.4 Hz, 1H), 7.11 (td, J = 7.7, 1.4 Hz, 1H), 7.34 (d, J = 7.7 Hz, 1H), 7.43 (d, J = 8.1 Hz, 2H), 7.82 (s, 1H), 7.87 (d, J = 8.1 Hz, 2H), 10.46 (br s, 1H) |
| N-(2-Aminophenyl)-4-[3-(benzimidazol-2-yl)-1-[3-(morpholin-4-yl)propyl]ureidomethyl]benzamide (Compound No. 1-163)<br>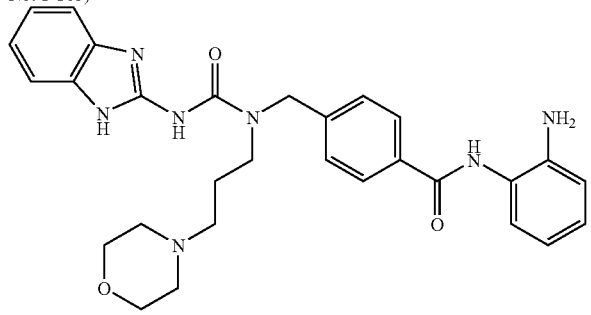 | $^1$H-NMR (400 MHz, CDCl$_3$) δ 1.80 (m, 2H), 2.45 (t, J = 6.1 Hz, 2H), 2.51 (br s, 4H), 3.45 (t, J = 5.6 Hz, 2H), 3.88 (br s, 2H), 4.08 (br s, 4H), 4.66 (s, 2H), 6.86 (dd, J = 7.7, 1.4 Hz, 1H), 6.86 (t, J = 7.7, 1.4 Hz, 1H), 6.86 (t, J = 7.7 Hz, 1H), 7.10 (td, J = 7.7, 1.4 Hz, 1H), 7.13-7.20 (m, 2H), 7.28-7.57 (m, 3H), 7.35 (d, J = 7.7 Hz, 1H), 7.41 (d, J = 7.6 Hz, 2H), 7.88 (d, J = 7.6 Hz, 2H), 7.88 (s, 1H), 10.98 (br s, 1H) |
| N-(2-Aminophenyl)-4-[3-[4-(morpholin-4-yl)phenyl]-1-[3-(morpholin-4-yl)propyl]ureidomethyl]benzamide (Compound No. 1-164)<br>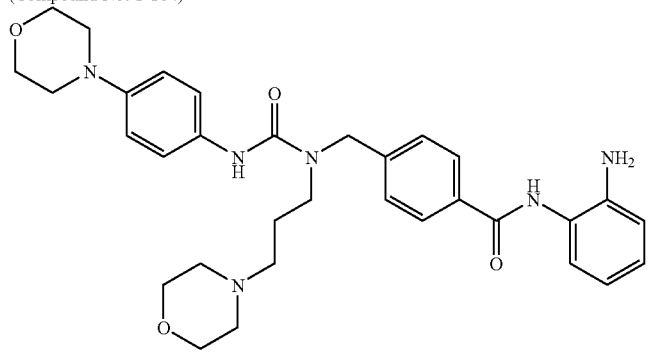 | $^1$H-NMR (500 MHz, CDCl$_3$) δ 1.73 (m, 2H), 2.43 (br s, 4H), 2.46 (t, J = 6.1 Hz, 2H), 3.11 (t, J = 4.8 Hz, 4H), 3.37 (t, J = 5.7 Hz, 2H), 3.64 (t, J = 4.4 Hz, 4H), 3.86 (t, J = 4.8 Hz, 4H), 3.89 (br s, 2H), 4.63 (s, 2H), 6.85 (dd, J = 7.6, 1.2 Hz, 1H), 6.85 (t, J = 7.6 Hz, 1H), 6.89 (d, J = 8.9 Hz, 2H), 7.10 (td, J = 7.6, 1.2 Hz, 1H), 7.32 (d, J = 8.9 Hz, 2H), 7.33 (m, 1H), 7.45 (d, J = 8.1 Hz, 2H), 7.85 (br s, 1H), 7.85 (d, J = 8.1 Hz, 2H), 8.80 (br s, 1H) |

| | |
|---|---|
| N-(2-Aminophenyl)-4-[1-(3-(morpholin-4-yl)propyl]-3-(5-nitrothiazol-2-yl)ureidomethyl]benzamide (Compound No. 1-165)<br>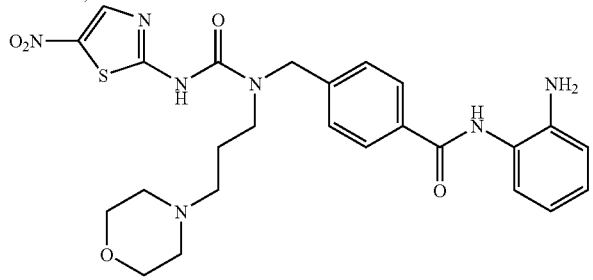 | $^1$H-NMR (400 MHz, CDCl$_3$) δ 1.79 (m, 2H), 2.46 (t, J = 6.0 Hz, 2H), 2.53 (br s, 4H), 3.39 (t, J = 5.5 Hz, 2H), 3.84 (br s, 2H), 4.01 (br s, 4H), 4.66 (s, 2H), 6.84-6.90 (m, 2H), 7.11 (td, J = 7.6, 1.4 Hz, 1H), 7.27 (br s, 1H), 7.36 (d, J = 7.6 Hz, 1H), 7.45 (d, J = 8.2 Hz, 2H), 7.82 (br s, 1H), 7.90 (d, J = 8.2 Hz, 2H), 8.26 (s, 1H) |
| N-(2-Aminophenyl)-4-[1-[3-(morpholin-4-yl)propyl]-3-(4,5,6,7-tetrahydrobenzothiazol-2-yl)ureidomethyl]-benzamide (Compound No. 1-166)<br>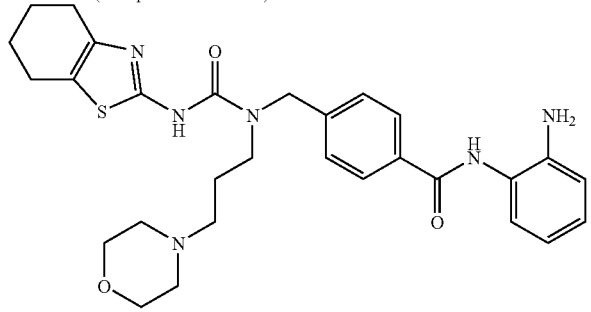 | $^1$H-NMR (400 MHz, CDCl$_3$) δ 1.72 (m, 2H), 1.79-1.88 (m, 4H), 2.41 (t, J = 6.0 Hz, 2H), 2.48 (br s, 4H), 2.56-2.69 (m, 4H), 3.36 (t, J = 5.4 Hz, 2H), 3.87 (br s, 2H), 4.00 (br s, 4H), 4.65 (s, 2H), 6.82-6.88 (m, 2H), 7.10 (td, J = 7.7, 1.4 Hz, 1H), 7.34 (d, J = 7.7 Hz, 1H), 7.42 (d, J = 8.1 Hz, 2H), 7.83 (br s, 1H), 7.86 (d, J = 8.1 Hz, 2H), 11.26 (br s, 1H) |
| N-(2-Aminophenyl)-4-[3-(4-dimethylaminophenyl)-1-[3-(pyrrolidin-1-yl)propyl]-ureidomethyl]benzamide (Compound No. 1-167)<br>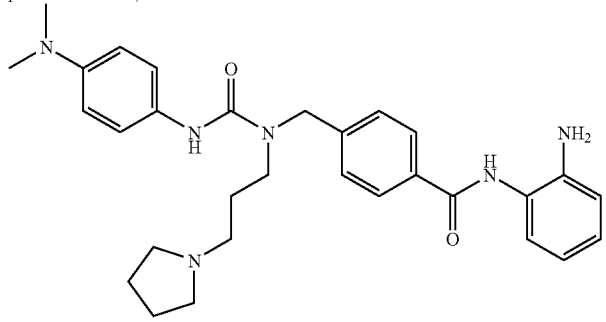 | $^1$H-NMR (500 MHz, DMSO-d$_6$) δ 1.67 (m, 2H), 1.71 (m, 4H), 2.40-2.47 (m, 6H), 2.82 (s, 6H), 3.32 (m, 2H), 4.57 (s, 2H), 4.88 (s, 2H), 6.59 (t, J = 7.6 Hz, 1H), 6.67 (d, J = 9.2 Hz, 2H), 6.78 (dd, J = 7.6, 1.5 Hz, 1H), 6.97 (td, J = 7.6, 1.5 Hz, 1H), 7.16 (d, J = 7.6 Hz, 1H), 7.22 (d, J = 9.2 Hz, 2H), 7.40 (d, J = 8.2 Hz, 2H), 7.95 (d, J = 8.2 Hz, 2H), 8.99 (s, 1H), 9.62 (s, 1H) |
| N-(2-Aminophenyl)-4-[3-(3,4-difluorophenyl)-1-[3-(pyrrolidin-1-yl)propyl]ureidomethyl]benzamide (Compound No. 1-168)<br>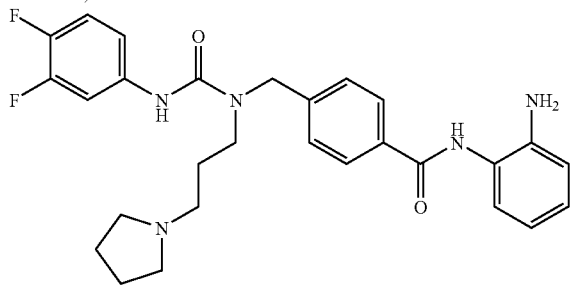 | $^1$H-NMR (500 MHz, DMSO-d$_6$) δ 1.69 (t, J = 6.4 Hz, 2H), 1.71-1.74 (m, 4H), 2.40 (t, J = 6.4 Hz, 2H), 2.44 (m, 4H), 3.36 (t, J = 5.5 Hz, 2H), 4.60 (s, 2H), 4.88 (s, 2H), 6.59 (t, J = 7.6 Hz, 1H), 6.78 (d, J = 7.6 Hz, 1H), 6.97 (td, J = 7.6, 1.5 Hz, 1H), 7.13 (m, 1H), 7.16 (d, J = 7.6, Hz, 1H), 7.34 (m, 1H), 7.40 (d, J = 8.0 Hz, 2H), 7.66 (ddd, J = 13.7, 7.5, 2.6 Hz, 1H), 7.95 (d, J = 8.0 Hz, 2H), 9.46 (s, 1H), 9.63 (s, 1H) |

| | |
|---|---|
| N-(2-Aminophenyl)-4-[3-(2,3-dihydrobenzo[1,4]dioxin-6-yl)-1-[3-(pyrrolidin-1-yl)propyl]ureidomethyl]benzamide (Compound No. 1-169)<br>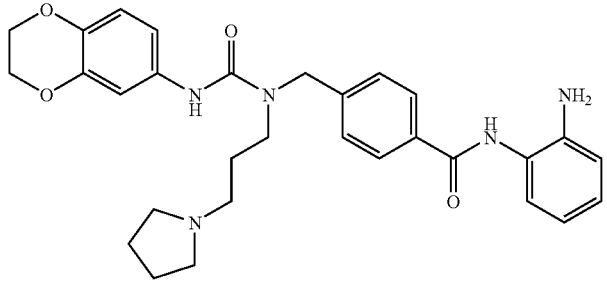 | $^1$H-NMR (500 MHz, DMSO-d$_6$) δ 1.68 (m, 2H), 1.72 (m, 4H), 2.41 (t, J = 6.3 Hz, 2H), 2.44 (m, 4H), 3.33 (m, 2H), 4.17-4.21 (m, 4H), 4.56 (s, 2H), 4.88 (s, 2H), 6.59 (t, J = 7.6 Hz, 1H), 6.73 (d, J = 8.9 Hz, 1H), 6.78 (dd, J = 7.6, 1.5 Hz, 1H), 6.83 (dd, J = 8.9, 2.6 Hz, 1H), 6.97 (td, J = 7.6, 1.5 Hz, 1H), 7.03 (d, J = 2.6 Hz, 1H), 7.16 (d, J = 7.6 Hz, 1H), 7.39 (d, J = 8.0 Hz, 2H), 7.94 (d, J = 8.0 Hz, 2H), 9.12 (s, 1H), 9.62 (s, 1H) |
| N-(2-Aminophenyl)-4-[3-(4-dimethylaminophenyl)-1-[3-(4-hydroxypiperidin-1-yl)-propyl]ureidomethyl]benzamide (Compound No. 1-170)<br>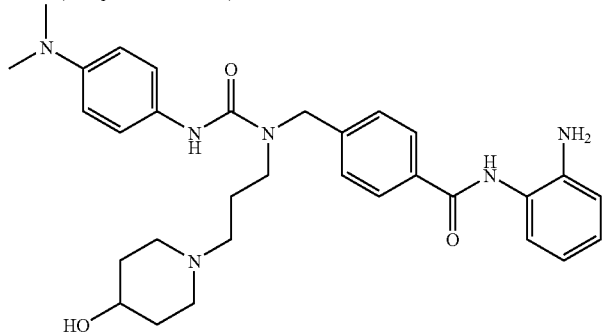 | $^1$H-NMR (400 MHz, CDCl$_3$) δ 1.50 (m, 2H), 1.63 (m, 2H), 1.71 (m, 2H), 1.79 (m, 2H), 2.44 (t, J = 5.4 Hz, 2H), 2.73 (m, 2H), 2.90 (s, 6H), 3.36 (t, J = 5.6 Hz, 2H), 3.70 (m, 1H), 3.77 (s, 2H), 4.60 (s, 2H), 6.71 (d, J = 9.0 Hz, 2H), 6.84 (dd, J = 7.6, 1.4 Hz, 1H), 6.84 (t, J = 7.6 Hz, 1H), 7.09 (td J = 7.6, 1.4 Hz, 1H), 7.23 (d, J = 9.0 Hz, 2H), 7.33 (d, J = 7.6 Hz, 1H), 7.43 (d, J = 8.2 Hz, 2H), 7.84 (d, J = 8.2 Hz, 2H), 7.97 (s, 1H), 8.87 (s, 1H) |
| N-(2-Aminophenyl)-4-[3-(3,4-difluorophenyl)-1-[3-(4-hydroxypiperidin-1-yl)-propyl]ureidomethyl]benzamide (Compound No. 1-171)<br>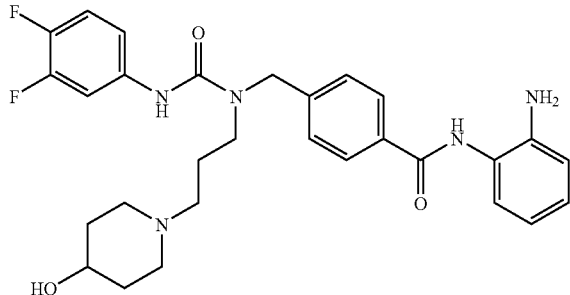 | $^1$H-NMR (400 MHz, CDCl$_3$) δ 1.45 (m, 2H), 1.74 (m, 2H), 1.84 (m, 2H), 2.27 (m, 2H), 2.46 (m, 2H), 2.72 (m, 2H), 3.37 (m, 2H), 3.77 (s, 2H), 4.28 (m, 1H), 4.60 (s, 2H), 6.85-6.87 (m, 3H), 6.99-7.11 (m, 3H), 7.34 (d, J = 8.3 Hz, 1H), 7.43 (d, J = 8.3 Hz, 2H), 7.52 (m, 1H), 7.70 (s, 1H), 7.86 (d, J = 8.3 Hz, 2H), 9.18 (s, 1H) |

-continued

| | |
|---|---|
| N-(2-Aminophenyl)-4-[3-(4-dimethylaminophenyl)-1-[3-(N-ethyl-N-methylamino)-propyl]ureidomethyl]benzamide (Compound No. 1-172)<br>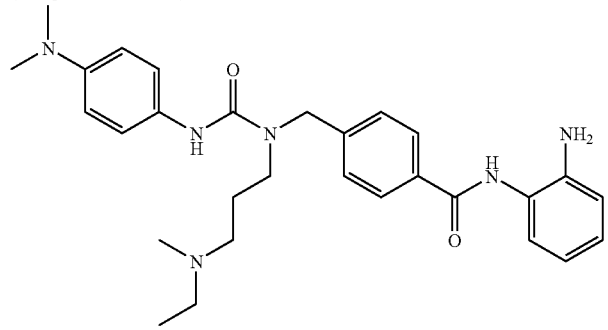 | $^1$H-NMR (400 MHz, CDCl$_3$)<br>δ 1.05 (t, J = 7.1 Hz, 3H), 1.50 (s, 9H), 1.68 (m, 2H), 2.25 (s, 3H), 2.42 (t, J = 6.0 Hz, 2H), 2.51 (q, J = 7.1 Hz, 2H), 2.89 (s, 6H), 3.36 (t, J = 5.7 Hz, 2H), 4.61 (s, 2H), 6.71 (d, J = 9.0 Hz, 2H), 6.92 (s, 1H), 7.16 (td, J = 7.7, 1.7 Hz, 1H), 7.21 (td, J = 7.7, 1.7 Hz, 1H), 7.29 (d, J = 9.0 Hz, 2H), 7.31 (m, 1H), 7.42 (d, J = 8.3 Hz, 2H), 7.74 (dd, J = 7.7, 1.7 Hz, 1H), 7.90 (d, J = 8.3 Hz, 2H), 9.12 (br s, 1H), 9.44 (br s, 1H) |

Example 2

N-(2-Aminophenyl)-4-[1-(2-dimethylaminoethyl)-3-(indan-5-yl)ureidomethyl]benzamide (Compound No. 2-1)

HATU (250 mg, 0.66 mmol) was added to a solution of 4-[1-(2-dimethylaminoethyl)-3-(indan-5yl)ureidomethyl]benzoic acid (Reference Compound No. 10-1, 250 mg, 0.66 mmol), o-phenylenediamine (140 mg, 1.3 mmol), and N,N-diisopropylethylamine (0.33 mL, 2.0 mmol) in DMF (5.0 mL), and then the mixture was stirred at room temperature for 16 hours. Ethyl acetate (100 mL) was added thereto, and then the whole was washed with brine (50 mL) three times. The organic layer was dried over anhydrous magnesium sulfate, and then the solvent was evaporated under reduced pressure. After the residue was purified by silica gel column chromatography (chloroform-methanol), the resulting solid was collected by filtration with ethyl acetate, and then it was dried under reduced pressure to give 230 mg of the title compound as a pale yellow-white solid. (Yield 74%)

| | |
|---|---|
| 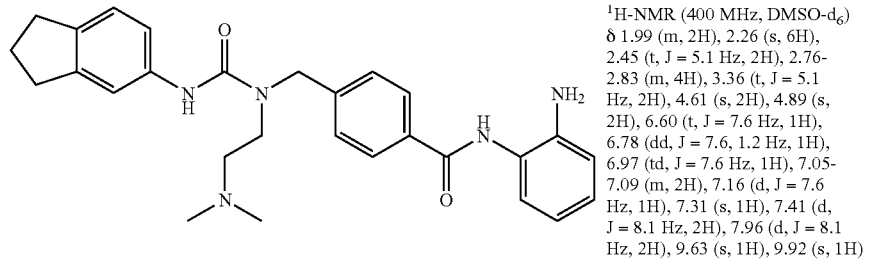 | $^1$H-NMR (400 MHz, DMSO-d$_6$)<br>δ 1.99 (m, 2H), 2.26 (s, 6H), 2.45 (t, J = 5.1 Hz, 2H), 2.76-2.83 (m, 4H), 3.36 (t, J = 5.1 Hz, 2H), 4.61 (s, 2H), 4.89 (s, 2H), 6.60 (t, J = 7.6 Hz, 1H), 6.78 (dd, J = 7.6, 1.2 Hz, 1H), 6.97 (td, J = 7.6 Hz, 1H), 7.05-7.09 (m, 2H), 7.16 (d, J = 7.6 Hz, 1H), 7.31 (s, 1H), 7.41 (d, J = 8.1 Hz, 2H), 7.96 (d, J = 8.1 Hz, 2H), 9.63 (s, 1H), 9.92 (s, 1H) |

By using any compounds selected from Reference Compounds No. 10-2 to 10-6, commercially available compounds, and known compounds, the following Compounds No. 2-2 to 2-6 were obtained by a method similar to that of Compound No. 2-1.

| | |
|---|---|
| N-(2-Aminophenyl)-4-[3-(3,4-difluorophenyl)-1-(3-dimethylaminopropyl)ureidomethyl]benzamide (Compound No. 2-2)<br>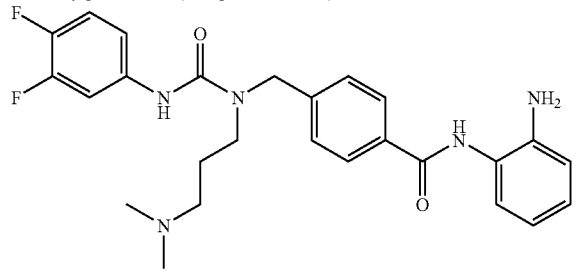 | $^1$H-NMR (400 MHz, CD$_3$OD)<br>δ 1.78 (m, 2H), 2.27 (s, 6H). 2.37 (t, J = 6.6 Hz, 2H), 3.42 (t, J = 6.3 Hz, 2H), 4.67 (s, 2H), 6.77 (dd, J = 7.6, 7.3 Hz, 1H), 6.89 (dd, J = 8.0, 1.2 Hz, 1H), 7.02-7.21 (m, 4H), 7.46 (d, J = 8.2 Hz, 2H), 7.53 (m, 1H), 7.96 (d, J = 8.2 Hz, 2H) |

| | |
|---|---|
| N-(2-Aminophenyl)-4-[1-(3-dimethylaminopropyl)-3-(2-methoxyphenyl)ureidomethyl]benzamide (Compound No. 2-3) 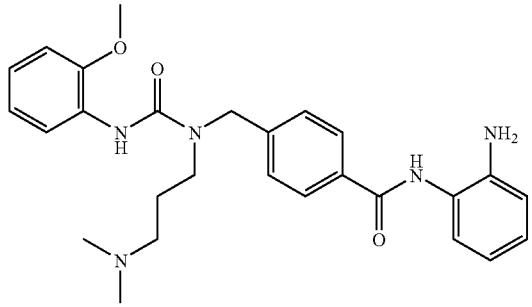 | ¹H-NMR (400 MHz, CD₃OD) δ 1.75 (m, 2H), 2.26 (s, 6H), 2.42 (t, J = 6.9 Hz, 2H), 3.49 (t, J = 6.9 Hz, 2H), 3.82 (s, 3H), 4.70 (s, 2H), 6.75 (dd, J = 7.6, 7.3 Hz, 1H), 6.87-6.91 (m, 2H), 6.95 (dd, J = 8.2, 1.3 Hz, 1H), 7.01-7.10 (m, 2H), 7.18 (m, 1H), 7.50 (d, J = 8.3 Hz, 2H), 7.76 (dd, J = 8.0, 1.5 Hz, 1H), 7.99 (d, J = 8.3 Hz, 2H) |
| N-(2-Aminophenyl)-4-[1-(3-dimethylaminopropyl)-3-ethoxycarbonylmethylureidomethyl]benzamide (Compound No. 2-4) 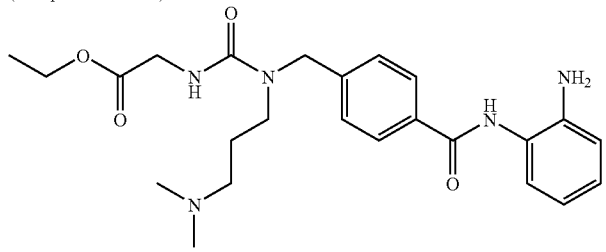 | ¹H-NMR (400 MHz, CD₃OD) δ 1.28 (t, J = 7.1 Hz, 3H), 1.75 (m, 2H), 2.31 (s, 6H), 2.43 (t, J = 6.9 Hz, 2H), 3.33 (t, J = 6.9 Hz, 2H), 3.89 (s, 2H0, 4.19 (q, J = 7.1 Hz, 2H), 4.62 (s, 2H), 6.77 (dd, J = 7.8, 7.3 Hz, 1H), 6.90 (dd, J = 7.8, 1.2 Hz, 1H), 7.08 (m, 1H), 7.18 (dd, J = 8.0, 1.2 Hz, 1H), 7.44 (d, J = 8.3 Hz, 2H), 7.95 (d, J = 8.3 Hz, 2H) |
| N-(2-Aminophenyl)-4-[3-t-butyl-1-(3-dimethylaminopropyl)ureidomethyl]benzamide (Compound No. 2-5) 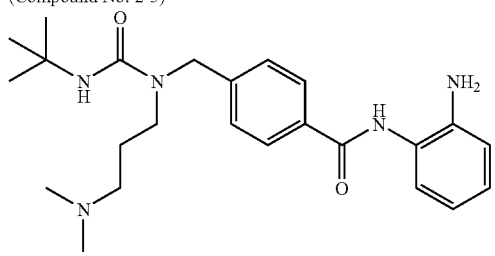 | ¹H-NMR (400 MHz, CD₃OD) δ 1.34 (s, 9H), 1.70 (m, 2H), 2.24 (s, 6H), 2.31 (t, J = 6.7 Hz, 2H), 3.29 (m, 2H), 4.55 (s, 2H), 6.75 (ddd, J = 7.8, 7.3, 1.5 Hz, 1H), 6.90 (dd, J = 7.8, 1.5 Hz, 1H), 7.07 (ddd, J = 7.8, 7.3, 1.5 Hz, 1H), 7.18 (dd, J = 7.8, 1.5 Hz, 1H), 7.39 (d, J = 8.2 Hz, 2H), 7.95 (d, J = 8.2 Hz, 2H) |
| N-(2-Aminophenyl)-4-[1-(2-hydroxyethyl)-3-(indan-5-yl)ureidomethyl]benzamide (Compound No. 2-6) 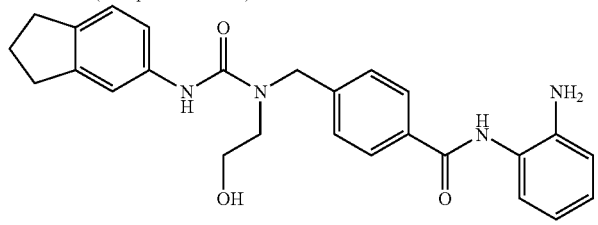 | ¹H-NMR (500 MHz, DMSO-d₆) δ 1.99 (m, 2H), 2.76-2.82 (m, 4H), 3.39 (t, J = 5.3 Hz, 2H), 3.57-3.59 (m, 2H), 4.65 (s, 2H), 4.89 (s, 2H), 5.31 (s, 1H), 6.60 (td, J = 7.5, 1.2 Hz, 1H), 6.78 (dd, J = 7.5, 1.2 Hz, 1H), 6.97 (td, J = 7.5, 1.2 Hz, 1H), 7.07 (d, J = 8.2 Hz, 1H), 7.11 (dd, J = 8.2, 2.0 Hz, 1H), 7.16 (d, J = 7.5 Hz, 1H), 7.31 (s, 1H), 7.40 (d, J = 8.2 Hz, 2H), 7.95 (d, J = 8.2 Hz, 2H), 8.62 (s, 1H), 9.62 (s, 1H) |

Example 3

N-(2-Aminophenyl)-4-[1-(3-dimethylaminopropyl)-3-(3-hydroxyphenyl)ureidomethyl]benzamide (Compound No. 3-1)

10% Palladium on carbon (100 mg) was added to a solution of N-(2-aminophenyl)-4-[3-(3-benzyloxyphenyl)-1-(3-dimethylaminopropyl)ureidomethyl]benzamide (Compound No. 1-76, 640 mg, 1.2 mmol) in a mixed solvent (ethyl acetate (10 mL), methanol (10 mL), and DMF (10 mL)), and then the reaction mixture was stirred under a hydrogen atmosphere at room temperature for 32 hours. After the insoluble was filtered off, water (100 mL) was added to the filtrate, the whole was extracted with ethyl acetate (100 mL) twice, and then the organic layer was washed with brine (100 mL) twice. The organic layer was dried over anhydrous magnesium sulfate, and then the solvent was evaporated under reduced pressure to give 480 mg of the title compound as a white amorphous product. (Yield 88%)

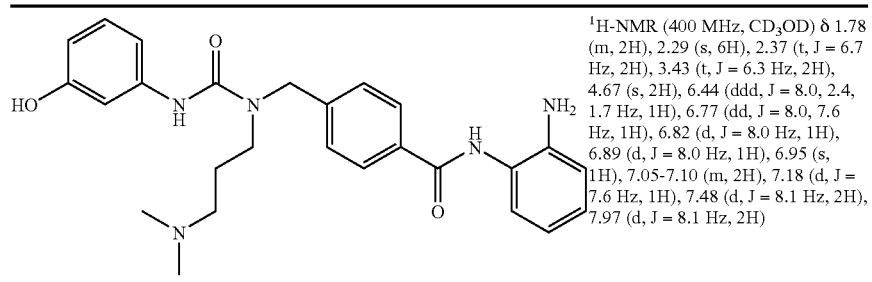

$^1$H-NMR (400 MHz, CD$_3$OD) δ 1.78 (m, 2H), 2.29 (s, 6H), 2.37 (t, J = 6.7 Hz, 2H), 3.43 (t, J = 6.3 Hz, 2H), 4.67 (s, 2H), 6.44 (ddd, J = 8.0, 2.4, 1.7 Hz, 1H), 6.77 (dd, J = 8.0, 7.6 Hz, 1H), 6.82 (d, J = 8.0 Hz, 1H), 6.89 (d, J = 8.0 Hz, 1H), 6.95 (s, 1H), 7.05-7.10 (m, 2H), 7.18 (d, J = 7.6 Hz, 1H), 7.48 (d, J = 8.1 Hz, 2H), 7.97 (d, J = 8.1 Hz, 2H)

By using any compounds selected from Compounds No. 1-81, commercially available compounds, and known compounds, the following Compounds No. 3-2 was obtained by a method similar to that of Compound No. 3-1.

N-(2-Aminophenyl)-4-[1-(3-dimethylaminopropyl)-3-(4-hydroxyphenyl)ureidomethyl]benzamide (Compound No. 3-2)

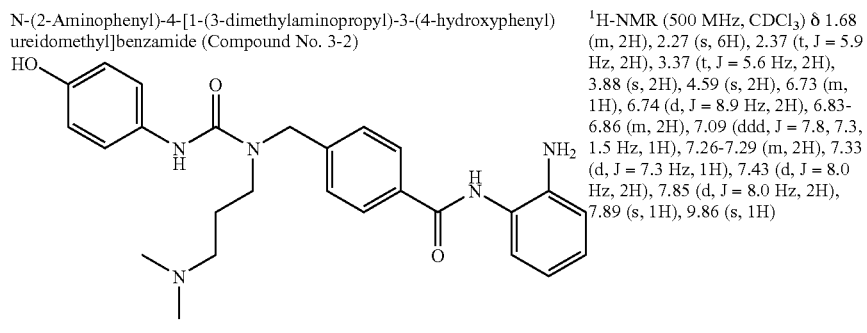

$^1$H-NMR (500 MHz, CDCl$_3$) δ 1.68 (m, 2H), 2.27 (s, 6H), 2.37 (t, J = 5.9 Hz, 2H), 3.37 (t, J = 5.6 Hz, 2H), 3.88 (s, 2H), 4.59 (s, 2H), 6.73 (m, 1H), 6.74 (d, J = 8.9 Hz, 2H), 6.83-6.86 (m, 2H), 7.09 (ddd, J = 7.8, 7.3, 1.5 Hz, 1H), 7.26-7.29 (m, 2H), 7.33 (d, J = 7.3 Hz, 1H), 7.43 (d, J = 8.0 Hz, 2H), 7.85 (d, J = 8.0 Hz, 2H), 7.89 (s, 1H), 9.86 (s, 1H)

Example 4

N-(2-Aminophenyl)-4-[3-(4-carboxyphenyl)-1-(3-dimethylaminopropyl)ureidomethyl]benzamide (Compound No. 4-1)

1.0 M aqueous sodium hydroxide solution (6.0 mL) was added to a solution of N-(2-aminophenyl)-4-[1-(3-dimethylaminopropyl)-3-(4-methoxycarbonylphenyl)ureidomethyl]benzamide (Compound No. 1-46, 62 mg, 0.12 mmol) in a mixed solvent (methanol (30 mL)-THF (5.0 mL)), and then the reaction mixture was stirred at room temperature for 7 days. After the reaction mixture was neutralized with 1.0 M hydrochloric acid, the solvent was evaporated under reduced pressure. The residue was purified by silica gel column chromatography (chloroform-methanol) to give 60 mg of the title compound as a white solid quantitatively.

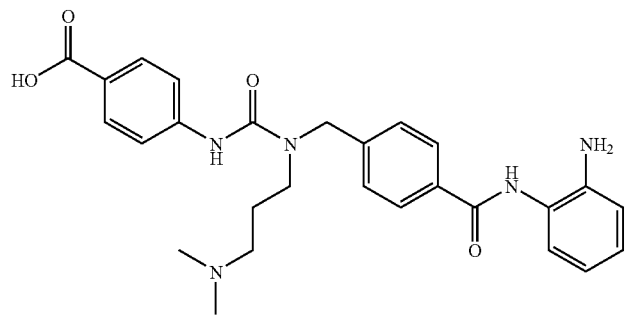

$^1$H-NMR (500 MHz, DMSO-d$_6$) δ 1.83 (br s, 2H), 2.35-2.41 (m, 8H), 3.41 (br s, 2H), 4.68 (s, 2H), 4.91 (s, 2H), 6.59 (m, 1H), 6.78 (dd, J = 7.9, 1.5 Hz, 1H), 6.96 (ddd, J = 7.9, 7.7, 1.5 Hz, 1H), 7.17 (d, J = 7.3 Hz, 1H), 7.42 (d, J = 8.4 Hz, 2H), 7.63 (d, J = 7.8 Hz, 2H), 7.83 (d, J = 8.4 Hz, 2H), 7.98 (d, J = 7.8 Hz, 2H), 9.70 (s, 1H), 12.48 (br s, 1H)

By using any compounds selected from Compounds No. 2-4, commercially available compounds, and known compounds, the following Compounds No. 4-2 was obtained by a method similar to that of Compound No. 4-1.

N-(2-Aminophenyl)-4-[3-carboxymethyl-1-(3-dimethylaminopropyl)ureidomethyl]benzamide (Compound No. 4-2)

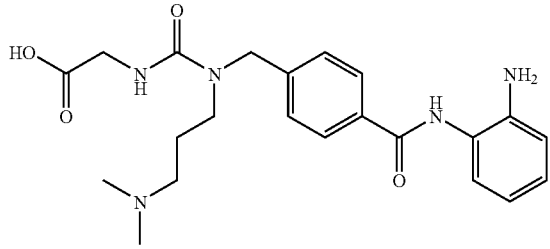

$^1$H-NMR (500 MHz, CD$_3$OD) δ 1.80 (m, 2H), 2.43 (s, 6H), 2.60 (br s, 2H), 3.39 (t, J = 6.7 Hz, 2H), 3.75 (s, 2H), 4.62 (s, 2H), 6.76 (m, 1H), 6.89 (dd, J = 8.1, 1.4 Hz, 1H), 7.07 (m, 1H), 7.16 (d, J = 6.7 Hz, 1H), 7.45 (d, J = 8.0 Hz, 2H), 7.96 (d, J = 8.0 Hz, 2H)

Example 5

N-(2-Aminophenyl)-4-[3-[4-(2-dimethylaminoethylaminocarbonyl)phenyl]-1-(3-dimethylaminopropyl)ureidomethyl]benzamide (Compound No. 5-1)

1-[Bis(dimethylamino)methylene]-5-chloro-1H-benzo triazolium 3-oxide hexafluorophosphate (49 mg, 0.067 mmol) was added to a suspension of N-(2-aminophenyl)-4-[3-(4-carboxyphenyl)-1-(3-dimethylaminopropyl)ureidomethyl]benzamide (Compound No. 4-1, 33 mg, 0.067 mmol), N,N-dimethylaminoethylenediamine (0.30 mL, 2.8 mmol) and N,N-diisopropylethylamine (0.023 mL, 0.13 mmol) in DMF (5.0 mL), and then the mixture was stirred at room temperature for 80 minutes. Saturated aqueous sodium hydrogen carbonate solution (30 mL) was added thereto, the whole was extracted with ethyl acetate (20 mL) twice, and then the organic layer was washed with brine (30 mL) twice. The organic layer was dried over anhydrous magnesium sulfate and evaporated under reduced pressure. The residue was purified by silica gel column chromatography (chloroform-methanol) to give 21 mg of the title compound as colorless oil. (Yield 57%)

(15 mL) and dichloromethane (15 mL) three times alternately, and then dried under reduced pressure to give 4.3 g of intermediate [II].

The intermediate [II] (1.2 g, 1.3 mmol) was swollen with dichloromethane (15 mL). N,N-Diisopropylethylamine (1.1 mL, 6.5 mmol) and methanesulfonyl chloride (0.30 mL, 3.9 mmol) were added thereto, and then the mixture was shaken at room temperature for 40 minutes. The reaction mixture was filtered, and then the resin was washed with DMF (10 mL) and dichloromethane (10 mL) three times alternately, with DMF (10 mL) twice additionally. DMF (15 mL) and 2-aminoethyl-1-pyrrolidine (0.83 mL, 6.5 mmol) were added to the resin, and then the mixture was shaken at room temperature for 15 hours. The reaction mixture was filtered, the resin was washed with DMF (10 mL), dichloromethane (10 mL), and methanol (10 mL) three times alternately, and then dried under reduced pressure to give intermediate [III].

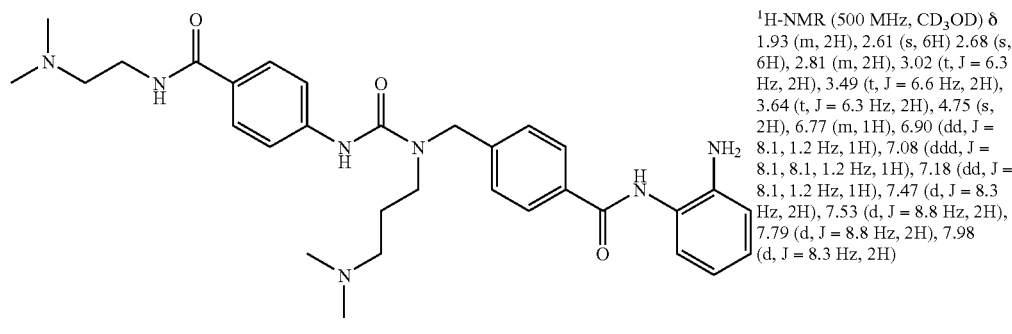

$^1$H-NMR (500 MHz, CD$_3$OD) δ 1.93 (m, 2H), 2.61 (s, 6H) 2.68 (s, 6H), 2.81 (m, 2H), 3.02 (t, J = 6.3 Hz, 2H), 3.49 (t, J = 6.6 Hz, 2H), 3.64 (t, J = 6.3 Hz, 2H), 4.75 (s, 2H), 6.77 (m, 1H), 6.90 (dd, J = 8.1, 1.2 Hz, 1H), 7.08 (ddd, J = 8.1, 8.1, 1.2 Hz, 1H), 7.18 (dd, J = 8.1, 1.2 Hz, 1H), 7.47 (d, J = 8.3 Hz, 2H), 7.53 (d, J = 8.8 Hz, 2H), 7.79 (d, J = 8.8 Hz, 2H), 7.98 (d, J = 8.3 Hz, 2H)

Example 6

N-(2-Aminophenyl)-4-[3-(4-chlorophenyl)-1-[2-(pyrrolidin-1-yl)ethyl]ureidomethyl]benzamide (Compound No. 6-1)

2-Chlorotritylchloride polystylene resin (3.0 g, 4.2 mmol) was swollen with dichloromethane (30 mL). o-Phenylenediamine (1.4 g, 13 mmol), and N,N-diisopropylethylamine (4.4 mL, 25 mmol) were added thereto, and then the mixture was shaken at room temperature for 18 hours. The reaction mixture was filtered, the resin was washed with DMF (15 mL) and dichloromethane (15 mL) three times alternately, and then dried under reduced pressure to give intermediate [I].

All the amount of the intermediate [I] was swollen with DMF (30 mL). 4-Hydroxymethylbenzoic acid (1.9 g, 13 mmol), N,N-diisopropylethylamine (4.4 mL, 25 mmol) and HATU (4.8 g, 13 mmol) were added thereto, and then the mixture was shaken at room temperature for 4 hours. The reaction mixture was filtered, the resin was washed with DMF The intermediate [III] (150 mg, 0.15 mmol) was swollen with dichloromethane (2.0 mL). 4-Chlorophenylisocyanate (120 mg, 0.75 mmol) was added thereto, and then the mixture was shaken at room temperature for 16 hours. The reaction mixture was filtered, the resin was washed with DMF (3.0 mL), dichloromethane (3.0 mL) and methanol (3.0 mL) three times alternately, and then dried under reduced pressure to give intermediate [IV].

5.0% Trifluoroacetic acid-dichloromethane solution (1.5 mL) was added to all the amount of the intermediate [IV], and then the mixture was shaken at room temperature for 25 minutes. The resin was filtered off, the filtrate was washed with saturated aqueous sodium hydrogen carbonate solution (3.0 mL), and then the organic layer was concentrated under reduced pressure. The residue was purified by silica gel column chromatography (chloroform-methanol) to give 7.2 mg of the title compound as yellow oil. (Yield 9.8%)

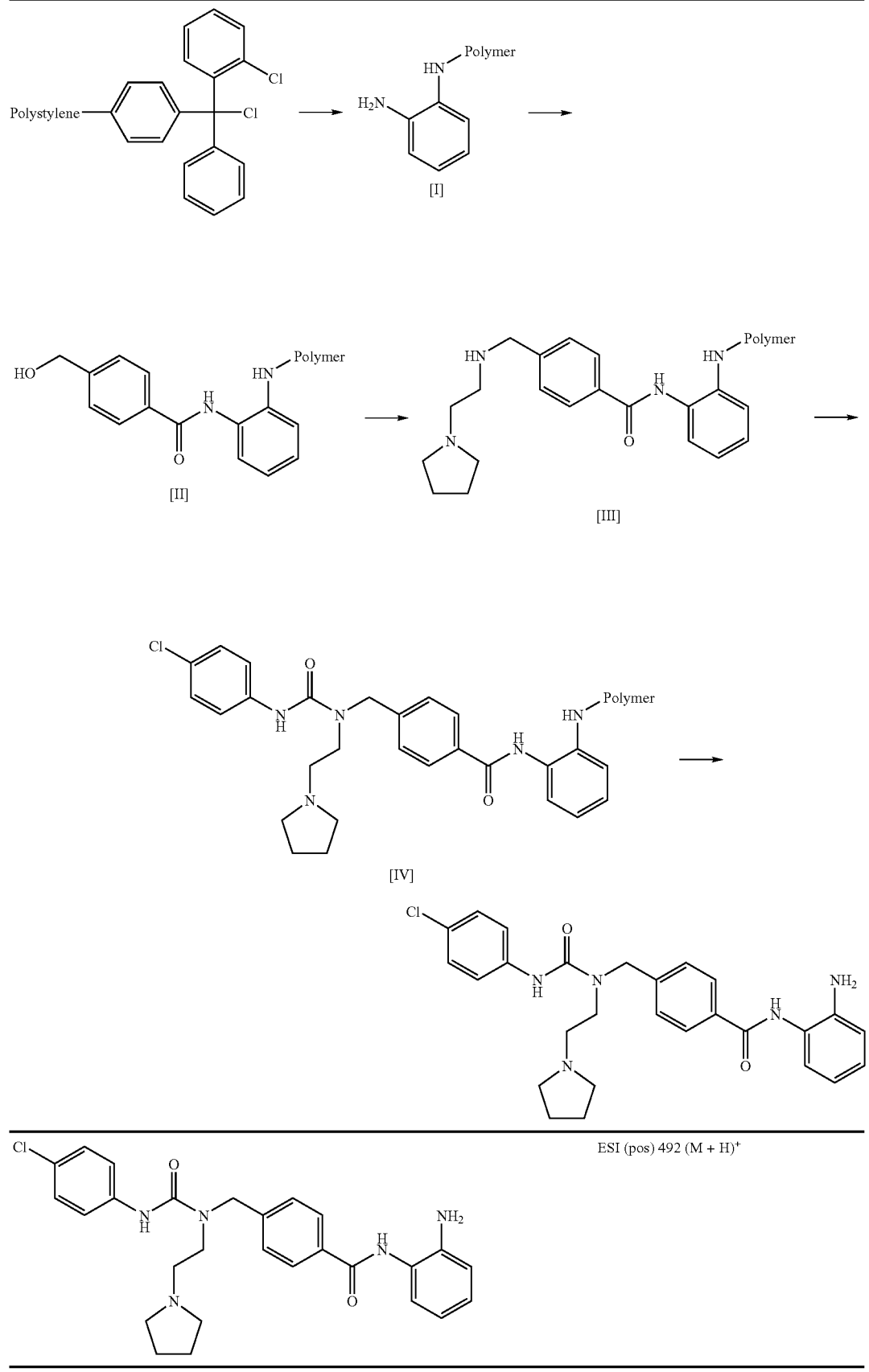
ESI (pos) 492 (M + H)+

By using any compounds selected from commercially available compounds and known compounds, the following Compounds No. 6-2 to 6-5 were obtained by a method similar to that of Compound No. 6-1.

N-(2-Aminophenyl)-4-[3-t-butyl-1-(2-pyrrolidin-1-ylethyl)ureidomethyl]benzamide (Compound No. 6-2)

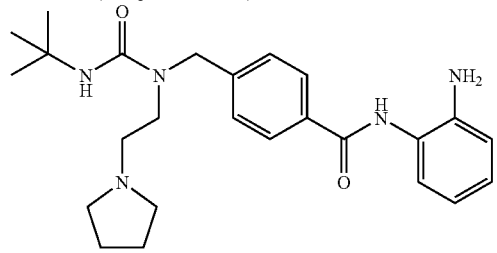

ESI (pos) 438 (M + H)⁺

N-(2-Aminophenyl)-4-[3-phenyl-1-(2-pyrrolidin-1-ylethyl)ureidomethyl]benzamide (Compound No. 6-3)

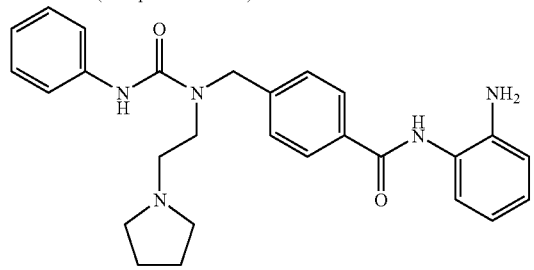

ESI (pos) 458 (M + H)⁺

N-(2-Aminophenyl)-4-[3-benzyl-1-(2-pyrrolidin-1-ylethyl)ureidomethyl]benzamide (Compound No. 6-4)

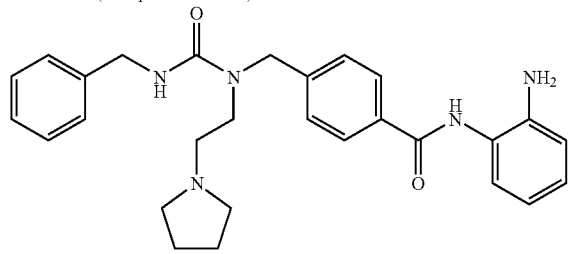

ESI (pos) 472 (M + H)⁺

N-(2-Aminophenyl)-4-[3-phenyl-1-(2-pyrrolidin-1-ylethyl)ureidomethyl]benzamide (Compound No. 6-5)

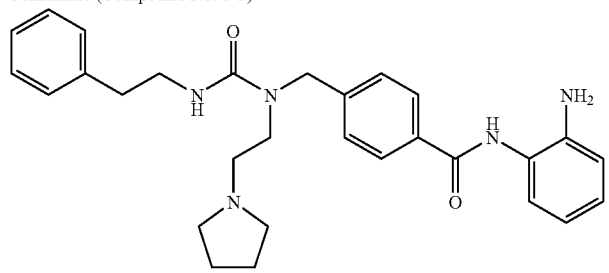

ESI (pos) 486 (M + H)⁺

Preparation Examples

Hereinafter, typical preparation examples of the present compound will be described.

| 1) Tablet (in 150 mg) | |
| --- | --- |
| Present compound | 1 mg |
| Lactose | 100 mg |
| Cornstarch | 40 mg |
| Carboxymethyl cellulose calcium | 4.5 mg |
| Hydroxypropyl cellulose | 4 mg |
| Magnesium stearate | 0.5 mg |

A tablet of the above-mentioned formulation is coated using 3 mg of a coating agent (for example, a conventional coating agent such as hydroxypropylmethyl cellulose, macrogol, or a silicone resin), whereby an objective tablet can be obtained. In addition, a desired tablet can be obtained by appropriately changing the type and/or amount of the present compound and additives.

| 2) Capsule (in 150 mg) | |
| --- | --- |
| Present compound | 5 mg |
| Lactose | 135 mg |
| Carboxymethyl cellulose calcium | 4.5 mg |
| Hydroxypropyl cellulose | 4 mg |
| Magnesium stearate | 1.5 mg |

A desired capsule can be obtained by appropriately changing the type and/or amount of the present compound and additives.

| 3) Eye drop (in 100 ml) | |
| --- | --- |
| Present compound | 100 mg |
| Sodium chloride | 900 mg |
| Polysorbate 80 | 500 mg |
| Sodium hydroxide | q.s. |
| Hydrochloric acid | q.s. |
| Sterile purified water | q.s. |

A desired eye drop can be obtained by appropriately changing the type and/or amount of the present compound and additives.

[Pharmacological Test]

1. Test for Evaluation of Effect of Morphological Change on Trabecular Meshwork Cells As a method for evaluating a cellular morphological change, an evaluation system using the cell shape index (hereinafter referred to as "CSI") as an index has been reported in The Journal of Clinical Investigation, 103, 1141-1150 (1999). Therefore, according to the method described in the above document, an effect of morphological change of the present compounds on trabecular meshwork cells was evaluated.

(Used Cells)

A human trabecular meshwork cell line (hereinafter referred to as "TM-1 cells") reported in Investigative Opthalmology & Visual Science, 43, 151-161 (2002) was used.

(Preparation of Reagents)

Culture medium 1: A reagent was prepared by adding fetal bovine serum (10%), L-glutamine (2 mM), amphotericin B (2.5 µg/mL), and gentamicin (25 µg/mL) to Dulbecco's modified Eagle medium (hereinafter referred to as "D-MEM").

Culture medium 2: Fetal bovine serum (3%), L-glutamine (2 mM), amphotericin B (2.5 µg/mL), and gentamicin (25 µg/mL) were added to D-MEM.

Cell staining liquid: A mixed liquid of Calcein-AM (16 µM) and Hoechst 33342 (40 µM) was prepared by diluting a Calcein-AM solution (cytoplasmic staining reagent, manufactured by Dojindo Laboratories) and a Hoechst 33342 solution (nuclear staining reagent, manufactured by Dojindo Laboratories) with D-MEM containing L-glutamine (2 mM), amphotericin B (2.5 µg/mL), and gentamicin (25 µg/mL).

(Preparation of Cells)

TM-1 cells subcultured at 37° C. in a 8% carbon dioxide gas atmosphere were treated with a trypsin/EDTA solution (0.05% trypsin and 0.53 mM tetrasodium ethylenediaminetetraacetate) at 24 hours before performing a drug treatment mentioned below and seeded on a 96-well culture plate. The culture medium 1 was used for the subculture of the cells. The culture medium 2 was used for the cell culture after seeding the cells on the plate.

(Preparation of Test Compound Solution)

A test compound was dissolved in dimethyl sulfoxide, whereby a 5 mM solution was prepared. Then, the resulting solution was diluted with the culture medium 2, whereby a 200 µM test compound solution was prepared.

(Preparation of Positive Control Compound Solution)

It has been reported that Y-27632 which is a Rho kinase inhibitor induces a morphological change in trabecular meshwork cells in Investigative Ophthalmology & Visual Science, 42, 137-144 (2001). Therefore, Y-27632 (produced according to the method described in WO 90/05723) was used as a positive control, and dissolved in dimethyl sulfoxide in the same manner as the test compound, whereby a 5 mM solution was prepared, and then, the resulting solution was diluted with the culture medium 2, whereby a 200 µM positive control compound solution was prepared.

(Test Method and Measurement Method)

1) To a 96-well culture plate, a solution of TM-1 cells adjusted to a cell density of $1.6 \times 10^4$ cells/mL was added in an amount of 95 µL ($1.5 \times 10^4$ cells) per well.

2) Incubation was performed at 37° C. in a 8% carbon dioxide gas atmosphere for 24 hours.

3) The test compound solution or positive control compound solution was added in an amount of 5 µL per well (the final concentration of the test compound or positive control compound was 10 µM). As a control, the culture medium 2 containing dimethyl sulfoxide (4%) was added in an amount of 5 µL per well.

4) Incubation was performed at 37° C. in a 8% carbon dioxide gas atmosphere for 24 hours.

5) The cell staining liquid was added in an amount of 10 µL per well.

6) Incubation was performed at 37° C. in a 8% carbon dioxide gas atmosphere for 1 hour to stain the cells.

7) A 37% formaldehyde solution was added in an amount of 10 µL per well.

8) Incubation was performed at room temperature for 1 hour to fix the cells.

9) Washing with phosphate-buffered saline was performed.

10) Using Array Scan Vti HCS reader (manufactured by Cellomics), images of stained cells magnified with a 20 times objective lens were captured in 80 fields (10 fields×8 wells) per test compound addition group.

11) CSI was calculated for each cell and an average value was obtained for each test compound addition group.

(Calculation Equation for CSI)

CSI was calculated using the following equation.

$$CSI = 4\pi \times (\text{Cell Area})/(\text{Cell Perimeter})^2$$

(Test Results and Discussion)

As an example of the test results, the CSI values of the respective test compound (Compound 1-2, Compound 1-4, Compound 1-5, Compound 1-16, Compound 1-22, Compound 1-23, Compound 1-28, Compound 1-31, Compound 1-34, Compound 1-36, Compound 1-38, Compound 1-39, Compound 1-43, Compound 1-46, Compound 1-47, Compound 1-49, Compound 1-50, Compound 1-53, Compound 1-58, Compound 1-59, Compound 1-60, Compound 1-66, Compound 1-76, Compound 1-80, Compound 1-94, Compound 1-97, Compound 1-102, Compound 1-104, Compound 1-107, Compound 1-113, Compound 1-128, Compound 1-134, Compound 1-135, Compound 1-165, Compound 1-169, Compound 2-2, Compound 2-3, Compound 2-4, Compound 2-5, Compound 3-1) addition groups and Y-27632 addition group are shown in Table I.

TABLE I

| Test compound | CSI |
| --- | --- |
| Control | 0.730 |
| Compound 1-2 | 0.599 |
| Compound 1-4 | 0.545 |
| Compound 1-5 | 0.636 |
| Compound 1-16 | 0.616 |
| Compound 1-22 | 0.619 |
| Compound 1-23 | 0.534 |
| Compound 1-28 | 0.514 |
| Compound 1-31 | 0.632 |
| Compound 1-34 | 0.681 |
| Compound 1-36 | 0.539 |
| Compound 1-38 | 0.616 |
| Compound 1-39 | 0.615 |
| Compound 1-43 | 0.679 |
| Compound 1-46 | 0.581 |
| Compound 1-47 | 0.613 |
| Compound 1-49 | 0.630 |
| Compound 1-50 | 0.617 |
| Compound 1-53 | 0.538 |
| Compound 1-58 | 0.610 |
| Compound 1-59 | 0.571 |
| Compound 1-60 | 0.608 |
| Compound 1-66 | 0.624 |
| Compound 1-76 | 0.649 |
| Compound 1-80 | 0.543 |
| Compound 1-94 | 0.595 |
| Compound 1-97 | 0.595 |
| Compound 1-102 | 0.538 |
| Compound 1-104 | 0.609 |
| Compound 1-107 | 0.663 |
| Compound 1-113 | 0.585 |
| Compound 1-128 | 0.554 |
| Compound 1-134 | 0.580 |
| Compound 1-135 | 0.555 |
| Compound 1-165 | 0.578 |
| Compound 1-169 | 0.566 |
| Compound 2-2 | 0.585 |
| Compound 2-3 | 0.618 |
| Compound 2-4 | 0.664 |
| Compound 2-5 | 0.570 |
| Compound 3-1 | 0.616 |
| Y-27632 | 0.600 |

2. Test for Evaluation of Intraocular Pressure-Lowering Effect

In order to evaluate an intraocular pressure-lowering effect of the present compounds, a test for evaluation of intraocular pressure-lowering effect of intracameral administration of a drug using male Japanese White rabbits was performed.

(Preparation of Test Compound Administration Liquid)

A test compound was dissolved or suspended in physiological saline containing 0.5% dimethyl sulfoxide, whereby a 1 mM test compound administration liquid was prepared.

(Test Method and Measurement Method)

One drop of 0.4% oxybuprocaine hydrochloride eye drop was instilled into both eyes of each male Japanese White rabbit to achieve local anesthesia, and thereafter, the intraocular pressure was measured using an applanation tonometer. Then, by using a syringe fitted with a 30-gauge needle, the test compound administration liquid (20 µL) was intracamerally administered to one eye. As a control, 20 µL of the vehicle (physiological saline containing 0.5% dimethyl sulfoxide) for the test compound was intracamerally administered. After the lapse of a certain period of time from the administration of the test compound or vehicle, one drop of 0.4% oxybuprocaine hydrochloride eye drop was instilled into the administered eye to achieve local anesthesia, and thereafter, the intraocular pressure was measured using an applanation tonometer.

(Calculation Equation for Intraocular Pressure Reduction Rate)

The intraocular pressure-lowering effect of each test compound was evaluated by calculating an intraocular pressure reduction rate. The intraocular pressure reduction rate (%) was calculated using the following equation.

(Intraocular Pressure Reduction rate(%))=100×(Average Value of Intraocular Pressure of Control Group)−(Average Value of Intraocular Pressure of Each Test Compound Administration Group)/(Average Value of Intraocular Pressure of Control Group)

(Test Results)

As an example of the test results, the intraocular pressure reduction rates of the respective test compound administration groups at 9 hours after administering the respective test compounds (Compound 1-59, Compound 1-80, and Compound 2-2) are shown in Table II (one group consisting of 6 cases).

TABLE II

| Test Compound | Intraocular Pressure Reduction Rate (%) |
| --- | --- |
| Compound 1-59 | 19 |
| Compound 1-80 | 18 |
| Compound 2-2 | 13 |

As shown in Table I, the present compounds have an excellent effect of cellular morphological change on trabecular meshwork cells equal to or greater than that of Y-27632 used as the positive control. Further, as shown in Table II, the present compounds have an excellent intraocular pressure-lowering effect also in the test using actual animal models. Accordingly, the present compounds can be used as an intraocular pressure-lowering agent and are expected to be useful as a preventive and/or therapeutic agent for diseases associated with intraocular pressure, particularly as a preventive and/or therapeutic agent for glaucoma, ocular hypertension, etc.

The invention claimed is:

1. A compound represented by the following formula (1) or pharmaceutically acceptable salt thereof:

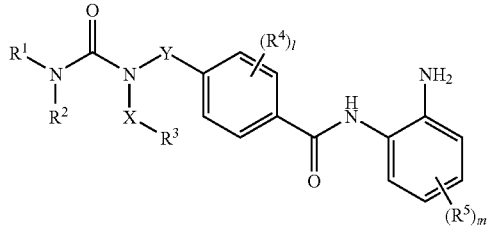
(1)

wherein $R^1$ and $R^2$ are the same or different and represent a hydrogen atom, a lower alkyl group which may have a substituent, or a group represented by the following formula (2);

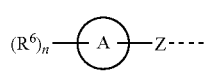
(2)

$R^3$ represents a hydroxy group, a lower alkoxy group which may have a substituent, a lower cycloalkyloxy group which may have a substituent, an aryloxy group which may have a substituent, —$NR^aR^b$, or a group represented by the following formula (3);

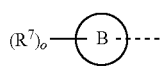
(3)

$R^4$ and $R^5$ are the same or different and represent a halogen atom, a lower alkyl group which may have a substituent, a hydroxy group, or a lower alkoxy group which may have a substituent;

$R^6$ represents a halogen atom, a lower alkyl group which may have a substituent, a lower cycloalkyl group which may have a substituent, an aryl group which may have a substituent, a heterocyclic group which may have a substituent, a hydroxy group, a lower alkoxy group which may have a substituent, a lower cycloalkyloxy group which may have a substituent, an aryloxy group which may have a substituent, a formyl group, a lower alkylcarbonyl group which may have a substituent, a carboxy group, a lower alkoxycarbonyl group which may have a substituent, a nitro group, a cyano group, —$NR^cR^d$, or —$NR^e(COR^f)$;

$R^7$ represents a lower alkyl group which may have a substituent, a lower cycloalkyl group which may have a substituent, an aryl group which may have a substituent, a hydroxy group, a lower alkoxy group which may have a substituent, a lower cycloalkyloxy group which may have a substituent, or an aryloxy group which may have a substituent;

$R^a$, $R^b$, $R^c$, $R^d$, $R^e$, and $R^f$ are the same or different and represent a hydrogen atom, a lower alkyl group which may have a substituent, a lower cycloalkyl group which may have a substituent, or an aryl group which may have a substituent;

the ring A represents a hydrocarbon ring or a heterocyclic ring;

the ring B represents a heterocyclic ring having one or plural heteroatoms selected from the group consisting of a nitrogen atom, an oxygen atom, and a sulfur atom in the ring;

X represents a lower alkylene group which may have a substituent;

Y and Z are the same or different and represent a single bond or a lower alkylene group which may have a substituent; and l, m, n, and o are the same or different and represent 0, 1, 2, or 3, in the case where l, m, n, and o represent 2 or 3, the respective groups represented by $R^4$, $R^5$, $R^6$, or $R^7$ may be the same or different.

2. The compound or pharmaceutically acceptable salt thereof according to claim 1, wherein in the formula (1), $R^1$ and $R^2$ are the same or different and represent a hydrogen atom, a lower alkyl group, a lower alkyl group having a carboxy group as a substituent, a lower alkyl group having a lower alkoxycarbonyl group as a substituent, or a group represented by the following formula (2);

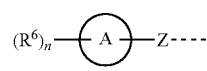
(2)

$R^3$ represents a hydroxy group, a lower alkoxy group, a lower alkoxy group having a hydroxy group as a substituent, a lower alkoxy group having a lower alkoxy group as a substituent, a lower cycloalkyloxy group, an aryloxy group, —$NR^aR^b$, or a group represented by the following formula (3)

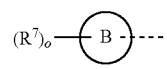
(3)

$R^4$ and $R^5$ are the same or different and represent a halogen atom, a lower alkyl group, a hydroxy group or a lower alkoxy group;

$R^6$ represents a halogen atom, a lower alkyl group, a lower alkyl group having a halogen atom as a substituent, a lower alkyl group having a cyano group as a substituent, a lower cycloalkyl group, an aryl group, a heterocyclic group, a heterocyclic group having a lower alkyl group as a substituent, a hydroxy group, a lower alkoxy group, a lower alkoxy group having a halogen atom as a substituent, a lower alkoxy group having a lower cycloalkyl group as a substituent, a lower alkoxy group having an aryl group as a substituent, a lower cycloalkyloxy group, an aryloxy group, a formyl group, a lower alkylcarbonyl group, a carboxy group, a lower alkoxycarbonyl group, a nitro group, a cyano group, —$NR^cR^d$, or —$NR^e(COR^f)$;

$R^7$ represents a lower alkyl group, a lower cycloalkyl group, an aryl group, a hydroxy group, a lower alkoxy group, a lower cycloalkyloxy group, or an aryloxy group;

$R^a$, $R^b$, $R^c$, $R^d$, $R^e$, and $R^f$ are the same or different and represent a hydrogen atom, a lower alkyl group, a lower alkyl group having —$NR^gR^h$ as a substituent, a lower cycloalkyl group, or an aryl group;

$R^g$ and $R^h$ are the same or different and represent a hydrogen atom or a lower alkyl group;

the ring A represents a hydrocarbon ring or a heterocyclic ring;

the ring B represents a heterocyclic ring having one or plural heteroatoms selected from the group consisting of a nitrogen atom and an oxygen atom in the ring;

X represents a lower alkylene group, a lower alkylene group having a hydroxy group as a substituent, or a lower alkylene group having a lower alkoxy group as a substituent;

Y and Z are the same or different and represent a single bond or a lower alkylene group; and l, m, n, and o are the same or different and represent 0, 1, 2, or 3, in the case where l, m, n, and o represent 2 or 3, the respective groups represented by $R^4$, $R^5$, $R^6$, or $R^7$ may be the same or different.

3. The compound or pharmaceutically acceptable salt thereof according to claim 1, wherein in the formula (1), $R^1$ represents a lower alkyl group, a lower alkyl group having a carboxy group as a substituent, a lower alkyl group having a lower alkoxycarbonyl group as a substituent, or a group represented by the following formula (2);

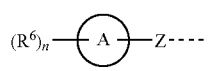

(2)

$R^2$ represents a hydrogen atom;

$R^3$ represents a hydroxy group, a lower alkoxy group, a lower alkoxy group having a hydroxy group as a substituent, —$NR^aR^b$, or a group represented by the following formula (3);

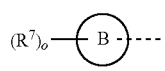

(3)

$R^5$ represents a halogen atom or a lower alkoxy group;

$R^6$ represents a halogen atom, a lower alkyl group, a lower alkyl group having a halogen atom as a substituent, a lower alkyl group having a cyano group as a substituent, a heterocyclic group, a heterocyclic group having a lower alkyl group as a substituent, a hydroxy group, a lower alkoxy group, a lower alkoxy group having a halogen atom as a substituent, a lower alkoxy group having an aryl group as a substituent, a lower alkylcarbonyl group, a carboxy group, a lower alkoxycarbonyl group, a nitro group, a cyano group, or —$NR^cR^d$;

$R^7$ represents a lower alkyl group or a hydroxy group;

$R^a$, $R^b$, $R^c$, and $R^d$ are the same or different and represent a hydrogen atom or a lower alkyl group;

the ring A represents a hydrocarbon ring or a heterocyclic ring;

the ring B represents a heterocyclic ring having one or plural heteroatoms selected from the group consisting of a nitrogen atom and an oxygen atom in the ring;

X represents a lower alkylene group or a lower alkylene group having a hydroxy group as a substituent;

Y represents a lower alkylene group;

Z represents a single bond or a lower alkylene group;

l represents 0;

m represents 0 or 1;

n represents 0, 1, or 2, in the case where n represents 2, the two groups represented by $R^6$ may be the same or different; and o represents 0 or 1.

4. The compound or pharmaceutically acceptable salt thereof according to claim 1, wherein in the formula (1), the ring A represents a ring selected from the group consisting of cyclopentane, benzene, indan, 1,2,3,4-tetrahydronaphthalene, furan, thiophene, isoxazole, thiazole, benzo[1,3]dioxole, 2,3-dihydrobenzo[1,4]dioxin, pyridine, dihydrobenzofuran, benzimidazole, 4,5,6,7-tetrahydrobenzothiazole, and quinoline.

5. The compound or pharmaceutically acceptable salt thereof according to claim 1, wherein in the formula (1), the ring B represents a ring selected from the group consisting of pyrrolidine, morpholine, piperazine piperidine, 2-pyrrolidone, and pyridine.

6. A compound or pharmaceutically acceptable salt thereof of formula (1) according to claim 1 and selected from the group consisting of N-(2-Aminophenyl)-4-[1-(2-dimethylaminoethyl)-3-phenylureidomethyl]benzamide;

N-(2-Aminophenyl)-4-[1-(2,3-dihydroxypropyl)-3-(indan-5-yl)ureidomethyl]benzamide;

N-(2-Amino-5-methoxyphenyl)-4-[1-(2-dimethylaminoethyl)-3-(indan-5-yl)ureidomethyl]benzamide;

N-(2-Aminophenyl)-4-[3-cyclopentyl-1-(2-methylaminoethyl)ureidomethyl]benzamide;

N-(2-Aminophenyl)-4-[3-t-butyl-1-(3-dimethylaminopropyl)ureidomethyl]benzamide;

N-(2-Aminophenyl)-4-[3-(4-dimethylaminophenyl)-1-[3-(morpholin-4-yl)propyl]ureidomethyl]benzamide;

N-(2-Aminophenyl)-4-[3-(4-cyanomethylphenyl)-1-(3-dimethylamino-2,2-dimethylpropyl)ureidomethyl]benzamide;

N-(2-Aminophenyl)-4-[1-(3-aminopropyl)-]-(2,3-dihydrobenzo[1,4] dioxin-6-yl)ureidomethyl]benzamide;

N-(2-Aminophenyl)-4-[3-(3,4-difluorophenyl)-1-(3-dimethylaminopropyl)ureidomethyl]benzamide;

N-(2-Aminophenyl)-4-[1-(3-dimethylaminopropyl)-3-(4-methoxycarbonylphenyl)ureidomethyl]benzamide;

N-(2-Aminophenyl)-4-[3-(4-dimethylaminophenyl)-1-(2-hydroxyethyl)ureidomethyl]benzamide;

N-(2-Aminophenyl)-4-[1-(2-hydroxyethyl)-3-phenethylureidomethyl]benzamide;

N-(2-Aminophenyl)-4-[3-(2,3-dihydrobenzo[1,4]dioxin-6-yl)-1-(1-ethylpyrrolidin-2-ylmethyl)ureidomethyl]benzamide;

N-(2-Aminophenyl)-4-[3-(3-methoxyphenyl)-1-[3-(morpholin-4-yl)propyl]ureidomethyl]benzamide;

N-(2-Aminophenyl)-4-[3-(4-difluoromethoxyphenyl)-1-[3-(morpholin-4-yl)propyl]ureidomethyl]benzamide;

N-(2-Aminophenyl)-4-[1-(3-dimethylaminopropyl)-3-(3-hydroxyphenyl)ureidomethyl]benzamide;

N-(2-Aminophenyl)-4-[3-(3,4-difluorophenyl)-1-[2-(1-methylpyrrolidin-2-yl)ethyl]ureidomethyl]benzamide;

N-(2-Aminophenyl)-4-[1-(3-dimethylaminopropyl)-3-(pyridin-3-yl)ureidomethyl]benzamide;

N-(2-Aminophenyl)-4-[3-]benzyl-1-(2-dimethylaminoethyl)ureidomethyl]benzamide;

N-(2-Aminophenyl)-4-[3-(4-chlorophenyl)-1-(piperidin-4-ylmethyl)ureidomethyl]benzamide;

N-(2-Aminophenyl)-4-[1-(3-dimethylaminopropyl)-3-(2-methoxyphenyl)ureidomethyl]benzamide;

N-(2-Aminophenyl)-4-[1-(3-dimethylaminopropyl)-3-ethoxycarbonylmethylureidomethyl]benzamide;

N-(2-Aminophenyl)-4-[3-(4-dimethylaminophenyl)-1-[3-(pyrrolidin-2-on-1-yl)propyl]ureidomethyl]benzamide;
N-(2-Aminophenyl)-4-[1-(4-dimethylaminobutyl)-3-(4-dimethylaminophenyl)ureidomethyl]benzamide;
N-(2-Aminophenyl)-4-[3-[2-(benzo[1,3]dioxol-5-yl)ethyl]-1-[3-(morpholin-4-yl)propyl]ureidomethyl]benzamide;
N-(2-Aminophenyl)-4-[3-(4-aminophenyl)-1-[3-(morpholin-4-yl)propyl]ureidomethyl]benzamide;
N-(2-Aminophenyl)-4-[3-(3-benzyloxyphenyl)-1-(3-dimethylaminopropyl)ureidomethyl]benzamide;
N-(2-Aminophenyl)-4-[1-(2-dimethylaminoethyl)-3-phenethylureidomethyl]benzamide;
N-(2-Aminophenyl)-4-[3-(2,3-dihydrobenzo[1,4]dioxin-6-yl)-1-(2-methylaminoethyl)ureidomethyl]benzamide;
N-(2-Aminophenyl)-4-[1-(3-dimethylaminopropyl)-3-phenethylureidomethyl]benzamide;
N-(2-Aminophenyl)-4-[3-(3,4-dimethoxyphenyl)-1-(3-dimethylamino-2,2-dimethylpropyl)ureidomethyl]benzamide;
N-(2-Aminophenyl)-4-[3-(2,3-dihydrobenzo[1,4]dioxin-6-yl)-1-(2-dimethylaminoethyl)ureidomethyl]benzamide;
N-(2-Aminophenyl)-4-[3-(2,3-dihydrobenzo[1,4]dioxin-6-yl)-1-[2-(4-methylpiperazin-1-yl)ethyl]ureidomethyl]benzamide;
N-(2-Aminophenyl)-4-[1-(3-dimethylaminopropyl)-3-(4-fluoro-3-nitrophenyl)ureidomethyl]benzamide;
N-(2-Aminophenyl)-4-[3-(2,3-dihydrobenzo[1,4]dioxin-6-yl)-1-[3-(pyrrolidin-1-yl)propyl]ureidomethyl]benzamide;
N-(2-Aminophenyl)-4-[3-(3,4-difluorophenyl)-1-[2-(4-methylpiperazin-1-yl)ethyl]ureidomethyl]benzamide;
N-(2-Aminophenyl)-4-[1-[3-(morpholin-4-yl)propyl-3-(3-phenylpropyl)]ureidomethyl]benzamide;
N-(2-Aminophenyl)-4-[3-(2,3-dihydrobenzo[1,4]dioxin-6-yl)-1-[3-(4-methylpiperidin-1-yl)propyl]ureidomethyl]benzamide;
N-(2-Aminophenyl)-4-[1-[3-(morpholin-4-yl)propyl]-3-(thiophen-3-yl)ureidomethyl]benzamide;
N-(2-Aminophenyl)-4-[3-(4-fluoro-3-methylphenyl)-1-[3-(morpholin-4-yl)propyl]ureidomethyl]benzamide and
N-(2-Aminophenyl)-4-[1-[3-(morpholin-4-yl)propyl]-3-(5-nitrothiazol-2-yl)ureidomethyl]benzamide.

7. A pharmaceutical composition comprising the compound or pharmaceutically acceptable salt thereof according to claim 1 and a pharmaceutical carrier.

8. A method for enhancing aqueous humor outflow comprising administering to a patient a pharmaceutically effective amount of the compound or pharmaceutically acceptable salt according to claim 1.

9. A method for lowering intraocular pressure comprising administering to a patient a pharmaceutically effective amount of the compound or pharmaceutically acceptable salt thereof according to claim 1.

10. A method for treating glaucoma or ocular hypertension comprising administering to a patient a pharmaceutically effective amount of the compound or pharmaceutically acceptable salt thereof according to claim 1.

11. The compound or pharmaceutically acceptable salt thereof according to claim 2, wherein in the formula (1), $R^1$ represents a lower alkyl group, a lower alkyl group having a carboxy group as a substituent, a lower alkyl group having a lower alkoxycarbonyl group as a substituent, or a group represented by the following formula (2);

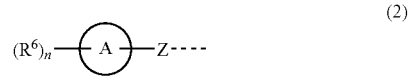

$R^2$ represents a hydrogen atom;
$R^3$ represents a hydroxy group, a lower alkoxy group, a lower alkoxy group having a hydroxy group as a substituent, —$NR^aR^b$, or a group represented by the following formula (3);

$R^5$ represents a halogen atom or a lower alkoxy group;
$R^6$ represents a halogen atom, a lower alkyl group, a lower alkyl group having a halogen atom as a substituent, a lower alkyl group having a cyano group as a substituent, a heterocyclic group, a heterocyclic group having a lower alkyl group as a substituent, a hydroxy group, a lower alkoxy group, a lower alkoxy group having a halogen atom as a substituent, a lower alkoxy group having an aryl group as a substituent, a lower alkylcarbonyl group, a carboxy group, a lower alkoxycarbonyl group, a nitro group, a cyano group, or —$NR^cR^d$;
$R^7$ represents a lower alkyl group or a hydroxy group;
$R^a$, $R^b$, $R^c$, and $R^d$ are the same or different and represent a hydrogen atom or a lower alkyl group;
the ring A represents a hydrocarbon ring or a heterocyclic ring;
the ring B represents a heterocyclic ring having one or plural heteroatoms selected from the group consisting of a nitrogen atom and an oxygen atom in the ring;
X represents a lower alkylene group or a lower alkylene group having a hydroxy group as a substituent;
Y represents a lower alkylene group;
Z represents a single bond or a lower alkylene group;
l represents 0;
m represents 0 or 1;
n represents 0, 1, or 2, in the case where n represents 2, the two groups represented by $R^6$ may be the same or different; and
o represents 0 or 1.

12. The compound or pharmaceutically acceptable salt thereof according to claim 2, wherein in the formula (1), the ring A represents a ring selected from the group consisting of cyclopentane, benzene, indan, 1,2,3,4-tetrahydronaphthalene, furan, thiophene, isoxazole, thiazole, benzo[1,3]dioxole, 2,3-dihydrobenzo[1,4]dioxin, pyridine, dihydrobenzofuran, benzimidazole, 4,5,6,7-tetrahydrobenzothiazole and quinoline.

13. The compound or pharmaceutically acceptable salt thereof according to claim 3, wherein in the formula (1), the ring A represents a ring selected from the group consisting of cyclopentane, benzene, indan, 1,2,3,4-tetrahydronaphthalene, furan, thiophene, isoxazole, thiazole, benzo[1,3]dioxole, 2,3-dihydrobenzo[1,4]dioxin, pyridine, dihydrobenzofuran, benzimidazole, 4,5,6,7-tetrahydrobenzothiazole, and quinoline.

14. The compound or pharmaceutically acceptable salt thereof according to claim 11, wherein in the formula (1), the ring A represents a ring selected from the group consisting of cyclopentane, benzene, indan, 1,2,3,4-tetrahydronaphthalene, furan, thiophene, isoxazole, thiazole, benzo[1,3]dioxole, 2,3-dihydrobenzo[1,4]dioxin, pyridine, dihydrobenzofuran, benzimidazole, 4,5,6,7-tetrahydrobenzothiazole, and quinoline.

15. The compound or pharmaceutically acceptable salt thereof according to claim 2, wherein in the formula (1), the ring B represents a ring selected from the group consisting of pyrrolidine, morpholine, piperazine, piperidine, 2-pyrrolidone, and pyridine.

16. The compound or pharmaceutically acceptable salt thereof according to claim 3, wherein in the formula (1), the ring B represents a ring selected from the group consisting of pyrrolidine, morpholine, piperazine, piperidine, 2-pyrrolidone, and pyridine.

17. The compound or pharmaceutically acceptable salt thereof according to claim 11, wherein in the formula (1), the ring B represents a ring selected from the group consisting of pyrrolidine, morpholine, piperazine, piperidine, 2-pyrrolidone, and pyridine.

18. A pharmaceutical composition comprising the compound or pharmaceutically acceptable salt thereof according to claim 6 and a pharmaceutical carrier.

19. A method for treating glaucoma or ocular hypertension comprising administering to a patient a pharmaceutically effective amount of the compound or pharmaceutically acceptable salt thereof according to claim 6.

* * * * *